US006403331B1

(12) United States Patent
Christianson et al.

(10) Patent No.: US 6,403,331 B1
(45) Date of Patent: *Jun. 11, 2002

(54) MUTANT PROTEOLYTIC ENZYMES AND METHOD OF PRODUCTION

(75) Inventors: Teresa Christianson, Cotati; Dean Goddette, Rohnert Park; Beth Frances Ladin, Santa Rosa; Maria R. Lau, Fairfield; Christian Paech, Santa Rosa; Robert B. Reynolds, Santa Rosa; Charles R. Wilson, Santa Rosa; Shiow-Shong Yang, Santa Rosa, all of CA (US)

(73) Assignee: Henkel Konnarditgesellshaft auf Aktien, Duesseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/585,798

(22) Filed: May 31, 2000

Related U.S. Application Data

(60) Continuation of application No. 08/980,135, filed on Nov. 26, 1997, now Pat. No. 6,136,553, which is a division of application No. 08/618,446, filed on Mar. 19, 1996, now Pat. No. 5,985,639, which is a division of application No. 08/254,021, filed on Jun. 2, 1994, now Pat. No. 5,500,364, which is a division of application No. 07/706,691, filed on May 29, 1991, now Pat. No. 5,340,735.

(51) Int. Cl.$^7$ .............................. C12Q 1/37; G06F 19/00

(52) U.S. Cl. .................. 435/23; 435/219; 435/220; 435/221; 435/24; 702/19

(58) Field of Search .................... 435/18, 19, 23, 435/24, 212, 219, 220, 221, 222; 702/19, 22

(56) References Cited

U.S. PATENT DOCUMENTS

| 4,760,025 A | 7/1988 | Estell et al. ................. 435/222 |
| 4,853,871 A | 8/1989 | Pantoliano et al. .......... 364/496 |
| 4,908,773 A | 3/1990 | Pantoliano et al. .......... 364/496 |
| 4,914,031 A | 4/1990 | Zukowski et al. ........... 435/222 |

FOREIGN PATENT DOCUMENTS

| EP | 0130756 | 1/1985 |
| EP | 0247647 | 12/1987 |
| EP | 0251446 | 1/1988 |
| EP | 0260105 | 3/1988 |
| EP | 0328229 | 8/1989 |
| JP | 1137972 | 5/1989 |
| WO | 87 04461 | 7/1987 |
| WO | 87 05050 | 8/1987 |
| WO | 88 07578 | 10/1988 |
| WO | 88 08028 | 10/1988 |
| WO | 88 08033 | 10/1988 |
| WO | 89 06279 | 7/1989 |
| WO | 89 09819 | 10/1989 |
| WO | 89 09830 | 10/1989 |

OTHER PUBLICATIONS

Oligonucleotide–directed mutagenesis using M13–derived vectors . . . , Zoller et al., Nucleic Acids Research, vol. 10, 6487–6500 (1982).
Construction of improved M13 vectors using oligodeoxynucleotide–directed mutagenesis, Norrander et al., Gene, 26, 101–106 (1983).
"Improvement of oligonucleotide–directed site–specific mutagenesis using double–stranded plasmid DNA", Morinaga et al., Bio/Technology 2:636–639 (1984).
"The gapped duplex DNA approach to oligonucleotide–directed mutation construction", Kramer et al., Nucleic Acids Research, 12:9441–9456 (1984).
"Improved oligonucleotide site–directed mutagenesis using M13 vectors", Carter et al., Nucleic Acids Research, 13:4431–4443 (1985).
"Rapid and efficient site–specific mutagenesis without phenotypic selection", Kunkel et al., Proc. Natl. Acad. Sci. USA, 82:488–492 (1985).
"Site–directed mutagenesis and the role of the oxyanion hole in subtilisin", Bryan et al., Proc. Natl. Acad. Sci. USA, 83:3743–3745 (1986).
Replacement of the *Bacillus subtilis* Subtilisin Structural Gene with an In–Vitro–Derived Deletion Mutation, Stahl et al., J. Bacteriol. 158:411–418 1984.
"Genes for Alkaline Protease and Neutral Protease . . . Mature Protein", Vasantha et al., J. Bacteriol, 159:811–819 (1984).
Cloning, sequencing and expression of subtilisin Carlsberg from *Bacillus lincheniformis*, Jacobs et al., Nucleic Acids Research, 13:8913–8926 (1985).
Determination of the Complete Amino–Acid Sequence of Subtilisin DY . . . Carlsberg and Amylosacchariticus, Nedkov et al., Biol. Chem. Hoppe Seyler, 366:421–430.
"Subtilisin Amylosacchariticus", Kurihara et al., Journal of Biological Chemistry, 247:5619–5631 (1972).
"Complete amino acid sequence of alkaline mesentericopeptidase", Svendsen et al., FEBS Lett., 196:228–232 (1986).
"Complete primary structure of thermitase from *Thermoactinomyces vulgaris* . . . " Meloun et al., FEBS Lett. 183:195–200 (1985).
Proteinase K from *Tritirachium album* Limber, Jany et al., Biol. Chem Hoppe–Seyler, 366:485–492, (1985).
"Designing substrate specificity by protein engineering of electrostatic interactions", Wells et al., Proc. Natl. Acad. Sci. USA 84:1219–1223 (1987).

(List continued on next page.)

Primary Examiner—Nashaat T. Nashed
(74) Attorney, Agent, or Firm—Glenn E. J. Murphy; Dilworth & Barrese, LLP

(57) ABSTRACT

Mutant *Bacillus lentus* DSM 5483 proteases are derived by the replacement of at least one amino acid residue of the mature form of the *B. lentus* DSM 5483 alkaline protease. The mutant proteases are expressed by genes which are mutated by site-specific mutagenesis. The amino acid sites selected for replacement are identified by means of a computer based method which compares the three dimensional structure of the wild-type protease and a reference protease.

23 Claims, 18 Drawing Sheets

OTHER PUBLICATIONS

"Crystal Structure of Thermitase at 14A Resolution", Teplyakov et al., J. Mol. Biol., 214:261–279 (1990).

"The Three–dimensional Structure of *Bacillus amyloliquefaciens* Subtilisin . . . ", Bott et al., J. Biol. Chem. 263:7895–7906 (1988).

"Refined 1.2 A crystal structure of the complex formed between subtilisin Carlsberg . . . interaction with subtilisin", Bode et al., EMBO Journal, 5:813–818 (1986).

"Cleavage at Asn–Gly Bonds with Hydroxylamine", Bornstein et al., Methods Enzymol. 47:132–145 (1977).

"The Effect on Subtilisin Activity of Oxidizing a Methionine Residue", Stauffer, et al., J. Biol. Chem., 244:5333–5338 (1969).

"Rational modification of enzyme catalysis by engineering surface charge", Russell et al., Nature, 328:496–500 (1987).

"Electrostatic Effects on Modification of Charged Groups . . . by Protein Engineering" Russell et al., J. Mol. Biol., 193:803:813 (1987).

Enhanced protein thermostability for site–directed mutations . . . , Mathews et al., Proc. Natl. Acad. Sci., 84:6663–6667 (1987).

"Influence of Interior Packing and Hydrophobicity on the Stability of a Protein", Sandberg et al., Science, 245:54–57 (1989).

"Contribution of hydrophobic interactions to protein stability", Kellis et al., Nature, 333:784–786 (1988).

"Structural invariants in protein folding", Cyrus Chothia, Nature, 254:304–308, (1975).

"Deciphering the Message in Protein Sequences: Tolerance to Amino Acid Substitutions", Bowie et al., Science, 247:1306–1310 (1990).

"Efficient oligonucleotide–directed construction of mutations . . . using alternating selectable markers", Stanssens, Nucleic Acids Res., 17:4441–4454 (1989).

Construction of a *Bacillus subtilis* Double Mutant Deficient in Extracellular . . . Proteases, Kawamura et al., J. Bacteriol., 160:442–444 (1984).

"Areas, Volumes, Packing, and Protein Structure", F. M. Richards, Ann. Rev. Biophys. Bioeng., 6:151–176 (1977).

A Computational Procedure for Determining Energetically Favorable Binding Sites . . . Macromolecules, P. J. Goodford, J. Med. Chem., 28:849–857 (1985).

"Charakterisierung einer Proteases aus *Thermoactinomyces vulgaris* (Thermitase)", Froemmel, et al., Acta biol. med. germ., 37:1193–1204 (1978).

"Optimal alignments in linear space", Myers et al., Comput. Applic. Biosci., 4:11–17 (1988).

"Improved tools for biological sequence comparison", Pearson et al., Proc. Natl. Acad. Sci USA, 85:2444–2448, (1988).

"Knowledge based modelling of homologous proteins, part I: . . . multiple structures", Sutcliffe et al., Protein Eng., 1:377–384 (1987).

"A solution for the best rotation to relate two sets of vectors", W. Kabsch., Acta Cryst., A32:922–923 (1976).

"Suggestions for 'Safe' Residue Substitutions in Site–directed Mutagenesis", Bordo, et al., J. Mol. Biol., 217:721–729 (1991).

"Engineering Thermostability in Subtilisin BPN' by In Vitro Mutagenesis", Rollence et al., Critical Rev. Biotechnol. 8:217–224, (1988).

The Protein Data Bank: A Computer–based Archival File for Macromolecular Structures, Bernstein et al., J. Mol. Biol. 112:535–542, (1977).

Inorganic Phosphate Determination in the Presence of a Labile Organic Phosphate: . . . Phosphatase Activity, Black et al., Anal. Biochem. 135:233–238 (1983).

"Proteases of Enhanced Stability: Characterization of a Thermostable Variant of Subtilisin", Bryan et al., Proteins: Struct. Funct. Genet. 1:326–334 (1986).

"Engineering Enzyme Specificity by 'Substrate–Assisted Catalysis'", Carter et al., Science, 237:394–399 (1987).

"Improvement in the alkaline stability of subtilisin using an efficient . . . screening procedure", Cunningham et al., Peotein Eng. 1:319–325 (1987).

"A Sensitive New Substrate for Chymotrypsin", DelMar et al., Anal. Biochem., 99:316–320 (1979).

"Engineering an Enzyme by Site–directed Mutagenesis to be Resistant to Chemical Oxidation", J. Biol. Chem. 260:6518–6521 (1985).

"Determination of Serum Proteins by Means of the Biuret Reaction", Gornall et al., J. Biol. Chem. 177:751–766 (1948).

"Biological Function for 6–Methyladenine Residues in the DNA of *Escherichia coli* K12", Marinus et al., J. Mol. Biol., 85:309–322 (1974).

"Protein Engineering of Disulfide Bonds in Subtilisin BPN", Mitchinson et al., Biochemistry, 28:4807–4815 (1989).

Protein Engineering of Subtilisin BPN': Enhanced Stabilization through . . . Disulfide Bond:, Pantoliano et al., Biochemistry, 26:2077–2082 (1987).

"Large Increases in General Stability for Subtilisin BPN' through . . . Free Energy of Unfolding", Pantoliano et al., Biochemistry, 28:7205–7213 (1989).

"The Engineering of Binding Affinity at Metal Ion Binding Sites . . . Subtilisin as a Test Case", Pantoliano e al., Biochemistry, 27:8311–8317 (1988).

"Mutant Subtilisin E with Enhanced Protease Activity Obtained by Site–directed Mutagenesis", Takagi et al., J. Biol. Chem. 263:19592–19596 (1988).

"The Role of Pro–230 in the Catalysis and Heat Stability of Subtilisin E", Takagi et al., J. Biochem. 105:953–956 (1989).

"Importance of hydrogen–bond formation in stabilizing the transition state of subtilisin", Wells et al., Phil. Trans. R. Soc. Lond., A317:415–423 (1986).

"Recruitment of substrate–specificity properties from one enzyme . . . by protein engineering", Wells et al., Proc. Natl. Acad. Sci USA, 84:5167–5171 (1987).

"In Vivo Formation and Stability of Engineered Disulfide Bonds in Subtilisin", Wells et al., J. Biol. Chem. 261:6564–6570 (1986).

"DNA mismatch–repair in *Escherichia coli* counteracting the hdyrolytic deamination of 5–methyl–cytosine residues", Zell et al., EMBO J. 6:1809–1815 (1987).

Society for Industrial Microbiology Annual Meeting, Abstract P60, B. Ladin, et al. (1990).

| | | | | | | | | | | |
|---|---|---|---|---|---|---|---|---|---|---|
| 1 | GLY | | C | 27.985 | 27.065 | 7.578 | 8 | ILE | O | 29.238 | 35.790 | 21.181 |
| 1 | GLY | | O | 26.834 | 26.692 | 7.822 | 9 | SER | N | 28.255 | 36.591 | 19.284 |
| 1 | GLY | | N | 27.785 | 25.660 | 5.657 | 9 | SER | CA | 29.270 | 37.572 | 19.075 |
| 1 | GLY | | CA | 28.517 | 26.825 | 6.143 | 9 | SER | CB | 29.158 | 38.161 | 17.652 |
| 2 | GLN | | N | 28.745 | 27.585 | 8.522 | 9 | SER | OG | 29.411 | 37.107 | 16.718 |
| 2 | GLN | | CA | 28.205 | 27.868 | 9.851 | 9 | SER | C | 29.191 | 38.684 | 20.145 |
| 2 | GLN | | CB | 29.179 | 27.265 | 10.835 | 9 | SER | O | 30.236 | 39.113 | 20.660 |
| 2 | GLN | | CG | 28.905 | 27.589 | 12.287 | 10 | ARG | N | 27.977 | 39.085 | 20.540 |
| 2 | GLN | | CD | 29.834 | 26.805 | 13.151 | 10 | ARG | CA | 27.775 | 40.132 | 21.537 |
| 2 | GLN | | OE1 | 29.476 | 25.685 | 13.540 | 10 | ARG | CB | 26.288 | 40.423 | 21.686 |
| 2 | GLN | | NE2 | 31.008 | 27.317 | 13.461 | 10 | ARG | CG | 25.946 | 41.656 | 22.562 |
| 2 | GLN | | C | 28.045 | 29.384 | 10.049 | 10 | ARG | CD | 26.666 | 42.953 | 22.101 |
| 2 | GLN | | O | 28.927 | 30.159 | 9.642 | 10 | ARG | NE | 26.378 | 43.300 | 20.705 |
| 3 | SER | | N | 26.940 | 29.781 | 10.693 | 10 | ARG | CZ | 25.394 | 44.138 | 20.338 |
| 3 | SER | | CA | 26.568 | 31.160 | 10.999 | 10 | ARG | NH1 | 25.226 | 44.365 | 19.048 |
| 3 | SER | | CB | 25.036 | 31.390 | 10.712 | 10 | ARG | NH2 | 24.604 | 44.767 | 21.215 |
| 3 | SER | | OG | 24.576 | 30.913 | 9.455 | 10 | ARG | C | 28.351 | 39.782 | 22.893 |
| 3 | SER | | C | 26.815 | 31.424 | 12.488 | 10 | ARG | O | 28.942 | 40.673 | 23.476 |
| 3 | SER | | O | 26.464 | 30.580 | 13.314 | 11 | VAL | N | 28.222 | 38.532 | 23.377 |
| 4 | VAL | | N | 27.371 | 32.570 | 12.897 | 11 | VAL | CA | 28.862 | 38.186 | 24.642 |
| 4 | VAL | | CA | 27.534 | 32.913 | 14.309 | 11 | VAL | CB | 28.127 | 37.003 | 25.339 |
| 4 | VAL | | CB | 28.860 | 33.625 | 14.552 | 11 | VAL | CG1 | 26.664 | 37.416 | 25.538 |
| 4 | VAL | | CG1 | 29.008 | 33.965 | 16.045 | 11 | VAL | CG2 | 28.227 | 35.723 | 24.530 |
| 4 | VAL | | CG2 | 30.006 | 32.739 | 14.035 | 11 | VAL | C | 30.343 | 37.832 | 24.471 |
| 4 | VAL | | C | 26.397 | 33.869 | 14.655 | 11 | VAL | O | 31.021 | 37.393 | 25.404 |
| 4 | VAL | | O | 26.344 | 34.990 | 14.097 | 12 | GLN | N | 30.868 | 37.944 | 23.261 |
| 5 | PRO | | N | 25.384 | 33.471 | 15.449 | 12 | GLN | CA | 32.288 | 37.745 | 22.957 |
| 5 | PRO | | CD | 25.140 | 32.114 | 15.924 | 12 | GLN | CB | 33.129 | 38.763 | 23.772 |
| 5 | PRO | | CA | 24.313 | 34.393 | 15.856 | 12 | GLN | CG | 32.773 | 40.196 | 23.319 |
| 5 | PRO | | CB | 23.404 | 33.524 | 16.740 | 12 | GLN | CD | 33.643 | 41.252 | 23.997 |
| 5 | PRO | | CG | 23.629 | 32.110 | 16.189 | 12 | GLN | OE1 | 34.842 | 41.403 | 23.753 |
| 5 | PRO | | C | 24.823 | 35.677 | 16.538 | 12 | GLN | NE2 | 33.145 | 42.035 | 24.926 |
| 5 | PRO | | O | 25.816 | 35.601 | 17.282 | 12 | GLN | C | 32.806 | 36.330 | 23.186 |
| 6 | TRP | | N | 24.126 | 36.804 | 16.302 | 12 | GLN | O | 33.978 | 36.104 | 23.557 |
| 6 | TRP | | CA | 24.597 | 38.070 | 16.867 | 13 | ALA | N | 31.938 | 35.350 | 22.940 |
| 6 | TRP | | CB | 23.589 | 39.231 | 16.567 | 13 | ALA | CA | 32.333 | 33.978 | 23.095 |
| 6 | TRP | | CG | 22.313 | 39.360 | 17.414 | 13 | ALA | CB | 31.189 | 33.004 | 22.890 |
| 6 | TRP | | CD2 | 22.238 | 40.080 | 18.588 | 13 | ALA | C | 33.418 | 33.589 | 22.084 |
| 6 | TRP | | CE2 | 20.905 | 39.872 | 18.955 | 13 | ALA | O | 34.293 | 32.789 | 22.477 |
| 6 | TRP | | CE3 | 23.091 | 40.874 | 19.364 | 14 | PRO | N | 33.507 | 34.053 | 20.808 |
| 6 | TRP | | CD1 | 21.120 | 38.755 | 17.097 | 14 | PRO | CD | 32.522 | 34.799 | 20.020 |
| 6 | TRP | | NE1 | 20.274 | 39.089 | 18.047 | 14 | PRO | CA | 34.622 | 33.646 | 19.943 |
| 6 | TRP | | CZ2 | 20.485 | 40.458 | 20.142 | 14 | PRO | CB | 34.311 | 34.283 | 18.601 |
| 6 | TRP | | CZ3 | 22.638 | 41.455 | 20.536 | 14 | PRO | CG | 32.806 | 34.270 | 18.606 |
| 6 | TRP | | CH2 | 21.339 | 41.249 | 20.918 | 14 | PRO | C | 35.977 | 34.034 | 20.525 |
| 6 | TRP | | C | 24.859 | 38.028 | 18.378 | 14 | PRO | O | 36.900 | 33.216 | 20.393 |
| 6 | TRP | | O | 25.812 | 38.610 | 18.854 | 15 | ALA | N | 36.096 | 35.170 | 21.257 |
| 7 | GLY | | N | 24.056 | 37.299 | 19.142 | 15 | ALA | CA | 37.383 | 35.545 | 21.881 |
| 7 | GLY | | CA | 24.171 | 37.250 | 20.597 | 15 | ALA | CB | 37.253 | 36.887 | 22.612 |
| 7 | GLY | | C | 25.488 | 36.591 | 21.015 | 15 | ALA | C | 37.837 | 34.470 | 22.892 |
| 7 | GLY | | O | 26.135 | 36.993 | 22.000 | 15 | ALA | O | 39.024 | 34.129 | 22.980 |
| 8 | ILE | | N | 25.911 | 35.557 | 20.242 | 16 | ALA | N | 36.899 | 33.826 | 23.591 |
| 8 | ILE | | CA | 27.125 | 34.811 | 20.543 | 16 | ALA | CA | 37.248 | 32.758 | 24.508 |
| 8 | ILE | | CB | 27.250 | 33.554 | 19.559 | 16 | ALA | CB | 36.057 | 32.436 | 25.368 |
| 8 | ILE | | CG2 | 28.525 | 32.760 | 19.882 | 16 | ALA | C | 37.632 | 31.505 | 23.705 |
| 8 | ILE | | CG1 | 26.016 | 32.625 | 19.654 | 16 | ALA | O | 38.587 | 30.787 | 24.026 |
| 8 | ILE | | CD | 25.683 | 32.107 | 21.080 | 17 | HIS | N | 36.927 | 31.180 | 22.610 |
| 8 | ILE | | C | 28.303 | 35.772 | 20.363 | 17 | HIS | CA | 37.206 | 29.941 | 21.872 |

FIG.1A

| | | | | | | | | | | |
|---|---|---|---|---|---|---|---|---|---|---|
| 17 | HIS | CB | 36.283 | 29.667 | 20.715 | 27 | LYS | N | 29.799 | 19.815 | 32.589 |
| 17 | HIS | CG | 34.810 | 29.669 | 21.066 | 27 | LYS | CA | 28.459 | 19.291 | 32.434 |
| 17 | HIS | CD2 | 33.823 | 29.867 | 20.140 | 27 | LYS | CB | 28.206 | 18.148 | 33.370 |
| 17 | HIS | ND1 | 34.240 | 29.557 | 22.260 | 27 | LYS | CG | 29.146 | 17.001 | 33.191 |
| 17 | HIS | CE1 | 32.932 | 29.701 | 22.082 | 27 | LYS | CD | 28.427 | 15.942 | 33.969 |
| 17 | HIS | NE2 | 32.694 | 29.881 | 20.807 | 27 | LYS | CE | 29.530 | 15.137 | 34.529 |
| 17 | HIS | C | 38.557 | 30.109 | 21.246 | 27 | LYS | NZ | 29.022 | 14.047 | 35.345 |
| 17 | HIS | O | 39.290 | 29.114 | 21.115 | 27 | LYS | C | 27.394 | 20.331 | 32.719 |
| 18 | ASN | N | 38.978 | 31.354 | 20.903 | 27 | LYS | O | 27.368 | 20.968 | 33.797 |
| 18 | ASN | CA | 40.320 | 31.583 | 20.379 | 28 | VAL | N | 26.512 | 20.472 | 31.730 |
| 18 | ASN | CB | 40.420 | 32.976 | 19.792 | 28 | VAL | CA | 25.435 | 21.471 | 31.738 |
| 18 | ASN | CG | 39.771 | 33.007 | 18.426 | 28 | VAL | CB | 25.628 | 22.534 | 30.583 |
| 18 | ASN | OD1 | 39.324 | 34.072 | 17.991 | 28 | VAL | CG1 | 24.502 | 23.560 | 30.598 |
| 18 | ASN | ND2 | 39.604 | 31.952 | 17.631 | 28 | VAL | CG2 | 26.989 | 23.220 | 30.749 |
| 18 | ASN | C | 41.377 | 31.382 | 21.454 | 28 | VAL | C | 24.121 | 20.739 | 31.512 |
| 18 | ASN | O | 42.545 | 31.105 | 21.147 | 28 | VAL | O | 23.947 | 20.067 | 30.475 |
| 19 | ARG | N | 41.007 | 31.481 | 22.726 | 29 | ALA | N | 23.203 | 20.933 | 32.446 |
| 19 | ARG | CA | 41.934 | 31.108 | 23.756 | 29 | ALA | CA | 21.900 | 20.311 | 32.385 |
| 19 | ARG | CB | 41.579 | 31.808 | 25.055 | 29 | ALA | CB | 21.478 | 19.832 | 33.763 |
| 19 | ARG | CG | 41.755 | 33.269 | 24.901 | 29 | ALA | C | 20.906 | 21.382 | 31.920 |
| 19 | ARG | CD | 41.327 | 33.963 | 26.212 | 29 | ALA | O | 20.919 | 22.490 | 32.454 |
| 19 | ARG | NE | 41.469 | 35.388 | 26.008 | 30 | VAL | N | 20.038 | 21.127 | 30.938 |
| 19 | ARG | CZ | 40.620 | 36.280 | 26.485 | 30 | VAL | CA | 19.069 | 22.069 | 30.421 |
| 19 | ARG | NH1 | 40.880 | 37.535 | 26.211 | 30 | VAL | CB | 19.123 | 22.097 | 28.835 |
| 19 | ARG | NH2 | 39.567 | 35.963 | 27.217 | 30 | VAL | CG1 | 18.017 | 22.967 | 28.267 |
| 19 | ARG | C | 41.924 | 29.600 | 23.992 | 30 | VAL | CG2 | 20.480 | 22.654 | 28.369 |
| 19 | ARG | O | 42.655 | 29.144 | 24.864 | 30 | VAL | C | 17.731 | 21.519 | 30.928 |
| 20 | GLY | N | 41.166 | 28.766 | 23.312 | 30 | VAL | O | 17.275 | 20.467 | 30.425 |
| 20 | GLY | CA | 41.105 | 27.344 | 23.620 | 31 | LEU | N | 17.155 | 22.192 | 31.928 |
| 20 | GLY | C | 40.056 | 26.959 | 24.682 | 31 | LEU | CA | 15.899 | 21.751 | 32.514 |
| 20 | GLY | O | 40.026 | 25.824 | 25.187 | 31 | LEU | CB | 15.878 | 22.118 | 33.997 |
| 21 | LEU | N | 39.130 | 27.872 | 25.003 | 31 | LEU | CG | 16.523 | 21.135 | 34.997 |
| 21 | LEU | CA | 38.098 | 27.626 | 26.023 | 31 | LEU | CD1 | 18.034 | 21.230 | 34.828 |
| 21 | LEU | CB | 38.012 | 28.796 | 26.984 | 31 | LEU | CD2 | 16.177 | 21.487 | 36.457 |
| 21 | LEU | CG | 39.321 | 29.049 | 27.732 | 31 | LEU | C | 14.832 | 22.501 | 31.724 |
| 21 | LEU | CD1 | 39.370 | 30.463 | 28.219 | 31 | LEU | O | 14.647 | 23.705 | 31.887 |
| 21 | LEU | CD2 | 39.469 | 28.017 | 28.815 | 32 | ASP | N | 14.163 | 21.816 | 30.801 |
| 21 | LEU | C | 36.767 | 27.463 | 25.284 | 32 | ASP | CA | 13.254 | 22.474 | 29.860 |
| 21 | LEU | O | 36.254 | 28.371 | 24.622 | 32 | ASP | CB | 14.173 | 23.197 | 28.850 |
| 22 | THR | N | 36.294 | 26.227 | 25.368 | 32 | ASP | CG | 13.567 | 24.470 | 28.221 |
| 22 | THR | CA | 35.094 | 25.767 | 24.713 | 32 | ASP | OD1 | 14.128 | 25.565 | 28.394 |
| 22 | THR | CB | 35.488 | 24.785 | 23.658 | 32 | ASP | OD2 | 12.549 | 24.352 | 27.538 |
| 22 | THR | OG1 | 36.139 | 23.695 | 24.331 | 32 | ASP | C | 12.331 | 21.405 | 29.226 |
| 22 | THR | CG2 | 36.341 | 25.467 | 22.585 | 32 | ASP | O | 12.057 | 20.382 | 29.870 |
| 22 | THR | C | 34.069 | 25.126 | 25.622 | 33 | THR | N | 11.874 | 21.602 | 27.972 |
| 22 | THR | O | 33.010 | 24.745 | 25.146 | 33 | THR | CA | 10.956 | 20.709 | 27.245 |
| 23 | GLY | N | 34.304 | 24.953 | 26.918 | 33 | THR | CB | 10.237 | 21.562 | 26.131 |
| 23 | GLY | CA | 33.327 | 24.232 | 27.761 | 33 | THR | OG1 | 11.275 | 22.099 | 25.255 |
| 23 | GLY | C | 33.680 | 22.769 | 27.973 | 33 | THR | CG2 | 9.394 | 22.669 | 26.737 |
| 23 | GLY | O | 32.931 | 22.033 | 28.642 | 33 | THR | C | 11.600 | 19.465 | 26.594 |
| 24 | SER | N | 34.808 | 22.329 | 27.403 | 33 | THR | O | 10.948 | 18.766 | 25.806 |
| 24 | SER | CA | 35.218 | 20.939 | 27.546 | 34 | GLY | N | 12.919 | 19.306 | 26.830 |
| 24 | SER | CB | 36.565 | 20.776 | 26.874 | 34 | GLY | CA | 13.720 | 18.216 | 26.294 |
| 24 | SER | OG | 36.819 | 19.378 | 26.828 | 34 | GLY | C | 14.758 | 18.794 | 25.334 |
| 24 | SER | C | 35.310 | 20.485 | 29.016 | 34 | GLY | O | 14.875 | 20.030 | 25.242 |
| 24 | SER | O | 35.830 | 21.218 | 29.880 | 35 | ILE | N | 15.492 | 17.921 | 24.630 |
| 25 | GLY | N | 34.786 | 19.290 | 29.245 | 35 | ILE | CA | 16.417 | 18.299 | 23.557 |
| 25 | GLY | CA | 34.688 | 18.702 | 30.571 | 35 | ILE | CB | 17.881 | 18.366 | 24.013 |
| 25 | GLY | C | 33.657 | 19.387 | 31.517 | 35 | ILE | CG2 | 18.614 | 19.017 | 22.822 |
| 25 | GLY | O | 33.562 | 19.018 | 32.697 | 35 | ILE | CG1 | 18.149 | 19.249 | 25.273 |
| 26 | VAL | N | 32.861 | 20.356 | 31.079 | 35 | ILE | CD | 19.589 | 19.096 | 25.859 |
| 26 | VAL | CA | 31.862 | 20.949 | 31.956 | 35 | ILE | C | 16.257 | 17.256 | 22.439 |
| 26 | VAL | CB | 31.863 | 22.501 | 31.794 | 35 | ILE | O | 16.348 | 16.042 | 22.687 |
| 26 | VAL | CG1 | 30.812 | 23.111 | 32.729 | 36 | SER | N | 15.873 | 17.729 | 21.243 |
| 26 | VAL | CG2 | 33.281 | 23.055 | 32.071 | 36 | SER | CA | 15.797 | 16.830 | 20.099 |
| 26 | VAL | C | 30.488 | 20.382 | 31.604 | 36 | SER | CB | 14.885 | 17.400 | 19.036 |
| 26 | VAL | O | 30.089 | 20.375 | 30.446 | 36 | SER | OG | 13.589 | 17.293 | 19.580 |

FIG.1B

| | | | | | | | | | | |
|---|---|---|---|---|---|---|---|---|---|---|
| 36 | SER | C | 17.166 | 16.572 | 19.462 | 44 | ARG | C | 24.399 | 12.088 | 27.123 |
| 36 | SER | O | 18.018 | 17.473 | 19.331 | 44 | ARG | O | 24.863 | 11.030 | 27.534 |
| 37 | THR | N | 17.380 | 15.298 | 19.076 | 45 | GLY | N | 23.168 | 12.489 | 27.392 |
| 37 | THR | CA | 18.541 | 14.930 | 18.274 | 45 | GLY | CA | 22.286 | 11.766 | 28.306 |
| 37 | THR | CB | 18.300 | 13.522 | 17.755 | 45 | GLY | C | 21.220 | 12.697 | 28.867 |
| 37 | THR | OG1 | 18.169 | 12.722 | 18.926 | 45 | GLY | O | 21.009 | 13.824 | 28.377 |
| 37 | THR | CG2 | 19.401 | 13.039 | 16.808 | 46 | GLY | N | 20.524 | 12.208 | 29.871 |
| 37 | THR | C | 18.675 | 15.912 | 17.089 | 46 | GLY | CA | 19.453 | 12.976 | 30.489 |
| 37 | THR | O | 17.670 | 16.153 | 16.374 | 46 | GLY | C | 18.430 | 12.113 | 31.221 |
| 38 | HIS | N | 19.880 | 16.435 | 16.837 | 46 | GLY | O | 18.632 | 10.912 | 31.445 |
| 38 | HIS | CA | 20.021 | 17.474 | 15.806 | 47 | ALA | N | 17.313 | 12.744 | 31.558 |
| 38 | HIS | CB | 19.786 | 18.868 | 16.461 | 47 | ALA | CA | 16.222 | 12.120 | 32.291 |
| 38 | HIS | CG | 19.722 | 20.046 | 15.486 | 47 | ALA | CB | 16.461 | 12.192 | 33.779 |
| 38 | HIS | CD2 | 20.803 | 20.545 | 14.801 | 47 | ALA | C | 14.953 | 12.896 | 31.997 |
| 38 | HIS | ND1 | 18.655 | 20.775 | 15.114 | 47 | ALA | O | 15.007 | 14.081 | 31.604 |
| 38 | HIS | CE1 | 19.051 | 21.670 | 14.239 | 48 | SER | N | 13.817 | 12.215 | 32.075 |
| 38 | HIS | NE2 | 20.348 | 21.530 | 14.048 | 48 | SER | CA | 12.537 | 12.888 | 31.947 |
| 38 | HIS | C | 21.432 | 17.344 | 15.305 | 48 | SER | CB | 11.680 | 12.343 | 30.801 |
| 38 | HIS | O | 22.341 | 17.174 | 16.118 | 48 | SER | OG | 10.390 | 12.945 | 30.842 |
| 39 | PRO | N | 21.740 | 17.555 | 14.025 | 48 | SER | C | 11.760 | 12.680 | 33.243 |
| 39 | PRO | CD | 20.795 | 17.752 | 12.918 | 48 | SER | O | 11.740 | 11.558 | 33.791 |
| 39 | PRO | CA | 23.135 | 17.467 | 13.571 | 49 | PHE | N | 11.224 | 13.808 | 33.696 |
| 39 | PRO | CB | 23.084 | 17.619 | 12.070 | 49 | PHE | CA | 10.358 | 13.821 | 34.885 |
| 39 | PRO | CG | 21.744 | 18.261 | 11.799 | 49 | PHE | CB | 10.967 | 14.782 | 35.924 |
| 39 | PRO | C | 24.112 | 18.457 | 14.195 | 49 | PHE | CG | 12.302 | 14.253 | 36.403 |
| 39 | PRO | O | 25.318 | 18.260 | 14.162 | 49 | PHE | CD1 | 13.454 | 14.844 | 35.923 |
| 40 | ASP | N | 23.645 | 19.520 | 14.832 | 49 | PHE | CD2 | 12.383 | 13.128 | 37.204 |
| 40 | ASP | CA | 24.583 | 20.488 | 15.375 | 49 | PHE | CE1 | 14.676 | 14.300 | 36.225 |
| 40 | ASP | CB | 24.218 | 21.897 | 14.900 | 49 | PHE | CE2 | 13.616 | 12.590 | 37.509 |
| 40 | ASP | CG | 25.453 | 22.801 | 14.740 | 49 | PHE | CZ | 14.760 | 13.176 | 37.008 |
| 40 | ASP | OD1 | 26.526 | 22.264 | 14.551 | 49 | PHE | C | 8.915 | 14.206 | 34.546 |
| 40 | ASP | OD2 | 25.389 | 24.037 | 14.740 | 49 | PHE | O | 8.115 | 14.601 | 35.418 |
| 40 | ASP | C | 24.561 | 20.439 | 16.874 | 50 | VAL | N | 8.571 | 14.104 | 33.248 |
| 40 | ASP | O | 24.918 | 21.450 | 17.480 | 50 | VAL | CA | 7.230 | 14.424 | 32.796 |
| 41 | LEU | N | 24.080 | 19.327 | 17.430 | 50 | VAL | CB | 7.264 | 15.245 | 31.450 |
| 41 | LEU | CA | 24.102 | 19.142 | 18.883 | 50 | VAL | CG1 | 5.869 | 15.427 | 30.821 |
| 41 | LEU | CB | 22.713 | 19.260 | 19.513 | 50 | VAL | CG2 | 7.766 | 16.635 | 31.755 |
| 41 | LEU | CG | 21.938 | 20.541 | 19.465 | 50 | VAL | C | 6.512 | 13.085 | 32.594 |
| 41 | LEU | CD1 | 20.485 | 20.249 | 19.882 | 50 | VAL | O | 6.894 | 12.336 | 31.695 |
| 41 | LEU | CD2 | 22.642 | 21.595 | 20.331 | 51 | PRO | N | 5.443 | 12.724 | 33.315 |
| 41 | LEU | C | 24.635 | 17.780 | 19.265 | 51 | PRO | CD | 4.826 | 13.553 | 34.344 |
| 41 | LEU | O | 24.417 | 16.802 | 18.530 | 51 | PRO | CA | 4.805 | 11.411 | 33.232 |
| 42 | ASN | N | 25.298 | 17.707 | 20.415 | 51 | PRO | CB | 3.632 | 11.476 | 34.218 |
| 42 | ASN | CA | 25.792 | 16.443 | 20.953 | 51 | PRO | CG | 4.118 | 12.525 | 35.235 |
| 42 | ASN | CB | 27.341 | 16.452 | 21.066 | 51 | PRO | C | 4.358 | 10.971 | 31.854 |
| 42 | ASN | CG | 27.960 | 15.195 | 21.667 | 51 | PRO | O | 4.621 | 9.848 | 31.454 |
| 42 | ASN | OD1 | 29.168 | 15.169 | 21.967 | 52 | GLY | N | 3.693 | 11.820 | 31.082 |
| 42 | ASN | ND2 | 27.260 | 14.090 | 21.803 | 52 | GLY | CA | 3.269 | 11.377 | 29.746 |
| 42 | ASN | C | 25.176 | 16.272 | 22.354 | 52 | GLY | C | 4.368 | 11.323 | 28.690 |
| 42 | ASN | O | 25.590 | 16.890 | 22.332 | 52 | GLY | O | 4.117 | 10.848 | 27.575 |
| 43 | ILE | N | 24.152 | 15.442 | 22.457 | 53 | GLU | N | 5.606 | 11.757 | 28.996 |
| 43 | ILE | CA | 23.458 | 15.252 | 23.736 | 53 | GLU | CA | 6.645 | 11.848 | 28.005 |
| 43 | ILE | CB | 21.958 | 15.077 | 23.423 | 53 | GLU | CB | 6.909 | 13.311 | 27.676 |
| 43 | ILE | CG2 | 21.208 | 14.865 | 24.766 | 53 | GLU | CG | 5.740 | 13.985 | 27.008 |
| 43 | ILE | CG1 | 21.451 | 16.284 | 22.605 | 53 | GLU | CD | 5.991 | 15.433 | 26.597 |
| 43 | ILE | CD | 20.150 | 16.044 | 21.857 | 53 | GLU | OE1 | 7.145 | 15.826 | 26.393 |
| 43 | ILE | C | 24.075 | 14.023 | 24.422 | 53 | GLU | OE2 | 5.012 | 16.167 | 26.462 |
| 43 | ILE | O | 24.160 | 12.963 | 23.781 | 53 | GLU | C | 7.901 | 11.202 | 28.519 |
| 44 | ARG | N | 24.520 | 14.131 | 25.675 | 53 | GLU | O | 8.803 | 11.919 | 28.919 |
| 44 | ARG | CA | 25.246 | 13.030 | 26.309 | 54 | PRO | N | 8.059 | 9.880 | 28.483 |
| 44 | ARG | CB | 26.332 | 13.557 | 27.250 | 54 | PRO | CD | 7.103 | 8.945 | 27.908 |
| 44 | ARG | CG | 27.060 | 14.753 | 26.730 | 54 | PRO | CA | 9.245 | 9.200 | 29.004 |
| 44 | ARG | CD | 27.731 | 14.330 | 25.467 | 54 | PRO | CB | 8.817 | 7.745 | 28.993 |
| 44 | ARG | NE | 29.007 | 13.812 | 25.844 | 54 | PRO | CG | 7.964 | 7.702 | 27.752 |
| 44 | ARG | CZ | 30.106 | 14.554 | 25.653 | 54 | PRO | C | 10.548 | 9.487 | 28.240 |
| 44 | ARG | NH1 | 31.274 | 14.034 | 26.023 | 54 | PRO | O | 11.625 | 9.172 | 28.750 |
| 44 | ARG | NH2 | 30.099 | 15.758 | 25.065 | 55 | SER | N | 10.497 | 10.048 | 27.015 |

FIG.1C

| | | | | | | | | | | |
|---|---|---|---|---|---|---|---|---|---|---|
|55|SER|CA|11.678|10.360|26.197|65|HIS|CA|16.749|26.168|20.989|
|55|SER|CB|11.310|10.444|24.730|65|HIS|CB|15.534|27.012|20.769|
|55|SER|OG|12.390|10.759|23.870|65|HIS|CG|15.850|28.409|28.237|
|55|SER|C|12.250|11.702|26.559|65|HIS|CD2|15.686|28.794|18.918|
|55|SER|O|11.469|12.540|27.001|65|HIS|ND1|16.319|29.457|20.941|
|56|THR|N|13.533|11.968|26.265|65|HIS|CE1|16.438|30.455|20.096|
|56|THR|CA|14.084|13.315|26.487|65|HIS|NE2|16.056|30.048|18.887|
|56|THR|CB|15.596|13.250|26.945|65|HIS|C|17.672|26.657|22.118|
|56|THR|OG1|16.283|12.433|25.998|65|HIS|O|18.820|27.073|21.904|
|56|THR|CG2|15.743|12.741|28.390|66|VAL|N|17.220|26.535|23.376|
|56|THR|C|13.978|14.192|25.225|66|VAL|CA|18.084|26.803|24.544|
|56|THR|O|14.370|15.358|25.250|66|VAL|CB|17.351|26.378|25.832|
|57|GLN|N|13.331|13.623|24.170|66|VAL|CG1|18.194|26.482|27.092|
|57|GLN|CA|13.252|14.317|22.886|66|VAL|CG2|16.264|27.335|25.994|
|57|GLN|CB|12.743|13.375|21.797|66|VAL|C|19.427|26.062|24.466|
|57|GLN|CG|13.825|12.370|21.360|66|VAL|O|20.494|26.687|24.586|
|57|GLN|CD|15.108|13.013|20.762|67|ALA|N|19.347|24.730|24.292|
|57|GLN|OE1|15.091|13.752|19.766|67|ALA|CA|20.534|23.878|24.204|
|57|GLN|NE2|16.267|12.793|21.390|67|ALA|CB|20.081|22.462|23.828|
|57|GLN|C|12.314|15.495|23.027|67|ALA|C|21.526|24.393|23.140|
|57|GLN|O|11.395|15.425|23.858|67|ALA|O|22.732|24.464|23.385|
|58|ASP|N|12.508|16.545|22.256|68|GLY|N|21.028|24.843|21.978|
|58|ASP|CA|11.724|17.738|22.451|68|GLY|CA|21.890|25.373|20.923|
|58|ASP|CB|12.619|18.910|22.214|68|GLY|C|22.602|26.682|21.221|
|58|ASP|CG|12.036|20.302|22.427|68|GLY|O|23.730|26.888|20.726|
|58|ASP|OD1|10.950|20.447|23.006|69|THR|N|22.009|27.580|22.020|
|58|ASP|OD2|12.737|21.245|22.032|69|THR|CA|22.727|28.785|22.414|
|58|ASP|C|10.499|17.854|21.573|69|THR|CB|21.703|29.733|23.084|
|58|ASP|O|10.627|18.076|20.358|69|THR|OG1|20.690|29.972|22.076|
|59|GLY|N|9.311|17.809|22.191|69|THR|CG2|22.339|31.046|23.576|
|59|GLY|CA|8.021|17.992|21.500|69|THR|C|23.902|28.431|23.353|
|59|GLY|C|7.601|19.445|21.318|69|THR|O|24.986|29.042|23.288|
|59|GLY|O|6.527|19.731|20.754|70|ILE|N|23.686|27.426|24.235|
|60|ASN|N|8.431|20.374|21.802|70|ILE|CA|24.771|26.952|25.107|
|60|ASN|CA|8.085|21.787|21.793|70|ILE|CB|24.305|25.947|26.219|
|60|ASN|CB|8.166|22.340|23.222|70|ILE|CG2|25.501|25.525|27.092|
|60|ASN|CG|7.768|23.804|23.268|70|ILE|CG1|23.197|26.607|27.065|
|60|ASN|OD1|8.585|24.702|23.090|70|ILE|CD|22.458|25.687|28.103|
|60|ASN|ND2|6.503|24.085|23.545|70|ILE|C|25.820|26.222|24.285|
|60|ASN|C|8.971|22.642|20.883|70|ILE|O|27.014|26.530|24.398|
|60|ASN|O|8.525|23.378|20.022|71|ALA|N|25.447|25.251|23.451|
|61|GLY|N|10.269|22.585|21.093|71|ALA|CA|26.467|24.349|22.986|
|61|GLY|CA|11.202|23.372|20.337|71|ALA|CB|26.523|23.129|23.948|
|61|GLY|C|12.035|24.187|21.318|71|ALA|C|26.352|23.895|21.578|
|61|GLY|O|13.231|24.429|21.115|71|ALA|O|26.869|22.805|21.295|
|62|HIS|N|11.417|24.583|22.439|72|ALA|N|25.785|24.709|20.671|
|62|HIS|CA|12.068|25.515|23.336|72|ALA|CA|25.772|24.252|19.280|
|62|HIS|CB|11.034|25.886|24.385|72|ALA|CB|25.105|25.252|18.367|
|62|HIS|CG|11.450|27.020|25.268|72|ALA|C|27.223|24.056|18.832|
|62|HIS|CD2|11.218|28.363|25.048|72|ALA|O|28.112|24.803|19.205|
|63|HIS|ND1|11.969|26.858|26.498|73|LEU|N|27.412|22.934|18.090|
|62|HIS|CE1|12.011|28.039|27.067|73|LEU|CA|28.744|22.458|17.726|
|62|HIS|NE2|11.572|28.932|26.189|73|LEU|CB|28.630|21.030|17.087|
|62|HIS|C|13.371|24.957|23.944|73|LEU|CG|27.913|19.969|17.918|
|62|HIS|O|14.409|25.642|23.918|73|LEU|CD1|27.805|18.638|17.193|
|63|GLY|N|13.351|23.723|24.453|73|LEU|CD2|28.650|19.898|19.221|
|63|GLY|CA|14.577|23.186|25.039|73|LEU|C|29.465|23.384|16.782|
|63|GLY|C|15.709|23.028|24.021|73|LEU|O|28.857|23.968|15.858|
|63|GLY|O|16.870|23.232|24.356|74|ASN|N|30.768|23.410|17.002|
|64|THR|N|15.375|22.712|22.746|74|ASN|CA|31.650|24.268|16.196|
|64|THR|CA|16.392|22.485|21.700|74|ASN|CB|32.829|24.736|17.002|
|64|THR|CB|15.729|21.894|20.395|74|ASN|CG|33.638|25.786|16.240|
|64|THR|OG1|15.057|20.682|20.709|74|ASN|OD1|33.278|26.358|15.207|
|64|THR|CG2|16.823|21.570|19.338|74|ASN|ND2|34.798|26.098|16.774|
|64|THR|C|17.078|23.790|21.373|74|ASN|C|32.170|23.435|15.022|
|64|THR|O|18.287|23.840|21.192|74|ASN|O|33.097|22.639|15.197|
|65|HIS|N|16.252|24.838|21.308|75|ASN|N|31.602|23.663|13.836|

FIG.1D

| | | | | | | | | | | |
|---|---|---|---|---|---|---|---|---|---|---|
|75|ASN|CA|31.833|22.805|12.665|85|SER|C|31.718|21.142|25.147|
|75|ASN|CB|30.957|21.533|12.702|85|SER|O|32.117|20.128|25.689|
|75|ASN|CG|29.491|21.798|13.007|86|ALA|N|30.806|21.904|25.738|
|75|ASN|OD1|28.914|22.891|12.815|86|ALA|CA|30.151|21.459|26.967|
|75|ASN|ND2|28.869|20.780|13.605|86|ALA|CB|29.153|22.489|27.391|
|75|ASN|C|31.502|23.581|11.415|86|ALA|C|29.408|20.122|26.787|
|75|ASN|O|31.582|24.793|11.490|86|ALA|O|28.914|19.771|25.689|
|76|SER|N|31.121|22.947|10.298|87|GLU|N|29.338|19.367|27.882|
|76|SER|CA|30.794|23.635|9.055|87|GLU|CA|28.637|18.102|27.917|
|76|SER|CB|31.452|22.852|7.920|87|GLU|CB|29.274|17.235|28.985|
|76|SER|OG|32.867|22.956|8.023|87|GLU|CG|30.727|16.977|28.652|
|76|SER|C|29.308|23.826|8.771|87|GLU|CD|31.359|15.911|29.523|
|76|SER|O|28.913|24.172|7.628|87|GLU|OE1|30.638|15.142|30.165|
|77|ILE|N|28.486|23.612|9.815|87|GLU|OE2|32.580|15.850|29.550|
|77|ILE|CA|27.049|23.710|9.658|87|GLU|C|27.172|18.407|28.237|
|77|ILE|CB|26.315|22.283|9.597|87|GLU|O|26.787|18.788|29.353|
|77|ILE|CG2|26.735|21.594|8.269|88|LEU|N|26.340|18.241|27.230|
|77|ILE|CG1|26.604|21.393|10.803|88|LEU|CA|24.949|18.654|27.326|
|77|ILE|CD|25.657|20.178|10.887|88|LEU|CB|24.566|19.080|25.910|
|77|ILE|C|26.407|24.494|10.799|88|LEU|CG|23.561|20.137|25.626|
|77|ILE|O|26.960|24.700|11.891|88|LEU|CD1|23.929|21.475|26.321|
|78|GLY|N|25.199|24.925|10.501|88|LEU|CD2|23.521|20.293|24.093|
|78|GLY|CA|24.338|25.534|11.486|88|LEU|C|24.042|17.570|27.876|
|78|GLY|C|24.874|26.773|12.159|88|LEU|O|24.093|16.491|27.282|
|78|GLY|O|25.345|27.713|11.542|89|TYR|N|23.223|17.777|28.919|
|79|VAL|N|24.781|26.721|13.475|89|TYR|CA|22.249|16.807|29.449|
|79|VAL|CA|25.226|27.840|14.293|89|TYR|CB|22.538|16.474|30.942|
|79|VAL|CB|23.977|28.470|15.058|89|TYR|CG|23.828|15.673|31.047|
|79|VAL|CG1|23.105|29.130|14.034|89|TYR|CD1|25.048|16.317|30.920|
|79|VAL|CG2|23.172|27.468|15.841|89|TYR|CE1|26.230|15.627|30.860|
|79|VAL|C|26.342|27.460|15.258|89|TYR|CD2|23.797|14.292|31.142|
|79|VAL|O|27.035|26.445|15.015|89|TYR|CE2|24.974|13.578|31.070|
|80|LEU|N|26.574|28.266|16.310|89|TYR|CZ|26.175|14.250|30.937|
|80|LEU|CA|27.681|28.023|17.216|89|TYR|OH|27.340|13.513|30.872|
|80|LEU|CB|28.856|28.882|16.777|89|TYR|C|20.847|17.347|29.318|
|80|LEU|CG|30.090|28.886|17.612|89|TYR|O|20.561|18.513|29.646|
|80|LEU|CD1|30.630|27.510|17.592|90|ALA|N|20.000|16.511|28.733|
|80|LEU|CD2|31.076|29.900|17.113|90|ALA|CA|18.613|16.880|28.538|
|80|LEU|C|28.436|18.614|90|ALA|CB|17.991|16.206|27.306|
|80|LEU|O|26.667|29.536|18.725|90|ALA|C|17.794|16.453|29.749|
|81|GLY|N|27.333|27.597|19.625|90|ALA|O|17.565|15.260|29.984|
|81|GLY|CA|26.928|28.085|20.924|91|VAL|N|17.307|17.405|30.542|
|81|GLY|C|28.076|28.805|21.662|91|VAL|CA|16.489|17.070|31.706|
|81|GLY|O|29.253|28.863|21.248|91|VAL|CB|17.050|17.737|32.979|
|82|VAL|N|27.794|29.222|22.883|91|VAL|CG1|16.278|17.172|34.186|
|82|VAL|CA|28.824|29.876|23.663|91|VAL|CG2|18.529|17.434|33.152|
|82|VAL|CB|28.207|30.550|24.929|91|VAL|C|15.086|17.576|31.413|
|82|VAL|CG1|29.266|31.108|25.913|91|VAL|O|14.803|18.789|31.545|
|82|VAL|CG2|27.250|31.691|24.395|92|LYS|N|14.186|16.716|30.935|
|82|VAL|C|29.915|28.926|24.085|92|LYS|CA|12.860|17.211|30.608|
|82|VAL|O|31.102|29.295|24.118|92|LYS|CB|12.271|16.257|29.604|
|83|ALA|N|29.504|27.716|24.494|92|LYS|CG|10.802|16.621|29.273|
|83|ALA|CA|30.437|26.706|24.970|92|LYS|CD|10.070|15.579|28.398|
|83|ALA|CB|30.194|26.444|26.456|92|LYS|CE|10.580|15.652|26.970|
|83|ALA|C|30.270|25.404|24.181|92|LYS|NZ|9.873|14.730|26.095|
|83|ALA|O|29.605|24.459|24.615|92|LYS|C|12.009|17.347|31.892|
|84|PRO|N|30.827|25.356|22.956|92|LYS|O|11.719|16.396|32.624|
|84|PRO|CD|31.627|26.423|22.334|93|VAL|N|11.659|18.596|32.162|
|84|PRO|CA|30.449|24.325|21.985|93|VAL|CA|10.834|18.966|33.299|
|84|PRO|CB|30.988|24.826|20.658|93|VAL|CB|11.520|19.956|34.315|
|84|PRO|CG|31.954|25.925|20.928|93|VAL|CG1|12.719|19.267|34.948|
|84|PRO|C|30.900|22.929|22.328|93|VAL|CG2|11.808|21.301|33.634|
|84|PRO|O|30.460|21.987|21.673|93|VAL|C|9.545|19.632|32.844|
|85|SER|N|31.795|22.800|23.311|93|VAL|O|8.636|19.907|33.627|
|85|SER|CA|32.303|21.525|23.810|94|LEU|N|9.434|19.988|31.564|
|85|SER|CB|33.826|21.574|23.944|94|LEU|CA|8.253|20.628|31.023|
|85|SER|OG|34.358|21.691|22.630|94|LEU|CB|8.576|22.025|30.524|

FIG.1E

| | | | | | | | | | | |
|---|---|---|---|---|---|---|---|---|---|---|
| 94 | LEU | CG | 9.291 | 22.983 | 31.432 | 105 | ILE | CA | 11.308 | 20.992 | 38.055 |
| 94 | LEU | CD1 | 9.772 | 24.188 | 30.604 | 105 | ILE | CB | 10.782 | 22.425 | 38.033 |
| 94 | LEU | CD2 | 8.380 | 23.374 | 32.555 | 105 | ILE | CG2 | 12.002 | 23.365 | 38.118 |
| 94 | LEU | C | 7.783 | 19.781 | 29.830 | 105 | ILE | CG1 | 9.919 | 22.652 | 36.794 |
| 94 | LEU | O | 8.605 | 19.154 | 29.150 | 105 | ILE | CD | 9.191 | 24.036 | 36.796 |
| 95 | GLY | N | 6.479 | 19.754 | 29.581 | 105 | ILE | C | 12.186 | 20.703 | 39.293 |
| 95 | GLY | CA | 5.913 | 18.985 | 28.494 | 105 | ILE | O | 13.406 | 20.539 | 39.166 |
| 95 | GLY | C | 5.987 | 19.713 | 27.150 | 106 | ALA | N | 11.585 | 20.494 | 40.484 |
| 95 | GLY | O | 6.394 | 20.881 | 27.052 | 106 | ALA | CA | 12.324 | 20.165 | 41.677 |
| 96 | ALA | N | 5.518 | 18.995 | 26.112 | 106 | ALA | CB | 11.347 | 20.164 | 42.870 |
| 96 | ALA | CA | 5.460 | 19.485 | 24.733 | 106 | ALA | C | 13.009 | 18.797 | 41.505 |
| 96 | ALA | CB | 4.826 | 18.408 | 23.824 | 106 | ALA | O | 14.185 | 18.706 | 41.872 |
| 96 | ALA | C | 4.659 | 20.791 | 24.611 | 107 | GLN | N | 12.452 | 17.715 | 40.904 |
| 96 | ALA | O | 4.945 | 21.657 | 23.772 | 107 | GLN | CA | 13.267 | 16.487 | 40.797 |
| 97 | ASP | N | 3.680 | 20.986 | 25.508 | 107 | GLN | CB | 12.484 | 15.170 | 40.501 |
| 97 | ASP | CA | 2.957 | 22.248 | 25.636 | 107 | GLN | CG | 11.380 | 14.761 | 41.453 |
| 97 | ASP | CB | 1.637 | 22.010 | 26.330 | 107 | GLN | CD | 10.582 | 13.516 | 41.085 |
| 97 | ASP | CG | 1.665 | 21.267 | 27.665 | 107 | GLN | OE1 | 9.435 | 13.412 | 41.526 |
| 97 | ASP | OD1 | 2.704 | 20.782 | 28.130 | 107 | GLN | NE2 | 11.040 | 12.542 | 40.292 |
| 97 | ASP | OD2 | 0.596 | 21.183 | 28.270 | 107 | GLN | C | 14.299 | 16.625 | 39.702 |
| 97 | ASP | C | 3.645 | 23.410 | 26.351 | 107 | GLN | O | 15.333 | 15.973 | 39.804 |
| 97 | ASP | O | 3.058 | 24.477 | 26.509 | 108 | GLY | N | 14.058 | 17.494 | 38.722 |
| 98 | GLY | N | 4.885 | 23.232 | 26.820 | 108 | GLY | CA | 15.068 | 17.832 | 37.732 |
| 98 | GLY | CA | 5.597 | 24.264 | 27.561 | 108 | GLY | C | 16.281 | 18.376 | 38.456 |
| 98 | GLY | C | 5.223 | 24.311 | 29.038 | 108 | GLY | O | 17.409 | 17.922 | 38.169 |
| 98 | GLY | O | 5.866 | 24.997 | 29.828 | 109 | LEU | N | 16.086 | 19.337 | 39.380 |
| 99 | ARG | N | 4.228 | 23.548 | 29.442 | 109 | LEU | CA | 17.203 | 19.921 | 40.151 |
| 99 | ARG | CA | 3.746 | 23.492 | 30.813 | 109 | LEU | CB | 16.703 | 21.098 | 40.941 |
| 99 | ARG | CB | 2.274 | 23.049 | 30.885 | 109 | LEU | CG | 16.358 | 22.306 | 40.103 |
| 99 | ARG | CG | 1.275 | 23.728 | 29.965 | 109 | LEU | CD1 | 15.553 | 23.267 | 40.958 |
| 99 | ARG | CD | 1.373 | 25.198 | 30.169 | 109 | LEU | CD2 | 17.613 | 22.976 | 39.579 |
| 99 | ARG | NE | 0.065 | 25.771 | 29.978 | 109 | LEU | C | 17.899 | 18.952 | 41.088 |
| 99 | ARG | CZ | -0.085 | 27.070 | 29.703 | 109 | LEU | O | 19.137 | 18.923 | 41.163 |
| 99 | ARG | NH1 | -1.339 | 27.516 | 29.555 | 110 | GLU | N | 17.146 | 18.078 | 41.739 |
| 99 | ARG | NH2 | 0.956 | 27.923 | 29.560 | 110 | GLU | CA | 17.767 | 16.997 | 42.502 |
| 99 | ARG | C | 4.518 | 22.498 | 31.672 | 110 | GLU | CB | 16.706 | 16.208 | 43.295 |
| 99 | ARG | O | 4.851 | 21.418 | 31.175 | 110 | GLU | CG | 16.044 | 17.043 | 44.443 |
| 100 | GLY | N | 4.746 | 22.767 | 32.962 | 110 | GLU | CD | 16.869 | 17.518 | 45.693 |
| 100 | GLY | CA | 5.370 | 21.790 | 33.846 | 110 | GLU | OE1 | 16.284 | 18.250 | 46.507 |
| 100 | GLY | C | 5.043 | 22.002 | 35.327 | 110 | GLU | OE2 | 18.058 | 17.205 | 45.884 |
| 100 | GLY | O | 4.933 | 23.136 | 35.803 | 110 | GLU | C | 18.562 | 16.049 | 41.616 |
| 101 | ALA | N | 4.881 | 20.881 | 36.029 | 110 | GLU | O | 19.674 | 15.702 | 42.025 |
| 101 | ALA | CA | 4.592 | 20.897 | 37.462 | 111 | TRP | N | 18.111 | 15.691 | 40.389 |
| 101 | ALA | CB | 4.090 | 19.544 | 37.966 | 111 | TRP | CA | 18.867 | 14.850 | 39.469 |
| 101 | ALA | C | 5.844 | 21.210 | 38.278 | 111 | TRP | CB | 18.049 | 14.586 | 38.169 |
| 101 | ALA | O | 6.945 | 20.745 | 37.930 | 111 | TRP | CG | 18.743 | 13.709 | 37.091 |
| 102 | ILE | N | 5.672 | 21.920 | 39.412 | 111 | TRP | CD2 | 19.617 | 14.121 | 36.111 |
| 102 | ILE | CA | 6.812 | 22.262 | 40.268 | 111 | TRP | CE2 | 19.919 | 12.914 | 35.467 |
| 102 | ILE | CB | 6.297 | 23.134 | 41.461 | 111 | TRP | CE3 | 20.195 | 15.302 | 35.658 |
| 102 | ILE | CG2 | 7.414 | 23.536 | 42.429 | 111 | TRP | CD1 | 18.535 | 12.343 | 37.029 |
| 102 | ILE | CG1 | 5.672 | 24.383 | 40.856 | 111 | TRP | NE1 | 19.264 | 11.895 | 36.042 |
| 102 | ILE | CD | 6.675 | 25.257 | 40.045 | 111 | TRP | CZ2 | 20.803 | 12.903 | 34.389 |
| 102 | ILE | C | 7.555 | 21.016 | 40.763 | 111 | TRP | CZ3 | 21.073 | 15.292 | 34.585 |
| 102 | ILE | O | 8.790 | 21.014 | 40.848 | 111 | TRP | CH2 | 21.370 | 14.099 | 33.959 |
| 103 | SER | N | 6.839 | 19.922 | 41.067 | 111 | TRP | C | 20.160 | 15.563 | 39.124 |
| 103 | SER | CA | 7.477 | 18.691 | 41.459 | 111 | TRP | O | 21.198 | 14.910 | 39.072 |
| 103 | SER | CB | 6.399 | 17.659 | 41.711 | 112 | ALA | N | 20.134 | 16.881 | 38.876 |
| 103 | SER | OG | 5.570 | 17.479 | 40.562 | 112 | ALA | CA | 21.331 | 17.620 | 38.528 |
| 103 | SER | C | 8.451 | 18.211 | 40.361 | 112 | ALA | CB | 21.029 | 19.102 | 38.310 |
| 103 | SER | O | 9.575 | 17.820 | 40.676 | 112 | ALA | C | 22.411 | 17.530 | 39.612 |
| 104 | SER | N | 8.068 | 18.299 | 39.085 | 112 | ALA | O | 23.578 | 17.183 | 39.356 |
| 104 | SER | CA | 8.950 | 17.948 | 37.972 | 113 | GLY | N | 22.019 | 17.742 | 40.859 |
| 104 | SER | CB | 8.185 | 18.077 | 36.660 | 113 | GLY | CA | 22.962 | 17.686 | 41.947 |
| 104 | SER | OG | 7.214 | 17.048 | 36.535 | 113 | GLY | C | 23.404 | 16.258 | 42.205 |
| 104 | SER | C | 10.230 | 18.802 | 37.897 | 113 | GLY | O | 24.567 | 16.052 | 42.565 |
| 104 | SER | O | 11.330 | 18.272 | 37.756 | 114 | ASN | N | 22.524 | 15.285 | 42.009 |
| 105 | ILE | N | 10.136 | 20.124 | 38.041 | 114 | ASN | CA | 22.901 | 13.872 | 42.191 |

FIG.1F

| | | | | | | | | | | |
|---|---|---|---|---|---|---|---|---|---|---|
| 114 | ASN | CB | 21.735 | 12.858 | 42.176 | 123 | SER | OG | 16.514 | 29.408 | 29.479 |
| 114 | ASN | CG | 20.764 | 12.994 | 43.318 | 123 | SER | C | 13.240 | 29.029 | 31.383 |
| 114 | ASN | OD1 | 21.095 | 13.531 | 44.373 | 123 | SER | O | 12.521 | 28.751 | 30.400 |
| 114 | ASN | ND2 | 19.511 | 12.575 | 43.163 | 124 | LEU | N | 12.818 | 29.236 | 32.647 |
| 114 | ASN | C | 23.820 | 13.339 | 41.111 | 124 | LEU | CA | 11.426 | 29.119 | 33.059 |
| 114 | ASN | O | 24.532 | 12.346 | 41.311 | 124 | LEU | CB | 11.093 | 27.646 | 33.233 |
| 115 | ASN | N | 23.767 | 13.953 | 39.923 | 124 | LEU | CG | 12.008 | 26.810 | 34.115 |
| 115 | ASN | CA | 24.558 | 13.494 | 38.817 | 124 | LEU | CD1 | 11.540 | 26.904 | 35.610 |
| 115 | ASN | CB | 23.678 | 13.382 | 37.576 | 124 | LEU | CD2 | 11.993 | 25.356 | 33.606 |
| 115 | ASN | CG | 22.871 | 12.090 | 37.637 | 124 | LEU | C | 11.200 | 29.897 | 34.347 |
| 115 | ASN | OD1 | 23.296 | 11.044 | 37.144 | 124 | LEU | O | 12.165 | 30.261 | 35.045 |
| 115 | ASN | ND2 | 21.716 | 12.088 | 38.291 | 125 | GLY | N | 9.951 | 30.177 | 34.709 |
| 115 | ASN | C | 25.761 | 14.354 | 38.510 | 125 | GLY | CA | 9.733 | 31.019 | 35.884 |
| 115 | ASN | O | 26.352 | 14.277 | 37.428 | 125 | GLY | C | 8.243 | 31.204 | 36.140 |
| 116 | GLY | N | 26.126 | 15.225 | 39.431 | 125 | GLY | O | 7.396 | 31.003 | 35.252 |
| 116 | GLY | CA | 27.354 | 15.971 | 39.331 | 126 | SER | N | 7.991 | 31.643 | 37.370 |
| 116 | GLY | C | 27.372 | 16.991 | 38.204 | 126 | SER | CA | 6.640 | 31.772 | 37.888 |
| 116 | GLY | O | 28.450 | 17.247 | 37.614 | 126 | SER | CB | 6.331 | 30.503 | 38.752 |
| 117 | MET | N | 26.235 | 17.614 | 37.909 | 126 | SER | OG | 5.242 | 30.673 | 39.682 |
| 117 | MET | CA | 26.210 | 18.667 | 36.878 | 126 | SER | C | 6.623 | 33.055 | 38.707 |
| 117 | MET | CB | 24.807 | 19.105 | 36.509 | 126 | SER | O | 7.650 | 33.353 | 39.302 |
| 117 | MET | CG | 23.929 | 18.029 | 35.895 | 127 | PRO | N | 5.544 | 33.844 | 38.839 |
| 117 | MET | SD | 24.529 | 17.426 | 34.290 | 127 | PRO | CD | 4.300 | 33.663 | 38.088 |
| 117 | MET | CE | 24.874 | 15.741 | 34.705 | 127 | PRO | CA | 5.458 | 35.005 | 39.740 |
| 117 | MET | C | 26.888 | 19.893 | 37.466 | 127 | PRO | CB | 4.310 | 35.813 | 39.157 |
| 117 | MET | O | 26.805 | 20.170 | 38.688 | 127 | PRO | CG | 3.377 | 34.706 | 38.715 |
| 118 | HIS | N | 27.549 | 20.672 | 36.615 | 127 | PRO | C | 5.258 | 34.663 | 41.234 |
| 118 | HIS | CA | 28.186 | 21.879 | 37.094 | 127 | PRO | O | 5.342 | 35.518 | 42.119 |
| 118 | HIS | CB | 29.481 | 22.174 | 36.318 | 128 | SER | N | 4.904 | 33.408 | 41.511 |
| 118 | HIS | CG | 30.504 | 21.026 | 36.418 | 128 | SER | CA | 4.673 | 32.939 | 42.860 |
| 118 | HIS | CD2 | 30.795 | 20.176 | 35.397 | 128 | SER | CB | 3.340 | 32.142 | 42.821 |
| 118 | HIS | ND1 | 31.283 | 20.653 | 37.437 | 128 | SER | OG | 2.292 | 33.013 | 42.389 |
| 118 | HIS | CE1 | 32.020 | 19.622 | 37.044 | 128 | SER | C | 5.845 | 32.100 | 43.399 |
| 118 | HIS | NE2 | 31.715 | 19.339 | 35.797 | 128 | SER | O | 6.430 | 31.293 | 42.646 |
| 118 | HIS | C | 27.256 | 23.067 | 36.967 | 129 | PRO | N | 6.223 | 32.275 | 44.678 |
| 118 | HIS | O | 27.293 | 23.989 | 37.781 | 129 | PRO | CD | 5.713 | 33.322 | 45.595 |
| 119 | VAL | N | 26.349 | 23.070 | 35.989 | 129 | PRO | CA | 7.185 | 31.419 | 45.363 |
| 119 | VAL | CA | 25.540 | 24.246 | 35.723 | 129 | PRO | CB | 7.492 | 32.187 | 46.641 |
| 119 | VAL | CB | 26.124 | 25.082 | 34.533 | 129 | PRO | CG | 6.138 | 32.757 | 46.937 |
| 199 | VAL | CG1 | 25.194 | 26.267 | 34.244 | 129 | PRO | C | 6.639 | 29.999 | 45.605 |
| 119 | VAL | CG2 | 27.537 | 25.612 | 34.864 | 129 | PRO | O | 5.416 | 29.779 | 45.693 |
| 119 | VAL | C | 24.194 | 23.670 | 35.344 | 130 | SER | N | 7.567 | 29.069 | 45.789 |
| 119 | VAL | O | 24.123 | 22.627 | 34.674 | 130 | SER | CA | 7.242 | 27.724 | 46.139 |
| 120 | ALA | N | 23.150 | 24.305 | 35.817 | 130 | SER | CB | 7.197 | 26.894 | 44.888 |
| 120 | ALA | CA | 21.801 | 23.917 | 35.457 | 130 | SER | OG | 7.387 | 25.528 | 45.215 |
| 120 | ALA | CB | 21.074 | 23.434 | 36.689 | 130 | SER | C | 8.260 | 27.146 | 47.092 |
| 120 | ALA | C | 21.128 | 25.170 | 34.893 | 130 | SER | O | 9.462 | 27.127 | 46.751 |
| 120 | ALA | O | 21.156 | 26.255 | 35.503 | 131 | ALA | N | 7.759 | 26.596 | 48.220 |
| 121 | ASN | N | 20.621 | 25.061 | 33.673 | 131 | ALA | CA | 8.619 | 25.896 | 49.154 |
| 121 | ASN | CA | 19.917 | 26.133 | 32.994 | 131 | ALA | CB | 7.818 | 25.334 | 50.312 |
| 121 | ASN | CB | 20.330 | 26.144 | 31.516 | 131 | ALA | C | 9.445 | 24.755 | 48.557 |
| 121 | ASN | CG | 19.771 | 27.348 | 30.778 | 131 | ALA | O | 10.670 | 24.654 | 48.755 |
| 121 | ASN | OD1 | 20.464 | 28.304 | 30.514 | 132 | THR | N | 8.761 | 23.973 | 47.716 |
| 121 | ASN | ND2 | 18.511 | 27.315 | 30.418 | 132 | THR | CA | 9.373 | 22.810 | 47.044 |
| 121 | ASN | C | 18.399 | 25.942 | 33.133 | 132 | THR | CB | 8.274 | 22.155 | 46.232 |
| 121 | ASN | O | 17.793 | 24.936 | 32.715 | 132 | THR | OG1 | 7.351 | 21.804 | 47.256 |
| 122 | LEU | N | 17.740 | 26.917 | 33.768 | 132 | THR | CG2 | 8.667 | 20.937 | 45.371 |
| 122 | LEU | CA | 16.277 | 26.942 | 33.962 | 132 | THR | C | 10.547 | 23.223 | 46.156 |
| 122 | LEU | CB | 15.895 | 27.041 | 35.454 | 132 | THR | O | 11.674 | 22.711 | 46.213 |
| 122 | LEU | CG | 16.010 | 25.856 | 36.340 | 133 | LEU | N | 10.257 | 24.266 | 45.394 |
| 122 | LEU | CD1 | 15.879 | 26.350 | 37.770 | 133 | LEU | CA | 11.185 | 24.742 | 44.396 |
| 122 | LEU | CD2 | 14.914 | 24.875 | 36.068 | 133 | LEU | CB | 10.467 | 25.753 | 43.511 |
| 122 | LEU | C | 15.706 | 28.182 | 33.264 | 133 | LEU | CG | 11.231 | 26.287 | 42.326 |
| 122 | LEU | O | 15.618 | 29.298 | 33.808 | 133 | LEU | CD1 | 11.504 | 25.174 | 41.324 |
| 123 | SER | N | 15.297 | 28.013 | 32.012 | 133 | LEU | CD2 | 10.395 | 27.377 | 41.663 |
| 123 | SER | CA | 14.756 | 29.116 | 31.232 | 133 | LEU | C | 12.393 | 25.365 | 45.081 |
| 123 | SER | CB | 15.184 | 28.969 | 29.748 | 133 | LEU | O | 13.539 | 25.053 | 44.693 |

FIG.1G

| | | | | | | | | | | | |
|---|---|---|---|---|---|---|---|---|---|---|---|
| 134 | GLU | N | 12.164 | 26.195 | 46.111 | 143 | ARG | NE | 22.030 | 17.901 | 45.589 |
| 134 | GLU | CA | 13.276 | 26.827 | 46.768 | 143 | ARG | CZ | 21.037 | 17.422 | 44.816 |
| 134 | GLU | CB | 12.749 | 27.786 | 47.793 | 143 | ARG | NH1 | 20.140 | 18.281 | 44.355 |
| 134 | GLU | CG | 13.795 | 28.476 | 48.645 | 143 | ARG | NH2 | 20.887 | 16.134 | 44.524 |
| 134 | GLU | CD | 13.249 | 29.330 | 49.814 | 143 | ARG | C | 26.745 | 20.456 | 44.602 |
| 134 | GLU | OE1 | 14.013 | 30.014 | 50.482 | 143 | ARG | O | 27.216 | 19.708 | 43.740 |
| 134 | GLU | OE2 | 12.046 | 29.337 | 50.036 | 144 | GLY | N | 27.007 | 21.760 | 44.635 |
| 134 | GLU | C | 14.181 | 25.795 | 47.420 | 144 | GLY | CA | 27.925 | 22.456 | 43.737 |
| 134 | GLU | O | 15.396 | 25.915 | 47.353 | 144 | GLY | C | 27.365 | 22.887 | 42.396 |
| 135 | GLN | N | 13.598 | 24.770 | 48.060 | 144 | GLY | O | 28.139 | 23.324 | 41.539 |
| 135 | GLN | CA | 14.373 | 23.701 | 48.651 | 145 | VAL | N | 26.048 | 22.782 | 42.186 |
| 135 | GLN | CB | 13.350 | 22.830 | 49.331 | 145 | VAL | CA | 25.465 | 22.150 | 40.874 |
| 135 | GLN | CG | 13.897 | 21.596 | 59.006 | 145 | VAL | CB | 24.118 | 22.435 | 40.672 |
| 135 | GLN | CD | 12.823 | 20.790 | 50.764 | 145 | VAL | CG1 | 23.521 | 22.778 | 39.291 |
| 135 | GLN | OE1 | 11.779 | 20.305 | 50.258 | 145 | VAL | CG2 | 24.324 | 20.921 | 40.792 |
| 135 | GLN | NE2 | 13.143 | 20.692 | 52.060 | 145 | VAL | C | 25.262 | 24.680 | 40.827 |
| 135 | GLN | C | 15.248 | 22.952 | 47.620 | 145 | VAL | O | 24.836 | 25.282 | 41.840 |
| 135 | GLN | O | 16.434 | 22.651 | 47.868 | 146 | LEU | N | 25.677 | 25.350 | 39.742 |
| 136 | ALA | N | 14.690 | 22.749 | 46.420 | 146 | LEU | CA | 25.317 | 26.759 | 39.578 |
| 136 | ALA | CA | 15.406 | 22.071 | 45.337 | 146 | LEU | CB | 26.351 | 27.518 | 38.740 |
| 136 | ALA | CB | 14.430 | 21.762 | 44.225 | 146 | LEU | CG | 26.005 | 28.987 | 38.374 |
| 136 | ALA | C | 16.556 | 22.950 | 44.802 | 146 | LEU | CD1 | 25.819 | 29.816 | 39.604 |
| 136 | ALA | O | 17.676 | 22.465 | 44.513 | 146 | LEU | CD2 | 27.114 | 29.556 | 37.506 |
| 137 | VAL | N | 16.313 | 24.272 | 44.677 | 146 | LEU | C | 23.979 | 26.800 | 38.875 |
| 137 | VAL | CA | 17.375 | 25.224 | 44.305 | 146 | LEU | O | 23.873 | 26.371 | 37.710 |
| 137 | VAL | CB | 16.834 | 26.694 | 44.238 | 147 | VAL | N | 22.940 | 27.297 | 39.523 |
| 137 | VAL | CG1 | 17.988 | 27.738 | 44.134 | 147 | VAL | CA | 21.611 | 27.371 | 38.926 |
| 137 | VAL | CG2 | 15.876 | 26.776 | 43.047 | 147 | VAL | CB | 20.552 | 27.093 | 40.011 |
| 137 | VAL | C | 18.531 | 25.152 | 45.317 | 147 | VAL | CG1 | 19.153 | 27.272 | 39.387 |
| 137 | VAL | O | 19.711 | 24.982 | 44.974 | 147 | VAL | CG2 | 20.649 | 25.642 | 40.526 |
| 138 | ASN | N | 18.136 | 25.179 | 46.588 | 147 | VAL | C | 21.405 | 28.740 | 38.305 |
| 138 | ASN | CA | 19.136 | 25.146 | 47.616 | 147 | VAL | O | 21.480 | 29.768 | 38.965 |
| 138 | ASN | CB | 18.498 | 25.457 | 48.973 | 148 | VAL | N | 21.138 | 28.776 | 37.003 |
| 138 | ASN | CG | 18.125 | 26.934 | 49.063 | 148 | VAL | CA | 21.007 | 30.019 | 36.251 |
| 138 | ASN | OD1 | 18.598 | 27.789 | 48.320 | 148 | VAL | CB | 21.982 | 30.003 | 35.055 |
| 138 | ASN | ND2 | 17.258 | 27.299 | 49.985 | 148 | VAL | CG1 | 21.916 | 31.349 | 34.328 |
| 138 | ASN | C | 19.869 | 23.832 | 47.685 | 148 | VAL | CG2 | 23.403 | 29.791 | 35.562 |
| 138 | ASN | O | 21.103 | 23.849 | 47.846 | 148 | VAL | C | 19.557 | 30.040 | 35.781 |
| 139 | SER | N | 19.209 | 22.709 | 47.506 | 148 | VAL | O | 19.127 | 29.064 | 35.128 |
| 139 | SER | CA | 19.937 | 21.466 | 47.610 | 149 | ALA | N | 18.826 | 31.120 | 36.019 |
| 139 | SER | CB | 19.001 | 20.303 | 47.649 | 149 | ALA | CA | 17.387 | 31.187 | 35.758 |
| 139 | SER | OG | 18.203 | 20.407 | 46.479 | 149 | ALA | CB | 16.610 | 31.028 | 37.063 |
| 139 | SER | C | 20.860 | 21.316 | 46.403 | 149 | ALA | C | 16.952 | 32.515 | 35.111 |
| 139 | SER | O | 22.027 | 20.902 | 46.586 | 149 | ALA | O | 17.539 | 33.555 | 35.396 |
| 140 | ALA | N | 20.431 | 21.663 | 45.160 | 150 | ALA | N | 15.931 | 32.454 | 34.249 |
| 140 | ALA | CA | 21.392 | 21.545 | 44.053 | 150 | ALA | CA | 15.375 | 33.605 | 33.549 |
| 140 | ALA | CB | 20.755 | 21.895 | 42.723 | 150 | ALA | CB | 14.427 | 33.109 | 32.448 |
| 140 | ALA | C | 22.593 | 22.460 | 44.264 | 150 | ALA | C | 14.588 | 34.558 | 34.469 |
| 140 | ALA | O | 23.740 | 22.070 | 44.057 | 150 | ALA | O | 13.789 | 34.092 | 35.290 |
| 141 | THR | N | 22.377 | 23.682 | 44.756 | 151 | SER | N | 14.717 | 35.878 | 34.313 |
| 141 | THR | CA | 23.473 | 24.599 | 45.081 | 151 | SER | CA | 13.991 | 36.841 | 35.145 |
| 141 | THR | CB | 22.851 | 25.918 | 45.587 | 151 | SER | CB | 14.526 | 38.284 | 34.979 |
| 141 | THR | OG1 | 22.034 | 26.472 | 44.549 | 151 | SER | OG | 14.430 | 38.730 | 33.630 |
| 141 | THR | CG2 | 23.908 | 26.914 | 45.924 | 151 | SER | C | 12.485 | 36.873 | 34.867 |
| 141 | THR | C | 24.419 | 23.994 | 46.121 | 151 | SER | O | 11.692 | 37.218 | 35.761 |
| 141 | THR | O | 25.644 | 24.054 | 45.907 | 152 | GLY | N | 12.062 | 36.534 | 33.633 |
| 142 | SER | N | 23.975 | 23.363 | 47.202 | 152 | GLY | CA | 10.646 | 36.425 | 33.269 |
| 142 | SER | CA | 24.937 | 22.839 | 48.134 | 152 | GLY | C | 10.382 | 37.457 | 32.193 |
| 142 | SER | CB | 24.216 | 22.599 | 49.442 | 152 | GLY | O | 11.117 | 38.447 | 32.024 |
| 142 | SER | OG | 23.086 | 21.786 | 49.207 | 153 | ASN | N | 9.271 | 37.263 | 31.499 |
| 142 | SER | C | 25.620 | 21.592 | 47.583 | 153 | ASN | CA | 8.969 | 38.082 | 30.352 |
| 142 | SER | O | 26.616 | 21.131 | 48.150 | 153 | ASN | CB | 8.689 | 37.237 | 29.116 |
| 143 | ARG | N | 25.155 | 21.025 | 46.447 | 153 | ASN | CG | 9.865 | 36.443 | 28.658 |
| 143 | ARG | CA | 25.865 | 19.945 | 45.761 | 153 | ASN | OD1 | 11.041 | 36.707 | 28.880 |
| 143 | ARG | CB | 24.848 | 18.907 | 45.261 | 153 | ASN | ND2 | 9.501 | 35.396 | 27.943 |
| 143 | ARG | CG | 24.269 | 18.107 | 46.467 | 153 | ASN | C | 7.759 | 38.990 | 30.526 |
| 143 | ARG | CD | 23.132 | 17.127 | 46.152 | 153 | ASN | O | 7.190 | 39.421 | 29.524 |

FIG.1H

| | | | | | | | | | | | |
|---|---|---|---|---|---|---|---|---|---|---|---|
| 154 | SER | N | 7.390 | 39.398 | 31.739 | 164 | ARG | CB | 12.939 | 36.127 | 43.071 |
| 154 | SER | CA | 6.193 | 40.206 | 31.915 | 164 | ARG | CG | 12.741 | 37.084 | 44.237 |
| 154 | SER | CB | 5.577 | 39.973 | 33.284 | 164 | ARG | CD | 13.377 | 38.408 | 43.906 |
| 154 | SER | OG | 6.365 | 40.558 | 34.319 | 164 | ARG | NE | 13.251 | 39.367 | 44.988 |
| 154 | SER | C | 6.534 | 41.682 | 31.798 | 164 | ARG | CZ | 14.206 | 39.530 | 45.901 |
| 154 | SER | O | 5.599 | 42.468 | 31.793 | 164 | ARG | NH1 | 14.020 | 40.475 | 46.838 |
| 155 | GLY | N | 7.805 | 42.092 | 31.773 | 164 | ARG | NH2 | 15.289 | 38.737 | 45.965 |
| 155 | GLY | CA | 8.154 | 43.499 | 31.759 | 164 | ARG | C | 15.032 | 35.123 | 43.973 |
| 155 | GLY | C | 8.028 | 44.150 | 33.143 | 164 | ARG | O | 15.559 | 35.875 | 44.807 |
| 155 | GLY | O | 8.292 | 45.349 | 33.278 | 165 | TYR | N | 15.147 | 33.808 | 44.046 |
| 156 | ALA | N | 7.640 | 43.439 | 34.195 | 165 | TYR | CA | 15.787 | 33.157 | 45.176 |
| 156 | ALA | CA | 7.476 | 44.065 | 35.498 | 165 | TYR | CB | 15.503 | 31.609 | 45.150 |
| 156 | ALA | CB | 6.649 | 43.170 | 36.405 | 165 | TYR | CG | 14.046 | 31.230 | 45.501 |
| 156 | ALA | C | 8.814 | 44.359 | 36.187 | 165 | TYR | CD1 | 13.399 | 31.807 | 46.600 |
| 156 | ALA | O | 9.864 | 43.754 | 35.891 | 165 | TYR | CE1 | 12.084 | 31.484 | 46.885 |
| 157 | SER | N | 8.746 | 45.315 | 37.132 | 165 | TYR | CD2 | 13.379 | 30.328 | 44.696 |
| 157 | SER | CA | 9.857 | 45.747 | 37.932 | 165 | TYR | CE2 | 12.067 | 30.003 | 44.992 |
| 157 | SER | CB | 9.592 | 47.150 | 38.402 | 165 | TYR | CZ | 11.444 | 30.587 | 46.078 |
| 157 | SER | OG | 8.442 | 47.158 | 39.213 | 165 | TYR | OH | 10.133 | 30.227 | 46.357 |
| 157 | SER | C | 10.085 | 44.828 | 39.123 | 165 | TYR | C | 17.293 | 33.408 | 45.179 |
| 157 | SER | O | 10.623 | 45.251 | 40.147 | 165 | TYR | O | 17.996 | 33.477 | 44.141 |
| 158 | SER | N | 9.695 | 43.568 | 39.049 | 166 | ALA | N | 17.829 | 33.600 | 46.368 |
| 158 | SER | CA | 10.126 | 42.600 | 40.061 | 166 | ALA | CA | 19.222 | 33.986 | 46.544 |
| 158 | SER | CB | 9.046 | 42.518 | 41.150 | 166 | ALA | CB | 19.552 | 34.070 | 48.042 |
| 158 | SER | OG | 7.823 | 41.997 | 40.640 | 166 | ALA | C | 20.231 | 33.070 | 45.878 |
| 158 | SER | C | 10.335 | 41.293 | 39.275 | 166 | ALA | O | 21.192 | 33.553 | 45.278 |
| 158 | SER | O | 9.682 | 41.091 | 38.225 | 167 | ASN | N | 19.920 | 31.767 | 45.871 |
| 159 | ILE | N | 11.265 | 40.413 | 39.718 | 167 | ASN | CA | 20.860 | 30.806 | 45.280 |
| 159 | ILE | CA | 11.600 | 39.245 | 38.894 | 167 | ASN | CB | 20.778 | 29.446 | 46.048 |
| 159 | ILE | CB | 13.164 | 39.024 | 38.847 | 167 | ASN | CG | 21.566 | 29.545 | 47.374 |
| 159 | ILE | CG2 | 13.801 | 40.300 | 38.272 | 167 | ASN | OD1 | 22.592 | 30.238 | 47.502 |
| 159 | ILE | CG1 | 13.729 | 38.612 | 40.201 | 167 | ASN | ND2 | 21.130 | 28.931 | 48.461 |
| 159 | ILE | CD | 15.208 | 38.246 | 40.013 | 167 | ASN | C | 20.712 | 30.572 | 43.776 |
| 159 | ILE | C | 10.906 | 37.978 | 39.381 | 167 | ASN | O | 21.411 | 29.727 | 43.205 |
| 159 | ILE | O | 10.454 | 37.888 | 40.528 | 168 | ALA | N | 19.760 | 31.248 | 43.121 |
| 160 | SER | N | 10.806 | 36.974 | 38.510 | 168 | ALA | CA | 19.673 | 31.167 | 41.683 |
| 160 | SER | CA | 10.114 | 35.754 | 38.841 | 168 | ALA | CB | 18.206 | 31.007 | 41.284 |
| 160 | SER | CB | 9.658 | 35.097 | 37.513 | 168 | ALA | C | 20.259 | 32.481 | 41.121 |
| 160 | SER | OG | 10.700 | 34.817 | 36.581 | 168 | ALA | O | 19.961 | 33.600 | 41.595 |
| 160 | SER | C | 10.947 | 34.777 | 39.691 | 169 | MET | N | 21.005 | 32.366 | 40.015 |
| 160 | SER | O | 12.152 | 34.921 | 39.958 | 169 | MET | CA | 21.563 | 33.497 | 39.321 |
| 161 | TYR | N | 10.265 | 33.738 | 40.148 | 169 | MET | CB | 22.854 | 33.069 | 38.636 |
| 161 | TYR | CA | 10.867 | 32.645 | 40.876 | 169 | MET | CG | 23.476 | 34.273 | 37.972 |
| 161 | TYR | CB | 9.887 | 32.231 | 41.988 | 169 | MET | SD | 25.057 | 33.851 | 37.212 |
| 161 | TYR | CG | 9.698 | 33.315 | 43.030 | 169 | MET | CE | 25.641 | 35.532 | 37.199 |
| 161 | TYR | CD1 | 10.614 | 33.397 | 44.072 | 169 | MET | C | 20.493 | 33.939 | 38.305 |
| 161 | TYR | CE1 | 10.459 | 34.368 | 45.057 | 169 | MET | O | 19.998 | 33.150 | 37.484 |
| 161 | TYR | CD2 | 8.619 | 34.189 | 42.939 | 170 | ALA | N | 20.047 | 35.196 | 38.436 |
| 161 | TYR | CE2 | 8.459 | 35.175 | 43.906 | 170 | ALA | CA | 18.956 | 35.777 | 37.681 |
| 161 | TYR | CZ | 9.384 | 35.241 | 44.953 | 170 | ALA | CB | 18.208 | 36.758 | 38.591 |
| 161 | TYR | OH | 9.270 | 36.241 | 45.896 | 170 | ALA | C | 19.430 | 36.504 | 36.432 |
| 161 | TYR | C | 11.101 | 31.499 | 39.865 | 170 | ALA | O | 20.278 | 37.405 | 36.596 |
| 161 | TYR | O | 10.257 | 31.307 | 38.975 | 171 | VAL | N | 18.927 | 36.158 | 35.241 |
| 162 | PRO | N | 12.153 | 30.681 | 39.954 | 171 | VAL | CA | 19.332 | 36.739 | 33.966 |
| 162 | PRO | CD | 12.388 | 29.536 | 39.042 | 171 | VAL | CB | 19.862 | 35.590 | 33.075 |
| 162 | PRO | CA | 13.162 | 30.687 | 41.003 | 171 | VAL | CG1 | 20.380 | 36.267 | 31.766 |
| 162 | PRO | CB | 13.715 | 29.232 | 40.966 | 171 | VAL | CG2 | 20.946 | 34.749 | 33.786 |
| 162 | PRO | CG | 13.726 | 28.915 | 39.470 | 171 | VAL | C | 18.192 | 37.445 | 33.235 |
| 162 | PRO | C | 14.243 | 31.756 | 40.879 | 171 | VAL | O | 17.145 | 36.824 | 32.979 |
| 162 | PRO | O | 15.044 | 31.845 | 41.789 | 172 | GLY | N | 18.474 | 38.712 | 32.887 |
| 163 | ALA | N | 14.352 | 32.580 | 39.814 | 172 | GLY | CA | 17.594 | 39.568 | 32.123 |
| 163 | ALA | CA | 15.393 | 33.575 | 39.716 | 172 | GLY | C | 18.038 | 39.553 | 30.640 |
| 163 | ALA | CB | 15.165 | 34.416 | 38.441 | 172 | GLY | O | 19.106 | 39.023 | 30.302 |
| 163 | ALA | C | 15.538 | 34.529 | 40.935 | 173 | ALA | N | 17.231 | 40.184 | 29.781 |
| 163 | ALA | O | 16.640 | 34.874 | 41.399 | 173 | ALA | CA | 17.461 | 40.220 | 28.347 |
| 164 | ARG | N | 14.417 | 34.878 | 41.559 | 173 | ALA | CB | 16.278 | 39.626 | 27.617 |
| 164 | ARG | CA | 14.385 | 35.740 | 42.745 | 173 | ALA | C | 17.667 | 41.631 | 27.812 |

FIG. 1I

| | | | | | | | | | | | |
|---|---|---|---|---|---|---|---|---|---|---|---|
| 173 | ALA | O | 16.987 | 42.599 | 28.169 | 182 | SER | CB | 9.735 | 46.338 | 25.967 |
| 174 | THR | N | 18.639 | 41.714 | 26.910 | 182 | SER | OG | 9.316 | 45.472 | 24.927 |
| 174 | THR | CA | 18.993 | 42.944 | 26.178 | 182 | SER | C | 10.061 | 44.602 | 27.814 |
| 174 | THR | CB | 20.504 | 43.281 | 26.349 | 182 | SER | O | 9.557 | 44.957 | 28.879 |
| 174 | THR | OG1 | 21.329 | 42.130 | 26.074 | 183 | PHE | N | 10.058 | 43.321 | 27.403 |
| 174 | THR | CG2 | 20.733 | 43.727 | 27.767 | 183 | PHE | CA | 9.501 | 42.231 | 28.191 |
| 174 | THR | C | 18.715 | 42.787 | 24.688 | 183 | PHE | CB | 9.261 | 40.999 | 27.282 |
| 174 | THR | O | 18.622 | 41.662 | 24.148 | 183 | PHE | CG | 10.501 | 40.486 | 26.518 |
| 175 | ASP | N | 18.674 | 43.934 | 24.029 | 183 | PHE | CD1 | 11.508 | 39.734 | 27.142 |
| 175 | ASP | CA | 18.518 | 43.907 | 22.588 | 183 | PHE | CD2 | 10.653 | 40.840 | 25.173 |
| 175 | ASP | CB | 17.388 | 44.840 | 22.148 | 183 | PHE | CE1 | 12.617 | 39.325 | 26.421 |
| 175 | ASP | CG | 17.584 | 46.353 | 22.386 | 183 | PHE | CE2 | 11.782 | 40.415 | 24.478 |
| 175 | ASP | OD1 | 18.675 | 46.844 | 22.682 | 183 | PHE | CZ | 12.774 | 39.665 | 25.095 |
| 175 | ASP | OD2 | 16.579 | 47.047 | 22.291 | 183 | PHE | C | 10.359 | 41.795 | 29.380 |
| 174 | ASP | C | 19.794 | 44.258 | 21.834 | 183 | PHE | O | 9.889 | 41.025 | 30.246 |
| 175 | ASP | O | 20.844 | 44.480 | 22.440 | 184 | SER | N | 11.615 | 42.247 | 29.427 |
| 176 | GLN | N | 19.724 | 44.498 | 20.516 | 184 | SER | CA | 12.551 | 41.670 | 30.410 |
| 176 | GLN | CA | 20.938 | 44.742 | 19.737 | 184 | SER | CB | 13.998 | 42.030 | 30.045 |
| 176 | GLN | CB | 20.702 | 44.722 | 18.237 | 184 | SER | OG | 14.926 | 41.420 | 30.947 |
| 176 | GLN | CG | 20.123 | 43.400 | 17.797 | 184 | SER | C | 12.281 | 42.125 | 31.843 |
| 176 | GLN | CD | 18.592 | 43.272 | 17.887 | 184 | SER | O | 12.450 | 43.331 | 32.137 |
| 176 | GLN | OE1 | 17.837 | 44.022 | 18.543 | 185 | GLN | N | 11.911 | 41.197 | 32.727 |
| 176 | GLN | NE2 | 18.083 | 42.254 | 17.196 | 185 | GLN | CA | 11.652 | 41.622 | 34.089 |
| 176 | GLN | C | 21.534 | 46.084 | 20.056 | 185 | GLN | CB | 11.034 | 40.489 | 34.904 |
| 176 | GLN | O | 22.690 | 46.302 | 19.783 | 185 | GLN | CG | 9.595 | 40.335 | 34.482 |
| 177 | ASN | N | 20.836 | 46.989 | 20.719 | 185 | GLN | CD | 8.912 | 39.174 | 35.165 |
| 177 | ASN | CA | 21.382 | 48.288 | 21.098 | 185 | GLN | OE1 | 8.817 | 39.005 | 36.377 |
| 177 | ASN | CB | 20.321 | 49.300 | 20.975 | 185 | GLN | NE2 | 8.397 | 38.320 | 34.331 |
| 177 | ASN | CG | 19.832 | 49.550 | 19.587 | 185 | GLN | C | 12.960 | 42.075 | 34.773 |
| 177 | ASN | OD1 | 20.577 | 49.605 | 18.631 | 185 | GLN | O | 14.066 | 41.606 | 34.458 |
| 177 | ASN | ND2 | 18.526 | 49.678 | 19.484 | 186 | TYR | N | 12.871 | 43.046 | 35.676 |
| 177 | ASN | C | 21.895 | 48.299 | 22.521 | 186 | TYR | CA | 14.048 | 43.618 | 36.349 |
| 177 | ASN | O | 22.380 | 49.322 | 23.026 | 186 | TYR | CB | 14.488 | 44.924 | 35.634 |
| 178 | ASN | N | 21.875 | 47.139 | 23.202 | 186 | TYR | CG | 13.385 | 45.992 | 35.576 |
| 178 | ASN | CA | 22.256 | 47.033 | 24.623 | 186 | TYR | CD1 | 12.362 | 45.872 | 34.635 |
| 178 | ASN | CB | 23.735 | 47.479 | 24.896 | 186 | TYR | CE1 | 11.347 | 46.805 | 34.553 |
| 178 | ASN | CG | 24.734 | 46.515 | 24.314 | 186 | TYR | CD2 | 13.385 | 47.049 | 36.468 |
| 178 | ASN | OD1 | 24.433 | 45.324 | 24.210 | 186 | TYR | CE2 | 12.386 | 47.988 | 36.396 |
| 178 | ASN | ND2 | 25.920 | 46.928 | 23.917 | 186 | TYR | CZ | 11.376 | 47.855 | 35.450 |
| 178 | ASN | C | 21.345 | 47.835 | 25.547 | 186 | TYR | OH | 10.418 | 48.846 | 35.328 |
| 178 | ASN | O | 21.747 | 48.392 | 26.576 | 186 | TYR | C | 13.735 | 43.925 | 37.819 |
| 179 | ASN | N | 20.081 | 47.806 | 25.174 | 186 | TYR | O | 12.616 | 43.620 | 38.262 |
| 179 | ASN | CA | 19.000 | 48.319 | 26.009 | 186 | GLY | N | 14.620 | 44.547 | 38.575 |
| 179 | ASN | CB | 18.044 | 49.165 | 25.243 | 187 | GLY | CA | 14.330 | 44.849 | 39.958 |
| 179 | ASN | CG | 18.566 | 50.593 | 25.088 | 187 | GLY | C | 15.232 | 44.062 | 40.892 |
| 179 | ASN | OD1 | 19.289 | 51.155 | 25.949 | 187 | GLY | O | 16.318 | 43.548 | 40.541 |
| 179 | ASN | ND2 | 18.250 | 51.181 | 23.925 | 188 | ALA | N | 14.782 | 43.915 | 42.140 |
| 179 | ASN | C | 18.230 | 47.101 | 26.490 | 188 | ALA | CA | 15.616 | 43.340 | 43.172 |
| 179 | ASN | O | 18.246 | 46.016 | 25.872 | 188 | ALA | CB | 14.891 | 43.435 | 44.515 |
| 180 | ARG | N | 17.579 | 47.276 | 27.645 | 188 | ALA | C | 15.973 | 41.884 | 42.894 |
| 180 | ARG | CA | 16.734 | 46.241 | 28.230 | 188 | ALA | O | 15.134 | 41.065 | 42.549 |
| 180 | ARG | CB | 16.050 | 46.746 | 29.525 | 189 | GLY | N | 17.263 | 41.594 | 42.986 |
| 180 | ARG | CG | 15.269 | 45.653 | 30.233 | 189 | GLY | CA | 17.747 | 40.223 | 42.778 |
| 180 | ARG | CD | 14.562 | 46.201 | 31.492 | 189 | GLY | C | 18.299 | 39.938 | 41.358 |
| 180 | ARG | NE | 13.537 | 47.146 | 31.076 | 189 | GLY | O | 18.911 | 38.873 | 41.139 |
| 180 | ARG | CZ | 12.271 | 46.850 | 30.720 | 190 | LEU | N | 18.128 | 40.857 | 40.397 |
| 180 | ARG | NH1 | 11.476 | 47.846 | 30.339 | 190 | LEU | CA | 18.646 | 40.601 | 39.064 |
| 180 | ARG | NH2 | 11.709 | 45.650 | 30.752 | 190 | LEU | CB | 18.023 | 41.621 | 38.094 |
| 180 | ARG | C | 15.639 | 45.909 | 27.213 | 190 | LEU | CG | 18.302 | 41.454 | 36.607 |
| 180 | ARG | O | 14.991 | 46.855 | 26.715 | 190 | LEU | CD1 | 17.688 | 40.163 | 36.140 |
| 181 | ALA | N | 15.377 | 44.644 | 26.848 | 190 | LEU | CD2 | 17.844 | 42.716 | 35.848 |
| 181 | ALA | CA | 14.225 | 44.338 | 26.002 | 190 | LEU | C | 20.169 | 40.671 | 39.079 |
| 181 | ALA | CB | 14.266 | 42.883 | 25.663 | 190 | LEU | O | 20.776 | 41.624 | 39.589 |
| 181 | ALA | C | 12.942 | 44.677 | 26.771 | 191 | ASP | N | 20.847 | 39.677 | 38.505 |
| 181 | ALA | O | 12.873 | 44.495 | 28.009 | 191 | ASP | CA | 22.285 | 39.597 | 38.558 |
| 182 | SER | N | 11.894 | 45.172 | 26.133 | 191 | ASP | CB | 22.732 | 38.168 | 38.777 |
| 182 | SER | CA | 10.757 | 45.650 | 26.927 | 191 | ASP | CG | 22.428 | 37.668 | 40.182 |

FIG.1J

| | | | | | | | | | | |
|---|---|---|---|---|---|---|---|---|---|---|
| 191 | ASP | OD1 | 22.903 | 38.250 | 41.148 | 201 | SER | CA | 19.476 | 28.584 | 17.356 |
| 191 | ASP | OD2 | 21.685 | 36.717 | 40.309 | 201 | SER | CB | 19.283 | 28.528 | 18.891 |
| 191 | ASP | C | 23.037 | 40.095 | 37.355 | 201 | SER | OG | 20.089 | 27.563 | 19.530 |
| 191 | ASP | O | 24.122 | 40.674 | 37.449 | 201 | SER | C | 18.875 | 27.346 | 16.701 |
| 192 | ILE | N | 22.464 | 39.842 | 36.171 | 201 | SER | O | 18.062 | 27.448 | 15.779 |
| 192 | ILE | CA | 23.192 | 40.070 | 34.908 | 202 | THR | N | 19.318 | 26.189 | 17.171 |
| 192 | ILE | CB | 24.291 | 38.919 | 34.852 | 202 | THR | CA | 18.879 | 24.880 | 16.747 |
| 192 | ILE | CG2 | 23.628 | 37.619 | 34.325 | 202 | THR | CB | 19.769 | 23.760 | 17.461 |
| 192 | ILE | CG1 | 25.513 | 39.314 | 34.012 | 202 | THR | OG1 | 19.869 | 24.043 | 18.866 |
| 192 | ILE | CD | 26.686 | 38.323 | 34.226 | 202 | THR | CG2 | 21.204 | 23.712 | 16.888 |
| 192 | ILE | C | 22.176 | 40.008 | 33.774 | 202 | THR | C | 17.412 | 24.706 | 17.082 |
| 192 | ILE | O | 21.020 | 39.545 | 33.967 | 202 | THR | O | 16.901 | 25.159 | 18.115 |
| 193 | VAL | N | 22.644 | 40.477 | 32.608 | 203 | TYR | N | 16.712 | 23.986 | 16.227 |
| 193 | VAL | CA | 21.847 | 40.379 | 31.392 | 203 | TYR | CA | 15.286 | 23.728 | 16.398 |
| 193 | VAL | CB | 21.246 | 41.745 | 30.945 | 203 | TYR | CB | 14.508 | 24.820 | 15.615 |
| 193 | VAL | CG1 | 20.189 | 42.187 | 31.967 | 203 | TYR | CG | 13.165 | 25.140 | 16.239 |
| 193 | VAL | CG2 | 22.326 | 42.772 | 30.755 | 203 | TYR | CD1 | 13.129 | 25.884 | 17.421 |
| 193 | VAL | C | 22.653 | 39.820 | 30.203 | 203 | TYR | CE1 | 11.918 | 26.223 | 17.992 |
| 193 | VAL | O | 23.885 | 39.799 | 30.174 | 203 | TYR | CD2 | 11.996 | 24.708 | 15.619 |
| 194 | ALA | N | 21.891 | 39.376 | 29.204 | 203 | TYR | CE2 | 10.770 | 25.044 | 16.193 |
| 194 | ALA | CA | 22.453 | 38.810 | 28.000 | 203 | TYR | CZ | 10.757 | 25.798 | 17.369 |
| 194 | ALA | CB | 22.770 | 37.303 | 28.253 | 203 | TYR | OH | 9.560 | 26.166 | 17.949 |
| 194 | ALA | C | 21.446 | 38.965 | 26.837 | 203 | TYR | C | 14.941 | 22.322 | 15.901 |
| 194 | ALA | O | 20.264 | 39.273 | 27.044 | 203 | TYR | O | 15.658 | 21.779 | 15.040 |
| 195 | PRO | N | 21.872 | 38.794 | 25.576 | 204 | PRO | N | 13.905 | 21.662 | 16.450 |
| 195 | PRO | CD | 23.294 | 38.583 | 25.188 | 204 | PRO | CD | 13.057 | 22.111 | 17.596 |
| 195 | PRO | CA | 21.018 | 38.880 | 24.377 | 204 | PRO | CA | 13.468 | 20.319 | 15.980 |
| 195 | PRO | CB | 21.899 | 38.465 | 23.180 | 204 | PRO | CB | 12.178 | 20.026 | 16.797 |
| 195 | PRO | CG | 23.321 | 38.854 | 23.643 | 204 | PRO | CG | 12.414 | 20.819 | 18.098 |
| 195 | PRO | C | 19.802 | 38.002 | 24.479 | 204 | PRO | C | 13.249 | 20.306 | 14.463 |
| 195 | PRO | O | 19.931 | 36.816 | 24.761 | 204 | PRO | O | 12.965 | 21.337 | 13.825 |
| 196 | GLY | N | 18.648 | 38.574 | 24.192 | 205 | GLY | N | 13.473 | 19.119 | 13.895 |
| 196 | GLY | CA | 17.403 | 37.833 | 24.257 | 205 | GLY | CA | 13.358 | 18.927 | 12.435 |
| 196 | GLY | C | 16.401 | 38.217 | 23.175 | 205 | GLY | C | 14.643 | 19.310 | 11.724 |
| 196 | GLY | O | 15.214 | 37.925 | 23.303 | 205 | GLY | O | 14.632 | 19.630 | 10.535 |
| 197 | VAL | N | 16.829 | 38.890 | 22.088 | 206 | SER | N | 15.770 | 19.252 | 12.442 |
| 197 | VAL | CA | 15.888 | 39.285 | 21.035 | 206 | SER | CA | 17.067 | 19.586 | 11.924 |
| 197 | VAL | CB | 15.690 | 40.877 | 21.010 | 206 | SER | CB | 17.523 | 18.417 | 11.036 |
| 197 | VAL | CG1 | 14.919 | 41.323 | 19.738 | 206 | SER | OG | 17.461 | 17.216 | 11.797 |
| 197 | VAL | CG2 | 15.038 | 41.327 | 22.327 | 206 | SER | C | 17.098 | 20.931 | 11.175 |
| 197 | VAL | C | 16.483 | 38.785 | 19.727 | 206 | SER | O | 17.591 | 21.045 | 10.047 |
| 197 | VAL | O | 17.672 | 38.897 | 19.432 | 207 | THR | N | 16.566 | 21.968 | 11.842 |
| 198 | ASN | N | 15.627 | 38.173 | 18.937 | 207 | THR | CA | 16.518 | 23.294 | 11.258 |
| 198 | ASN | CA | 15.957 | 37.626 | 17.630 | 207 | THR | CB | 15.070 | 23.518 | 10.667 |
| 198 | ASN | CB | 16.220 | 38.703 | 16.520 | 207 | THR | OG1 | 15.190 | 24.695 | 9.866 |
| 198 | ASN | CG | 15.814 | 38.095 | 15.160 | 207 | THR | CG2 | 13.924 | 23.606 | 11.700 |
| 198 | ASN | OD1 | 15.010 | 37.149 | 15.093 | 207 | THR | C | 16.928 | 24.275 | 12.354 |
| 198 | ASN | ND2 | 16.255 | 38.621 | 14.013 | 207 | THR | O | 17.600 | 23.908 | 13.342 |
| 198 | ASN | C | 17.160 | 36.718 | 17.695 | 208 | TYR | N | 16.632 | 25.546 | 12.113 |
| 198 | ASN | O | 18.147 | 36.910 | 16.978 | 208 | TYR | CA | 17.071 | 26.693 | 12.914 |
| 199 | VAL | N | 17.039 | 35.746 | 18.605 | 208 | TYR | CB | 18.333 | 27.321 | 12.307 |
| 199 | VAL | CA | 18.096 | 34.791 | 18.849 | 208 | TYR | CG | 19.364 | 26.245 | 12.061 |
| 199 | VAL | CB | 18.135 | 34.490 | 20.377 | 208 | TYR | CD1 | 19.428 | 25.565 | 10.842 |
| 199 | VAL | CG1 | 19.303 | 33.623 | 20.702 | 208 | TYR | CE1 | 20.274 | 24.513 | 10.648 |
| 199 | VAL | CG2 | 18.493 | 35.732 | 21.205 | 208 | TYR | CD2 | 20.152 | 25.869 | 13.110 |
| 199 | VAL | C | 17.872 | 33.522 | 18.017 | 208 | TYR | CE2 | 20.978 | 24.825 | 12.917 |
| 199 | VAL | O | 16.912 | 32.776 | 18.194 | 208 | TYR | CZ | 21.039 | 24.151 | 11.713 |
| 200 | GLN | N | 18.706 | 33.324 | 17.005 | 208 | TYR | OH | 21.935 | 23.103 | 11.601 |
| 200 | GLN | CA | 18.771 | 32.144 | 16.138 | 208 | TYR | C | 15.936 | 27.689 | 12.911 |
| 200 | GLN | CB | 19.584 | 32.515 | 14.908 | 208 | TYR | O | 15.224 | 27.863 | 11.906 |
| 200 | GLN | CG | 19.819 | 31.348 | 13.964 | 209 | ALA | N | 15.728 | 28.316 | 14.076 |
| 200 | GLN | CD | 20.240 | 31.677 | 12.544 | 209 | ALA | CA | 14.653 | 29.234 | 14.266 |
| 200 | GLN | OE1 | 21.324 | 32.176 | 12.338 | 209 | ALA | CB | 13.489 | 28.384 | 14.707 |
| 200 | GLN | NE2 | 19.592 | 31.494 | 11.476 | 209 | ALA | C | 15.041 | 30.312 | 15.266 |
| 200 | GLN | C | 19.433 | 30.946 | 16.796 | 209 | ALA | O | 16.021 | 30.178 | 16.019 |
| 200 | GLN | O | 20.567 | 31.114 | 17.277 | 210 | SER | N | 14.378 | 31.450 | 15.089 |
| 201 | SER | N | 18.810 | 29.768 | 16.799 | 210 | SER | CA | 14.567 | 32.642 | 15.914 |

FIG.1K

| | | | | | | | | | | |
|---|---|---|---|---|---|---|---|---|---|---|
| 210 | SER | CB | 14.614 | 33.893 | 15.065 | 220 | HIS | CG | 23.307 | 34.345 | 25.237 |
| 210 | SER | OG | 15.788 | 33.756 | 14.342 | 220 | HIS | CD2 | 24.010 | 34.501 | 24.048 |
| 210 | SER | C | 13.456 | 32.819 | 16.920 | 220 | HIS | ND1 | 21.999 | 34.359 | 24.936 |
| 210 | SER | O | 12.255 | 32.689 | 16.610 | 220 | HIS | CE1 | 21.849 | 34.518 | 23.642 |
| 211 | SER | N | 13.895 | 33.079 | 18.152 | 220 | HIS | NE2 | 23.064 | 34.607 | 23.115 |
| 211 | LEU | CA | 12.990 | 33.304 | 19.244 | 220 | HIS | C | 25.048 | 32.824 | 28.410 |
| 211 | LEU | CB | 12.963 | 32.089 | 20.118 | 220 | HIS | O | 26.276 | 32.626 | 28.383 |
| 211 | LEU | CG | 12.368 | 30.848 | 19.535 | 221 | VAL | N | 24.370 | 32.933 | 29.566 |
| 211 | LEU | CD1 | 12.346 | 29.857 | 20.657 | 221 | VAL | CA | 25.084 | 32.989 | 30.830 |
| 211 | LEU | CD2 | 10.940 | 31.056 | 19.033 | 221 | VAL | CB | 24.180 | 33.727 | 31.843 |
| 211 | LEU | C | 13.372 | 34.503 | 20.110 | 221 | VAL | CG1 | 24.746 | 33.674 | 33.267 |
| 211 | LEU | O | 14.547 | 34.927 | 20.110 | 221 | VAL | CG2 | 24.119 | 35.194 | 31.366 |
| 212 | ASN | N | 12.439 | 35.024 | 20.912 | 221 | VAL | C | 25.477 | 31.606 | 31.299 |
| 212 | ASN | CA | 12.734 | 36.191 | 21.741 | 221 | VAL | O | 26.612 | 31.424 | 31.734 |
| 212 | ASN | CB | 11.883 | 37.403 | 21.413 | 222 | ALA | N | 24.617 | 30.614 | 31.120 |
| 212 | ASN | CG | 11.961 | 37.853 | 19.972 | 222 | ALA | CA | 24.981 | 29.223 | 31.421 |
| 212 | ASN | OD1 | 12.979 | 38.246 | 19.415 | 222 | ALA | CB | 23.871 | 28.283 | 31.032 |
| 212 | ASN | ND2 | 10.841 | 37.797 | 19.283 | 222 | ALA | C | 26.229 | 28.786 | 30.670 |
| 212 | ASN | C | 12.354 | 35.787 | 23.156 | 222 | ALA | O | 27.129 | 28.121 | 31.204 |
| 212 | ASN | O | 11.336 | 35.119 | 23.350 | 223 | GLY | N | 26.258 | 29.180 | 29.388 |
| 213 | GLY | N | 13.070 | 36.197 | 24.217 | 223 | GLY | CA | 27.463 | 28.928 | 28.649 |
| 213 | GLY | CA | 12.648 | 35.928 | 25.599 | 223 | GLY | C | 28.715 | 29.661 | 29.070 |
| 213 | GLY | C | 13.834 | 35.974 | 26.520 | 223 | GLY | O | 29.806 | 29.064 | 29.098 |
| 213 | GLY | O | 14.990 | 35.843 | 26.099 | 224 | ALA | N | 28.557 | 30.955 | 29.357 |
| 214 | THR | N | 13.583 | 36.141 | 27.832 | 224 | ALA | CA | 29.708 | 31.677 | 29.842 |
| 214 | THR | CA | 14.658 | 36.016 | 28.829 | 224 | ALA | CB | 29.313 | 33.106 | 30.058 |
| 214 | THR | CB | 14.204 | 36.523 | 30.242 | 224 | ALA | C | 30.261 | 31.051 | 31.147 |
| 214 | THR | OG1 | 12.998 | 35.812 | 30.594 | 224 | ALA | O | 31.463 | 30.894 | 31.314 |
| 214 | THR | CG2 | 14.014 | 38.055 | 30.271 | 225 | ALA | N | 29.387 | 30.580 | 32.016 |
| 214 | THR | C | 15.128 | 34.527 | 28.894 | 225 | ALA | CA | 29.771 | 29.836 | 33.221 |
| 214 | THR | O | 16.253 | 34.214 | 29.302 | 225 | ALA | CB | 28.560 | 29.321 | 34.020 |
| 215 | SER | N | 14.304 | 33.607 | 28.380 | 225 | ALA | C | 30.593 | 28.603 | 32.864 |
| 215 | SER | CA | 14.663 | 32.187 | 28.217 | 225 | ALA | O | 31.630 | 28.374 | 33.487 |
| 215 | SER | CB | 13.425 | 31.449 | 27.696 | 226 | ALA | N | 30.248 | 27.816 | 31.843 |
| 215 | SER | OG | 12.324 | 31.235 | 28.564 | 226 | ALA | CA | 31.033 | 26.664 | 31.490 |
| 215 | SER | C | 15.860 | 31.981 | 27.237 | 226 | ALA | CB | 30.292 | 25.958 | 30.380 |
| 215 | SER | O | 16.588 | 30.993 | 27.305 | 226 | ALA | C | 32.446 | 27.078 | 31.054 |
| 216 | MET | N | 16.039 | 32.907 | 26.272 | 226 | ALA | O | 33.421 | 26.381 | 31.370 |
| 216 | MET | CA | 17.165 | 32.901 | 25.324 | 227 | LEU | N | 32.587 | 28.209 | 30.328 |
| 216 | MET | CB | 16.776 | 33.575 | 24.055 | 227 | LEU | CA | 33.888 | 28.734 | 29.901 |
| 216 | MET | CG | 15.843 | 32.791 | 23.121 | 227 | LEU | CB | 33.691 | 29.983 | 28.955 |
| 216 | MET | SD | 14.133 | 32.519 | 23.660 | 227 | LEU | CG | 32.901 | 29.762 | 27.666 |
| 216 | MET | CE | 14.311 | 30.783 | 23.925 | 227 | LEU | CD1 | 32.816 | 31.015 | 26.813 |
| 216 | MET | C | 18.372 | 33.638 | 25.885 | 227 | LEU | CD2 | 33.598 | 28.704 | 26.902 |
| 216 | MET | O | 19.506 | 33.386 | 25.460 | 227 | LEU | C | 34.782 | 29.060 | 31.088 |
| 217 | ALA | N | 18.136 | 34.558 | 26.845 | 227 | LEU | O | 35.954 | 28.623 | 31.131 |
| 217 | ALA | CA | 19.249 | 35.257 | 27.465 | 228 | VAL | N | 34.176 | 29.711 | 32.105 |
| 217 | ALA | CB | 18.739 | 36.485 | 28.240 | 228 | VAL | CA | 34.951 | 30.076 | 33.286 |
| 217 | ALA | C | 19.991 | 34.343 | 28.432 | 228 | VAL | CB | 34.114 | 31.094 | 34.168 |
| 217 | ALA | O | 21.223 | 34.249 | 28.386 | 228 | VAL | CG1 | 34.822 | 31.451 | 35.502 |
| 218 | THR | N | 19.211 | 33.574 | 29.199 | 228 | VAL | CG2 | 33.950 | 32.402 | 33.362 |
| 218 | THR | CA | 19.756 | 32.657 | 30.231 | 228 | VAL | C | 35.340 | 28.814 | 34.074 |
| 218 | THR | CB | 18.587 | 31.860 | 30.888 | 228 | VAL | O | 36.468 | 28.777 | 34.573 |
| 218 | THR | OG1 | 17.719 | 32.837 | 31.429 | 229 | LYS | N | 34.502 | 27.781 | 34.115 |
| 218 | THR | CG2 | 19.040 | 30.887 | 31.979 | 229 | LYS | CA | 34.817 | 26.566 | 34.865 |
| 218 | THR | C | 20.824 | 31.704 | 29.700 | 229 | LYS | CB | 33.575 | 25.679 | 34.978 |
| 218 | THR | O | 21.912 | 31.648 | 30.275 | 229 | LYS | CG | 33.758 | 24.324 | 35.713 |
| 219 | PRO | N | 20.683 | 31.008 | 28.586 | 229 | LYS | CD | 34.180 | 24.479 | 37.170 |
| 219 | PRO | CD | 19.479 | 30.843 | 27.793 | 229 | LYS | CE | 34.230 | 23.097 | 37.844 |
| 219 | PRO | CA | 21.708 | 30.099 | 28.089 | 229 | LYS | NZ | 34.394 | 23.211 | 39.298 |
| 219 | PRO | CB | 21.074 | 29.384 | 26.909 | 229 | LYS | C | 35.919 | 25.792 | 34.170 |
| 219 | PRO | CG | 19.943 | 30.268 | 26.471 | 229 | LYS | O | 36.804 | 25.233 | 34.841 |
| 219 | PRO | C | 23.027 | 30.765 | 27.704 | 230 | GLN | N | 35.915 | 25.679 | 32.835 |
| 219 | PRO | O | 24.060 | 30.108 | 27.745 | 230 | GLN | CA | 37.001 | 24.957 | 32.188 |
| 220 | HIS | N | 22.994 | 32.051 | 27.346 | 230 | GLN | CB | 36.692 | 24.852 | 30.683 |
| 220 | HIS | CA | 24.239 | 32.770 | 27.094 | 230 | GLN | CG | 37.819 | 24.181 | 29.916 |
| 220 | HIS | CB | 23.997 | 34.219 | 26.600 | 230 | GLN | CD | 37.806 | 24.343 | 28.410 |

FIG.1L

| | | | | | | | | | | |
|---|---|---|---|---|---|---|---|---|---|---|
| 230 | GLN | OE1 | 36.941 | 24.907 | 27.731 | 238 | VAL | C | 30.741 | 31.770 | 43.322 |
| 230 | GLN | NE2 | 38.866 | 23.779 | 27.864 | 238 | VAL | O | 30.584 | 32.955 | 42.971 |
| 230 | GLN | C | 38.324 | 25.710 | 32.453 | 239 | GLN | N | 31.903 | 31.146 | 43.181 |
| 230 | GLN | O | 39.365 | 25.106 | 32.722 | 239 | GLN | CA | 33.058 | 31.865 | 42.654 |
| 231 | LYS | N | 38.320 | 27.043 | 32.369 | 239 | GLN | CB | 34.348 | 31.007 | 42.712 |
| 231 | LYS | CA | 39.482 | 27.877 | 32.678 | 239 | GLN | CG | 34.787 | 30.771 | 44.165 |
| 231 | LYS | CB | 39.085 | 29.347 | 32.389 | 239 | GLN | CD | 36.001 | 29.847 | 44.293 |
| 231 | LYS | CG | 40.041 | 30.518 | 32.637 | 239 | GLN | OE1 | 35.946 | 28.629 | 44.354 |
| 231 | LYS | CD | 41.380 | 30.478 | 31.945 | 239 | GLN | NE2 | 37.174 | 30.441 | 44.326 |
| 231 | LYS | CE | 42.078 | 31.872 | 31.997 | 239 | GLN | C | 32.811 | 32.264 | 41.203 |
| 231 | LYS | NZ | 42.377 | 32.352 | 33.343 | 239 | GLN | O | 33.124 | 33.398 | 40.784 |
| 231 | LYS | C | 39.970 | 27.715 | 34.142 | 240 | ILE | N | 32.261 | 31.291 | 40.463 |
| 231 | LYS | O | 41.173 | 27.658 | 34.409 | 240 | ILE | CA | 31.950 | 31.500 | 39.047 |
| 232 | ASN | N | 39.023 | 27.635 | 35.097 | 240 | ILE | CB | 31.410 | 30.186 | 38.368 |
| 232 | ASN | CA | 39.292 | 27.588 | 36.520 | 240 | ILE | CG2 | 31.025 | 30.399 | 36.876 |
| 232 | ASN | CB | 38.801 | 28.848 | 37.227 | 240 | ILE | CG1 | 32.503 | 29.161 | 38.463 |
| 232 | ASN | CG | 39.339 | 30.115 | 36.617 | 240 | ILE | CD | 32.041 | 27.775 | 37.973 |
| 232 | ASN | OD1 | 40.486 | 30.464 | 36.859 | 240 | ILE | C | 30.902 | 32.584 | 38.896 |
| 232 | ASN | ND2 | 38.537 | 30.834 | 35.845 | 240 | ILE | O | 31.087 | 33.511 | 38.104 |
| 232 | ASN | C | 38.595 | 26.402 | 37.158 | 241 | ARG | N | 29.819 | 32.484 | 39.667 |
| 232 | ASN | O | 37.635 | 26.555 | 37.907 | 251 | ARG | CA | 28.769 | 33.495 | 39.638 |
| 233 | PRO | N | 39.057 | 25.173 | 36.945 | 241 | ARG | CB | 27.701 | 33.092 | 40.655 |
| 233 | PRO | CD | 40.245 | 24.847 | 36.150 | 241 | ARG | CG | 26.634 | 34.192 | 40.895 |
| 233 | PRO | CA | 38.320 | 23.978 | 37.376 | 241 | ARG | CD | 25.462 | 33.692 | 41.771 |
| 233 | PRO | CB | 39.053 | 22.819 | 36.729 | 241 | ARG | NE | 24.364 | 34.639 | 41.945 |
| 233 | PRO | CG | 40.441 | 23.367 | 36.519 | 241 | ARG | CZ | 23.323 | 34.340 | 42.749 |
| 233 | PRO | C | 38.155 | 23.820 | 38.863 | 241 | ARG | NH1 | 22.325 | 35.215 | 42.920 |
| 233 | PRO | O | 37.266 | 23.094 | 39.274 | 241 | ARG | NH2 | 23.252 | 33.149 | 43.371 |
| 234 | SER | N | 38.962 | 24.489 | 39.675 | 241 | ARG | C | 29.313 | 34.923 | 39.937 |
| 234 | SER | CA | 38.725 | 24.374 | 41.124 | 241 | ARG | O | 29.037 | 35.874 | 39.200 |
| 234 | SER | CB | 40.005 | 24.643 | 41.961 | 242 | ASN | N | 30.153 | 35.073 | 40.959 |
| 234 | SER | OG | 40.378 | 26.007 | 41.847 | 242 | ASN | CA | 30.649 | 36.413 | 41.277 |
| 234 | SER | C | 37.635 | 25.309 | 41.680 | 242 | ASN | CB | 31.391 | 36.455 | 42.609 |
| 234 | SER | O | 37.203 | 25.124 | 42.824 | 242 | ASN | CG | 30.386 | 36.371 | 43.746 |
| 235 | TRP | N | 37.151 | 26.270 | 40.878 | 242 | ASN | OD1 | 29.177 | 36.652 | 43.659 |
| 235 | TRP | CA | 36.213 | 27.246 | 41.393 | 242 | ASN | ND2 | 30.877 | 35.881 | 44.877 |
| 235 | TRP | CB | 36.022 | 28.366 | 40.435 | 242 | ASN | C | 31.591 | 36.931 | 40.225 |
| 235 | TRP | CG | 37.165 | 29.323 | 40.391 | 242 | ASN | O | 31.631 | 38.152 | 39.938 |
| 235 | TRP | CD2 | 37.103 | 30.539 | 39.761 | 243 | HIS | N | 32.330 | 36.012 | 39.584 |
| 235 | TRP | CE2 | 38.384 | 31.011 | 39.929 | 243 | HIS | CA | 33.284 | 36.451 | 38.593 |
| 235 | TRP | CE3 | 36.167 | 31.261 | 39.083 | 243 | HIS | CB | 34.183 | 35.327 | 38.178 |
| 235 | TRP | CD1 | 38.405 | 29.059 | 40.930 | 243 | HIS | CG | 35.409 | 35.790 | 37.413 |
| 235 | TRP | NE1 | 39.136 | 30.109 | 40.623 | 243 | HIS | CD2 | 36.367 | 36.638 | 37.902 |
| 235 | TRP | CZ2 | 38.726 | 32.237 | 39.404 | 243 | HIS | ND1 | 35.770 | 35.447 | 36.181 |
| 235 | TRP | CZ3 | 36.502 | 32.474 | 38.559 | 243 | HIS | CE1 | 36.908 | 36.044 | 35.892 |
| 235 | TRP | CH2 | 37.775 | 32.956 | 38.720 | 243 | HIS | NE2 | 37.250 | 36.757 | 36.945 |
| 235 | TRP | C | 34.862 | 26.643 | 41.637 | 243 | HIS | C | 32.559 | 36.966 | 37.370 |
| 235 | TRP | O | 34.427 | 25.726 | 40.941 | 243 | HIS | O | 32.988 | 37.984 | 36.820 |
| 236 | SER | N | 34.206 | 27.137 | 42.669 | 244 | LEU | N | 31.473 | 36.265 | 36.963 |
| 236 | SER | CA | 32.884 | 26.712 | 43.011 | 244 | LEU | CA | 30.709 | 36.649 | 35.801 |
| 236 | SER | CB | 32.771 | 26.915 | 44.541 | 244 | LEU | CB | 29.576 | 35.636 | 35.501 |
| 236 | SER | OG | 32.691 | 28.301 | 44.902 | 244 | LEU | CG | 29.971 | 34.234 | 34.958 |
| 236 | SER | C | 31.891 | 27.549 | 42.200 | 244 | LEU | CD1 | 28.719 | 33.367 | 34.841 |
| 236 | SER | O | 32.195 | 28.606 | 41.637 | 244 | LEU | CD2 | 30.649 | 34.360 | 33.602 |
| 237 | ASN | N | 30.645 | 27.084 | 42.278 | 244 | LEU | C | 30.147 | 38.007 | 36.104 |
| 237 | ASN | CA | 29.495 | 27.743 | 41.705 | 244 | LEU | O | 30.189 | 38.853 | 35.217 |
| 237 | ASN | CB | 28.255 | 26.923 | 42.112 | 245 | LYS | N | 29.690 | 38.289 | 37.328 |
| 237 | ASN | CG | 27.966 | 26.679 | 43.605 | 245 | LYS | CA | 29.178 | 39.632 | 37.654 |
| 237 | ASN | OD1 | 28.706 | 27.112 | 44.495 | 245 | LYS | CB | 28.452 | 39.593 | 38.993 |
| 237 | ASN | ND2 | 26.851 | 26.017 | 43.928 | 245 | LYS | CG | 27.193 | 38.687 | 38.928 |
| 237 | ASN | C | 29.388 | 29.219 | 42.117 | 245 | LYS | CD | 26.536 | 38.412 | 40.289 |
| 237 | ASN | O | 29.255 | 30.109 | 41.266 | 245 | LYS | CE | 25.811 | 39.677 | 40.573 |
| 238 | VAL | N | 29.592 | 29.555 | 43.414 | 245 | LYS | NZ | 25.221 | 39.607 | 41.886 |
| 238 | VAL | CA | 29.576 | 30.945 | 43.876 | 245 | LYS | C | 30.300 | 40.665 | 37.714 |
| 238 | VAL | CB | 29.553 | 30.919 | 45.442 | 245 | LYS | O | 30.125 | 41.805 | 37.257 |
| 238 | VAL | CG1 | 29.767 | 32.294 | 46.097 | 246 | ASN | N | 31.462 | 40.279 | 38.199 |
| 238 | VAL | CG2 | 28.199 | 30.344 | 45.805 | 246 | ASN | CA | 32.579 | 41.194 | 38.352 |

FIG.1M

| | | | | | | | | | | |
|---|---|---|---|---|---|---|---|---|---|---|
| 246 | ASN | CB | 33.697 | 40.568 | 39.196 | 256 | LEU | CG | 16.565 | 49.634 | 34.134 |
| 246 | ASN | CG | 33.286 | 40.502 | 40.651 | 256 | LEU | CD1 | 16.919 | 50.482 | 32.887 |
| 246 | ASN | OD1 | 32.445 | 41.245 | 41.165 | 256 | LEU | CD2 | 15.095 | 49.321 | 34.182 |
| 246 | ASN | ND2 | 33.814 | 39.538 | 41.375 | 256 | LEU | C | 18.284 | 46.162 | 34.546 |
| 246 | ASN | C | 33.188 | 41.620 | 37.046 | 256 | LEU | O | 17.798 | 45.300 | 33.803 |
| 246 | ASN | O | 33.819 | 42.686 | 36.960 | 257 | TYR | N | 19.566 | 46.246 | 34.888 |
| 247 | THR | N | 33.020 | 40.781 | 36.033 | 257 | TYR | CA | 20.590 | 45.390 | 34.268 |
| 247 | THR | CA | 33.574 | 41.115 | 34.734 | 257 | TYR | CB | 21.608 | 46.225 | 33.447 |
| 247 | THR | CB | 34.386 | 39.916 | 34.179 | 257 | TYR | CG | 20.957 | 47.106 | 32.389 |
| 247 | THR | OG1 | 33.492 | 38.818 | 34.055 | 257 | TYR | CD1 | 20.349 | 46.459 | 31.337 |
| 247 | THR | CG2 | 35.608 | 39.565 | 35.059 | 257 | TYR | CE1 | 19.733 | 47.179 | 30.384 |
| 247 | THR | C | 32.516 | 41.547 | 33.737 | 257 | TYR | CD2 | 20.951 | 48.503 | 32.449 |
| 247 | THR | O | 32.865 | 41.792 | 32.575 | 257 | TYR | CE2 | 20.330 | 49.219 | 31.446 |
| 248 | ALA | N | 31.252 | 41.714 | 34.123 | 257 | TYR | CZ | 19.731 | 48.536 | 30.426 |
| 248 | ALA | CA | 30.213 | 42.085 | 33.162 | 257 | TYR | OH | 19.142 | 49.131 | 29.335 |
| 248 | ALA | CB | 28.829 | 41.914 | 33.800 | 257 | TYR | C | 21.424 | 44.557 | 35.226 |
| 248 | ALA | C | 30.385 | 43.558 | 32.731 | 257 | TYR | O | 22.226 | 43.739 | 34.776 |
| 248 | ALA | O | 30.961 | 44.395 | 33.440 | 258 | GLY | N | 21.305 | 44.756 | 36.542 |
| 249 | THR | N | 29.950 | 43.949 | 31.551 | 258 | GLY | CA | 22.222 | 44.130 | 37.496 |
| 249 | THR | CA | 30.001 | 45.323 | 31.096 | 258 | GLY | C | 23.630 | 44.552 | 37.201 |
| 249 | THR | CB | 29.955 | 45.301 | 29.552 | 258 | GLY | O | 23.896 | 45.710 | 36.877 |
| 249 | THR | OG1 | 31.151 | 44.706 | 29.080 | 259 | SER | N | 24.511 | 43.586 | 37.273 |
| 249 | THR | CG2 | 29.830 | 46.690 | 28.965 | 259 | SER | CA | 25.897 | 43.856 | 36.955 |
| 249 | THR | C | 28.830 | 46.105 | 31.676 | 259 | SER | CB | 26.747 | 42.633 | 37.239 |
| 249 | THR | O | 27.664 | 45.760 | 31.425 | 259 | SER | OG | 26.779 | 42.518 | 38.660 |
| 250 | SER | N | 29.067 | 47.214 | 32.412 | 259 | SER | C | 26.153 | 44.278 | 35.527 |
| 250 | SER | CA | 27.941 | 47.994 | 32.947 | 259 | SER | O | 27.225 | 44.856 | 35.285 |
| 250 | SER | CB | 28.405 | 49.102 | 33.875 | 260 | GLY | N | 25.225 | 44.013 | 34.600 |
| 250 | SER | OG | 27.267 | 49.862 | 34.279 | 260 | GLY | CA | 25.413 | 44.431 | 33.222 |
| 250 | SER | C | 27.136 | 48.631 | 31.822 | 260 | GLY | C | 25.476 | 43.210 | 32.331 |
| 250 | SER | O | 27.687 | 49.164 | 30.857 | 260 | GLY | O | 24.999 | 42.106 | 32.672 |
| 251 | LEU | N | 25.824 | 48.523 | 31.929 | 261 | LEU | N | 26.036 | 43.461 | 31.151 |
| 251 | LEU | CA | 24.949 | 49.115 | 30.934 | 261 | LEU | CA | 26.105 | 42.461 | 30.087 |
| 251 | LEU | CB | 24.067 | 48.019 | 30.342 | 261 | LEU | CB | 26.274 | 43.195 | 28.721 |
| 251 | LEU | CG | 24.737 | 46.908 | 29.627 | 261 | LEU | CG | 26.349 | 42.381 | 27.424 |
| 251 | LEU | CD1 | 23.663 | 46.020 | 29.043 | 261 | LEU | CD1 | 25.064 | 41.598 | 27.191 |
| 251 | LEU | CD2 | 25.595 | 47.430 | 28.481 | 261 | LEU | CD2 | 26.675 | 43.372 | 26.282 |
| 251 | LEU | C | 24.069 | 50.231 | 31.462 | 261 | LEU | C | 27.234 | 41.470 | 30.309 |
| 251 | LEU | O | 23.214 | 50.787 | 30.769 | 261 | LEU | O | 28.410 | 41.842 | 30.426 |
| 252 | GLY | N | 24.239 | 50.606 | 32.703 | 262 | VAL | N | 26.851 | 40.192 | 30.263 |
| 252 | GLY | CA | 23.317 | 51.538 | 33.279 | 262 | VAL | CA | 27.872 | 39.161 | 30.432 |
| 252 | GLY | C | 22.880 | 50.976 | 34.613 | 262 | VAL | CB | 27.227 | 37.754 | 30.407 |
| 252 | GLY | O | 23.651 | 50.372 | 35.376 | 262 | VAL | CG1 | 26.633 | 37.448 | 29.036 |
| 253 | SER | N | 21.614 | 51.241 | 34.872 | 262 | VAL | CG2 | 28.305 | 36.734 | 30.824 |
| 253 | SER | CA | 20.958 | 50.918 | 36.106 | 262 | VAL | C | 28.935 | 39.300 | 29.331 |
| 253 | SER | CB | 19.470 | 51.165 | 35.891 | 262 | VAL | O | 28.661 | 39.699 | 28.193 |
| 253 | SER | OG | 18.813 | 51.273 | 37.150 | 263 | ASN | N | 30.181 | 39.070 | 29.700 |
| 253 | SER | C | 21.195 | 49.492 | 36.567 | 263 | ASN | CA | 31.271 | 39.216 | 28.755 |
| 253 | SER | O | 20.900 | 48.587 | 35.786 | 263 | ASN | CB | 31.866 | 40.599 | 28.993 |
| 254 | THR | N | 21.694 | 49.321 | 37.796 | 263 | ASN | CG | 33.072 | 40.880 | 28.136 |
| 254 | THR | CA | 21.773 | 48.021 | 38.431 | 263 | ASN | OD1 | 33.666 | 40.009 | 27.502 |
| 254 | THR | CB | 22.417 | 48.071 | 39.869 | 263 | ASN | ND2 | 33.498 | 42.124 | 28.143 |
| 254 | THR | OG1 | 23.694 | 48.691 | 39.803 | 263 | ASN | C | 32.250 | 38.068 | 28.945 |
| 254 | THR | CG2 | 22.671 | 46.670 | 40.414 | 263 | ASN | O | 33.119 | 37.994 | 29.826 |
| 254 | THR | C | 20.311 | 47.594 | 38.557 | 264 | ALA | N | 32.136 | 37.126 | 28.030 |
| 254 | THR | O | 20.041 | 46.419 | 38.445 | 264 | ALA | CA | 32.947 | 35.931 | 28.088 |
| 255 | ASN | N | 19.316 | 48.480 | 38.694 | 264 | ALA | CB | 32.528 | 34.857 | 27.080 |
| 255 | ASN | CA | 17.930 | 48.038 | 38.783 | 264 | ALA | C | 34.404 | 36.250 | 27.801 |
| 255 | ASN | CB | 17.061 | 49.253 | 39.031 | 264 | ALA | O | 35.259 | 35.517 | 28.331 |
| 255 | ASN | CG | 15.600 | 48.927 | 39.271 | 265 | GLU | N | 34.752 | 37.304 | 27.054 |
| 255 | ASN | OD1 | 15.191 | 48.158 | 40.157 | 265 | GLU | CA | 36.169 | 37.625 | 26.884 |
| 255 | ASN | ND2 | 14.771 | 49.580 | 38.459 | 265 | GLU | CB | 36.346 | 38.768 | 25.842 |
| 255 | ASN | C | 17.441 | 47.296 | 37.526 | 265 | GLU | CG | 37.790 | 39.302 | 25.597 |
| 255 | ASN | O | 16.752 | 46.279 | 37.550 | 265 | GLU | CD | 38.470 | 40.138 | 26.723 |
| 256 | LEU | N | 17.889 | 47.805 | 36.389 | 265 | GLU | OE1 | 39.623 | 39.854 | 27.100 |
| 256 | LEU | CA | 17.437 | 47.297 | 35.108 | 265 | GLU | OE2 | 37.835 | 41.060 | 27.255 |
| 256 | LEU | CB | 17.435 | 48.386 | 34.041 | 265 | GLU | C | 36.745 | 38.057 | 28.227 |

FIG.1N

| | | | | | | | | | | |
|---|---|---|---|---|---|---|---|---|---|---|
| 265 | GLU | O | 37.766 | 37.524 | 28.689 | 307 | H2O | OH2 | 26.065 | 37.253 | 43.741 |
| 266 | ALA | N | 36.098 | 39.020 | 28.897 | 308 | H2O | OH2 | 11.945 | 45.684 | 23.380 |
| 266 | ALA | CA | 36.698 | 39.536 | 30.109 | 309 | H2O | OH2 | 19.643 | 10.507 | 40.112 |
| 266 | ALA | CB | 35.959 | 40.800 | 30.534 | 310 | H2O | OH2 | 38.430 | 41.954 | 36.077 |
| 266 | ALA | C | 36.677 | 38.485 | 31.228 | 311 | H2O | OH2 | 13.501 | 39.873 | 16.866 |
| 266 | ALA | O | 37.562 | 38.418 | 32.099 | 312 | H2O | OH2 | 16.785 | 49.578 | 21.745 |
| 267 | ALA | N | 35.677 | 37.593 | 31.161 | 313 | H2O | OH2 | 28.911 | 19.876 | 22.976 |
| 267 | ALA | CA | 35.566 | 36.560 | 32.179 | 314 | H2O | OH2 | 29.797 | 51.940 | 35.038 |
| 267 | ALA | CB | 34.165 | 35.963 | 32.078 | 315 | H2O | OH2 | 8.968 | 16.983 | 43.770 |
| 267 | ALA | C | 36.616 | 35.454 | 32.087 | 316 | H2O | OH2 | 21.830 | 26.021 | 49.724 |
| 267 | ALA | O | 36.811 | 34.737 | 33.081 | 317 | H2O | OH2 | 18.231 | 35.980 | 44.119 |
| 268 | THR | N | 37.257 | 35.279 | 30.927 | 318 | H2O | OH2 | 17.725 | 35.088 | 15.203 |
| 268 | THR | CA | 38.227 | 34.187 | 30.751 | 319 | H2O | OH2 | 34.481 | 23.007 | 20.146 |
| 268 | THR | CB | 37.888 | 33.276 | 29.515 | 320 | H2O | OH2 | 19.764 | 37.086 | 46.005 |
| 268 | THR | OG1 | 37.799 | 34.092 | 28.362 | 321 | H2O | OH2 | 13.211 | 26.583 | 10.242 |
| 268 | THR | CG2 | 36.575 | 32.530 | 29.710 | 322 | H2O | OH2 | 10.729 | 31.502 | 26.207 |
| 268 | THR | C | 39.617 | 34.741 | 30.576 | 323 | H2O | OH2 | 22.023 | 36.663 | 14.105 |
| 268 | THR | O | 40.534 | 33.996 | 30.218 | 324 | H2O | OH2 | 26.324 | 19.922 | 21.851 |
| 269 | THR | N | 39.728 | 36.045 | 30.801 | 325 | H2O | OH2 | 30.661 | 17.697 | 22.182 |
| 269 | ARG | CA | 41.008 | 36.690 | 30.810 | 326 | H2O | OH2 | 8.433 | 17.883 | 24.882 |
| 269 | ARG | CB | 40.656 | 38.156 | 30.839 | 327 | H2O | OH2 | 32.021 | 21.783 | 19.092 |
| 269 | ARG | CG | 41.824 | 39.000 | 30.472 | 328 | H2O | OH2 | 32.606 | 20.038 | 14.623 |
| 269 | ARG | CD | 41.544 | 40.401 | 29.949 | 329 | H2O | OH2 | 27.918 | 17.370 | 24.830 |
| 269 | ARG | NE | 42.811 | 40.930 | 29.432 | 330 | H2O | OH2 | 17.445 | 14.094 | 24.149 |
| 269 | ARG | CZ | 43.324 | 42.136 | 29.787 | 331 | H2O | OH2 | 16.527 | 18.554 | 15.250 |
| 269 | ARG | NH1 | 44.518 | 43.533 | 29.265 | 332 | H2O | OH2 | 15.380 | 14.546 | 15.873 |
| 269 | ARG | NH2 | 42.681 | 42.951 | 30.667 | 333 | H2O | OH2 | 12.129 | 16.040 | 17.903 |
| 269 | ARG | C | 41.844 | 36.161 | 32.014 | 334 | H2O | OH2 | 13.873 | 16.685 | 15.209 |
| 269 | ARG | OT1 | 41.328 | 35.597 | 32.990 | 335 | H2O | OH2 | 6.048 | 18.751 | 34.243 |
| 269 | ARG | OT2 | 43.070 | 36.206 | 31.952 | 336 | H2O | OH2 | 4.411 | 16.951 | 35.536 |
| 270 | CM | CM | 27.629 | 24.423 | 14.043 | 337 | H2O | OH2 | 6.528 | 15.046 | 39.508 |
| 271 | CM | CM | 18.482 | 35.001 | 42.551 | 338 | H2O | OH2 | 4.188 | 15.102 | 37.754 |
| 272 | H2O | OH2 | 35.625 | 16.277 | 36.682 | 339 | H2O | OH2 | 7.267 | 13.144 | 37.517 |
| 273 | H2O | OH2 | 19.773 | 36.339 | 42.049 | 340 | H2O | OH2 | 7.231 | 10.169 | 35.676 |
| 274 | H2O | OH2 | 28.438 | 25.352 | 47.303 | 341 | H2O | OH2 | 9.229 | 11.210 | 38.524 |
| 275 | H2O | OH2 | 25.023 | 30.639 | 43.381 | 342 | H2O | OH2 | 13.492 | 9.745 | 35.358 |
| 276 | H2O | OH2 | 23.352 | 28.163 | 42.310 | 343 | H2O | OH2 | 12.026 | 44.524 | 42.622 |
| 277 | H2O | OH2 | 21.594 | 35.893 | 18.729 | 344 | H2O | OH2 | 11.004 | 41.120 | 45.663 |
| 278 | H2O | OH2 | 22.058 | 31.111 | 19.688 | 345 | H2O | OH2 | 10.220 | 39.693 | 42.722 |
| 279 | H2O | OH2 | 18.752 | 45.063 | 40.645 | 346 | H2O | OH2 | 12.059 | 47.753 | 40.959 |
| 280 | H2O | OH2 | 18.039 | 30.216 | 23.124 | 347 | H2O | OH2 | 9.164 | 48.300 | 42.769 |
| 281 | H2O | OH2 | 14.078 | 9.380 | 32.356 | 348 | H2O | OH2 | 11.958 | 43.338 | 44.851 |
| 282 | H2O | OH2 | 15.449 | 19.938 | 28.355 | 349 | H2O | OH2 | 11.239 | 46.641 | 44.371 |
| 283 | H2O | OH2 | 15.927 | 25.605 | 30.476 | 350 | H2O | OH2 | 4.931 | 44.533 | 41.923 |
| 284 | H2O | OH2 | 12.858 | 32.346 | 37.185 | 351 | H2O | OH2 | 6.403 | 36.291 | 34.865 |
| 285 | H2O | OH2 | 11.544 | 33.624 | 27.713 | 352 | H2O | OH2 | 5.564 | 39.764 | 36.611 |
| 286 | H2O | OH2 | 11.580 | 8.103 | 31.642 | 353 | H2O | OH2 | 8.066 | 29.304 | 32.467 |
| 287 | H2O | OH2 | 42.076 | 35.854 | 14.697 | 401 | H2O | OH2 | 23.985 | 29.300 | 19.050 |
| 288 | H2O | OH2 | 8.591 | 11.660 | 25.062 | 402 | H2O | OH2 | 22.840 | 42.988 | 23.949 |
| 289 | H2O | OH2 | 34.301 | 29.140 | 15.200 | 403 | H2O | OH2 | 24.648 | 47.653 | 34.651 |
| 290 | H2O | OH2 | 30.440 | 24.492 | 43.369 | 404 | H2O | OH2 | 22.155 | 15.174 | 18.497 |
| 291 | H2O | OH2 | 35.793 | 42.916 | 26.272 | 405 | H2O | OH2 | 22.394 | 50.724 | 27.973 |
| 292 | H2O | OH2 | 30.881 | 38.720 | 32.534 | 406 | H2O | OH2 | 25.205 | 15.404 | 16.200 |
| 293 | H2O | OH2 | 29.323 | 24.894 | 39.464 | 407 | H2O | OH2 | 16.769 | 30.931 | 11.057 |
| 294 | H2O | OH2 | 30.053 | 41.242 | 26.124 | 408 | H2O | OH2 | 6.421 | 46.954 | 36.986 |
| 295 | H2O | OH2 | 26.029 | 30.946 | 34.554 | 409 | H2O | OH2 | 39.155 | 36.951 | 34.253 |
| 296 | H2O | OH2 | 23.950 | 42.830 | 40.424 | 410 | H2O | OH2 | 30.425 | 43.985 | 26.477 |
| 297 | H2O | OH2 | 22.857 | 33.906 | 20.288 | 411 | H2O | OH2 | 15.991 | 34.160 | 48.706 |
| 298 | H2O | OH2 | 29.750 | 12.657 | 20.465 | 412 | H2O | OH2 | 33.843 | 20.940 | 9.231 |
| 299 | H2O | OH2 | 16.182 | 42.867 | 32.920 | 413 | H2O | OH2 | 16.995 | 50.196 | 28.127 |
| 300 | H2O | OH2 | 20.509 | 35.549 | 16.195 | 415 | H2O | OH2 | 38.899 | 33.531 | 34.689 |
| 301 | H2O | OH2 | 21.065 | 41.688 | 15.225 | 416 | H2O | OH2 | 17.892 | 19.864 | 44.040 |
| 302 | H2O | OH2 | 12.353 | 41.495 | 42.254 | 417 | H2O | OH2 | 34.568 | 30.498 | 17.440 |
| 303 | H2O | OH2 | 11.733 | 34.741 | 14.055 | 419 | H2O | OH2 | 35.622 | 20.284 | 42.959 |
| 304 | H2O | OH2 | 7.156 | 35.456 | 31.880 | 420 | H2O | OH2 | 0.206 | 12.428 | 34.387 |
| 305 | H2O | OH2 | 7.914 | 47.871 | 34.970 | 421 | H2O | OH2 | 38.833 | 23.281 | 24.721 |
| 306 | H2O | OH2 | 5.154 | 42.915 | 39.674 | 422 | H2O | OH2 | 27.524 | 37.611 | 14.941 |

FIG.10

| | | | | | | | | | | |
|---|---|---|---|---|---|---|---|---|---|---|
|423|H2O|OH2|33.375|39.759|31.397|474|H2O|OH2|33.485|27.966|24.079|
|425|H2O|OH2|10.662|51.211|37.076|475|H2O|OH2|16.400|18.715|49.507|
|426|H2O|OH2|28.400|26.227|22.233|476|H2O|OH2|34.584|26.355|28.896|
|427|H2O|OH2|37.069|31.271|18.172|477|H2O|OH2|18.844|26.392|36.213|
|428|H2O|OH2|35.149|22.967|42.892|478|H2O|OH2|17.595|33.022|12.700|
|429|H2O|OH2|14.410|35.423|17.549|479|H2O|OH2|19.970|49.821|15.851|
|430|H2O|OH2|34.593|37.589|20.470|480|H2O|OH2|29.931|22.624|47.074|
|431|H2O|OH2|33.293|43.729|30.636|481|H2O|OH2|28.764|29.952|13.997|
|432|H2O|OH2|18.935|12.276|22.731|482|H2O|OH2|24.923|29.997|46.055|
|433|H2O|OH2|36.502|38.642|39.753|483|H2O|OH2|4.494|34.569|48.325|
|434|H2O|OH2|30.888|44.367|36.634|484|H2O|OH2|25.927|28.389|42.632|
|435|H2O|OH2|6.433|14.502|42.412|485|H2O|OH2|19.179|31.050|19.865|
|436|H2O|OH2|23.735|32.721|13.204|486|H2O|OH2|33.544|35.859|34.951|
|437|H2O|OH2|30.269|39.336|42.632|489|H2O|OH2|7.275|28.059|36.209|
|438|H2O|OH2|6.916|37.376|38.041|490|H2O|OH2|18.187|52.286|20.471|
|439|H2O|OH2|31.535|45.230|24.294|491|H2O|OH2|14.703|47.608|24.076|
|440|H2O|OH2|21.133|38.497|43.405|492|H2O|OH2|14.414|29.083|26.931|
|441|H2O|OH2|26.156|30.548|26.735|493|H2O|OH2|20.741|38.573|12.784|
|442|H2O|OH2|20.961|41.888|36.136|494|H2O|OH2|32.484|22.352|42.540|
|443|H2O|OH2|10.366|9.353|42.909|495|H2O|OH2|11.669|32.823|30.485|
|444|H2O|OH2|15.664|13.252|41.086|496|H2O|OH2|25.506|21.376|19.908|
|445|H2O|OH2|15.488|35.603|22.544|498|H2O|OH2|14.394|49.504|27.686|
|446|H2O|OH2|8.523|29.548|42.831|499|H2O|OH2|39.498|21.926|32.920|
|448|H2O|OH2|6.347|42.537|28.354|500|H2O|OH2|20.574|46.516|27.909|
|449|H2O|OH2|20.408|28.429|14.479|501|H2O|OH2|41.254|36.175|22.038|
|451|H2O|OH2|9.986|37.579|24.768|502|H2O|OH2|18.615|23.589|42.251|
|452|H2O|OH2|34.820|21.034|34.828|503|H2O|OH2|23.238|48.249|18.498|
|453|H2O|OH2|17.186|30.632|13.537|504|H2O|OH2|11.027|27.025|49.749|
|454|H2O|OH2|12.491|19.964|46.613|505|H2O|OH2|6.051|28.870|41.533|
|455|H2O|OH2|31.523|29.927|11.890|506|H2O|OH2|20.329|51.097|40.041|
|456|H2O|OH2|12.628|27.138|21.026|507|H2O|OH2|34.042|46.991|33.740|
|457|H2O|OH2|33.466|44.288|34.479|508|H2O|OH2|18.800|14.484|12.899|
|458|H2O|OH2|19.599|43.860|38.560|509|H2O|OH2|23.984|14.515|28.480|
|459|H2O|OH2|16.152|29.460|52.727|510|H2O|OH2|14.955|20.395|22.995|
|460|H2O|OH2|12.458|29.430|17.126|511|H2O|OH2|31.742|13.971|22.917|
|461|H2O|OH2|37.639|14.784|37.217|512|H2O|OH2|13.014|49.698|46.176|
|462|H2O|OH2|9.851|34.465|20.032|513|H2O|OH2|3.857|17.317|43.260|
|463|H2O|OH2|33.545|17.795|26.313|514|H2O|OH2|8.348|35.692|23.895|
|464|H2O|OH2|9.256|16.911|34.260|515|H2O|OH2|9.871|28.970|29.151|
|465|H2O|OH2|35.476|39.839|21.547|516|H2O|OH2|18.301|41.737|20.959|
|467|H2O|OH2|23.365|24.048|13.490|517|H2O|OH2|10.419|21.355|11.387|
|468|H2O|OH2|11.732|35.837|17.577|518|H2O|OH2|11.150|32.989|33.268|
|469|H2O|OH2|30.073|50.380|31.035|519|H2O|OH2|43.085|38.642|27.705|
|471|H2O|OH2|16.204|22.887|7.809|520|H2O|OH2|20.416|57.764|27.758|
|472|H2O|OH2|27.601|27.623|26.352|521|H2O|OH2|40.300|29.469|52.597|
|473|H2O|OH2|2.443|14.804|32.338| | | | | | |

FIG.1P

MUTANT PROTEOLYTIC ENZYMES AND METHOD OF PRODUCTION

This is a continuation application of application Ser. No. 08/980,135, filed Nov. 26, 1997 now U.S. Pat. No. 6,136,553 which was a divisional application of application Ser. No. 08/618,446, filed Mar. 19, 1996, now U.S. Pat. No. 5,985,639 which was a divisional application of application Ser. No. 08/254,021, filed Jun. 2, 1994, now U.S. Pat. No. 5,500,364, which was a divisional of application Ser. No. 07/706,691, filed May 29, 1991, now U.S. Pat. No. 5,340,735.

BACKGROUND OF THE INVENTION

1. Field of the Invention

This invention relates to mutant proteolytic enzymes having improved properties relative to the wild-type enzyme, to genetic constructs which code for the mutant proteolytic enzymes, to methods of predicting mutations which enhance the stability of the enzyme, and to methods of producing the mutant proteolytic enzymes.

2. Description of the Related Art

*Subtilisins* are a family of extracellular proteins having molecular weights in the range of 25,000–35,000 daltons and are produced by various Bacillus species. These proteins function as peptide hydrolases in that they catalyze the hydrolysis of peptide linkages in protein substrates at neutral and alkaline pH values. *Subtilisins* are termed serine proteases because they contain a specific serine residue which participates in the catalytic hydrolysis of peptide substrates. A *subtilisin* enzyme isolated from soil samples and produced by *Bacillus lentus* for use in detergent formulations having increased protease and oxidative stability over commercially available enzymes under conditions of pH 7 to 10 and at temperature of 10 to 60° C. in aqueous solutions has been disclosed in copending patent application Ser. No. 07/398,854, filed on Aug. 25, 1989. This *B. lentus* alkaline protease enzyme (BLAP, vide infra) is obtained in commercial quantities by cultivating a *Bacillus licheniformis* ATCC 53926 strain which had been transformed by an expression plasmid which contained the wild type BLAP gene and the *B. licheniformis* ATCC 53926 alkaline protease gene promoter.

Industrial processes generally are performed under physical conditions which require highly stable enzymes. Enzymes may be inactivated by high temperatures, pH extremes, oxidation, and surfactants. Even though *Bacillus subtilisin* proteases are currently used in many industrial applications, including detergent formulations, stability improvements are still needed. Market trends are toward more concentrated detergent powders, and an increase in liquid formulations. Increased shelf stability and oxidative stability, with retention of catalytic efficiency are needed. It is therefore desirable to isolate novel enzymes with increased stability, or to improve the stability of existing enzymes, including *subtilisin* proteases such as BLAP.

The stability of a protein is a function of its three dimensional structure. A protein folds into a three dimensional conformation based upon the primary amino acid sequence, and upon its surrounding environment. The function and stability of a protein are a direct result of its three dimensional structure.

A large body of information has been published which describes changes in enzyme properties as a result of alterations in the primary amino acid sequence of the enzyme. These alterations can result from random or site specific alterations of the gene which expresses the enzyme using genetic engineering techniques. Random approaches mutagenize total cellular DNA, followed by selection for the synthesis of an enzyme with improved properties. This approach requires neither knowledge of the three dimensional structure of the enzyme, nor any predictive capability on the part of the researcher. Site directed mutagenesis, on the other hand, requires a rational approach for the introduction of amino acid changes. In this approach one or more amino acids may be replaced by other residues by altering the DNA sequence which encodes the protein. This can be accomplished using oligonucleotide directed in vitro mutagenesis. The following references teach site-directed mutagenesis procedures used to generate specific amino acid substitution(s): Hines, J. C., and Ray, D. S. (1980) Gene 11:207–218; Zoller, M. J., and Smith, M. (1982) Nucleic Acids Res. 10:6487–6500; Norrander, J., et al. (1983) Gene 26:101–106; Morinaga, Y., et al. (1984) Bio/Technology 2:636–639; Kramer, W., et al. (1984) Nucleic Acids Res. 12:9441–9456; Carter, P., et al. (1985) Nucleic Acids Res. 13:4431–4443; Kunkel, T. A. (1985) Proc. Natl. Acad. Sci. USA 82:488–492; Bryan, P., et al. (1986) Proc. Natl. Acad. Sci. USA 83:3743–3745.

A rational approach may or may not require knowledge of a protein's structure. For example, patent application WO 89/06279 describes the comparison of the primary amino acid sequence of different *subtilisins* while contrasting differences in physical and chemical properties. The primary amino acid sequences of the different *subtilisins* are aligned for the greatest homology, while taking into account amino acid insertions, deletions, and total number of amino acids.

Currently, the amino acid sequences of at least 10 *subtilisin* proteases have been published. Eight of these *subtilisins* were isolated from species of Bacilli, and include *subtilisin* 168 (Stahl, M. L., and Ferrari, E. (1984) J. Bacteriol. 158:411–418), *subtilisin* BPN' (Vasantha, N., et al., (1984) J. Bacteriol. 159:811–819), *subtilisin* Carlsberg (Jacobs, M., et al. (1985) Nucleic Acids Res. 13:8913–8926), *subtilisin* DY (Nedkov, P., et al. (1985) Biol. Chem. Hoppe-Seyler 366:421–430), *subtilisin* amylosacchariticus (Kurihara, M., et al. (1972) J.Biol. Chem. 247:5619–5631), *subtilisin* mesenticopeptidase (Svendsen, I., et al. (1986) FEBS Lett. 196:228–232), *subtilisin* 147 and *subtilisin* 309 (Hastrup et al. (1989) WO 89/06279), *subtilisin* PB92 (Van Eekelen et al. (1989) EP 0328229), and *subtilisin* BLAP (Ladin, B., et al. (1990) Society for Industrial Microbiology Annual Meeting, Abstract P60). The remaining two *subtilisin* sequences are thermitase from the fungus *Thermoactinomyces vulgaris* (Meloun, B., et al. (1985) FEBS Lett. 183:195–200), and proteinase K from the fungus *Tritirachium album limber* (Jany, K. -D., and Mayer, B. (1985) Biol. Chem. Hoppe-Seyler 366:485–492).

Methods for obtaining optimum alignment of homologous proteins are described in Atlas of Protein Sequence and Structure, Vol. 5, Supplement 2 (1976) (Dayhoff, M. O., ed., Natl. Biomed. Res. Found., Silver Springs, Md.). This comparison is then used to identify specific amino acid alterations which might produce desirable improvements in the target enzyme. Wells, J. A., et al. (1987) Proc. Natl. Acad. Sci. USA 84:1219–1223, used primary sequence alignment to predict site directed mutations which affect the substrate specificity of a *subtilisin*. Using the alignment approach WO 89/06279 teaches the construction of mutant *subtilisins* having improved properties including an increased resistance to oxidation, increased proteolytic activity, and improved washing performance for laundry detergent applications. Patent applications WO 89/09819, and WO 89/09830 teach improvement in the thermal stability of *subtilisin* BPN' by the introduction of one or more amino acid changes based on the alignment of the primary amino acid sequences of *subtilisin* BPN' with the more thermal stable *subtilisin* Carlsberg. From hereon, amino acids will be referred to by the one or three letter code as defined in Table 1.

TABLE 1

One and Three Letter Code for Amino Acids

A = Ala = Alanine
C = Cys = Cysteine
D = Asp = Aspartic acid or aspartate
E = Glu = Glutamic acid or glutamate
F = Phe = Phenylalanine
G = Gly = Glycine
H = His = Histidine
I = Ile = Isoleucine
K = Lys = Lysine
L = Leu = Leucine
M = Met = Methionine
N = Asn = Asparagine
P = Pro = Proline
Q = Gln = Glutamine
R = Arg = Arginine
S = Ser = Serine
T = Thr = Threonine
V = Val = Valine
W = Trp = Tryptophan
Y = Tyr = Tyrosine Rational mutational approaches may also predict mutations which improve an enzyme property based upon the three dimensional structure of an enzyme, in addition to the alignment of primary amino acid sequences described above. One method for determining the three dimensional structure of a protein involves the growing of crystals of the protein, followed by X-ray crystallographic analysis. This technique has been successfully used to determine several high resolution *subtilisin* structures such as thermitase (Teplyakov, A. V., et al. (1990) 214:261–279), *subtilisin* BPN' (Bott, R., et. al. (1988) J. Biol. Chem. 263:7895–7906) and *subtilisin* Carlsberg (Bode, W., et al. (1986) EMBO J. 5:813–818), for example.

EP 0251446 teaches the construction of mutant carbonyl hydrolases (proteases) which have at least one property different from the parental carbonyl hydrolase. It describes mutations which effect (either improve or decrease) oxidative stability, substrate specificity, catalytic activity, thermal stability, alkaline stability, pH activity profile, and resistance to autoproteolysis. These mutations were selected for introduction into *Bacillus amyloliguefaciens subtilisin* BPN' after alignment of the primary sequences of BPN' and proteases from *B. subtilis, B. licheniformis,* and thermitase. Such alignment can then be used to select amino acids in these other proteases which differ, as substitutes for the equivalent amino acid in the *B. amyloliquefaciens* carbonyl hydrolase. This application also describes alignment on the basis of a 1.8 Å X-ray crystal structure of the *B. amyloliquefaciens* protease. Amino acids in the carbonyl hydrolase of *B. amyloliguefaciens* which when altered can affect stability, substrate specificity, or catalytic efficiency include: Met50, Met124, and Met222 for oxidative stability; Tyr104, Ala152, Glu156, Gly166, Gly169, Phe189, and Tyr217 for substrate specificity; N155 alterations were found to decrease turnover, and lower Km; Asp36, Ile107, Lys170, Asp197, Ser204, Lys213, and Met222 for alkaline stability; and Met199, and Tyr21 for thermal stability. Alteration of other amino acids was found to affect multiple properties of the protease. Included in this category are Ser24, Met50, Asp156, Gly166, Gly169, and Tyr217. Substitution at residues Ser24, Met50, Ile107, Glu156, Gly166, Gly169, Ser204, Lys213, Gly215, and Tyr217 was predicted to increase thermal and alkaline stability. An important point about this patent application is that with the exception of those mutations effecting substrate specificity, no rational mutational approach for improving the alkaline or temperature stability of a protease based upon computer simulations of an X-ray crystal structure is described.

WO 88/08028 teaches a method for redesigning proteins to increase stability by altering amino acid residues that are in close proximity to the protein's metal ion binding site. This application describes the alteration of a calcium ion binding site present within *subtilisin* BPN' through the substitution, insertion, or deletion of amino acid residue(s) in close proximity to that site so that the electrostatic attraction between the amino acids and the calcium ion is increased. The characterization of the calcium ion binding site is accomplished through the analysis of a 1.3 Å three dimensional structure of *subtilisin* BPN' using a high resolution computer graphics system. This approach allows the selection of amino acids acceptable for replacing the native amino acids in the protease by first simulating the change using the computer model. This allows for the identification of any problems including steric hindrance prior to the actual construction and testing of the mutant proteases.

U.S. Pat. Nos. 4,908,773 and 4,853,871 teach a computer based method for evaluating the three dimensional structure of a protein to select amino acid residues where the introduction of a novel disulfide bond will potentially stabilize the protein. Potentially acceptable amino acid residues can then be ranked, and replaced using computer simulation, prior to the actual construction of the mutant protein using site directed mutagenesis protocols.

Several patent applications combine published data on biochemical stability with computer analysis of three dimensional protease structures in order to predict mutations which stabilize the enzyme. U.S. Pat. No. 4,914,031 and WO 88/08033 and WO 87/04461 teach a method for improving the pH and thermal stability of *subtilisin* aprA by replacing asparagine residues present in asparagine/glycine pairs. Asparagine/glycine pairs in proteins have been shown to undergo cyclization to form cyclic imide anhydroaspartylglycine (Bornstein, P., and Balian, G. (1977) Methods Enzymol. 47:132–145). This cyclic imide is susceptible to base hydrolyzed cleavage leading to inactivation of the enzyme. Computer analysis of the three dimensional structure of the aprA protease also predicted that formation of the cyclic imide could lead to protease inactivation resulting from a shift of the side chain of the active site serine. The decision to replace the asparagine residue and not the glycine residue was based upon alignment of the aprA sequence with other *subtilisin*-like enzymes, cucumisin and proteinase K.

Sensitivity to oxidation is an important deficiency of serine proteases used in detergent applications (Stauffer, C. E., and Etson, D. (1969) J. Biol. Chem. 244:5333–5338). EP 0130756, EP 0247647, and U.S. Pat. No. 4,760,025 teach a saturation mutation method where one or multiple mutations are introduced into the *subtilisin* BPN' at amino acid residues Asp32, Asn155, Tyr104, Met222, Gly166, His64, Ser221, Gly169, Glu156, Ser33, Phe189, Tyr217, and/or Ala152. Using this approach mutant proteases exhibiting improved oxidative stability, altered substrate specificity, and/or altered pH activity profiles are obtained. A method is taught in which improved oxidative stability is achieved by substitution of methionine, cysteine, tryptophan, and lysine residues. These publications also teach that mutations within the active site region of the protease are also most likely to influence activity. Random or selected mutations can be introduced into a target gene using the experimental approach but neither EP 0130756, EP 0247647, nor U.S. Pat.

No. 4,760,025 teach a method for predicting amino acid alterations which will improve the thermal or surfactant stability of the protease.

WO 8705050 teaches a random mutagenesis approach for construction of *subtilisin* mutants exhibiting enhanced thermal stability. One or more random mutations are introduced into single stranded target DNA using the chemical mutagens sodium bisulfite, nitrous acid, and formic acid. Subsequently, the mutated DNA is transformed into a Bacillus host and at least 50,000 colonies are screened by a filter assay to identify proteases with improved properties. Site directed mutagenesis can then be used to introduce all possible mutations into a site identified through the random mutagenesis screen. No method for pre selection of amino acids to be altered is taught.

EP 0328229 teaches the isolation and characterization of PB92 *subtilisin* mutants with improved properties for laundry detergent applications based upon wash test results. it teaches that biochemical properties are not reliable parameters for predicting enzyme performance in the wash. Methods for selection of mutations involve the substitution of amino acids by other amino acids in the same category (polar, nonpolar, aromatic, charged, aliphatic, and neutral), the substitution of polar amino acids asparagine and glutamine by charged amino acids, and increasing the anionic character of the protease at sites not involved with the active site. No method for identifying which specific amino acids should be altered is taught, and no rational mutational approach is taught which is based on alignment of X-ray structures of homologous proteases with different properties.

EP 0260105 teaches the construction of *subtilisin* BPN' mutants with altered transesterification rate/hydrolysis rate ratios and nucleophile specificities by changing specific amino acid residues within 15 Å of the catalytic triad. Russell, A. J., and Fersht, A. R. (1987) Nature 328:496–500, and Russell, A. J., et al. (1987) J. Mol. Biol. 193:803–813, teach the isolation of a *subtilisin* BPN' mutant (D099S) that had a change in the surface charge 14–15 Å from the active site. This substitution causes an effect on the pH dependence of the *subtilisin's* catalytic reaction.

There are a number of different strategies for increasing protein stability. Many of these methods suggest types of substitutions to improve the stability of a protein but do not teach a method for identifying amino acid residues within a protein which should be substituted. From entropic arguments, many types of substitutions have been suggested such as Gly to Ala and any amino acid to Pro (Matthews, B. W., et al. (1987) Proc. Natl. Acad. Sci. 84:6663–6667). Likewise, while it is clear that increasing the apolar size of an amino acid in the core will add to stability, adverse packing effects may more than compensate for the hydrophobic effect, resulting in a decrease in protein stability (Sandberg,W. S., and Terwilliger, T. C. (1989) Science 245:54–57). Menéndez-Arias, L., and Argos, P. (1990) J. Mol. Biol. 206:397–406, performed a statistical evaluation of amino acid substitutions of thermophilic and mesophilic molecules and proposed that decreased flexibility and increased hydrophobicity in the α-helical regions contributes most towards increasing protein stability. From their data, they formulated a set of empirical rules to improve stability.

Increasing the-hydrophobicity of certain side chains has long been suggested as a means to improve protein stability. The hydrophobic exclusion of nonpolar amino acids is the largest force driving protein folding. This has been studied by examining the partitioning of amino acids or amino acid analogs from water to a hydrophobic medium. While the numbers vary depending on the work, these studies generally agree that burying a hydrophobic side chain increases protein stability. For example, Kellis, J. T., Jr., et al. (1988) Nature 333:784–786, estimated that the removal of a methyl group destabilizes the enzyme by 1.1 kcal/mole assuming no other structural perturbations occur. Conversely, this predicts that the addition of a methylene group should add 1.1 kcal/mol if no unfavorable contacts occur. Similarly, Sandberg, W. S., and Terwilliger, T. C. (1989) Science 245:54–57, showed that the effect of removing or adding methylene groups is the sum of the hydrophobic effect and structural distortions. Simply adding buried hydrophobic groups may not increase protein stability because the total effect of adding or deleting a methyl group on the local packing structure must be considered. As the protein interior has a para-crystalline structure (Chothia, C. (1975) Nature 254:304–308), small distortions in the remainder of the structure resulting from the addition methyl group may exact a high cost and reduce rather than increase stability.

Along the same lines, the core of λ repressor has been shown to be amazingly tolerant to apolar amino acid substitutions in a functional assay (Bowie, J. U., et al. (1990) Science 247:1306–1310). It is not clear that this is true for larger proteins. The constraints on the hydrophobic core of a small protein may be less stringent than a larger protein simply due to the volume of the core relative to the number of amino acids which need to pack into the region. As the volume of the hydrophobic core increases, the number of amino acids which must pack together correctly increases, requiring more specific nonlocal interactions.

It has been recognized that increasing the interior hydrophobicity of a protein as a means of increasing the stability is hampered by the difficulty of determining which positions in the protein will lead to stabilization when substituted (Sandberg, W. S., and Terwilliger, T. C. (1991) Trends Biotechnol. 9:59–63). The methods discussed above provide a means of determining what substitutions to make to improve stability but do not identify which sites in the protein are most important. The present invention provides a method of determining which positions in the protein will lead to stabilization when substituted.

SUMMARY OF THE INVENTION

Other than in the operating examples, or where otherwise indicated, all numbers expressing quantities of ingredients or reaction conditions used herein are to be understood as modified in all instances by the term "about".

The native or wild-type protease from which the mutant proteases according to the invention are derived is a *B. lentus* alkaline protease (BLAP) obtained from *B. lentus* DSM 5483 having 269 amino acid residues, a molecular mass of 26,823 daltons, and a calculated isoelectric point of 9.7 based on standard pK values. The BLAP gene is obtained by isolating the chromosomal DNA from the *B. lentus* strain DSM 5483, constructing DNA probes having homology to putative DNA sequences encoding regions of the *B. lentus* protease, preparing genomic libraries from the isolated chromosomal DNA, and screening the libraries for the gene of interest by hybridization to the probes.

Mutant *B. lentus* DSM 5483 proteases have been made which are derived by the replacement of at least one amino acid residue of the mature form of the *B. lentus* DSM 5483 alkaline protease. The sites for replacement are selected from the group consisting of Ser3, Val4, Ser36, Asn42, Ala47, Thr56, Thr69, Glu87, Ala96, Ala101, Ile102, Ser104, Asn114, His118, Ala120, Ser130, Ser139, Thr141, Ser142, Ser157, Ala188, Val193, Val199, Gly205, Ala224, Lys229, Ser236, Asn237, Asn242, His243, Asn255, Thr268. The replacement amino acid residues are listed in Table 2. The numbering of the mutant proteases is based on the *B. lentus* DSM 5483 wild-type protease as given in the SEQ ID NO:52.

Genes which express the mutant *B. lentus* DSM 5483 proteases according to the invention are made by altering one or more codons of the wild-type *B. lentus* DSM 5483 alkaline protease gene which encode for a protease derived by accomplishing at least one of the amino acid substitutions listed in Table 2.

The protease sites listed in Table 2 are sites predicted to affect thermal and surfactant stability relative to the wild-type protease. These sites are identified by means of a computer based method which compares the three dimensional structure of the wild-type protease (henceforth, the target protein) and a homologous protease (henceforth, the reference protein). The three dimensional coordinates of the wild-type protease are probed with an uncharged probe molecule to produce a probe-accessible surface which has an external surface the interior of which contains one or more probe-accessible internal cavities. The amino acids of the reference protein having side chains lying outside the solvent-accessible surface or inside the internal cavities of the target protein are identified by aligning the three dimensional coordinates of the target protein and the reference protein.

Proteins having greater thermal and surfactant stability are produced by replacing the amino acid in the target protein if the amino acid in the target protein can be changed without creating unacceptable steric effects. The amino acid in the target protein is altered by site directed mutagenesis of the gene which expresses the target protein.

Genetic constructs are made which contain in the direction of transcription a promoter, ribosomal binding site, initiation codon and the major portion of the pre region of the *Bacillus licheniformis* ATCC 53926 alkaline protease gene operably linked to a portion of the pre region and all of the pro and mature regions of the *Bacillus lentus* DSM 5483 alkaline protease gene followed by a 164 bp DNA fragment containing the transcription terminator from the ATCC 53926 alkaline protease gene. The *Bacillus lentus* DSM 5483 alkaline protease gene is altered to produce a mutant gene which encodes for a protease derived by accomplishing at least one of the amino acid substitutions listed in Table 2. Mutant protease is made by fermenting a Bacillus strain transformed with a genetic construct containing a mutated *Bacillus lentus* DSM 5483 alkaline protease gene.

BRIEF DESCRIPTION OF THE FIGURES

FIGS. 1A–1P shows the atomic coordinates for *Bacillus lentus* alkaline protease (BLAP) to 1.4 Å resolution.

DESCRIPTION OF THE PREFERRED EMBODIMENTS

Figure 2:
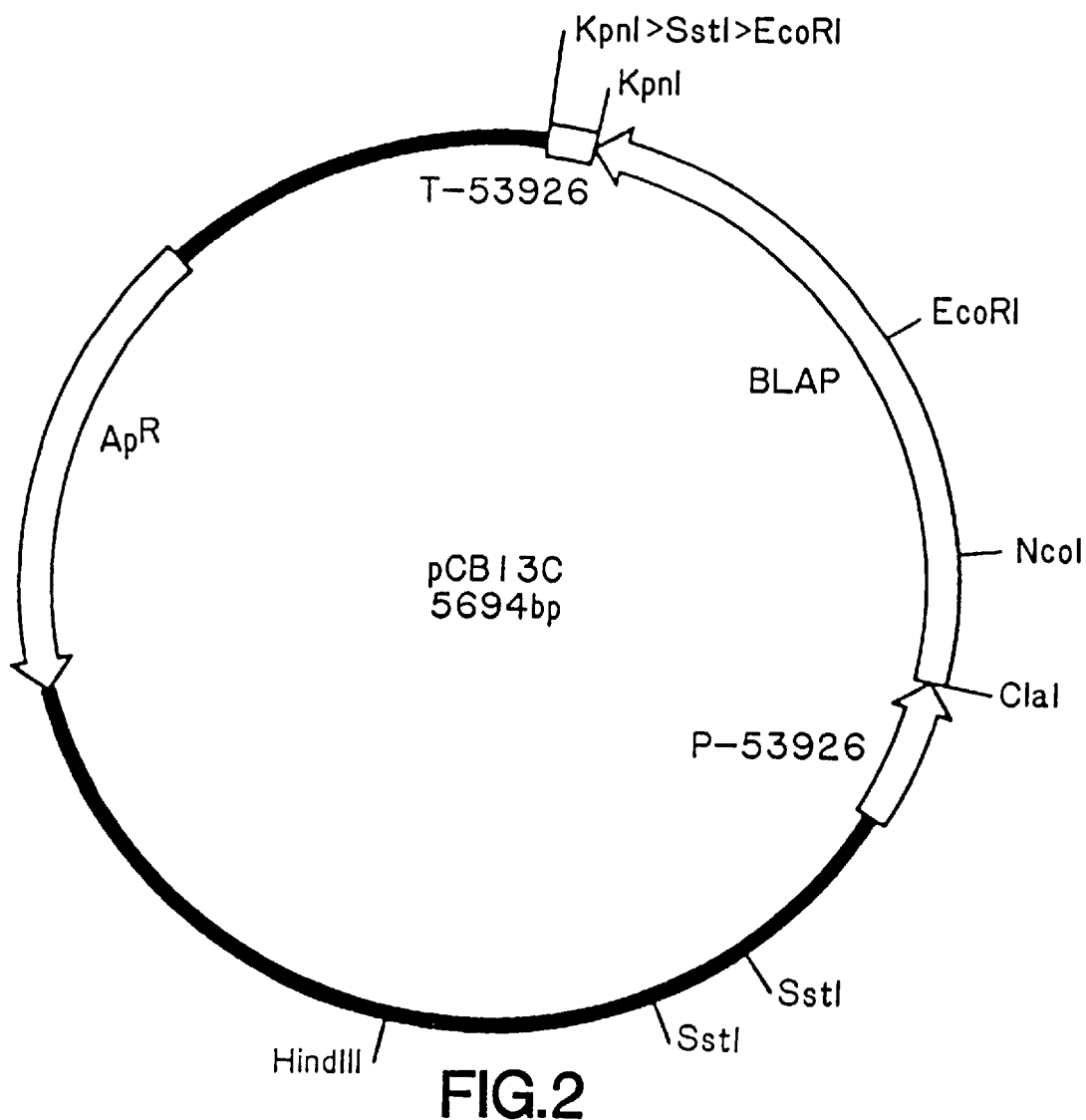
FIG. 2 shows the restriction map for plasmid pCB13C which contains a hybrid gene fusion between the *Bacillus licheniformis* ATCC 53926 protease gene and the *Bacillus lentus* DSM 5483 BLAP gene. The promoter, ribosomal binding site and presequence (P-53926) from ATCC 53926 were fused to the pro- and mature sequence of the BLAP gene. The transcription terminator of ATCC 53926 (T-53926) was appended to the BLAP coding region.

One aspect of the invention relates to mutant proteolytic enzymes which have superior thermal stability and surfactant stability relative to the wild-type protease as determined by laboratory tests. The mutant proteases according to the invention are those derived by the replacement of at least one amino acid residue of the mature *Bacillus lentus* DSM 5483 alkaline protease wherein said one amino acid residue which is selected from the group consisting of Ser3, Val4, Ser36, Asn42, Ala47, Thr56, Thr69, Glu87, Ala96, Ala101, Ile102, Ser104, Asn114, His118, Ala120, Ser130, Ser139, Thr141, Ser142, Ser157, Ala188, Val193, Val199, Gly205, Ala224, Lys229, Ser236, Asn237, Asn242, His243, Asn255, Thr268 is replaced with the amino acid residue listed in Table 2. Table 2 shows the identity and position of the wild-type amino acid and the amino acid residue(s) which replace it in the mutant protein. For example, the first entry in Table 2 shows Ser3, a serine residue at position 3 which can be replaced by threonine (abbreviated as T using the one letter code for amino acids) or any small amino acid. A small amino acid is defined as glycine, alanine, valine, serine, threonine or cysteine. A small hydrophobic amino acid is defined as glycine, alanine, threonine, valine or isoleucine. A charged amino acid is defined as lysine, arginine, histidine, glutamate or aspartate. The abbreviation a.a. stands for "amino acid" residue.

TABLE 2

| Residue | Replacement Amino Acid |
| --- | --- |
| Ser3 | T or any small, hydrophobic a.a. |
| Val4 | I, S or any small a.a. |
| Ser36 | A, T or any small a.a. |
| Ser42 | F, A, T, V, I, Y |
| Ala47 | W or any small a.a. except A |
| Thr56 | V, S or any small, hydrophobic a.a. |
| Thr69 | R, A or any charged a.a. |
| Glu87 | R, M or any charged a.a. |
| Ala96 | I, N, S or any small, hydrophobic a.a. |
| Ala101 | T, S or any small, hydrophobic a.a. |
| Ile102 | W or any small a.a. except P |
| Ser104 | T or any small, hydrophobic a.a. |
| Asn114 | S, Q or any small, hydrophobic a.a. |
| His118 | F or any a.a. except P and W |
| Ala120 | V or any small, hydrophobic a.a. |
| Ser130 | A, T or any small, hydrophobic a.a. |
| Ser139 | A, T, Y or any a.a. except P and W |
| Thr141 | W or any a.a. except P |
| Ser142 | A, T. or any small, hydrophobic a.a. |
| Ser157 | T or any small, hydrophobic a.a. |
| Ala188 | P or any small, hydrophobic a.a. |
| Val193 | M or any small, hydrophobic a.a. |
| Val199 | I or any small, hydrophobic a.a. |
| Gly205 | V or any small, hydrophobic a.a. |
| Ala224 | V or any small, hydrophobic a.a. |
| Lys229 | W or any a.a. except P |
| Ser236 | A, T or any small, hydrophobic a.a. |
| Asn237 | A, N, Q, M or any small, hydrophobic a.a. |
| Asn242 | A, N, Q, M or any small, hydrophobic a.a. |
| His243 | A, N, Q, M or any small, hydrophobic a.a. |
| Asn255 | P or any small, hydrophobic a.a. |
| Thr268 | V or any small, hydrophobic a.a. |

The amino acid sequences of the preferred proteolytic enzymes are given in SEQ ID NO:1 to SEQ ID NO:51. The preferred mutated *B. lentus* DSM 5483 proteases which are encoded for by genes according to the invention as disclosed above are given in SEQ ID NO: 53 to 105. These proteases are produced by bacterial strains which have been transformed with plasmids containing a native or hybrid gene, mutated at one or more nucleotide base pairs by known mutagenesis methods. These mutant genes encode for proteases in which selected amino acid residues have been substituted for by other amino acids.

The mutant proteases according to the invention are listed in Table 3.

TABLE 3

| Mutation | Temperature Stability 50° C., pH 11.0 t½ (min) | Temperature Stability 60° C., pH 10.0 t½ (min) | SDS Stability pH 10.5, 50° C. t½ (min) | SDS Stability pH 8.6, 50° C. t½ (min) |
|---|---|---|---|---|
| S3T, V4I, A188P, V193M, V199I | 120 | 67 | 3.2 | 12 |
| S3T, A188P, V193M, V199I | 95 | 60 | 3.75 | 18.5 |
| V4I, A188P, V193M, V199I | 72 | 39 | 1.75 | 3.75 |
| S139Y, A188P, V193M, V199I | 69 | 33 | 1.4 | 4.6 |
| S130T, S139Y, A188P, V193M, V199I | 64 | 22 | 2 | 6.3 |
| A188P, V193M, V199I | 55 | 23.5 | 3.0 | 12.5 |
| S3T, A188P, V193M | 54 | 21 | 1.5 | 3.4 |
| S157T | 52 | 17.5 | 1.2 | 0.95 |
| A188P, V193M | 50 | 27 | 2.5 | 7.25 |
| A188P | 48 | 19 | 1.4 | 2.8 |
| S3T, V4I, A188P, V193M | 43 | 21 | 1.4 | 3.7 |
| V193M | 42 | 16.6 | 1.2 | 3.0 |
| S104T | 42 | 8 | 1.0 | 1.8 |
| T69V | 41 | 12.3 | 0.8 | 1.8 |
| V4I, A188P, V193M | 40 | 19 | 1.25 | 2.7 |
| A224V | 39 | 15 | 0.9 | 1.1 |
| V199I | 38.5 | 11.6 | 1.0 | 2.0 |
| V4I | 32.5 | 10 | 0.75 | 1.0 |
| S3T | 32 | 6.6 | 1.2 | 2.8 |
| S139Y | 26 | 8.8 | 1.0 | 2.0 |
| N242A | 26 | 7.4 | 0.9 | 1.9 |
| S236T | 25.5 | 8.4 | 1.0 | 2.0 |
| S36A | 23.8 | 8.6 | 0.9 | 1.8 |

TABLE 3 (cont.)

| Mutation | Temperature Stability 50° C., pH 11.0 t½ (min) | Temperature Stability 60° C., pH 10.0 t½ (min) | SDS Stability pH 10.5, 50° C. t½ (min) | SDS Stability pH 8.6, 50° C. t½ (min) |
|---|---|---|---|---|
| H243A | 23 | 5.9 | 0.8 | 1.7 |
| A101T | 23 | 4.7 | 0.5 | 2.75 |
| S236A | 23 | 5.1 | 0.8 | 1.3 |
| E87R | 22.5 | 9.0 | 0.4 | 1.2 |
| N114S | 22 | 7.9 | 1.1 | 1.3 |
| A47W | 21 | 7.2 | 0.9 | 1.05 |
| A120S | 20.5 | 8.4 | 0.9 | 1.4 |
| T56V | 20 | 8.5 | 0.8 | 0.7 |
| A120V | 20 | 11.8 | 0.65 | 1.9 |
| G205V | 20 | 6.8 | 1.1 | 2.8 |
| S130A | 20 | 8.8 | 0.4 | 1.0 |
| S130T | 20 | 7.2 | 0.4 | 1.1 |
| A96I | 19 | 12 | 1.0 | 1.4 |
| S104T, S139Y, A224V | 18 | 9.5 | 1.0 | 1.8 |
| S139A | 18.5 | 7.8 | 0.5 | 0.8 |
| S142T | 17.5 | 11.5 | 0.9 | 1.7 |
| S139T | 16.5 | 4.3 | 0.5 | 0.5 |
| I102W | 16.5 | 7.2 | 0.7 | 1.6 |
| A96N | 16 | 6 | 0.9 | 0.95 |
| N42F | 16 | 5.9 | 1.0 | 1.4 |
| S142A | 16 | 9 | 1.0 | 1.7 |
| H118F | 15.8 | 5.1 | 1.0 | 1.3 |
| N237A | 15 | 7.8 | 0.67 | 1.3 |
| N255P | 15.0 | 5.3 | 1.2 | 1.25 |
| T141W, N237A | 14 | 5.4 | 0.33 | 1.1 |
| T268V | 14 | 3.8 | 0.75 | 1.1 |
| K229W | 13.4 | 4.6 | 1.0 | 1.4 |
| T141W | 12 | 6.5 | 0.6 | 1.4 |
| wildtype | 12.0 | 3.0 | 0.8 | 1.6 |

Any of the proteases listed in Table 3 will exhibit greater stability in some manner than the wild-type protease BLAP. The entries under the "Mutation" heading of Table 3 shows the identity of the wild-type amino acid (using the one letter code), its position, and the amino acid which replaces it in the mutant protease. For example, S3T signifies that the serine at position 3 of the mature protease is replaced with a threonine. Some of the preferred mutant proteases are single replacements at specific locations such as a protease wherein valine at position 4 is replaced by isoleucine to specific combinations of replacements such as a protease wherein threonine at position 141 is replaced by tryptophan and asparagine at position 237 is replaced by alanine. The latter protease containing two replacements is one of only a number of possibilities.

The preferred mutant proteases according to the invention are identified as: (S3T, V4I, A188P, V193M, V199I); E87R; (S3T, A188P, V193M, V199I); N114S; (V4I, A188P, V193M, V199I); A47W; (S139Y, A188P, V193M, V199I); A120S; (S130T, S139YF A188P, V193M, V199I); T56V; A120V;(A188P, V193M, V199I); G205V; (S3T, A188P, V193M); S130A; S130T; S157T; A96I; (S104T, S139Y, A224V); S139A; S142T; S139T; I102W; V193M; A96N; N42F; S142A; H118F; N237A; N255P; (T141W, N237A); T268V; K229W; T141W; (A188P, V193M); V4I; S3T; S139Y; N242A; S236T; S36A; H243A; A101T; S236A; A188P; (S3T, V4I, A188P, V193M); V193M; S104T; T69V; (V4I, A188P, V193M); A224V; V199I. The system used to designate the above preferred proteases first lists the amino acid residue in the mature form of the *B. lentus* DSM 5483 alkaline protease at the numbered position followed by the replacement amino acid residue using the one letter codes for amino acids. For example, V193M is a protease in which valine has been replaced by methionine at position 193 of the mature *B. lentus* DSM 5483 alkaline protease. A mutant protease identified by more than one such designation is a mutant protease which contains all of the indicated substitutions. For example, (A188P, V193M) is a protease in which valine has been replaced by methionine at position 193 of the mature *B. lentus* DSM 5483 protease and alanine at position 188 has been replaced by proline.

Mutant forms of the *B. lentus* DSM 5483 alkaline protease are prepared by site-specific mutagenesis of DNA encoding the mature form of either wild-type BLAP, or a mutant BLAP. The DNA fragment encoding the mature form of wild type BLAP was prepared using plasmid pCB13C. Plasmid pCB13C contains a hybrid fusion between the *B. licheniformis* ATCC 53926 protease gene and the *B. lentus* DSM 5483 BLAP gene, shown in FIG. 2. Specifically, this hybrid fusion contains DNA encoding the promoter, ribosomal binding site, and 21 residues of the pre sequence from the ATCC 53926 protease gene fused to a DNA sequence encoding the last five residues of the BLAP pre sequence and all of the pro and mature residues of BLAP. This fusion is referred to as the ClaI fusion because this restriction site is located at the juncture between the ATCC 53926 and DSM 5483 DNA's. A new ClaI restriction site had to be introduced into the ATCC 53926 alkaline protease gene near to the junction of the pre and pro sequences. The ClaI site was introduced into the ATCC 53926 alkaline protease gene by using a polymerase chain reaction (PCR) to amplify a DNA fragment containing sequence information from the N-terminal part of the ATCC 53926 alkaline protease gene. The amplified fragment included the ATCC 53926 alkaline protease promoter, ribosomal binding site, initiation codon, and most of the pre sequence. This 292 bp DNA fragment was flanked by AvaI and ClaI restriction sites at its 5' and 3' ends, respectively. The BLAP gene already contained a naturally occurring ClaI site at the corresponding position. Analysis of the DNA sequence across the fusion of the ATCC 53926 and BLAP genes confirmed the expected DNA and amino acid sequences.

Figure 3:
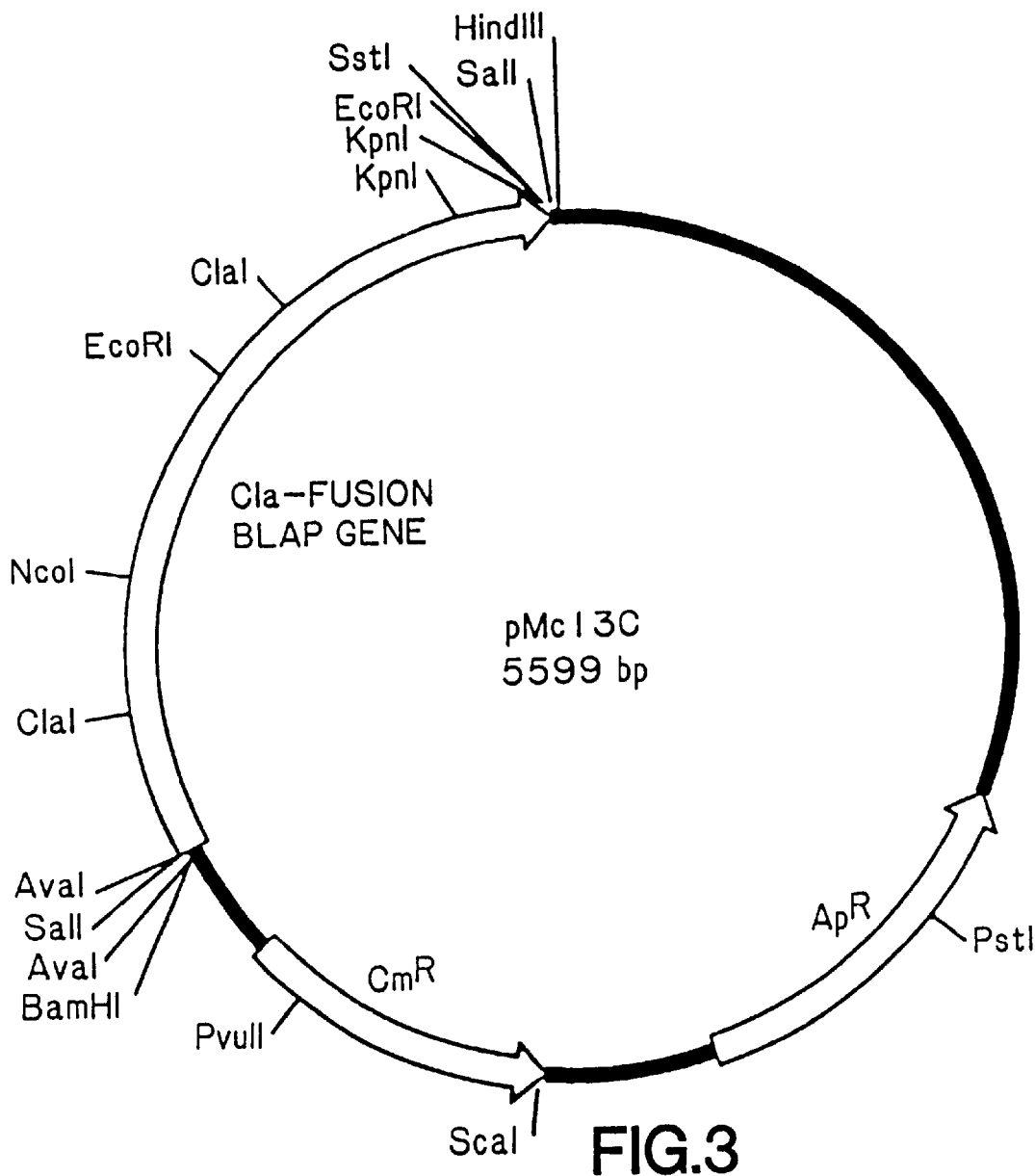
FIG. 3 shows the restriction map for plasmid pMc13C which is derived from pMac5-8 and contains the BLAP gene and carries an amber mutation in the $Ap^R$ gene which renders it inactive.

Before any mutagenesis can be carried out, the gene is subcloned into the mutagenesis vector pMa5-8. This is accomplished by synthesizing a DNA fragment containing the ClaI fusion gene and the ATCC 53926 transcription terminator as a SalI cassette using the PCR. The PCR was carried out using conditions as described by the manufacturer (Perkin Elmer Cetus, Norwalk, Conn.). In the PCR, two synthetic oligonucleotides bearing SalI sites are used as primers and *Escherichia coli* vector pCB13C DNA as a template. After cutting the PCR product with SalI, this fragment is cloned into the mutagenic plasmid pMc5-8 which has previously been cut with SalI and dephosphorylated with bacterial alkaline phosphatase. Plasmids pMc5-8, and pMa5-8 described below were obtained from H.-J. Fritz and are described by Stanssens, P., et al. (1989) Nucleic Acids Res. 17:4441–4454. SalI sites are chosen to allow the PCR fragment to be cloned into pMc5-8 in both orientations. The ligation mix is transformed into *E. coli* WK6. Chloramphenicol resistant ($Cm^R$) transformants are screened for the presence of an insert and a correct plasmid construct pMc13C is identified as shown in FIG. 3. once the gene is cloned into the pMc vector and desirable sites for mutation are identified, the mutation(s) is introduced using synthetic DNA oligonucleotides according to a modification of a published protocol (Stanssens, P., et al. (1989) Nucleic Acids Res. 17:4441–4454). The oligonucleotide containing the mutation(s) to be introduced is annealed to a gapped duplex (gd) structure which carries the BLAP gene on a segment of single stranded (ss) DNA. The gapped duplex can be formed by annealing linear ss DNA from pMc13C with denatured and restricted pMa5-8 DNA. Plasmid pMa5-8 contains an active ampicillin resistance gene but has an inactivating point mutation in the chloramphenicol resistance gene, whereas plasmid pMc13C contains, in addition to an intact BLAP gene, an active chloramphenicol resistance gene, but has an inactivating point mutation in the ampicillin resistance gene. The annealed product is the gd DNA which is a double stranded heteroduplex with a ss DNA gap spanning the entire cloned BLAP gene. The mutant oligonucleotide is able to anneal to homologous ss BLAP DNA within the gap and the remaining gap is filled in by DNA polymerase I (Klenow fragment) and ligated using T4 DNA ligase, purchased from New England Biolabs Inc., Beverly, Mass. The mutagenic efficiency of such a system can be improved by the use of Exonuclease III (Exo III) purchased from New England Biolabs Inc., Beverly, Mass. Exo III is an exodeoxyribonuclease that digests double stranded DNA from the 3' end. As a free 3' end is required, closed circular ss DNA or ds DNA is unaffected by this enzyme. A subsequent treatment of the product of the fill-in reaction with Exo III removes any species with only partially filled gaps. This significantly improves the mutagenic efficiency and is the preferred mutagenesis method. The product of the fill-in reaction is then transformed into a repair deficient *E. coli* strain such as WK6mutS and ampicillin resistant transformants ($Ap^R$) are selected. Replication of the transformed heteroduplex phasmid results in two different progenies. One progeny contains the wild type BLAP gene and the intact chloramphenicol resistance gene, but an inactive ampicillin resistance gene. The other progeny contains a BLAP gene carrying the mutation of interest and is resistant to ampicillin but not to chloramphenicol.

Selection of $AP^R$, $Cm^S$ mutant transformants with ampicillin is not sufficient to stop some background growth of the $Ap^S$, $Cm^R$ progeny carrying the wild type BLAP gene. Therefore, it is necessary to perform a second transformation into *E. coli* using plasmid DNA prepared from the $AP^R$ transformants of the WK6mutS strain. This second transformation uses a low plasmid concentration with a large number of recipient cells of a suppressor deficient strain of *E. coli* such as WK6. This approach decreases the likelihood of a recipient cell receiving plasmid DNA from both progeny. $Ap^R$ transformants are selected and plasmid DNA from several transformants is isolated and screened for the presence of the mutation. The pMa mutant derivative of the first mutagenesis round can be used for a second round of mutagenesis by preparing ss DNA of that species and annealing it to XbaI/HindIII restricted and denatured DNA of pMc5-8. Plasmid pMc5-8 is identical to pMa5-8 except that it contains an active chloramphenicol resistance gene and an inactive ampicillin resistance gene. The general procedure is the same as that described above.

The mutant BLAP proteases can be produced by transferring the mutant BLAP genes from their particular *E. coli* pMa13C derivative vector into a plasmid vector which can replicate in Bacillus. To accomplish this, the mutant BLAP genes are separated from their pMa13C plasmids by digestion with the restriction endonucleases AvaI and SstI, followed by ligation to the larger AvaI/SstI fragment from either plasmid pH70 or pC51. These AvaI/SstI fragments from pH70 and pC51 include the DNA sequences necessary for replication in Bacillus and encode either kanamycin resistance ($Km^R$) or tetracycline resistance ($Tc^R$) respectively. Plasmid pH70 is constructed by cloning the ATCC 53926 alkaline protease gene carried on a EcoRI/BamHI DNA fragment into the $Km^R$ plasmid pUB110 between the EcoRI and BamHI sites. Plasmid pC51 is constructed by cloning the ATCC 53926 protease gene carried on a EcoRI-BamHI fragment into the $Tc^R$ plasmid pBC16 between the EcoRI and BamHI sites. The larger AvaI-SstI fragment from either pH70 or pC51 used for cloning the mutant BLAP genes is first purified from other DNA fragments by high pressure liquid chromatography (HPLC) on a Gen-Pak FAX column (Waters, Milford, Mass.). The column is 4.6 mm by 100 mm in size and contains a polymer-based high performance anion-exchange resin. Conditions for elution of the DNA are a flow rate of 0.75 ml/min with a gradient of Buffer A (25 mM tris(hydroxymethyl) aminomethane (Tris) pH 8.0 containing 1 mM disodium ethylenediamine tetraacetic acid (EDTA)) and Buffer B (25 mM Tris pH 8.0, 1 mM EDTA, 1 M NaCl) starting at 50% each and reaching a final concentration of 30% Buffer A and 70% Buffer B.

After ligation the mutant BLAP plasmids are transformed into *B. subtilis* DB104. The genes encoding the major alkaline and neutral proteases present in this strain have been inactivated (Kawamura, F., and Doi, R. A. (1984) J. Bacteriol. 160:442–444). Cells of *B. subtilis* DB104 transformed by these plasmids grow on a nutrient-skim milk agar in the presence of either kanamycin or tetracycline. Transformants of DB104 that manufacture mutant protease are identified by the formation of clear zones of hydrolysis in the skim milk. Confirmation that the protease-producing transformants carry a plasmid-borne BLAP gene with the desired mutation(s) is accomplished by purifying plasmid DNA from a culture of each transformant. The plasmid DNA is purified away from cell protein and chromosomal DNA by SDS-salt precipitation followed by chromatography over a Qiagen ion-exchange column (Qiagen Corporation, Studio City, Calif.). AvaI-SstI digested plasmid DNAs from different transformants are compared with AvaI/SstI-digested derivatives of plasmid pH70 or pC51 known to carry an intact BLAP gene. Restriction digests of these plasmids are compared by agarose gel electrophoresis to identify plasmids that have the proper-sized AvaI/SstI DNA fragments. Selected plasmid DNAs are then sequenced across the region of the expected BLAP mutation(s) to confirm that the desired mutation(s) are present. One or more clones of each BLAP mutation are stored frozen in 15% glycerol at −70° C. and also cultivated in shake flasks (Example 4, Production of Proteases) to produce mutant protease for characterization.

Another aspect of the invention provides a computer based method for identifying the sites which affect the storage, thermal, SDS and pH stability of a protein. This method is based on the hypothesis that protein stability may be enhanced by decreasing the volume of internal cavities and improving surface packing of amino acid side chains. The interior of a protein contains many apolar amino acids which are tightly packed into a nearly crystalline state. One way in which these interior amino acids affect protein stability is through packing effects. These include van der Waal interactions, distortion of the remainder of the protein and electrostatic effects. Packing effects have been studied by measuring the contribution of methyl groups in the interior of a protein to the overall stability of the protein. It has been estimated that the removal of a methyl group from the interior of a protein destabilizes it by about 1.1 kcal/mol assuming no other perturbations occur (Kellis, J. T., Jr., et al. (1988) Nature 333:784–786). However, the inverse may not be true. Simply adding buried hydrophobic groups may not increase protein stability because the total effect of adding or deleting a methyl group on the local packing structure must be considered. As the protein interior has a para-crystalline structure (Chothia, C. (1975) Nature 254:304–308), small distortions in the remainder of the structure resulting from the addition methyl group may exact a high cost and reduce rather than increase stability.

While it is known in the art to make certain substitutions which may affect protein stability, there is no known way of identifying which sites in the protein will lead to stabilization when substituted. For example, it has been suggested that protein stability would be increased if alanine were substituted for glycine or serine; or if threonine were substituted for serine (Matthews, B. W., et al. (1987) Proc. Natl. Acad. Sci. 84:6663–6667); or if proline were substituted for glycine. However, the sites in which one or more of these substitutions should be made has been so far unpredictable. Other methods depend on comparisons of the amino acid sequences of different but related proteins. However, this does not show which sites are important to stability, only which positions are different.

There are two computer based methods for identifying the sites which affect the stability of a protein according to the invention.

In the first method for identifying sites which affect the stability of protein, the first step comprises generating a probe-accessible surface by analyzing the target protein coordinates with an uncharged probe molecule having a radius of about 0.9 to about 2.0 Å. It is important that no water molecules be included in the protein structure during this analysis. The second step of this method is the identification of the amino acids which form the boundaries of the internal cavities. These amino acids comprise a set of positions which, if mutated, may increase the stability of the protein. An increase in stability can be achieved by amino acid substitutions which decrease the volume of the internal cavities.

The molecular modeling program QUANTA (trademark of Polygen Corporation, 200 Fifth Ave., Waltham, Mass. 02254) was used to calculate probe-accessible surfaces as well as perform the alignment of the three dimensional coordinates of the proteins. These functions can be carried out equally well by other molecular modeling programs which are also commercially available. The following is a list of commercially available programs which can also be used to calculate probe-accessible surfaces: Insight or InsightII (trademark of Biosym Technologies, Inc., 10065 Barnes Canyon Road—Suite A, San Diego, Calif. 92121), BIOGRAF (trademark of Biodesign, Inc., 199 S. Los Robles Ave., #270, Pasadena, Calif. 91101) or Sybyl (trademark of Tripos Associates, 1699 S. Hanley Road, St. Louis, Mo. 63144)

The probe-accessible surface referred to in step 1 of the first method can be generated in several ways (Richards, F. M. (1977) Annu. Rev. Biophys. Bioeng. 6:151–176): A spherical probe of radius R (0.9 to 2.0 Å) is allowed to roll on the outside of a molecule while maintaining contact with the van der Waal surface. The surface defined by the center of the probe is defined as the probe-accessible surface. Alternatively, a similar surface can be generated by increasing the van der Waal radii of all the atoms in a protein by the radius of the probe. Overlapping surfaces are eliminated and the remaining surface represents the probe-accessible surface. In the preferred embodiment, a three-dimensional box of dimensions 50×50×50 Å with a 1 Å grid size in all three dimensions (x, y, and z) is centered on the center of mass of the target protein coordinates. Most preferably, the dimensions of the probe map are adjusted such that all of the protein atoms fall within the probe map's bounds. The grid size of 1 Å provides a sufficiently high resolution to clearly define the probe-accessible surface although another grid size could be used, ranging from 0.5 to 3.0 Å. An uncharged probe molecule is positioned at each grid point and the energy of interaction between the probe and the target protein atoms is determined. The energy of nonbonded interaction ($E_{nb}$) contains only the van der Waal component such that $$E_{nb} = \sum_{\substack{nonbonded \\ i, jpairs}} 4\varepsilon_{ij}\left[\left(\frac{\sigma_{ij}}{r}\right)^{12} - \left(\frac{\sigma_{ij}}{r}\right)^{6}\right] \quad \text{EQUATION (1)}$$

where r is the nonbonded distance, $\epsilon_{ij}$ is the dispersion well depth and $\sigma_{ij}$ is the Lennard-Jones diameter. The result is a map consisting of a box with energy values at each grid point. This map can be contoured at a particular energy value to generate surfaces which correspond to the solvent accessible surface and internal cavities (Goodford, P. J. (1985) J. Med. Chem. 28:849–857). The value at which to contour the maps can vary depending on the particular radius used and the parameters used to define the probe molecule and the particular method used to generate the probe. The preferred embodiment is to used a probe radius of 0.9 Å and contour the surface at 10 kcal/mol.

The external surface of the probe-accessible surface is also known as the solvent-accessible surface. Probe-accessible surfaces inside of the solvent accessible surface are defined as internal cavities and represent cavities large enough to accommodate a molecule with a radius equal to the probe radius. The presence of such a cavity on the inside of a protein does not imply that the cavity will in fact be filled by one or more solvent molecules.

The second step of the method for identifying sites which affect the stability of a protein is the identification of the amino acids which form the internal cavities. The internal cavities are defined by the amino acids which make up its boundaries. These amino acids comprise a set of positions which, if mutated, may increase the stability of the protein.

In a second method for identifying sites which affect the stability of a protein, the first step comprises generating a probe-accessible surface by analyzing the target protein coordinates with an uncharged probe molecule having a radius of about 0.9 to about 2.0 Å. It is important that no water molecules be included in the protein structure during this analysis. This step is the same as the first step of the method set forth above.

The second step involves aligning the three dimensional structure of the target protein and a reference protein by moving the three dimensional coordinates of the reference protein into the coordinate frame of the target protein. The reference protein is usually chosen so that a high degree of similarity exists between it and the target protein so that packing differences between the target and reference protein which potentially affect the stability of the target protein can be identified. The reference protein can be any protein for which a three dimensional structure is available which is homologous to the target protein. Examples of such proetins include but are not limited to *subtilisin* Carlsberg, *subtilisin* BPN', proteinase K, and Thermitase. When the target protein is BLAP, one preferred reference protein is Thermitase. Thermitase is an extra-cellular *subtilisin*-like serine protease isolated from *Thermoactinomyces vulgaris* (Frömmel, C., et al. (1978) Acta Biol. Med. Ger. 37:1193–1204). The protein amino acid sequence of thermitase is 42% identical to BLAP. The high degree of similarity between these two proteins provides an ideal system with which to examine packing differences that affect BLAP stability. In this second step the three dimensional structures of Thermitase and BLAP are aligned using the computer program QUANTA™. The three dimensional alignment is carried out by first aligning the primary sequences of the two proteins to determine which amino acids are equivalent. This is accomplished using FASTA (Myers, E. W., and Miller, W. (1988) Comput. Applic. Biosci. 4:11–17; Pearson, W. R., and Lipman, D. J. (1988) Proc. Natl. Acad. Sci. USA 85:2444–2448). Based on this alignment of the primary sequence, residues are matched for subsequent alignment of the three dimensional structures using MULTLSQ (Sutcliffe, M. J., et al. (1987) Protein Eng. 1:377–384; Kabsch, W. (1976) Acta Cryst. A32:922–923). This program uses one structure as fixed coordinates (the target protein coordinates) and then rotates and translates a second structure (the reference protein coordinates) so as to give the smallest root mean squared (r.m.s.) deviation between the two sets of three dimensional coordinates. For example, the alignment of the BLAP and thermitase three dimensional coordinates results in an r.m.s. deviation between equivalent $\alpha$-carbons of 0.8 Å. This demonstrates that the amino acid sequences of BLAP and thermitase fold into three dimensional structures which are extremely similar.

In the third step, the alignment of the three dimensional structures is used to identify sites which affect the stability of the target protein. This can be accomplished by a variety of methods. Using a computer program designed to display protein structures and surfaces such as QUANTA™, the structure of the reference protein can be displayed with the probe-accessible surface. The combined display of the reference protein and probe-accessible surface can then be visually examined to determine which amino acids in the reference protein fall outside of the solvent-accessible surface or inside internal cavities. An alternative method which can be used comprises coloring the atoms of the reference protein by determining whether amino acids in the reference protein fall outside of the solvent-accessible surface or inside internal cavities. The probe-accessible surface map (probe map) was used to color the atoms in the transformed *subtilisin* BPN' structure. In order to color each atom, an energy value needs to be interpolated from the probe map at each atomic coordinate.

The probe map consists of three dimensional grid with an energy value (E) at each grid point. In the preferred embodiment, the probe map is a 50×50×50 Å box centered on the center of mass of the protein with a 1 Å grid unit in all three dimensions (x, y, and z). In its optimal conception, the size of the probe map is adjusted such that all of the protein atoms fall within the probe map's bounds. The energy value at each protein atom position was approximated by interpolating from the energy values from the surrounded eight grid points in the probe map. Given the energy value at each point from the probe map, the grid spacing, and the atomic coordinate, it is a simple matter for any one skilled in the art to interpolate an energy value at each atomic coordinate.

In one such method, an energy value of zero is assigned arbitrarily if an atom falls outside the bounds of the map. From a given atomic coordinate (x,y,z), the eight closest grid points from the probe map which surround (x,y,z) are identified such that $(x_1<x<x_2)$, $(y_1<y<y_2)$, and $(z_1<z<z_2)$. The eight grid points are then A $(x_1, y_1, z_1)$, B $(x_1, y_1, z_2)$ C $(x_1, y_2, z_2)$, D $(x_1, y_2, z_1)$, E $(x_2, y_1, z_1)$ F $(x_2, y_1, z_2)$, G $(x_2, y_2, z_2)$, and H $(x_2, y_2, z_1)$. The energy value (E) at a given grid point such as $(x_1, y_1, z_1)$ is then $E_{(x_1,y_1,z_1)}$ or equivalently $E_A$. The energy at a specific atomic coordinate $E_{(x,y,z)}$ can be interpolated from the probe map given the eight nearest surrounding grid points (A through H, as described above) and the value at each grid point ($E_A$ through $E_H$). The equation which was used for calculating the energy at specific atomic coordinates, $E_{(x,y,z)}$, is shown in Equation (2). The energy value at each coordinate can then be stored and used to display the molecule.

$$E_{(x,y,z)} = \left(\frac{x-x_1}{x_2-x_1}\right)(E_o - E_k) + E_k \qquad \text{EQUATION (2)}$$

where $$E_o = \left(\frac{y-y_1}{y_2-y_1}\right)(E_m - E_l) + E_l; \text{ and}$$

$$E_k = \left(\frac{y-y_1}{y_2-y_1}\right)(E_j - E_i) + E_i;$$

and where $$E_i = \left(\frac{z-z_1}{z_2-z_1}\right)(E_F - E_E) + E_E;$$

$$E_j = \left(\frac{z-z_1}{z_2-z_1}\right)(E_G - E_H) + E_H;$$

$$E_l = \left(\frac{z-z_1}{z_2-z_1}\right)(E_B - E_A) + E_A;$$

$$E_m = \left(\frac{z-z_1}{z_2-z_1}\right)(E_C - E_D) + E_D;$$

The protein atoms were colored on the basis of this interpolated energy value. The protein was displayed using QUANTA™ and atoms with interpolated energies below 10 kcal/mol were colored as red. Atoms with interpolated energies above 10 kcal/mol were colored green. Visual inspection allowed identification of side chains which penetrated the solvent accessible surface or penetrated internal cavities.

There are also two computer based methods for increasing the stability of a protein. The first method comprises the steps of: (1) generating a probe-accessible surface of said target protein by probing the coordinates of said protein with an uncharged probe molecule having a radius of about 0.9 to about 2.0 Å, wherein said probe-accessible surface has an external surface the interior of which contains one or more probe-accessible internal cavities; (2) identifying the amino acids which make up the boundaries of the internal cavities, wherein said amino acids comprise a set of sites which when mutated increase the stability of the protein; (3) identifying an amino acid mutation which would decrease the volume of said internal cavities; (4) determining if said amino acid in said target protein can be changed without creating unacceptable steric interactions; (5) replacing the amino acid in said target protein by site-directed mutagenesis of the gene which expresses said target protein.

The first two steps of the above first method for improving the stability of a protein are the same as those disclosed above for the first computer based method for identifying the sites which affect the stability of a protein.

In step (3) an amino acid identified in step (2) is examined with the goal of identifying a mutation which would decrease the volume of said internal cavity. The size, shape and position of said internal cavity often defines and limits what mutations are acceptable and allowable given the distinct shape and size of each individual amino acid side chain. However, as a particular site in the proteih has been identified for mutation, appropriate mutations can be also be determined by applying any of the various heuristics which define generally acceptable mutations (Matthews, B. W., et al. (1987) Proc. Natl. Acad. Sci. 84:6663–6667; Menéndez-Arias, L., and Argos, P. (1990) J. Mol. Biol. 206:397–406; Sandberg, W. S., and Terwilliger, T. C. (1991) Trends Biotechnol. 9:59–63; Bordo, D., and Argos, P. (1991) J. Mol. Biol. 217:721–729).

In step (4) a determination is then made if the amino acid identified for change in the target protein can be mutated or changed without creating a conformation of the target protein having unacceptable steric interactions. The separation distance between two atoms considered unacceptably short is some percentage of the sum of the van der Waal radii of the two atoms in question. Values of 90–95% of the sum of the van der Waal radii are common though others could be used. Common atoms between the original and replacement amino acid side chain are located and fixed in the same position. The new amino acid is rotated to find the position with the least number of close contacts or unacceptable steric interactions (distances shorter than physically reasonable). The separation distance at which two atoms are considered unreasonably short is some percentage of the sum of the van der Waal radii of the two atoms in question. Values of 90–95% of the sum of the van der Waal radii are common though others could be used. If all conformations of the new amino acid have close contacts, the amino acid substitution is rejected. A conformation with no close contacts which can be matched to a preferred amino acid conformation as defined by Ponder, J. W., and Richards, F. M. (1987) J. Mol. Biol. 193:775–791, is most highly desirable. In step (6) the amino acid identified for change to the corresponding amino acid in the same position in the reference protein is changed by site-directed mutagenesis of the gene which expresses the target protein by the methods disclosed above.

The second method comprises the steps of: (1) generating a probe-accessible surface of said target protein by probing the three dimensional coordinates of said protein with an uncharged probe molecule having a radius of about 0.9 to about 2.0 Å, wherein said probe-accessible surface has an external surface the interior of which contains one or more probe-accessible internal cavities; (2) aligning said three dimensional coordinates of said target protein and a reference protein by moving the three dimensional coordinates of said reference protein into the coordinate frame of said target protein; (3) identifying an amino acid in said reference protein whose side chain lies outside said solvent-accessible surface of said protein or inside said internal cavities of said target protein; (4) identifying the amino acid in said target protein which occupies the equivalent position as said amino acid in said reference protein; (5) determining if said amino acid in said target protein can be changed without creating unacceptable steric effects; (6) replacing the amino acid in said target protein with the corresponding amino acid in the equivalent position in said reference protein by site-directed mutagenesis of the gene which expresses said target protein.

The first three steps of this method. are the same as steps (1), (2), and (3) of the second method for the second computer based method for identifying the sites which affect the stability of a protein.

In step (4) the amino acid in the target protein which occupies the equivalent position as the amino acid in the reference protein is identified. Equivalency is determined from the primary sequence alignment and three dimensional structure alignment described above. Given two protein structures, a target and a reference structure, which have been aligned, equivalent amino acids are defined as pairs of amino acids, one from the target and one from the reference protein, which may differ in identity but occupy close to the same position in the secondary and tertiary structure of the two proteins.

The following examples are meant to illustrate but not to limit the invention.

EXAMPLE 1

Identification of Sites in BLAP for Mutagenesis

The structure of BLAP was obtained by X-ray crystallography and solved to 1.4 Å. The atomic coordinates are shown in FIG. 1. Water molecules were removed from the structure and the protein coordinates were used to generate a probe-accessible surface using a computer program QUANTA™ (version 3.0). This program can be used to calculate a probe-interaction map. The coordinates of BLAP were read into the computer and the following parameters were set in order to perform the probe interaction grid calculation. A Van der Waal calculation was requested with a "proton" probe (radius of 0.9 Å) with a charge of 0.0. The box dimensions were set to 50 Å with a grid size of 1 Å centered on the a-carbon of residue 219. The maximum energy was set to 500 and the minimum to −100. This means that energy values which exceed 500 will be set to 500. An energy value will exceed 500 when the probe is very close to an atom in the protein. The calculations were performed on a Silicon Graphics Inc. (2105 Landings Drive, Suite 2105, Mountain View, Calif. 94043) 4D/220 PowerIris™ workstation. QUANTA™ was used to visualize the probe-accessible surface. The map was contoured at 50 kcal/mol but this value depends on the particular constants in use and the method used to generate the probe accessible surface. The map was displayed simultaneously with the structure of BLAP and amino acid side chains which defined the boundaries of the internal cavities were identified visually.

One such amino acid was threonine-69. This side chain is completely buried with only 2% of its surface being solvent accessible. The hydroxyl group of the side chain defined part of the border of two internal cavities. These particular cavities are occupied by water molecules 278 on one side, and 280 on the other. Mutating this amino acid to valine represents a conservative change which increases the hydrophobicity of the side chain while having little effect on size and shape. Using computer modeling, it was determined that mutating threonine-69 to valine would not create any close contacts with other protein atoms or significantly perturb the structure if the valine occupies the same position as the hydroxyl of threonine-69 in the wild type protein. An oligonucleotide was synthesized which carried a mutation of the codon for threonine-69 to valine (T69V). This oligonucleotide was used to create a site directed mutation in the BLAP gene which was subcloned into a Bacillus vector and expressed in *B. subtilis* DB104 (See Examples 4 and 5). Strains were identified which were expressing the mutant protease and several shake flasks were prepared to produce the mutant protein (See Example 5). The mutant protease was purified from the shake flask media and characterized for surfactant and temperature stability (See Examples 7, 10, and 11).

The mutation T69V resulted in a 340% increase in the half-life of the protease at 50° C., from 12 minutes to 41 minutes (See Table 3).

EXAMPLE 2

Identification of Sites in BLAP for Mutagenesis Based on Other Proteases (A) Comparison to *Subtilisin* Carlaberg The three dimensional coordinates of *subtilisin* Carlsberg (1CSE) were obtained from the Brookhaven Protein Database (Bernstein, F. C., et al. (1977) J. Mol. Biol. 112:535–542). The protease structures were aligned using the molecular modeling program QUANTA™. The BLaP coordinates were held fixed. The α-carbons of residues 1 to 32 of BLAP were matched to residues 1 to 32 of 1CSE, respectively; residues 40 to 60 of BLAP to residues 41 to 61 of 1CSE; residues 80 to 155 of BLAP to residues 82 to 157 of 1CSE; residues 170 to 269 of BLAP to residues 176 to 275 of 1CSE. The BLAP structure was held fixed, and the 1CSE structure was rotated and translated such that the r.m.s. deviation between the α-carbons of matched residues was minimized. The translation vector

| (0.17406  | −0.65535  | 0.73500   |
|-----------|-----------|-----------|
| −0.42119  | −0.72422  | −0.54599  |
| 0.89011   | −0.21454  | −0.40209) | were applied to the coordinates of 1CSE and the transformed coordinates were saved (henceforth, the transformed 1CSE structure). The final r.m.s. deviation between the matched 229 α-carbon pairs was 0.872 Å.

The probe-accessible surface map calculated in Example 1 was used to color the atoms in the transformed 1CSE structure. The entire map, which consists of three dimensional grid of (x, y, z) coordinates in space and an energy value at each position, was read into computer memory along with the protein coordinates (the transformed 1CSE structure). The energy value at each atom position was approximated by interpolating from the energy values of the surrounding eight nearest grid points in the probe map. The protein atoms were colored on the basis of this interpolated energy value. The protein was displayed using QUANTA™ and atoms were displayed in different colors depending on their interpolated energy value. For example, if the energy were greater than 400 the atoms were dark blue; between 300 and 400, light blue; 200 and 300, green; 200 to 100 yellow; and between −100 and 100, red. Visual inspection of such a display allowed identification of side chains which penetrated the solvent accessible surface or internal cavities.

One such amino acid was methionine-199 (LCSE numbering) in *subtilisin* Carlsberg. The amino acid was identified by visual inspection of the transformed 1CSE structure (as described above). Below, the coordinates of residue 199 from the transformed 1CSE structure are shown in the Brookhaven Protein Data Bank file format along with the interpolated energy values.

| Coordinates of Methionine-199 from the 1.2 Å structure of subtilisin Carlsberg. | | | | | | | |
|---|---|---|---|---|---|---|---|
| ATOM | 1364 | N  | MET 199 | 22.392 | 40.705 | 32.311 | 1.0 | 500.00 |
| ATOM | 1365 | CA | MET 199 | 21.675 | 40.581 | 31.054 | 1.0 | 500.00 |
| ATOM | 1366 | C  | MET 199 | 22.438 | 39.677 | 30.103 | 1.0 | 500.00 |
| ATOM | 1367 | O  | MET 199 | 23.689 | 39.601 | 30.254 | 1.0 | 500.00 |
| ATOM | 1368 | CB | MET 199 | 21.621 | 41.991 | 30.511 | 1.0 | 500.00 |
| ATOM | 1369 | CG | MET 199 | 20.868 | 42.994 | 31.426 | 1.0 | 500.00 |
| ATOM | 1370 | SD | MET 199 | 19.150 | 42.631 | 31.891 | 1.0 | 211.58 |
| ATOM | 1371 | CE | MET 199 | 18.273 | 43.395 | 30.493 | 1.0 | 41.68  |

Column 1 is the record type; column 2 is the atom number; column 3 is the atom name; column 4 is the residue name; column 5 is the residue number; columns 6, 7 & 8 are the x, y, z coordinates of the atom, respectively; column 9 is the occupancy; column 10 is normally the temperature factor but this has been replaced with the interpolated energy value. Note that a value of 500 in this column means that the atom in nearly completely within the van der Waal surface of the BLAP molecule. When the probe map was calculated (see Example 1), energy values greater than 500 were set to 500. As can be seen, atoms 1370 and 1371 have significantly lower energy values (column 10). The end of this methionine residue extends into an internal cavity in the BLAP molecule.

This residue is equivalent in secondary and tertiary structure to valine-193 in BLAP. Using computer modeling, valine-193 in BLAP was changed to methionine. The χ values for the new methionine side chain in BLAP were taken from the *subtilisin* BPN' structure. In this conformation, the new side chain had no close contacts except for the ε-carbon of the methionine which contacted a crystallographic water in the BLAP structure.

An oligonucleotide was synthesized which mutated the codon for valine-193 to methionine (V193M) in the BLAP gene. This oligonucleotide was used to create a site directed mutation in the BLAP gene which was subcloned into a Bacillus vector and expressed in *B. subtilis* DB104 (See Examples 3, 4, and 5). Strains were identified which were expressing the mutant protease and several shake flasks were prepared to produce the mutant protein (See Example 5). The mutant protease was purified from the shake flask media and characterized for temperature and surfactant stability (See Examples 6, 7, 10, and 11).

The mutation V193M resulted in a 350% increase in the half-life of the protease at 50° C., from 12 minutes to 42 minutes (See Table 3).

(B) Comparison to Thermitase.

The three-dimensional coordinates of thermitase (1TEC) were obtained from the Brookhaven Protein Database (Bernstein, F. C., et al. (1977) J. Mol. Biol. 112:535–542). The structures of BLAP and 1TEC were aligned using the molecular modeling program QUANTA™ by matching equivalent α-carbons as listed below.

| Matched α-carbons between BLAP and Thermitase (1TEC) | |
|---|---|
| BLAP | 1TEC |
| 5–20 | 12–27 |
| 23–34 | 29–41 |
| 43–72 | 52–81 |
| 75–227 | 85–237 |
| 232–256 | 240–264 |

The BLAP structure was held fixed and the 1TEC structure was rotated and translated such that the r.m.s. deviation between the α-carbons of matched residues was minimized. The translation vector (14.92521, 33.43270, 40.92134) and the rotation matrix

| (0.79048 | −0.20395 | −0.57753 |
|---|---|---|
| −0.01688 | 0.93532 | −0.35340 |
| 0.61225 | 0.28911 | 0.73591) | were applied to the coordinates of 1TEC and the transformed coordinates were saved (henceforth, the transformed 1TEC structure). The final r.m.s. deviation between the matched 236 α-carbon pairs was 1.384 Å.

The probe-accessible surface map was used to color the atoms in the transformed 1TEC structure. The entire probe map was read into computer memory along with the coordinates of the transformed 1TEC structure. The energy value at each atomic position was interpolated from the energy values of the eight surrounding grid points in the probe map. The protein was displayed using QUANTA™ and atoms were displayed in different colors as a function of their interpolated energy value. For example, if the energy were greater than 400 the atoms were dark blue; between 300 and 400, light blue; 200 and 300, green; 200 to 100 yellow; and between −100 and 100, red. Visual inspection of such a display allowed identification of side chains which penetrated the solvent accessible surface or internal cavities.

One such amino acid was tyrosine-149 (1TEC numbering) in thermitase. The amino acid was identified by visual inspection of the transformed 1TEC structure. Below, the coordinates of residue 149 from the transformed 1TEC structure are shown in the Brookhaven Protein Data Bank file format along with the interpolated energy values.

| Coordinates of Tyrosine-149 from the 2.0 Å structure of Thermitase. | | | | | | | |
|---|---|---|---|---|---|---|---|
| ATOM 1052 | N | TYR 149 | 19.783 | 23.026 | 47.326 | 1.0 | 500.00 |
| ATOM 1053 | CA | TYR 149 | 20.372 | 21.668 | 47.275 | 1.0 | 500.00 |
| ATOM 1054 | C | TYR 149 | 21.456 | 21.557 | 46.165 | 1.0 | 500.00 |
| ATOM 1055 | O | TYR 149 | 22.619 | 21.330 | 46.486 | 1.0 | 500.00 |
| ATOM 1056 | CB | TYR 149 | 19.282 | 20.595 | 47.169 | 1.0 | 500.00 |
| ATOM 1057 | CG | TYR 149 | 19.859 | 19.183 | 46.935 | 1.0 | 227.30 |
| ATOM 1058 | CD1 | TYR 149 | 20.262 | 18.427 | 48.038 | 1.0 | 79.13 |
| ATOM 1059 | CD2 | TYR 149 | 20.014 | 18.722 | 45.608 | 1.0 | 275.01 |
| ATOM 1060 | CE1 | TYR 149 | 20.762 | 17.146 | 47.807 | 1.0 | 10.99 |
| ATOM 1061 | CE2 | TYR 149 | 20.531 | 17.425 | 45.371 | 1.0 | 500.00 |
| ATOM 1062 | CZ | TYR 149 | 20.860 | 16.649 | 46.488 | 1.0 | 131.28 |
| ATOM 1063 | OH | TYR 149 | 21.165 | 15.337 | 46.252 | 1.0 | 147.29 |

Column 10 is normally the temperature factor but this has been replaced with the interpolated energy value. As can be seen, the phenyl ring of the tyrosine side chain has significantly lower energy values (column 10 of atoms CG, CD1, CD2, CE1, CE2 and CZ).

This residue is equivalent in secondary and tertiary structure to serine-139 in BLAP. Using computer modeling, serine-139 in BLAP was changed to tyrosine. The χ values for the new tyrosine side chain in BLAP were taken from the thermitase structure. In this conformation, the new side chain had no close contacts that could not be alleviated by small changes (less than 5°) of the χ values. The modeled tyrosine side chain in BLAP fits neatly into a crevice on the surface of the BLAP protein between two surface helices.

An oligonucleotide was synthesized which mutated the codon for serine-139 to tyrosine (S139Y) in the BLAP gene. This oligonucleotide was used to create a site directed mutation in the BIAP gene which was subcloned into a Bacillus vector and expressed in *B. subtilis* DB104 (See Examples 3, 4, and 5). Strains were identified which expressed the mutant protease and several shake flasks were prepared to produce the mutant protein (See Example 5). The mutant protease was purified from the shake flask culture and characterized for temperature and surfactant stability (See Examples 6, 7, 10, and 11).

The mutation S139Y resulted in a 216% increase in the half-life of the protease at 50° C., from 12 minutes to 26 minutes (See Table 3).

EXAMPLE 3

Site Directed Mutagenesis of the BLAP Gene

This mutagenesis procedure was first described by Stanssens, P., et al. (1989) Nucleic Acids Res. 17:4441–4454. While this is the preferred method, many other methods could be used to introduce oligonucleotide site-directed mutations, particularly those which use single stranded DNA. For example, the method of Kunkel (Kunkel, T. A. (1985) Proc. Natl. Acad. Sci. USA 82:488–492) has also been used.

A synthetic oligonucleotide was synthesized which mutates the codon of threonine-69 to the codon for valine.

The mutagenic oligonucleotide was annealed to a gapped duplex DNA which carries the BLAP gene on a segment of single stranded (ss) DNA. The gapped duplex (gd) was formed by denaturing linear DNA's from pMc13C and pMa5-8 followed by re-annealing. The mutagenic oligonucleotide annealed to homologous ss BLAP DNA within the gap and the remaining gap was filled in by a DNA polymerase and ligated using T4 DNA ligase. Subsequent treatment of the product of the fill-in reaction with ExoIII removed any species with only partially filled gaps.

The product of the fill-in reaction was then transformed into a repair deficient *E. coli* strain such as WK6mutS. Plasmid DNA from the recombinant *E. coli* WK6mutS was prepared and transformed in a low plasmid/recipient ratio into a suppressor deficient strain of *E. coli* such as WK6. Ampicillin resistant transformants were selected and plasmid DNA of several candidates was purified and checked for the presence of the mutation.

The mutant BLAP protease was expressed by transferring the mutant BLAP genes from their particular *E. coli* pMa13C derivative vector into a plasmid vector which can replicate in Bacillus such as pH70 or pC51. In the following example, the plasmids pc51 and pH70 can be used interchangeably with the exception that plasmid pH70 encodes resistance to kanamycin while plasmid pC51 encodes resistance to tetracycline. The mutant BLAP gene was separated from the pMa13C plasmids by digestion with the restriction endonucleases AvaI and SstI and then ligated with an AvaI-SstI cut fragment of plasmid pH70 that includes the regions necessary for kanamycin resistance and for replication in Bacillus. The pH70 AvaI-SstI fragment was purified by high pressure liquid chromatography (HPLC). After ligation the mutant BLAP plasmids were transformed into *B. subtilis* DB104, a strain that has been engineered to inactivate its own genes encoding the major alkaline and neutral proteases. *B. subtilis* DB104 transformed by these plasmids were grown on a nutrient-skim milk agar in the presence of the antibiotic kanamycin. Clones that manufactured mutant protease were identified by the formation of clear zones of hydrolysis in the skim milk. Plasmid DNA was purified from these clones to verify that the protease-producing clones carried the a plasmid-borne BLAP gene with the desired mutation. The plasmid DNA was purified away from cell protein and chromosomal DNA by SDS-salt precipitation followed by chromatography over a Qiagen ion-exchange column (Qiagen Corporation). AvaI-SstI digested plasmid DNAs from different clones were compared with AvaI/SstI-digested derivatives of plasmid pH70 known to carry an intact BLAP gene. Plasmid digests were compared by agarose gel electrophoresis to identify plasmids that have the proper-sized AvaI/SstI DNA fragments. Selected plasmid DNAs were then sequenced across the region of the particular BLAP mutation to confirm that the mutation was present. One or more clones of each BLAP mutation were stored frozen in 15% glycerol at −70° C. and also cultivated in shake flasks (Examples 4 and 5) to manufacture mutant protease for characterization.

EXAMPLE 4

Production of Proteases

Each strain of *B. subtilis* DB104 that carried a plasmid with one of the mutant BLAP genes was cultivated in shake flasks to make the mutant protease. Strains were grown in 50 ml precultures of (Difco) Luria Broth (LB) with the antibiotic kanamycin for pH70 derived clones or tetracycline for pC51 derived clones at 37° C. and 280 rpm in a New Brunswick Series 25 Incubator Shaker. After 7 to 8 hours of incubation 2.5 or 5.0 ml of the preculture was transferred to 50 or 100 ml of MLBSP medium (Table 5), respectively, with either 20 µg/ml of kanamycin, or 15 µg/ml of tetracycline in 500 ml (Bellco) baffled shake flasks for growth and eventual production of the protease. These main shake flask cultures were incubated at 240 rpm and 37° C. for 64 hours before the culture broths were treated to remove intact cells and cellular debris, and to reduce the pH to 5.8 before they were concentrated. The protease production of each culture was monitored by electrophoresis of culture supernatants with reverse polarity on 12.5% homogenous polyacrylamide gels with the Pharmacia PhastSystem.

EXAMPLE 5

Production of Mutant Proteases in Shake Flasks

A hot loop was used to streak each mutant strain from a frozen cryovial culture onto an LB-skim milk agar containing either 20 µg/ml of kanamycin or 15 µg/ml of tetracycline. The plates were incubated at 37° C. for 20 to 24 hours. A single, isolated colony producing a good zone of hydrolysis of the skim milk was picked into a 250 ml Erlenmeyer flask containing about 50 ml Luria Broth (LB) which contained either 20 µg/ml kanamycin or 15 µg/ml of tetracycline. The broth was incubated in a New Brunswick Series 25 Incubator Shaker at 37° C. with shaking at 280 rpm for 7 to 8 hours. Either 2.5 ml of the turbid preculture was transferred into 50 ml of MLBSP containing either 20 µg/ml kanamycin or 15 µg/ml of tetracycline in each of four baffled 500 ml flasks, or 5 ml of preculture was used as an inoculum for 100 ml of MLBSP broth with antibiotic contained in each of two 500 ml baffled flasks (a 5% v/v transfer). All flasks were incubated at 240 rpm and 37° C. for 64 hours. After 64 hours of incubation the set of flasks for each culture was consolidated, transferred to 50 ml centrifuge tubes, and centrifuged at 20,000 $g_{av}$ for 15 minutes at 4° C. The broth was filtered through Miracloth (Calbiochem Corp. #475855) into 400 ml beakers chilled on ice. The broth was slowly stirred on ice for 30 minutes before the broth pH was reduced to 5.8 by the slow addition of glacial acetic acid. More fine debris were removed by centrifugation again at 20,000 $g_{av}$ and the broth was filtered through Miracloth into graduated cylinders to measure the volume. Two sets of 1 ml samples were made for PhastSystem gels and activity assays. The broth was stored on ice until the protease could be purified. The MLBSP media used for the production of BLAP in shake flask cultures is described in Table 5.

TABLE 4

COMPOSITION OF MLBSP MEDIUM

| Component | Quantity (for 1 liter of media) |
| --- | --- |
| deionized water | 750 ml |
| Difco Casitone | 10 gm |
| Difco Tryptone | 20 gm |
| Difco Yeast Extract | 10 gm |
| NaCl | 5 gm |
| Sodium Succinate | 27 gm |

The media was adjusted to pH of 7.2 by addition of NaOH, the volume adjusted to 815 ml with water and autoclaved 15 minutes at 121° C. at 15 lbs/in$^2$. The media was cooled before adding the sterile stock solutions described in Appendix 1, while stirring.

TABLE 5 additions to MLBSP broth

| Component | | Quantity (for 1 L of media) |
|---|---|---|
| $MgSO_4.7H_2O$ | (100 mg/ml stock, autoclaved) | 1.0 ml |
| $CaCl_2.2H_2O$ | (30 mg/ml stock, autoclaved) | 2.5 ml |
| $FeSO_4.7H_2O$ | (1 mM stock, filter sterilized) | 0.5 ml |
| $MnCl_2.4H_2O$ | (1 mM stock, autoclaved) | 0.5 ml |
| Glucose | (25% (w/v) stock, autoclaved) | 80.0 ml |
| PIPES Buffer[1] | (pH 7.2, 1 M stock, autoclaved) | 50.0 ml |
| $KPO_4$ Buffer[2] | (1.5 M stock, autoclaved) | 50.0 ml |

[1]Piperazine-N,N'-bis(2-ethane sulfonic acid).
[2]A sufficient amount of 1.5 M dibasic phosphate ($K_2HPO_4$) was added to 200 ml of 1.5 M monobasic phosphate ($KH_2PO_4$) to adjust the pH to 6.0 using a Beckman pH144 pH meter equipped with a Beckman combination electrode (#3952C). The final pH was adjusted to 7.0 with 4 M KOH.

Either kanamycin or tetracycline antibiotic stock solutions were added to the media just before use to a final concentration of 20 µg/ml and 15 µg/ml respectively.

EXAMPLE 6

Purification of BLAP

Fermentation broth of transformed *B. subtilis* DB104, while still in the fermenter, was adjusted to pH 5.8 with 4 N $H_2SO_4$. The broth was collected and cooled to 4° C. If not mentioned otherwise, all subsequent steps were performed on ice or at 4° C. An aliquot of the broth material was clarified by centrifugation at $15,000 \times g_{av}$. for 60 min. Floating lipid material was removed by aspiration, and the supernatant filtered through Miracloth. The dark brown solution was placed in dialysis tubing (Spectrapor; #1, 6 to 8 kilodalton (kDa) molecular-weight-cut-off, 1.7 ml/cm) and dialyzed for 16 hours in 20 mM 2-(N-morpholino) ethanesulfonic acid (MES) containing 1 mM $CaCl_2$, adjusted with NaOH to pH 5.8 ('MES buffer'). The dialysate was clarified by centrifugation ($20,000 \times g_{av}$. for 10 min) and the pH of the solution was adjusted to 7.8 with 2 N NaOH. The enzyme solution containing approximately 0.9 g of protein in 1.2 liter was loaded at a flow rate of 150 ml/hour onto a column of S-Sepharose Fast Flow (SSFF, Pharmacia; 25 mm diameter, 260 mm long) previously equilibrated with 20 m N-(2-hydroxyethyl)piperazine-N'-(2-ethanesulfonic acid) [HEPES], containing 1 mM $CaCl_2$, adjusted with NaOH to pH 7.8 ('HEPES buffer'). After the application of the enzyme solution the column was washed with 2 column volumes (250 ml) of HEPES buffer and then developed at a flow rate of 140 ml/hour with a gradient of 0 to 0.25 M NaCl in 600 ml of HEPES buffer. The gradient eluate was fractionated into 5.2-ml aliquots which were collected into tubes containing 2 ml of 100 mM MES/$Na^+$, pH 5.8. The enzyme eluted between 0.12 and 0.15 M NaCl. Fractions containing the enzyme were pooled and protein was precipitated with ammonium sulfate at 52% of saturation. Solid salt (0.33 g per ml of solution) was added slowly with stirring over a period of 15 min, and stirring was continued for another 15 min. The precipitate was collected by centrifugation, the pellet was dissolved in MES buffer and the protein concentration in the solution was adjusted to 5 to 7 mg/ml. Following dialysis for 16 hours in MES buffer the solution was clarified by centrifugation and the pH of the supernatant was adjusted to 7.2. The protease was purified further by a second cation exchange separation on SSFF. All steps of this procedure were the same as above except that the pH of the HEPES buffer was 7.2 and that the NaCl gradient was from 0 to 0.25 M in 600 ml of HEPES buffer. Protein in pooled fractions was precipitated as above with ammonium sulfate and the enzyme was stored as ammonium sulfate precipitate at −70° C. Prior to use the ammonium sulfate precipitate of the enzyme was dissolved in an appropriate buffer, typically MES buffer, at the desired protein concentration, and dialyzed overnight in the buffer of choice.

EXAMPLE 7

Purification of BLAP Mutants

Fermentation broth from shake flasks, on average 180 ml, was collected and clarified by centrifugation at $20,000 \times g_{av}$. for 15 min. The supernatant was placed, with stirring, on ice and after 30 min the pH of the solution was adjusted to 5.8 with glacial acetic acid. If not mentioned otherwise; all subsequent steps were performed on ice or at 4° C. The solution was clarified again by centrifugation ($20,000 \times g_{av}$. for 15 min) and was concentrated approximately 4-fold by ultrafiltration (Amicon; YM30 membrane). The dark brown solution was placed in dialysis tubing (spectrapor; #1, 6 to 8 KDa molecular-weight-cut-off, 1.7 ml/cm) and dialyzed for 16 hours in 20 mM HEPES/$Na^+$, pH 7.8, containing 1 mM $CaCl_2$ ('HEPES buffer'). The dialysate was clarified by centrifugation ($20,000 \times g_{av}$. for 10 min) and the pH of the solution, if necessary, was adjusted to 7.8 with 2 N NaOH. The enzyme solution was loaded at a flow rate of 60 ml/hour onto a column of SSFF (15 mm diameter, 75 mm long), previously equilibrated with HEPES buffer. When all colored by-products were eluted, the column was washed with 50 ml of HEPES buffer. Then, the enzyme was eluted with 0.25 M NaCl in HEPES buffer. Fractions of 1.2 ml were collected into tubes containing 0.5 ml of 100 mM MES/$Na^+$, pH 5.8. Protein-content in fractions was monitored either by a UV detector set at 280 nm or by protein assay as described below. Pooled fractions containing protease protein were placed on ice and protein was precipitated with a 5 to 8-fold volume excess of acetone at −20° C. The protein was allowed to precipitate for 6 min, the mixture was centrifuged for 4 min at $6,600 \times g_{av}$., the supernatant was discarded, the pellet was briefly exposed to vacuum (water aspirator) to remove most of the acetone, and the pellet was dissolved in 20 mM MES/$Na^+$, pH 5.8, to give an approximate protein concentration of 30 mg/ml. Prior to any assays, the solution was centrifuged in an Eppendorf centrifuge for 3 min at full speed ($13,000 \times g_{max}$.).

EXAMPLE 8

Protein Determination

Protein was determined by a modified biuret method (Gornall, A. G., et al. (1948) J. Biol. Chem. 177:751–766). The protein in a total volume of 500 µl was mixed with 500 µl of biuret reagent and incubated for 10 min at 50° C. The solution was briefly chilled and its absorbance was measured at 540 nm. Typically, a reagent blank and three different protein aliquots in duplicates were measured and the recorded optical densities analyzed by linear regression. Bovine serum albumin (BSA, crystalline; Calbiochem) was used as protein standard. With purified BLAP protein the usefulness of BSA as protein standard in the biuret assay was confirmed. A BLAP sample was exhaustively dialyzed in 1 mM sodium phosphate, pH 5.8, and subsequently lyophilized. A sample of the solid material was weighed, dissolved in 1 mM sodium phosphate, pH 5.8, and used to generate a standard curve for the biuret assay. From the actual difference in phosphate content (Black, M. J., and Jones, M. E. (1983) Anal. Biochem. 135:233–238) of the final protein solution and the nominally 1 mM sodium phosphate solution used to dissolve the protein, the contribution of phosphate to the weight of solid BLAP was estimated and used to correct the standard curve.

EXAMPLE 9

Protease Assays

Two different protease assays were used. With the HPE method protease activity was established at a single concentration of casein (prepared according to Hammarsten; Merck, #2242) as substrate. In the AAPF-pNA assay initial rates of succinyl-L-alanyl-L-alanyl-L-prolyl-L-phenylalanyl-p-nitroanilide (AAPF-pNA; Bachem) supported catalysis were used to determine the kinetic parameters $K_m$, $k_{cat}$, and $k_{cat}/K_m$.

A. HPE Method

Culture supernatants or solutions of purified proteases were diluted with chilled buffer (10 mM MES/Na$^+$, pH 5.8) to give three different solutions with a protein concentration ratio of 1:3:5. The substrate solution contained 9.6 mg/ml casein, 24 mM Tris, and 0.4% (w/v) sodium tripolyphosphate, dissolved in synthetic tap water (STW; 0.029% (w/v) CaCl$_2$.2H$_2$O, 0.014% (w/v) MgCl$_2$. 6H$_2$O, and 0.021% (w/v) NaHCO$_3$ in deionized water) adjusted to pH 8.5 at 50° C., prepared as follows. With stirring for 10 min, 6 g of casein was dissolved in 350 ml of STW. To this, 50 ml of 0.3 M Tris in STW was added and stirring was continued for another 10 min. This solution was heated to 70° C., then allowed to cool slowly. At 50° C., the pH was adjusted to 8.5 with 0.1 N NaOH. When the solution reached room temperature, the volume was adjusted to 500 ml with STW, followed by the addition of 125 ml of 2% (w/v) pentasodium tripolyphosphate in STW, pH 8.5 (adjusted with 3 N HCl). The protease assay was started by adding 50 $\mu$l of protease solution to 750 $\mu$l of substrate solution placed in a 2.2 ml Eppendorf container preincubated for 10 min at 50° C. After 15 min, the reaction was terminated by the addition of 600 $\mu$l of trichloroacetic reagent (0.44 M trichloroacetic acid, 0.22 M sodium acetate in 3% (v/v) glacial acetic acid). The mixture was placed on ice for 15 min, the precipitated protein removed by centrifugation for 8 min (at 13,000$\times g_{max}$.) and a 900 $\mu$l aliquot of the supernatant was mixed with 600 $\mu$l of 2 N NaOH. The absorbance at 290 nm of this solution was recorded. Each dilution was assayed in duplicates and the data points for three different dilutions from one enzyme sample was analyzed by linear regression. A slope of 1 in this assay corresponds to 80 HPE units in the least diluted sample. In case of strongly colored culture supernatants with measurable quantities of UV absorbing material carried over by the diluted protease aliquot into the assay cuvette a control curve was constructed whose slope was subtracted from the slope of the protease assay before final HPE units were calculated.

B. AAPF-pNA Assay

Protease samples were diluted with 50% (v/v) 1,2-propanediol in 100 mM Tris, adjusted with 2 N HCl to pH 8.6 at 25° C. ('Tris-propanediol buffer'), in which they were stable for at least 6 h at room temperature. A stock solution of 160 mM AAPF-pNA was prepared in dimethylsulfoxide dried with a molecular sieve (Aldrich; 4 Å, 4–8 mesh) for at least 24 h prior to use. Fixed point assays were performed at 25° C. with 1.6 mM AAPF-pNA in 100 mM Tris, adjusted with 2 N HCl to pH 8.6 at 25° C., in a total volume of 1.020 ml. The substrate was added to the assay buffer 1 min prior to the assay initiation and the reaction was started by addition of enzyme at a final concentration of 20 ng to 1.3 $\mu$g of protein per ml (0.75 to 48.5 nM enzyme) depending on specific activity. Release of p-nitroanilide was monitored at 410 nm, and a molar extinction coefficient of 8,480 M$^{-1}$cm$^{-1}$ was used to calculate amount and concentration of product formed (DelMar, E. G., et al. (1979) Anal. Biochem. 99:316–320). Kinetic parameters were calculated from a velocity vs. substrate concentration plot constructed from initial rates measured once each at 12 different AAPF-pNA concentrations ranging from 0.16 to 3.2 mM. Data were fitted to a hyperbolic curve and proportionally weighted using the program ENZFITTER (Leatherbarrow, R. J. (1987) ENZFITTER, Biosoft, Cambridge, UK). A nominal molecular weight of 26.8 kDa was used in all calculations that required the interconversion of protein concentration and molarity of protease enzyme.

EXAMPLE 10

Temperature Stability of Purified Proteases

Stability of protease proteins was evaluated under two different conditions: (a) 100 mM glycine/Na$^+$, pH 10 at 60° C., and (b) 100 mM glycine/Na$^+$, pH 11 at 50° C. At t=0 min, the protein was diluted to approximately 0.25 mg/ml into incubation buffer maintained at the desired temperature. Periodically, an aliquot was removed from this incubation mixture and diluted into Tris-propanediol buffer chilled on ice. Residual protease activity was determined by the AAPF-pNA assay at a fixed AAPF-pNA concentration (1.6 mM). Stability is expressed as half-life ($t_{1/2}$) of activity determined from semi-logarithmic plots of residual activity as function of time. Each plot consisted of 6 data points with $t_{1/2}$ approximately in the center between experimental points.

EXAMPLE 11

Resistance of Proteases to Sodium Dodecylsulfate (SDS)

SDS was selected as representative of surfactants in general. Resistance of proteases to SDS was evaluated under two different conditions: (a) 100 mM Tris adjusted with 2 N HCl to pH 8.6 at 50° C., containing 1% (w/v) SDS, and (b) 50 mM sodium carbonate, pH 10.5 at 50° C., containing 1% (w/v) SDS. Protease proteins were incubated at a final protein concentration of 0.25 mg/ml. Data were collected and evaluated as described above under Example 10.

EXAMPLE 12

Polyacrylamide Gel Electrophoresis

Purity of protease samples was evaluated on 20% non-denaturing PhastSystem gels (Pharmacia) run with reversed polarity. The same system was used to monitor the protease content of crude shake flask and fermentation broths. Buffer strips were prepared as described in Application File No. 300 (Pharmacia).

Molecular weight determinations were performed on 20% SDS PhastSystem gels, using the following markers: bovine serum albumin, 66 kDa; egg albumin, 45 kDa; glyceraldehyde-phosphate dehydrogenase, 36 kDa; carbonic anhydrase, 29 kDa; trypsinogen, 24 kDa; trypsin inhibitor, 20.1 kDa; α-lactalbumin, 14.2 kDa (all from Sigma). Prior to SDS-PAGE, a protease sample was denatured with formic acid at a final concentration of 30 to 50% (v/v). Upon dilution of formic acid to 15% (v/v) protein was precipitated with trichloroacetic acid at a final concentration of 10%

(v/v). The collected pellet was washed once with water, then dissolved in 2% (w/v) SDS and heated for 2 min in a boiling waterbath. Gels were stained with Coomassie Brilliant Blue R-250 (Kodak).

Deposit of Microorganisms

Living cultures of the following have been accepted for deposit under the Budapest Treaty on the International Recognition of the Deposit of Microorganisms for the purposes of patent procedure by the American Type Culture Collection, 12301 Parklawn Drive, Rockville, Md. 20852 on May 8, 1991 (the accession number preceeds each deposit description): ATCC 68614—*Bacillus licheniformis* ATCC 53926 strain which contains a tetracycline-resistance plasmid originally derived from Bacillus plasmid pBC16 which carries the ATCC 53926 alkaline protease-BLAP ClaI fusion gene, whose structural gene has the mutations S3T, V4I, A188P, V193M, V199I; ATCC 68615—*E. coli* WK6 which carries phasmid pMc13C, a chloramphenicol-resistant derivative of phasmid pMc5-8, that contains the ATCC 53926 alkaline protease- BLAP ClaI fusion gene and a 164 bp KpnI 35 fragment carrying the ATCC 53926 alkaline protease gene's transcriptional terminator. The genotype of strain WK6 are Δlac-proAB, galE, strA, mutS::Tn10/F'lacI$^q$, ZΔM15, proA$^+$B$^+$ (Zell, R., and Fritz, H.-J. (1987) EMBO J. 6:1809–1815); ATCC 68616—*E. coli* GM33 which carries plasmid pCB13C, an ampicillin-resistant derivative of Pharmacia plasmid vector pTZ19R (Pharmacia) that contains the ATCC 53926 alkaline protease-ClaI fusion gene. The GM33 strain's genotype is dan3 (dam-methylase minus (Marinus, M. G. and Morris, N. R. (1974) J. Mol. Biol. 85:309–322)); ATCC 68617—*E. coli* WK6 which carries phasmid pMa5-8, an ampicillin-resistant mutagenesis vector described in Stanssens, P. et al. (1989) Nucleic Acids Research 17:4441–4454. The genotype of strain WK6 mutations are Δlac-proAB, galE, strA, mutS::Tn10/F'lacI$^q$, ZΔM15, proA$^+$B$^+$(Zell, R., and Fritz, H.-J. (1987) EMBO J. 6:1809–1815); ATCC 68618—an *E. coli* WK6 which carries phasmid pMc5-8, a chloramphenicol-resistant mutagenesis vector described in Stanssens, P., et al. (1989) Nucleic Acids Res. 17:4441–4454. The genotype of strain WK6 are Δlac-proAB, galE, strA, mutS::Tn10/F'lacI$^q$, ZΔM15, proA$^+$B$^+$ (Zell, R., and Fritz, H. -J. (1987) EMBO J. 6:1809–1815).

TABLE I

| EQUIVALENT BLAP AMINO ACID POSITION | TARGET SUBTILISIN | MUTATION IN TARGET SUBTILISIN | PATENT REFERENCE | JOURNAL REFERENCE |
|---|---|---|---|---|
| W006 | 147 | W005Y | 16 | — |
| W006 | 309 | W006Y | 16 | — |
| I008 | BPN' | V008I | 17, 18 | — |
| R019, G213 | 147 | R018G, G212C | 16 | — |
| R019, G213 | 309 | R019G, G213C | 16 | — |
| L021, T022, S085 | BPN' | Y021A, T022C, S087C | 3 | 80 |
| L021 | BPN' | Y021X, X = A, F, or L | 3 | — |
| L021, T022 | BPN' | Y021A, T022X, X = C OR K | 3 | 80 |
| T022 | BPN' | T022C | — | 58 |
| T022, S085, N212 | BPN' | T022C, S087C, N218S | 8, 9 | — |
| T022, S085 | BPN' | T022C, S087C | 8, 9 | 58 |
| T022, F049, S085, A163, L211, N212 | BPN' | T022C, M050F, S087C, G169A, Y217K, N218S | 17 | — |
| T022, F049, S085, A163, Q200, L211, N212 | BPN' | T022C, M050F, S087C, G169A, Q206C, Y217K, N218S | 17 | — |
| T022, S085, N212 | BPN' | T022C, S087C, N218D | 17 | — |
| T022, F049, S085, A163, N212 | BPN' | T022C, M050F, S087C, G169A, N218S | 17 | — |
| T022, S085, A163, N212 | BPN' | T022C, S087C, G169A, N218S | 17 | — |
| T022, N074 | BPN' | T022K, N076D | 17, 18 | — |
| T022, S085, Q200, S210 | BPN' | T022C, S087C, Q206C, A216C | 8, 9 | — |
| T022, S085, A163, A166 | BPN' | T022C, S087C, G169A, P172D | 17 | — |
| S024, S215 | BPN' | S024C, S221A | — | 31 |
| S024, D032, H062 | BPN' | S024C, D032A, H064A | — | 31 |
| S024, H062 | BPN' | S024C, H064A | 13 | 80 |
| S024, D032, H062, S215 | BPN' | S024C, D032A, H064, S221A | — | 31 |
| S024, D032 | BPN' | S024C, D032A | — | 31 |
| S024, S085 | BPN' | S024C, S087C | 8, 9 | — |
| S024 | BPN' | S024X, X = A or C | 3 | 80 |
| S024, S085 | BPN' | S024C, S087C | 3 | 80 |
| S024 | BPN' | S024C | 13 | 80 |
| V026, A226 | BPN' | V026C, A232C | — | 53 |
| V026 | BPN' | V026C | — | 53 |
| V026, K229 | BPN' | V026C, L235C | 8, 9 | — |
| V026 | BPN' | V026C | 8, 9 | — |
| K027, E087 | BPN' | K027C, S089C | 8, 9 | — |
| A029, M117 | BPN' | A029C, M119C | — | 53 |
| A029 | BPN' | A029C | — | 53 |
| L031 | 168 | I031L | 6 | 74 |
| L031 | 168 | I031X, X = A, C, F, G, S, T, V | — | 74 |
| D032 | BPN' | D032X, X = Q or S | 3 | — |
| T033 | BPN' | S033X, X = A, G, or T | 3 | — |
| D040, G078 | BPN' | D041C, G080C | — | 53 |
| D040 | aprA | D041X; X = D or E | 15 | — |
| D040 | BPN' | D041C | — | 53 |
| R044, A047 | BPN' | A045V, A048V | 3 | — |
| G045 | BPN' | G046V | 3 | — |
| A047 | BPN' | A048E | 13 | — |
| A047 | BPN' | A048X, X = E, R, or V | 3 | — |

TABLE I-continued

| EQUIVALENT BLAP AMINO ACID POSITION | TARGET SUBTILISIN | MUTATION IN TARGET SUBTILISIN | PATENT REFERENCE | JOURNAL REFERENCE |
|---|---|---|---|---|
| S048 | BPN' | S049X, X = C or L | 3 | — |
| S048, V093 | BPN' | S049C, V095C | 3 | — |
| S048, K092 | BPN' | S049C, K094C | 3 | — |
| F049, S154, A163, L211 | BPN' | M050F, E154S, G169A, Y217L | 3 | — |
| F049, Q107 | BPN' | M050C, N109C | 8, 9 | — |
| F049, N074, S076, A163, Q200, L211, N212 | BPN' | M050F, N076D, S078D, G169A, Q206C, Y217K, N218S | 17 | — |
| F049, G108 | BPN' | M050C, G110C | 3 | — |
| F049, N074, S076, A163, Q200, L211, N212 | BPN' | M050F, N076D, S078D, G169A, Q206C, Y217K, N218D | 17 | — |
| F049, V093 | BPN' | M050C, V095C | 3 | — |
| F049, S154, —, L211 | BPN' | M050F, E156X, G166X', Y217X", X = S or Q; X" = K or N; X" = K or L | 3 | — |
| F049, N074, A163, Q200, L211, N212 | BPN' | M050F, N076D, G169A, Q206C, Y217K, N218S | 17 | 59 |
| F049 | BPN' | M050X, X = C, F, I, K, L, P, or V | 3 | 33 |
| F049, L122, M216 | BPN' | M050F, M124X, M222X', X = I or L; X' = Q or A | 3 | — |
| F049, S154, L211 | BPN' | M050F, E156S, Y217L | 3 | — |
| F049, M216 | BPN' | M050F, M222Q | 3 | — |
| F049, L122 | BPN' | M050F, M124I | 3 | — |
| F049, I105, T207 | BPN' | M050F, I107V, K213R | 3 | 33 |
| F049, S154, A163, L211 | BPN' | M050F, E156S, G169A, Y217L | 3 | — |
| F049 | BPN' | M050F | 17, 18 | 59 |
| G052 | BPN' | S053T | 17, 18 | 64 |
| G059, A096 | 168 | G061C, S098C | 6 | — |
| G061, L211 | BPN' | S063D, Y217K | 18 | — |
| H062 | BPN' | H064A | 13 | 80 |
| H065 | 309 | H065X; X = D or E | 16 | — |
| H065 | 147 | H064X, X = D OR E | 16 | — |
| V066 | 309 | V066X; X = C or M | 16 | — |
| V066 | 147 | V065X, X = C or M | 16 | — |
| T069 | 147 | T068X, X = D or E | 16 | — |
| T069 | 309 | T069X; X = D or E | 16 | — |
| L073 | aprA | L075X; X = D or E | 15 | — |
| N074, N075, Q107, N212 | aprA | N076D, N077D, N109S, N218S | 15 | — |
| N074 | aprA | N076D | 15 | — |
| N074, P129 | BPN' | N076D, G131D | 14 | — |
| N074, I077, Q107, N212 | aprA | N076D, I079E, N109S, N218S | 15 | — |
| N074 | aprA | N076X; X = D or E | 15 | — |
| N074, I077 | aprA | N076D, I079E | 15 | — |
| N074 | BPN' | N076D | 14, 17 | 60 |
| N074, N075 | aprA | N076D, N077D | 15 | — |
| N074, S076 | BPN' | N076D, S078D | 14 | — |
| N074, A166 | BPN' | N076, P172X, X = D or E | 14 | — |
| N074, Q107, N212 | aprA | N076D, N109S, N218S | 15 | — |
| N075 | aprA | N077D | 15 | — |
| N075 | aprA | N077X; X = D or E | 15 | — |
| N075, Q107, N212 | aprA | N077D, N109S, N218S | 15 | — |
| N075 | BPN' | N077D | 3 | — |
| S076, A166 | BPN' | S078D, P172X, X = D or E | 14 | — |
| S076, P129 | BPN' | S078D, G131D | 14 | — |
| S076, P129, A166 | BPN' | S078D, G131D, P172X, X = D or E | 14 | — |
| S076 | BPN' | S078D | 14, 17 | — |
| S076 | aprA | S078X; X = D or E | 15 | — |
| I077 | aprA | I079E | 15 | — |
| I077 | aprA | I079X; X = D or E | 15 | — |
| I077, Q107, N212 | aprA | I079E, N109S, N218S | 15 | — |
| G078 | aprA | G080X; X = D or E | 15 | — |
| G078 | BPN' | G080C | — | 53 |
| V079 | aprA | V081X; X = D or E | 15 | — |
| A083, A226 | BPN' | A085C, A232C | 8, 9 | — |
| S085 | BPN' | S087C | — | 58 |
| S085 | BPN' | S087X, X = C or N | 3 | 80 |
| S085, Q200, S210 | BPN' | S087C, Q206C, A216C | 17 | — |
| K092 | BPN' | K094X, X = C, Q, or R | 3 | — |
| K093 | BPN' | K095X, X = C, I, or L | 3 | — |
| L094 | BPN' | L096D | 3 | — |
| D097 | BPN' | D099K | — | 65 |
| D097, S154 | BPN' | D099K, E154K | — | 65 |
| D097 | BPN' | D099S | — | 65 |
| D097, S154 | BPN' | D099S, E156S | — | 65 |
| I102 | BPN' | Y104X, X = any other amino acid | 3 | — |
| I102, S126 | BPN' | Y104V, G128S | 17, 18 | — |
| I105, T207 | BPN' | I107V, K213R | 3 | 33 |
| I105 | BPN' | I107V | 3 | 33 |
| Q107, N212 | aprA | N109S, N218S | 15 | — |
| Q107 | aprA | N109S | 15 | — |

TABLE I-continued

| EQUIVALENT BLAP AMINO ACID POSITION | TARGET SUBTILISIN | MUTATION IN TARGET SUBTILISIN | PATENT REFERENCE | JOURNAL REFERENCE |
|---|---|---|---|---|
| G108 | BPN' | G110X, X = C or R | 3 | — |
| N114, P129 | BPN' | A116T, G131D | 14 | 64 |
| N114 | BPN' | A116T | 14 | — |
| N114 | BPN' | A116E | 12, 17 | 64 |
| G116, S126, P127 | PB92 | G116V, S126Q, P127D | 5 | — |
| G116 | PB92 | G116X; X = A, I, L, or V | 5 | — |
| G116, S126, P127 | PB92 | G116V, S126V, P127M | 5 | — |
| G116, S126, P127, S128 | PB92 | G116V, S126R, P127S, S128P | 5 | — |
| G116 | PB92 | G116X; X = I, L, or V | 5 | — |
| G116, S126, P127, S128 | PB92 | G116V, or G116IG, or G116L; and at least one different aa at pos. | 5 | — |
| G116, S126, P127, S128 | PB92 | G116V, S126G, P127Q, S128I | 5 | |
| G116, S126, P127, S128 | PB92 | G116V, S126F, P127L, S128T | 5 | |
| G116, S126, P127, S128, S160 | PB92 | G116V, S126V, P127E, S128K, S160K | 5 | |
| G116, S126, P127, S128 | PB92 | G116V, S126Y, P127G, S128L | 5 | |
| G116, S126, P127, S128 | PB92 | G116V, S126L, P127Q, S128A | 5 | |
| G116, S126, P127, S128 | PB92 | G116V, S126N, P127H, S128I | 5 | |
| G116, S126, P127 | PB92 | G116V, S126H, P127Y | 5 | |
| G116, S126, P127, S128 | PB92 | G116V, S126V, P127E, S128K | 5 | |
| G116, S126, P127, S128 | PB92 | G116V, S126L, P127N, S128V | 5 | |
| G116, S126, P127, S128, S160 | PB92 | G116V, S126N, P127S, S128A, S160D | 5 | |
| G116, S126, P127 | PB92 | G116V, S126F, P127Q | 5 | |
| M117, H118, M216 | PB92 | M117L, H118D, M216Q | 5 | |
| M117, M216 | PB92 | M117L, M216Q | 5 | |
| M117, H118, M216 | PB92 | M117L, H118D, M216S | 5 | |
| M117, M216 | PB92 | M117L, M216S | 5 | |
| M117, H118 | PB92 | M117L, H118D | 5 | |
| M117 | BPN' | M119C | — | 53 |
| A120, V145 | BPN' | I122C, V147C | 8, 9 | — |
| L122, M216 | BPN' | M124X, M222Q, X = I or L | 3 | — |
| L122 | BPN' | M124X, X = A, I, K, or L | 3 | — |
| L124 | BPN' | L126I | 12, 17 | 64 |
| S126, P127, S128 | PB92 | S126M, P127A, S128G | 5 | — |
| S126, P127, S128 | PB92 | S126X, X = any other non-hydroxylated aa; P127X', X' = any other aa; | 5 | — |
| S126, P127, S128, S160 | PB92 | S126M, P127A, S128G, S160D | 5 | — |
| P129, N212, A248 | BPN' | G131D, N218S, T254A | 12, 17 | 64 |
| P129 | BPN' | G131E | 14 | — |
| P129, A166 | BPN' | G131D, P172X, X = D or E | 14 | 60 |
| P129 | BPN' | G131D | 12, 17 | 29 |
| P129, N212 | BPN' | G131D, N218S | 12 | 64 |
| P129 | BPN' | G131D | 14, 17 | 29 |
| P129, A166 | BPN' | G131D, P172D | 14 | 60 |
| E134 | PB92 | E134K | 5 | — |
| L146 | BPN' | V148C | — | 53 |
| L146, N237 | BPN' | V148C, N243C | — | 53 |
| A150 | BPN' | A152X, X = C, G, I, L, M, S, or T | 3 | — |
| S151, N212 | 309 | S151A, N212S | 16 | — |
| S151 | 147 | A150S | 16 | — |
| S151 | 309 | S151A | 16 | — |
| S151, N212 | 147 | A150S, S211N | 16 | — |
| N153, L211 | BPN' | N155Q, Y217K | — | 27 |
| N153, L211 | BPN' | N155H, Y217K | — | 27 |
| N153 | BPN' | N155X, X = H, Q, or R | — | 27 |
| N153 | BPN' | N155X, X = A, D, E, H, or T | 3 | 78 |
| N153 | BPN' | N155L | — | 28 |
| N153, L211 | BPN' | N155R, Y217K | — | 27 |
| S154 | BPN' | E156K | — | 65 |
| S154, A163 | BPN' | E156S, G169A | 3 | — |
| S154, A163, L211 | BPN' | E156S, G169A, Y217L | — | 79 |
| S154 | BPN' | E156S | 3 | 81 |
| S154 | BPN' | E156S | — | 65 |
| S154 | BPN' | E156X, X = A, L, M, Q, S, T, or Y | 3 | 81 |
| S154, L211 | BPN' | E156S, Y217L | — | 79 |
| S154, — | BPN' | E156X, G166X', X = Q or S and X' = D, K, or N | 3 | 81 |
| S160, M216 | PB92 | S160G, M216S | 5 | — |
| S160 | PB92 | S160D | 5 | — |
| S160, M216 | PB92 | S160D, M216Q | 5 | — |
| S160 | PB92 | S160C | 5 | — |
| S160 | PB92 | S160X; X = G, D, or E | 5 | — |
| S160 | PB92 | S160X, X = A, I, K, L, N, P, Q, R, T, Y | 5 | — |
| S160, N212 | PB92 | S160G, N212D | 5 | — |
| S160, M216 | PB92 | S160D, M216S | 5 | — |
| S160, M216 | PB92 | S160G, M216Q | 5 | — |
| P162 | 309 | P162A | 16 | — |
| P162 | 147 | P161A | 16 | — |

TABLE I-continued

| EQUIVALENT BLAP AMINO ACID POSITION | TARGET SUBTILISIN | MUTATION IN TARGET SUBTILISIN | PATENT REFERENCE | JOURNAL REFERENCE |
|---|---|---|---|---|
| A163 | BPN' | G169X, X = A or S | 1 | 79 |
| A163, M216 | BPN' | G169A, M222X, X = A or C | 3 | — |
| A163 | BPN' | G169X, X = any other amino acid | 3 | — |
| A163 | BPN' | G169A | 17, 18 | 59 |
| R164 | 309 | R164Y | 16 | — |
| R164 | 147 | R163Y | 16 | — |
| R164 | BPN' | K170X, X = E or R | 3 | 33 |
| Y165 | BPN' | Y171X, X = E, F, K, Q, or R | 3 | — |
| A166 | PB92 | A166X; X = D or E | 5 | — |
| A166 | BPN' | P172E | 14, 17 | 60 |
| A166 | BPN' | P172X, X = D, E, N, or Q | 3 | — |
| A166, M169 | PB92 | A166D, M169I | 5 | — |
| A166 | BPN' | P172D | 14, 17 | 60 |
| M169 | 147 | M168I | 16 | — |
| M169 | 309 | M169I | 16 | — |
| M169 | PB92 | M169S | 5 | — |
| M169, M216 | PB92 | M169I, M216S | 5 | — |
| M169 | PB92 | M169X; X = A, L, I, V, G, or P? | 5 | — |
| D175 | PB92 | D175N | 5 | — |
| S182 | BPN' | S188P | 12, 17 | 64 |
| F183 | BPN' | F189X, X = any other amino acid | 3 | — |
| G189 | 309 | G189D | 16 | — |
| G189 | 147 | E188X, X = G or D | 16 | — |
| G189 | 309 | G189E | 16 | — |
| G189, M216 | 147 | E188G, M215X, X = A or C | 16 | — |
| G189, M216 | 309 | G189E, M216X; X = A or C | 16 | — |
| D191 | BPN' | D197E | — | 60 |
| D191 | BPN' | D197X, X = A or R | 3 | — |
| V193 | BPN' | M199I | 3 | — |
| N198 | BPN' | S204X, X = C, L, P, or R | 3 | — |
| N198, T207 | BPN' | S204X, K213R, X = any amino acid | 3 | — |
| Q200 | BPN' | Q206C | 17, 18 | — |
| Q200, S210 | BPN' | Q206C, A216C | 8, 9 | — |
| Q200 | BPN' | Q206Y | 17, 18 | — |
| Q200 | BPN' | Q206Cox | 17 | 59 |
| T202 | aprA | T208X; X = D or E | 15 | — |
| P204 | BPN' | P210C | — | 53 |
| T207 | BPN' | K213X, X = R or T | 3 | 33 |
| T207 | PB92 | T207K | 5 | — |
| Y208 | aprA | Y214X; X = D or E | 15 | — |
| S210 | BPN' | A216C | — | 59 |
| L211, N212 | PB92 | L211Y, N212S | 5 | — |
| L211 | BPN' | Y217X, X = any other amino acid | 3 | — |
| L211 | BPN' | Y217K | 17, 18 | 59 |
| L211 | BPN' | Y217L | 3 | 79 |
| L211 | BPN' | Y217L | 17, 18 | — |
| L211 | PB92 | L211Y | 5 | — |
| N212 | aprA | N218S | 11 | — |
| N212 | PB92 | N212D | 5 | — |
| N212 | BPN' | N218D | 12, 17 | 29 |
| N212 | PB92 | N212S | 5 | — |
| N212 | aprA | N218S | 11, 15 | — |
| N212 | 147 | S211N | 16 | — |
| N212, A248 | BPN' | N218S, T254A | 12, 17 | 64 |
| N212 | PB92 | N212X, X = D or E | 5 | — |
| N212 | BPN' | N218X, X = S or D | 12 | 29 |
| N212 | 309 | N212S | 16 | — |
| N212 | aprA | N218X, X = C, E, I, V, T | 11 | — |
| N212 | BPN' | N218X, X = any other amino acid | 12 | 29 |
| N212 | BPN' | N218S | 12, 17 | 29 |
| G213 | 147 | G212M | 16 | — |
| G213, M216 | 147 | G212C, M215C | 16 | — |
| G213 | 309 | G213M | 16 | — |
| G213, M216 | 309 | G213C, M216C | 16 | — |
| S215 | BPN' | S221C | — | 27 |
| S215 | BPN' | S221X, X = A or C | 3 | — |
| M216 | 147 | M215X, X = C or A | 16 | — |
| M216 | BPN' | M222X, X = any other amino acid | 1 | 35 |
| M216 | PB92 | M216Q | 5 | — |
| M216 | BPN' | M222C | 1 | 35 |
| M216 | 309 | M216A | 16 | — |
| M216 | PB92 | M216X; X = any amino acid except M or C | 5 | — |
| M216 | PB92 | M216S | 5 | — |
| M216 | PB92 | M216-ox | 5 | — |
| M216 | BPN' | M222X, X = any other amino acid | 3 | 35 |
| M216 | 309 | M216C | 16 | — |

TABLE I-continued

| EQUIVALENT BLAP AMINO ACID POSITION | TARGET SUBTILISIN | MUTATION IN TARGET SUBTILISIN | PATENT REFERENCE | JOURNAL REFERENCE |
|---|---|---|---|---|
| M216 | PB92 | M216X, X = A, C, E, G, H, I, K, L, N, P, T, W, Y | 5 | — |
| A226 | BPN' | A232C | — | 53 |
| K229 | BPN' | L235C | 8, 9 | — |
| P233 | 168 | P239X, X = G, K, or R | — | 75 |
| E235 | PB92 | W235R | 5 | — |
| E235, S259 | PB92 | W235R, S259K | 5 | — |
| E235, H243 | PB92 | W235R, H243R | 5 | — |
| N237 | BPN' | N243C | — | 53 |
| N242, H243 | BPN' | S248D, S249R | 17, 18 | — |
| H243, A267 | BPN' | S249C, A273C | 8, 9 | — |
| H243, S259 | PB92 | H243R, S259K | 5 | — |

1. EP 0130756 (Bott, R. R., Ferrari, E., Wells, J. A., Estell, D. A., Henner, D. J. (1985) Procaryotic carbonyl hydrolases, methods, DNA, vectors and transformed hosts for producing them, and detergent compositions containing them).
2. EP 0247647 (Bott, R. R., Ferrari, E., Wells, J. A., Estell, D. A., Henner, D. J. (1987) DNA mutagenesis method).
3. EP 0251446 (Wells, J. A., Cunningham, B. C., Caldwell, R. M., Bott, R. R., Estell, D. A., Power, S. C. (1987) Non-human carbonyl hydrolase mutants, DNA sequences and vectors encoding same and hosts transformed with said vectors).
4. EP 0260105 (Arbige, M. V., Estell, D. A., Pepsin, M. J., Poulose, A. J. (1988) Preparation of enzymes having altered activity).
5. EP 0328229 (Van Eekelen, C. A. G., Mulleners, L. J. S. M., Van der Laan, J. C., Misset, O., Cuperus, R. A., Lensink, J. H. A. (1989) Novel proteolytic enzymes and their use in detergents).
6. JP 1137972 (Takagi, H., Takahashi, K., Momose, H., Morinaga, Y., Matsuzawa, H., Ota, T. (1989) New *subtilisin*, obtained by displacing one or two aminoacid(s) of wild *subtilisin*).
7. U.S. application Ser. No. 07/398,854, filed on Aug. 25, 1989
8. U.S. Pat. No. 4,853,871 (Pantoliano, M. W., Ladner, R. C. (1989) Computer-based method for designing stabilized proteins).
9. U.S. Pat. No. 4,908,773 (Pantoliano, M. L., Ladner, R. C. (1990) Computer designed stabilized proteins and method for producing same).
10. U.S. Pat. No. 4,914,031 (Zukowski, M. M., Stabinsky, Y., Levitt, M. (1990) Subtilisin analogs).
11. WO 87/04461 (Stabinsky, Y., Zukowski, M. M. (1987) Thermally stable and pH stable *subtilisin* analogs and method for production thereof).
12. WO 87/05050 (Bryan, P. N., Rollence, M. L., Pantoliano, M. W. (1987) Mutagenesis and screening method and product).
13. WO 88/07578 (Wells, J. A., Carter, P. J. (1988) Substrate assisted catalysis).
14. WO 88/08028 (Pantoliano, M. W., Finzel, B. C., Bryan, P. N. (1988) The engineering of electrostatic interactions at metal ion binding sites for the stabilization of proteins).
15. WO 88/08033 (Zurowski, M. M., Stabinsky, Y. (1988) Subtilisin analogs).
16. WO 89/06279 (Hastrup, S., Branner, S., Norris, F., Petersen, S. B., Nørskov-Lauridsen, L., Jensen, V. J., Aaslyng, D. (1989) Mutated *subtilisin* genes).
17. WO 89/09819 (Bryan, P. N., Pantoliano, M. W. (1989) Combinig mutations for stabilization of *subtilisin*).
18. WO 89/09830 (Bryan, P. N., Pantoliano, M. W. (1989) Subtilisin mutations).

JOURNAL AND BOOK REFERENCES

19. Atlas of Protein Sequence and Structure (1976) Vol. 5, Suppl. 2 (Dayhoff, M. O., ed., Natl. Biomed. Res. Found., Silver Springs, Md.)
20. Bernstein, F. C., Koetzle, T. F., Williams, G. J. B., Meyer, Jr., F. F., Brice, M. D., Rodgers, J. R., Kennard, O., Shimanouchi, T., Tasumi, M. (1977) The Protein Data Bank: a computer-based archival file for macromolecular structures. J. Mol. Biol. 112:535–542
21. Black, N. J., Jones, M. E. (1983) Inorganic phosphate determination in the presence of a labile organic phosphate: assay for carbamyl phosphate phosphatase activity. Anal. Biochem. 135:233–238
22. Bode, W., Papamokos, E. Musil, D., Seemueller, U., Fritz, H. (1986) Refined 1.2 Å crystal structure of the complex formed between *subtilisin* Carlsberg and the inhibitor eglin c. Molecular structure of eglin and its detailed interaction with *subtilisin*. EMBO J. 5:813–818
23. Bordo, D., Argos, P. (1991) Suggestions for 'safe' residue substitutions in site-directed mutagenesis. J. Mol. Biol. 217:721–729
24. Bornstein, P., Balian, G. (1977) Cleavage at Asn-Gly bonds with hydroxylamine. Methods Enzymol. 47:132–145
25. Bott, R., Ultsch, M., Kossiakoff, A., Graycar, T., Katz, B., Power, S. (1988) The three-dimensional structure of, *Bacillus amyloliquefaciens subtilisin* at 1.8 Å and an analysis of the structural consequences of peroxide inactivation. J. Biol. Chem. 263:7895–7906
26. Bowie, J. U., Reidhaar-Olson, J. F., Lim, W. A., Sauer, R. T. (1990) Deciphering the message in protein sequences: tolerance to amino acid substitutions. Science 247:1306–1310
27. Bryan, P. (1987) Somanase project. Office of Naval Research, Document No. AD-A182 669
28. Bryan, P., Pantoliano, M. W., Quill, S. G., Hsiao, H.-Y., Poulos, T. (1986) Site-directed mutagenesis and the role of the oxyanion hole in *subtilisin*. Proc. Natl. Acad. Sci. USA 83:3743–3745
29. Bryan, P. N., Rollence, M. L., Pantoliano, M. W., Wood, J., Finzel, B. C., Gilliland, G. L., Howard, A. J., Poulos, P. L. (1986) Proteases of enhanced stability: characterization of a thermostable variant of *subtilisin*. Proteins: struct. Funct. Genet. 1:326–334.
30. Carter, P., Bedouelle, H., Winter, G. (1985) Improved oligonucleotide site-directed mutagenesis using M13 vectors. Nucleic Acids Res. 13:4431–4443
31. Carter, P., Wells, J. A. (1987) Engineering enzyme specificity by 'substrate-assisted catalysis'. Science 237:394–399

32. Chothia, C. (1975) Structural invariants in protein folding. Nature 254:304–308
33. Cunningham, B. C., Wells, J. A. (1987) Improvement in the alkaline stability of subtilisin using an efficient random mutagenesis and screening procedure. Protein Eng. 1:319–325
34. DelMar, E. G., Largman, C., Brodrick, T. W., Geokas, M. C. (1979) A sensitive new substrate for chymotrypsin. Anal. Biochem. 99:316–320
35. Estell, D. A., Graycar, T. P., Wells, J. A. (1985) Engineering an enzyme by site-directed mutagenesis to be resistent to chemical oxidation. J. Biol. Chem. 260:6518–6521
36. Frömmel, C., Hausdorf, G., Höhne, W. E., Behnke, U., Rutloff, H. (1978) Characterization of a protease from *Thermoactinomyces vulgaris* (thermitase). 2. Single-step fine purification and protein-chemical characterization. Acta Biol. Med. Ger. 37:1193–1204
37. Goodford, P. J. (1985) A computational procedure for determining energetically favorable binding sites on biologically important macromolecules. J. Med. Chem. 28:849–857
38. Gornall, A. G., Bardawill, C. S., David, M. M. (1948) Determination of serum proteins by means of the biuret reaction. J. Biol. Chem. 177:751–766
39. Hines, J. C., Ray, D. S. (1980) Construction and characterization of new coliphage M13 cloning vectors. Gene 11:207–218
40. Jacobs, M., Eliasson, M., Uhlén, Flock, J.-I. (1985) Cloning, sequencing and expression of subtilisin Carlsberg from *Bacillus licheniformis*. Nucleic Acids Res. 13:8913–8926
41. Jany, K. -D., Mayer, B. (1985) Proteinase K from *Tritirachium album* Limber. I. Molecular mass and sequence around the active site serine residue. Biol. Chem. Hoppe-Seyler 366:485–492
42. Kabsch, W. (1976) A solution for the best rotation to relate two sets of vectors. Acta Cryst. A32:922–923
43. Kawamura, F., Doi, R. A. (1984) Construction of a *Bacillus subtilis* double mutant deficient in extracellular alkaline and neutral proteases. J. Bacteriol. 160:442–444
44. Kellis, J. T., Jr., Nyberg, K., Sali, D., Fersht, A. L. (1988) Contribution of hydrophobic interactions to protein stability. Nature 333:784–786
45. Kramer, W., Drutsa, V., Jansen, H.-W., Kramer, B., Pflugfelder, M., Fritz, H.-J. (1984) The gapped duplex DNA approach to oligonucleotide-directed mutation construction. Nucleic Acids Res. 12:9441–9456
46. Kunkel, T. A. (1985) Rapid and efficient site-specific mutagenesis without phenotypic selection. Proc. Natl. Acad. Sci. USA 82:488–492
47. Kurihara, M., Markland, F. S., Smith, E. L. (1972) Subtilisin Amylosacchariticus. III. Isolation and sequence of the chymotryptic peptides and the complete amino acid sequence. J. Biol. Chem. 247:5619–5631
48. Ladin, B., Hon, S., Markgraf, M., Mielenz, J., Wilson, R. (1990) The cloning and characterization of a *Bacillus lentus* alkaline protease. Society for Industrial Microbiology Annual Meeting, Abstract P60.
49. Leatherbarrow, R. J. (1987) ENZFITTER, Biosoft, Cambridge, UK
50. Marinus, M. G., Morris, N. R. (1974) Biological function for 6-methyladenine residues in the DNA of *Escherichia coli* K12. J. Mol. Biol. 85:309–322
51. Matthews, B. W., Nicholson, H., Becktel, W. J. (1987) Enhanced protein thermostability from site-directed mutations that decrease the entropy of unfolding. Proc. Natl. Acad. Sci. USA 84:6663–6667
52. Meloun, B., Baudyš, M., Kostka, V., Hausdorf, G. , Frömmel, C., Höhne, W. E. (1985) Complete primary structure of thermitase from *Thermoactinomyces vulgaris* and its structural features related to the subtilisin-type proteinases. FEBS Lett. 183:195–200
53. Menéndez-Arias, L., Argos, P. (1990) Engineering protein thermal stability. Sequence statistics point to residue substitutions in α-helices. J. Mol. Biol. 206:397–406
54. Mitchinson, C., Wells, J. A. (1989) Protein engineering of disulfide bonds in subtilisin BPN'. Biochemistry 28:4807–4815
55. Morinaga, Y., Franceschini, T., Inouye, S., Inouye, M. (1984) Improvement of oligonucleotide-directed site-specific mutagenesis using double-stranded plasmid DNA. Bio/Technology 2:636–639
56. Myers, E. W., Miller, W. (1988) Optimal alignments in linear space. Comput. Applic. Biosci. 4:11–17
57. Nedkov, P., Oberthür, W., Braunitzer, G. (1985) Determination of the complete amino-acid sequence of *subtilisin DY* and its comparison with the primary structures of the *subtilisins* BPN', Carlsberg and amylosacchariticus. Biol. Chem. Hoppe-Seyler 366:421–430
58. Norrander, J., Kempe, T., Messing, J. (1983) Construction of improved M13 vectors using oligonucleotide-directed mutagenesis. Gene 26:101–106
59. Pantoliano, M. W., Ladner, R. C., Bryan, P. N., Rollence, M. L., Wood, J. F., Poulos, T. L. (1987) Protein engineering of subtilisin BPN': enhanced stability through the introduction of two cysteines to form a disulfide bond. Biochemistry 26:2077–2082
60. Pantoliano, M. W., Whitlow, M., Wood, J. F., Dodd, S. W. Hardman, K. D., Rollence, M. L., Bryan, P. N. (1989) Large increases in general stability of subtilisin BPN' through incremental changes in the free energy of unfolding. Biochemistry 28:7205–7213
61. Pantoliano, M. W., Whitlow, M., Wood, J. F., Rollence, M. L., Finzel, B. C., Gilliland, G. L., Poulos, T. L., Bryan, P. N. (1988) The engineering of binding affinity at metal ion binding sites for the stabilization of proteins: subtilisin as a test case. Biochemistry 27:8311–8317
62. Pearson, W. R., Lipman, D. J. (1988) Improved tools for biological sequence comparison. Proc. Natl. Acad. Sci. USA 85:2444–2448
63. Ponder, J. W., Richards, F. M. (1987) Tertiary templates for proteins. Use of packing criteria in the enumeration of allowed sequences for different structural classes. J. Mol. Biol. 193:775–791)
64. Richards, F. M. (1977) Areas, volumes, packing, and protein structure. Annu. Rev. Biophys. Bioeng. 6:151–176
65. Rollence, M. L., Filpula, D., Pantoliano M. W., Bryan, P. N. (1988) Engineering thermostability in subtilisin BPN' by in vitro mutagenesis. C.R.C. Critical Rev. Biotechnol. 8:217–224
66. Russell, A. J., Fersht, A. R. (1987) Rational modification of enzyme catalysis by engineering surface charge. Nature 328:496–500
67. Russell, A. J., Thomas, P. G., Fersht, A. R. (1987) Electrostatic effects on modification of charged groups in the active site cleft of subtilisin by protein engineering. J. Mol. Biol. 193:803–813
68. Sandberg, W. S., Terwilliger, T. C. (1989) Influence of interior packing and hydrophobicity on the stability of a protein. Science 245:54–57
69. Sandberg, W. S., Terwilliger, T. C. (1991) Repacking protein interiors. Trends Biotechnol. 9:59–63
70. Stahl, M. L., Ferrari, E. (1984) Replacement of the *Bacillus subtilis* subtilisin structural gene with an in vitro-derived deletion mutation. J. Bacteriol. 158:411–418

71. Stanssens, P., Opsomer, C., McKeown, Y. M., Kramer, W., Zabeau, M., Fritz, H.-J. (1989) Efficient oligonucleotide-directed construction of mutations in expression vectors by the gapped duplex DNA method using alternating selectable markers. Nucleic Acids Res. 17:4441–4454)
72. Stauffer, C. F., Etson, D. (1969) The effect on *subtilisin* activity of oxidizing a methionine residue. J. Biol. Chem. 244:5333–5338
73. Sutcliffe, M. J., Haneef, I., Carney, D., Blundell, T. L. (1987) Knowledge based modelling of homologous proteins, part I: three-dimensional frameworks derived from the simultaneous superposition of multiple structures. Protein Eng. 1:377–384
74. Svendsen, I., Genov, N., Idakieva, K. (1986) Complete amino acid sequence of alkaline mesentericopeptidase. A *subtilisin* isolated from a strain of *Bacillus mesentericus*. FEBS Lett. 196:228–232
75. Takagi, H., Morinaga, Y., Ikemura, H., Inouye, M. (1988) Mutant *subtilisin* E with enhanced protease activity obtained by site-directed mutagenesis. J. Biol. Chem. 263:19592–19596
76. Takagi, H., Morinaga, Y., Ikemura, H., Inouye, M. (1989) The role of Pro-239 in the catalysis and heat stability of *subtilisin* E. J. Biochem. 105:953–956
77. Teplyakov, A. V., Kuranova, I. P., Harutyunyan, E. H., Vainshtein, B. K., Frömmel, C., Höhne, W. E., Wilson, K. S. (1990) Crystal structure of thermitase at 1.4 Å resolution. J. Mol. Biol. 214:261–279
78. Vasantha, N., Thompson, L. D., Rhodes, C., Banner, C., Nagle, J., Filpula, D. (1984) Genes for alkaline protease and neutral protease from *Bacillus amyloliquefaciens* contain a large open reading frame between the regions coding for signal sequence and mature protein. Bacteriol. 159:811–819
79. Wells, J. A., Cunningham, B. C., Graycar, T. P., Estell, D. A. (1986) Importance of hydrogen-bond formation in stabilizing the transition state of *subtilisin*. Phil. Trans. R. Soc. Lond. A 317:415–423
80. Wells, J. A., Cunningham, B. C., Graycar, T. P., Estell, D. A. (1987) Recruitment of substrate-specificity properties from one enzyme into a related one by protein engineering. Proc. Natl. Acad. Sci USA 84:5167–5171
81. Wells T. A., Powers, D. B. (1986) In vivo formation and stability of engineered disulfide bonds in *subtilisin*. J. Biol. Chem. 261:6564–6570
82. Wells, J. A., Powers, D. B., Bott, R. R., Graycar, T. P., Estell, D. A. (1987) Designing substrate specificity by protein engineering of electrostatic interactions. Proc. Natl. Acad. Sci. USA 84:1219–1223
83. Zell, R., Fritz, H.-J. (1987) DNA mismatch-repair in *Escherichia coli* counteracting the hydrolytic deamination of 5-methyl-cytosine residues. EMBO J. 6:1809–1815
84. Zoller, N. J., Smith, M. (1982) oligonucleotide-directed mutagenesis using M13-derived vectors: an efficient and general procedure for the production of point mutations in any fragment of DNA. Nucleic Acids Res. 10:6487–6500

What is claimed is:

1. A computer based method for identifying amino acid sites in a target protein which affect the stability of the target protein comprising the steps of (1) inputting the three dimensional coordinates of said target protein into a computer; (2) generating a probe-accessible surface of said target protein by probing the internal and external surfaces defined by the three dimensional coordinates of said protein with an uncharged probe molecule having a radius of about 0.9 to about 2.0 Å, wherein said probe-accessible surface has an external surface the interior of which contains one or more probe-accessible internal cavities; and (3) identifying the amino acids which make up the boundaries of the internal cavities, wherein said amino acids comprise a set of sites which when mutated affect the stability of the protein.

2. The computer based method of claim 1 wherein said target protein is *Bacillus lentus* DSM 5483 alkaline protease.

3. A computer based method for identifying amino acid sites in a target protein which affect the stability of the target protein comprising the steps of (1) inputting the three dimensional coordinates of said target protein into a computer; (2) generating a probe-accessible surface of said target protein by probing the internal and external surfaces defined by the three dimensional coordinates of said protein with an uncharged probe molecule having a radius of about 0.9 to about 2.0 Å, wherein said probe-accessible surface has an external surface the interior of which contains one or more probe-accessible internal cavities; (3) aligning said three dimensional coordinates of said target protein and a reference protein by moving the three dimensional coordinates of said reference protein into the coordinate frame of said target protein; and (4) identifying an amino acid in said reference protein whose side chain lies outside said external surface of said probe-accessible surface or inside said internal cavities of said probe-accessible surface.

4. The computer based method of claim 3 wherein said target protein is *Bacillus lentus* DSM 5483 alkaline protease.

5. The computer based method of claim 3 wherein said reference protein is any protein for which a three dimensional structure is available which is homologous to the target protein.

6. The computer based method of claim 3 wherein said reference protein is thermitase.

7. The computer based method of claim 3 wherein said reference protein is *subtilisin* Carlsberg.

8. The computer based method of claim 3 wherein said reference protein is *subtilisin* BPN'.

9. The computer based method of claim 3 wherein said reference protein is proteinase K.

10. A computer based method for affecting the stability of a protein comprising the steps of: (1) inputting the three dimensional coordinates of said protein into a computer; (2) generating a probe-accessible surface of said protein by probing the internal and external surfaces defined by the coordinates of said protein with an uncharged probe molecule having a radius of about 0.9 to about 2.0 Å, wherein said probe-accessible surface has an external surface the interior of which contains one or more probe-accessible internal cavities; (3) identifying the amino acids which make up the boundaries of the internal cavities, wherein said amino acids comprise a set of sites which when mutated affect the stability of the protein; (4) identifying an amino acid mutation which changes the volume of said internal cavities; (5) determining if said amino acid in said protein can be mutated without creating unacceptable steric interactions; and (6) replacing the amino acid in said protein by site directed mutagenesis of the gene which expresses said target protein.

11. The computer based method of claim 10 wherein said target protein is *Bacillus lentus* DSM 5483 alkaline protease.

12. The computer based method of claim 10 wherein said reference protein is any protein for which a three dimensional structure is available which is substantially homologous to the target protein.

13. The computer based method of claim 10 wherein said reference protein is thermitase.

14. The computer based method of claim 10 wherein said reference protein is *subtilisin* Carlsberg.

15. The computer based method of claim 10 wherein said reference protein is *subtilisin* BPN'.

16. The computer based method of claim 10 wherein said reference protein is proteinase K.

17. A computer based method for changing the stability of a target protein comprising the steps of (1) inputting the three dimensional coordinates of said target protein into a computer; (2) generating a probe-accessible surface of said target protein by probing the internal and external surfaces defined by the coordinates of said target protein with an uncharged probe molecule having a radius of about 0.9 to about 2.0 Å, wherein said probe-accessible surface has an external surface the interior of which contains one or more probe-accessible internal cavities; (3) aligning said three-dimensional coordinates of said target protein and a reference protein by moving the three dimensional coordinates of said reference protein into the coordinate frame of said target protein; (4) identifying an amino acid in said reference protein whose side chain lies outside said external surface of said probe-accessible surface or inside said internal cavities of said probe-accessible surface; (5) identifying the amino acid in said target protein which occupies the equivalent position as said amino acid in said reference protein; (6) determining if said amino acid in said target protein can be changed without creating unacceptable steric effects; and (7) replacing the amino acid in said target protein with the corresponding amino acid in the equivalent position in said reference protein by site-directed mutagenesis of the gene which expresses said target protein.

18. The computer based method of claim 17 wherein said target protein is *Bacillus lentus* DSM 5483 alkaline protease.

19. The computer based method of claim 17 wherein said reference protein is any protein for which a three dimensional structure is available which is homologous to the target protein.

20. The computer based method of claim 17 wherein said reference protein is thermitase.

21. The computer based method of claim 17 wherein said reference protein is *subtilisin* Carlsberg.

22. The computer based method of claim 17 wherein said reference protein is *subtilisin* BPN'.

23. The computer based method of claim 17 wherein said reference protein is proteinase K.

* * * * *

UNITED STATES PATENT AND TRADEMARK OFFICE
CERTIFICATE OF CORRECTION

PATENT NO. : 6,403,331 B1
DATED : June 11, 2002
INVENTOR(S) : Christianson et al.

It is certified that error appears in the above-identified patent and that said Letters Patent is hereby corrected as shown below:

<u>Title page,</u>
Item [73], Assignee, delete "Konnarditgesellschaft" and insert
-- Kommanditgesellschaft --.

Signed and Sealed this

Twenty-eighth Day of March, 2006

JON W. DUDAS
*Director of the United States Patent and Trademark Office*

```
                       SEQUENCE LISTING (1) GENERAL INFORMATION:

(iii) NUMBER OF SEQUENCES: 104

(2) INFORMATION FOR SEQ ID NO:1:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Serine P rotease
        (B) STRAIN: Bacillus l entus  DSM 5843

(vii) IMMEDIATE SOURCE:
        (B) CLONE: S3T, V4I, A188P, V193M, V199I (xi) SEQUENCE DESCRIPTION: SEQ ID NO:1:

Ala Gln Thr Ile Pro Trp Gly Ile Ser Arg V al Gln Ala Pro Ala Ala
1               5                   10                  15

His Asn Arg Gly Leu Thr Gly Ser Gly Val L ys Val Ala Val Leu Asp
            20                  25                  30

Thr Gly Ile Ser Thr His Pro Asp Leu Asn I le Arg Gly Gly Ala Ser
        35                  40                  45

Phe Val Pro Gly Glu Pro Ser Thr Gln Asp G ly Asn Gly His Gly Thr
    50                  55                  60
```

```
His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Arg Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
            115                 120                 125

Pro Ser Ala Thr Leu Glu Gln Ala Val Asn Ser Ala Thr Ser Arg Gly
            130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Pro Gly Leu Asp Ile
            180                 185                 190

Met Ala Pro Gly Val Asn Ile Gln Ser Thr Tyr Pro Gly Ser Thr Tyr
            195                 200                 205

Ala Ser Leu Asn Gly Thr Ser Met Ala Thr Pro His Val Ala Gly Ala
            210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265

(2) INFORMATION FOR SEQ ID NO:2:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Serine Protease
        (B) STRAIN: Bacillus lentus DSM 5843

(vii) IMMEDIATE SOURCE:
        (B) CLONE: S3T, A188P, V193M, V199I (xi) SEQUENCE DESCRIPTION: SEQ ID NO:2:

Ala Gln Thr Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
                20                  25                  30

Thr Gly Ile Ser Thr His Pro Asp Leu Asn Ile Arg Gly Gly Ala Ser
            35                  40                  45

Phe Val Pro Gly Glu Pro Ser Thr Gln Asp Gly Asn Gly His Gly Thr
        50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95
```

```
Asp Gly Arg Gly Ala Ile Ser Ser Ile Ala G ln Gly Leu Glu Trp Ala
            100                 105                 110

Gly Asn Asn Gly Met His Val Ala Asn Leu S er Leu Gly Ser Pro Ser
        115                 120                 125

Pro Ser Ala Thr Leu Glu Gln Ala Val Asn S er Ala Thr Ser Arg Gly
        130                 135                 140

Val Leu Val Val Ala Ser Gly Asn Ser G ly Ala Ser Ser Ile Ser
145                 150                 155                 160

Tyr Pro Ala Arg Tyr Ala Asn Ala Met Ala V al Gly Ala Thr Asp Gln
            165                 170                 175

Asn Asn Asn Arg Ala Ser Phe Ser Gln Tyr G ly Pro Gly Leu Asp Ile
            180                 185                 190

Met Ala Pro Gly Val Asn Ile Gln Ser Thr T yr Pro Gly Ser Thr Tyr
        195                 200                 205

Ala Ser Leu Asn Gly Thr Ser Met Ala Thr P ro His Val Ala Gly Ala
        210                 215                 220

Ala Ala Leu Val Lys Gln Lys Asn Pro Ser T rp Ser Asn Val Gln Ile
225                 230                 235                 240

Arg Asn His Leu Lys Asn Thr Ala Thr Ser L eu Gly Ser Thr Asn Leu
            245                 250                 255

Tyr Gly Ser Gly Leu Val Asn Ala Glu Ala A la Thr Arg
            260                 265

(2) INFORMATION FOR SEQ ID NO:3:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Serine P rotease
        (B) STRAIN: Bacillus l entus  DSM 5843

(vii) IMMEDIATE SOURCE:
        (B) CLONE: V4I, A188P,  V193M, V199I (

-continued

```
                  115                  120                      125
Pro Ser Ala Thr Leu Glu Gln Ala Val Asn Ser Ala Thr Ser Arg Gly
            130                 135                 140
Val Leu Val Val Ala Ala Ser Gly Asn Ser Gly Ala Ser Ser Ile Ser
145                 150                 155                     160
Tyr Pro Ala Arg Tyr Ala Asn Ala Met Ala Val Gly Ala Thr Asp Gln
                165                 170                 175
Asn Asn Asn Arg Ala Ser Phe Ser Gln Tyr Gly Pro Gly Leu Asp Ile
            180                 185                 190
Met Ala Pro Gly Val Asn Ile Gln Ser Thr Tyr Pro Gly Ser Thr Tyr
            195                 200                 205
Ala Ser Leu Asn Gly Thr Ser Met Ala Thr Pro His Val Ala Gly Ala
        210                 215                 220
Ala Ala Leu Val Lys Gln Lys Asn Pro Ser Trp Ser Asn Val Gln Ile
225                 230                 235                     240
Arg Asn His Leu Lys Asn Thr Ala Thr Ser Leu Gly Ser Thr Asn Leu
                245                 250                 255
Tyr Gly Ser Gly Leu Val Asn Ala Glu Ala Ala Thr Arg
            260                 265
```

(2) INFORMATION FOR SEQ ID NO:4:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Serine Protease
        (B) STRAIN: Bacillus lentus DSM 5843

(vii) IMMEDIATE SOURCE:
        (B) CLONE: S139Y, A188P, V193M, V199I (xi) SEQUENCE DESCRIPTION: SEQ ID NO:4:

```
Ala Gln Ser Val Pro Trp Gly Ile Ser Arg Val Gln Ala Pro Ala Ala
1               5                   10                  15
His Asn Arg Gly Leu Thr Gly Ser Gly Val Lys Val Ala Val Leu Asp
            20                  25                  30
Thr Gly Ile Ser Thr His Pro Asp Leu Asn Ile Arg Gly Gly Ala Ser
        35                  40                  45
Phe Val Pro Gly Glu Pro Ser Thr Gln Asp Gly Asn Gly His Gly Thr
    50                  55                  60
His Val Ala Gly Thr Ile Ala Ala Leu Asn Asn Ser Ile Gly Val Leu
65                  70                  75                  80
Gly Val Ala Pro Ser Ala Glu Leu Tyr Ala Val Lys Val Leu Gly Ala
                85                  90                  95
Asp Gly Arg Gly Ala Ile Ser Ser Ile Ala Gln Gly Leu Glu Trp Ala
            100                 105                 110
Gly Asn Asn Gly Met His Val Ala Asn Leu Ser Leu Gly Ser Pro Ser
        115                 120                 125
Pro Ser Ala Thr Leu Glu Gln Ala Val Asn Tyr Ala Thr Ser Arg Gly
    130                 135                 140
```

-continued

```
Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Pro Gly Leu Asp Ile
                180                 185                 190

Met Ala Pro Gly Val Asn Ile Gln Ser Thr Tyr Pro Gly Ser Thr Tyr
                195                 200                 205

Ala Ser Leu Asn Gly Thr Ser Met Ala Thr Pro His Val Ala Gly Ala
                210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
                260                 265
```

(2) INFORMATION FOR SEQ ID NO:5:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Serine Protease
        (B) STRAIN: Bacillus lentus DSM 5843

(vii) IMMEDIATE SOURCE:
        (B) CLONE: S130T, S139Y, A188P, V193M, V199I (xi) SEQUENCE DESCRIPTION: SEQ ID NO:5:

```
Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
                20                  25                  30

Thr Gly Ile Ser Thr His Pro Asp Leu Asn Ile Arg Gly Gly Ala Ser
                35                  40                  45

Phe Val Pro Gly Glu Pro Ser Thr Gln Asp Gly Asn Gly His Gly Thr
50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Arg Gly Ala Ile Ser Ser Ile Ala Gln Gly Leu Glu Trp Ala
                100                 105                 110

Gly Asn Asn Gly Met His Val Ala Asn Leu Ser Leu Gly Ser Pro Ser
                115                 120                 125

Pro Thr Ala Thr Leu Glu Gln Ala Val Asn Tyr Ala Thr Ser Arg Gly
                130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175
```

```
Asn Asn Asn Arg Ala Ser Phe Ser Gln Tyr G ly Pro Gly Leu Asp Ile
            180                 185                 190

Met Ala Pro Gly Val Asn Ile Gln Ser Thr T yr Pro Gly Ser Thr Tyr
            195                 200                 205

Ala Ser Leu Asn Gly Thr Ser Met Ala Thr P ro His Val Ala Gly Ala
            210                 215                 220

Ala Ala Leu Val Lys Gln Lys Asn Pro Ser T rp Ser Asn Val Gln Ile
225                 230                 235                 240

Arg Asn His Leu Lys Asn Thr Ala Thr Ser L eu Gly Ser Thr Asn Leu
            245                 250                 255

Tyr Gly Ser Gly Leu Val Asn Ala Glu Ala A la Thr Arg
            260                 265

(2) INFORMATION FOR SEQ ID NO:6:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Serine P rotease
        (B) STRAIN: Bacillus l entus  DSM 5843

(vii) IMMEDIATE SOURCE:
        (B) CLONE: A188P, V193 M, V199I (xi) SEQUENCE DESCRIPTION: SEQ ID NO:6:

Ala Gln Ser Val Pro Trp Gly Ile Ser Arg V al Gln Ala Pro Ala Ala
1                   5                  10                  15

His Asn Arg Gly Leu Thr Gly Ser Gly Val L ys Val Ala Val Leu Asp
            20                  25                  30

Thr Gly Ile Ser Thr His Pro Asp Leu Asn I le Arg Gly Gly Ala Ser
            35                  40                  45

Phe Val Pro Gly Glu Pro Ser Thr Gln Asp G ly Asn Gly His Gly Thr
            50                  55                  60

His Val Ala Gly Thr Ile Ala Ala Leu Asn A sn Ser Ile Gly Val Leu
65                  70                  75                  80

Gly Val Ala Pro Ser Ala Glu Leu Tyr Ala V al Lys Val Leu Gly Ala
            85                  90                  95

Asp Gly Arg Gly Ala Ile Ser Ser Ile Ala G ln Gly Leu Glu Trp Ala
            100                 105                 110

Gly Asn Asn Gly Met His Val Ala Asn Leu S er Leu Gly Ser Pro Ser
            115                 120                 125

Pro Ser Ala Thr Leu Glu Gln Ala Val Asn S er Ala Thr Ser Arg Gly
            130                 135                 140

Val Leu Val Val Ala Ala Ser Gly Asn Ser G ly Ala Ser Ser Ile Ser
145                 150                 155                 160

Tyr Pro Ala Arg Tyr Ala Asn Ala Met Ala V al Gly Ala Thr Asp Gln
            165                 170                 175

Asn Asn Asn Arg Ala Ser Phe Ser Gln Tyr G ly Pro Gly Leu Asp Ile
            180                 185                 190

Met Ala Pro Gly Val Asn Ile Gln Ser Thr T yr Pro Gly Ser Thr Tyr
```

```
                195                 200                 205
Ala Ser Leu Asn Gly Thr Ser Met Ala Thr Pro His Val Ala Gly Ala
        210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
                260                 265
```

(2) INFORMATION FOR SEQ ID NO:7:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Serine Protease
        (B) STRAIN: Bacillus lentus DSM 5843

(vii) IMMEDIATE SOURCE:
        (B) CLONE: S3T, A188P, V193M (xi) SEQUENCE DESCRIPTION: SEQ ID NO:7:

```
Ala Gln Thr Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
                20                  25                  30

Thr Gly Ile Ser Thr His Pro Asp Leu Asn Ile Arg Gly Gly Ala Ser
                35                  40                  45

Phe Val Pro Gly Glu Pro Ser Thr Gln Asp Gly Asn Gly His Gly Thr
        50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Arg Gly Ala Ile Ser Ser Ile Ala Gln Gly Leu Glu Trp Ala
                100                 105                 110

Gly Asn Asn Gly Met His Val Ala Asn Leu Ser Leu Gly Ser Pro Ser
                115                 120                 125

Pro Ser Ala Thr Leu Glu Gln Ala Val Asn Ser Ala Thr Ser Arg Gly
        130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Pro Gly Leu Asp Ile
                180                 185                 190

Met Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
        210                 215                 220
```

```
Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
                260                 265
```

(2) INFORMATION FOR SEQ ID NO:8:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Serine Protease
        (B) STRAIN: Bacillus lentus DSM 5843

(vii) IMMEDIATE SOURCE:
        (B) CLONE: S157T (xi) SEQUENCE DESCRIPTION: SEQ ID NO:8:

```
Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
                20                  25                  30

Thr Gly Ile Ser Thr His Pro Asp Leu Asn Ile Arg Gly Gly Ala Ser
            35                  40                  45

Phe Val Pro Gly Glu Pro Ser Thr Gln Asp Gly Asn Gly His Gly Thr
        50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Arg Gly Ala Ile Ser Ser Ile Ala Gln Gly Leu Glu Trp Ala
                100                 105                 110

Gly Asn Asn Gly Met His Val Ala Asn Leu Ser Leu Gly Ser Pro Ser
                115                 120                 125

Pro Ser Ala Thr Leu Glu Gln Ala Val Asn Ser Ala Thr Ser Arg Gly
130                 135                 140

Val Leu Val Val Ala Ala Ser Gly Asn Ser Gly Ala Thr Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
                180                 185                 190

Val Ala Pro Gly Val Asn Val Gln Ser Thr Tyr Pro Gly Ser Thr Tyr
                195                 200                 205

Ala Ser Leu Asn Gly Thr Ser Met Ala Thr Pro His Val Ala Gly Ala
                210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255
```

```
Tyr Gly Ser Gly Leu Val Asn Ala Glu Ala Ala Thr Arg
            260                 265
```

(2) INFORMATION FOR SEQ ID NO:9:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Serine P rotease
        (B) STRAIN: Bacillus l entus DSM 5843

(vii) IMMEDIATE SOURCE:
        (B) CLONE: A188P, V193 M (xi) SEQUENCE DESCRIPTION: SEQ ID NO:9:

```
Ala Gln Ser Val Pro Trp Gly Ile Ser Arg V al Gln Ala Pro Ala Ala
1               5                  10                  15

His Asn Arg Gly Leu Thr Gly Ser Gly Val L ys Val Ala Val Leu Asp
            20                  25                  30

Thr Gly Ile Ser Thr His Pro Asp Leu Asn I le Arg Gly Gly Ala Ser
        35                  40                  45

Phe Val Pro Gly Glu Pro Ser Thr Gln Asp G ly Asn Gly His Gly Thr
    50                  55                  60

His Val Ala Gly Thr Ile Ala Ala Leu Asn A sn Ser Ile Gly Val Leu
65                  70                  75                  80

Gly Val Ala Pro Ser Ala Glu Leu Tyr Ala V al Lys Val Leu Gly Ala
                85                  90                  95

Asp Gly Arg Gly Ala Ile Ser Ser Ile Ala G ln Gly Leu Glu Trp Ala
            100                 105                 110

Gly Asn Asn Gly Met His Val Ala Asn Leu S er Leu Gly Ser Pro Ser
        115                 120                 125

Pro Ser Ala Thr Leu Glu Gln Ala Val Asn S er Ala Thr Ser Arg Gly
    130                 135                 140

Val Leu Val Val Ala Ala Ser Gly Asn Ser G ly Ala Ser Ser Ile Ser
145                 150                 155                 160

Tyr Pro Ala Arg Tyr Ala Asn Ala Met Ala V al Gly Ala Thr Asp Gln
                165                 170                 175

Asn Asn Asn Arg Ala Ser Phe Ser Gln Tyr G ly Pro Gly Leu Asp Ile
            180                 185                 190

Met Ala Pro Gly Val Asn Val Gln Ser Thr T yr Pro Gly Ser Thr Tyr
        195                 200                 205

Ala Ser Leu Asn Gly Thr Ser Met Ala Thr P ro His Val Ala Gly Ala
    210                 215                 220

Ala Ala Leu Val Lys Gln Lys Asn Pro Ser T rp Ser Asn Val Gln Ile
225                 230                 235                 240

Arg Asn His Leu Lys Asn Thr Ala Thr Ser L eu Gly Ser Thr Asn Leu
                245                 250                 255

Tyr Gly Ser Gly Leu Val Asn Ala Glu Ala A la Thr Arg
            260                 265
```

(2) INFORMATION FOR SEQ ID NO:10:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Serine P rotease
        (B) STRAIN: Bacillus l entus  DSM 5843

(vii) IMMEDIATE SOURCE:
        (B) CLONE: A188P (xi) SEQUENCE DESCRIPTION: SEQ ID NO:10:

```
Ala Gln Ser Val Pro Trp Gly Ile Ser Arg V al Gln Ala Pro Ala Ala
1               5                  10                  15

His Asn Arg Gly Leu Thr Gly Ser Gly Val L ys Val Ala Val Leu Asp
            20                  25                  30

Thr Gly Ile Ser Thr His Pro Asp Leu Asn I le Arg Gly Gly Ala Ser
        35                  40                  45

Phe Val Pro Gly Glu Pro Ser Thr Gln Asp G ly Asn Gly His Gly Thr
    50                  55                  60

His Val Ala Gly Thr Ile Ala Ala Leu Asn A sn Ser Ile Gly Val Leu
65                  70                  75                  80

Gly Val Ala Pro Ser Ala Glu Leu Tyr Ala V al Lys Val Leu Gly Ala
                85                  90                  95

Asp Gly Arg Gly Ala Ile Ser Ser Ile Ala G ln Gly Leu Glu Trp Ala
            100                 105                 110

Gly Asn Asn Gly Met His Val Ala Asn Leu S er Leu Gly Ser Pro Ser
        115                 120                 125

Pro Ser Ala Thr Leu Glu Gln Ala Val Asn S er Ala Thr Ser Arg Gly
    130                 135                 140

Val Leu Val Val Ala Ala Ser Gly Asn Ser G ly Ala Ser Ser Ile Ser
145                 150                 155                 160

Tyr Pro Ala Arg Tyr Ala Asn Ala Met Ala V al Gly Ala Thr Asp Gln
                165                 170                 175

Asn Asn Asn Arg Ala Ser Phe Ser Gln Tyr G ly Pro Gly Leu Asp Ile
            180                 185                 190

Val Ala Pro Gly Val Asn Val Gln Ser Thr T yr Pro Gly Ser Thr Tyr
        195                 200                 205

Ala Ser Leu Asn Gly Thr Ser Met Ala Thr P ro His Val Ala Gly Ala
    210                 215                 220

Ala Ala Leu Val Lys Gln Lys Asn Pro Ser T rp Ser Asn Val Gln Ile
225                 230                 235                 240

Arg Asn His Leu Lys Asn Thr Ala Thr Ser L eu Gly Ser Thr Asn Leu
                245                 250                 255

Tyr Gly Ser Gly Leu Val Asn Ala Glu Ala A la Thr Arg
            260                 265
```

(2) INFORMATION FOR SEQ ID NO:11:

(i) SEQUENCE CHARACTERISTICS:
        (A) LENGTH: 269 amino acids
        (B) TYPE: amino acid (D) TOPOLOGY: unknown (ii) MOLECULE TYPE: protein (iii) HYPOTHETICAL: NO (iv) ANTI-SENSE: NO (vi) ORIGINAL SOURCE:
            (A) ORGANISM: Serine P rotease
            (B) STRAIN: Bacillus l entus  DSM 5843

(vii) IMMEDIATE SOURCE:
            (B) CLONE: S3T, V4I, A188P, V193M (xi) SEQUENCE DESCRIPTION: SEQ ID NO:11:

```
Ala Gln Thr Ile Pro Trp Gly Ile Ser Arg V al Gln Ala Pro Ala Ala
1               5                   10                  15

His Asn Arg Gly Leu Thr Gly Ser Gly Val L ys Val Ala Val Leu Asp
            20                  25                  30

Thr Gly Ile Ser Thr His Pro Asp Leu Asn I le Arg Gly Gly Ala Ser
        35                  40                  45

Phe Val Pro Gly Glu Pro Ser Thr Gln Asp G ly Asn Gly His Gly Thr
    50                  55                  60

His Val Ala Gly Thr Ile Ala Ala Leu Asn A sn Ser Ile Gly Val Leu
65                  70                  75                  80

Gly Val Ala Pro Ser Ala Glu Leu Tyr Ala V al Lys Val Leu Gly Ala
                85                  90                  95

Asp Gly Arg Gly Ala Ile Ser Ser Ile Ala G ln Gly Leu Glu Trp Ala
            100                 105                 110

Gly Asn Asn Gly Met His Val Ala Asn Leu S er Leu Gly Ser Pro Ser
        115                 120                 125

Pro Ser Ala Thr Leu Glu Gln Ala Val Asn S er Ala Thr Ser Arg Gly
    130                 135                 140

Val Leu Val Val Ala Ala Ser Gly Asn Ser G ly Ala Ser Ser Ile Ser
145                 150                 155                 160

Tyr Pro Ala Arg Tyr Ala Asn Ala Met Ala V al Gly Ala Thr Asp Gln
                165                 170                 175

Asn Asn Asn Arg Ala Ser Phe Ser Gln Tyr G ly Pro Gly Leu Asp Ile
            180                 185                 190

Met Ala Pro Gly Val Asn Val Gln Ser Thr T yr Pro Gly Ser Thr Tyr
        195                 200                 205

Ala Ser Leu Asn Gly Thr Ser Met Ala Thr P ro His Val Ala Gly Ala
    210                 215                 220

Ala Ala Leu Val Lys Gln Lys Asn Pro Ser T rp Ser Asn Val Gln Ile
225                 230                 235                 240

Arg Asn His Leu Lys Asn Thr Ala Thr Ser L eu Gly Ser Thr Asn Leu
                245                 250                 255

Tyr Gly Ser Gly Leu Val Asn Ala Glu Ala A la Thr Arg
            260                 265
```

(2) INFORMATION FOR SEQ ID NO:12:

(i) SEQUENCE CHARACTERISTICS:
(A) LENGTH: 269 amino acids
(B) TYPE: amino acid
(D) TOPOLOGY: unknown (ii) MOLECULE TYPE: protein (iii) HYPOTHETICAL: NO (iv) ANTI-SENSE: NO (vi) ORIGINAL SOURCE:
    (A) ORGANISM: Serine P rotease
    (B) STRAIN: Bacillus l entus  DSM 5843

(vii) IMMEDIATE SOURCE:
    (B) CLONE: V193M (xi) SEQUENCE DESCRIPTION: SEQ ID NO:12:

```
Ala Gln Ser Val Pro Trp Gly Ile Ser Arg V al Gln Ala Pro Ala Ala
 1               5                  10                  15

His Asn Arg Gly Leu Thr Gly Ser Gly Val L ys Val Ala Val Leu Asp
            20                  25                  30

Thr Gly Ile Ser Thr His Pro Asp Leu Asn I le Arg Gly Gly Ala Ser
        35                  40                  45

Phe Val Pro Gly Glu Pro Ser Thr Gln Asp G ly Asn Gly His Gly Thr
    50                  55                  60

His Val Ala Gly Thr Ile Ala Ala Leu Asn A sn Ser Ile Gly Val Leu
65                  70                  75                  80

Gly Val Ala Pro Ser Ala Glu Leu Tyr Ala V al Lys Val Leu Gly Ala
                85                  90                  95

Asp Gly Arg Gly Ala Ile Ser Ser Ile Ala G ln Gly Leu Glu Trp Ala
            100                 105                 110

Gly Asn Asn Gly Met His Val Ala Asn Leu S er Leu Gly Ser Pro Ser
        115                 120                 125

Pro Ser Ala Thr Leu Glu Gln Ala Val Asn S er Ala Thr Ser Arg Gly
    130                 135                 140

Val Leu Val Val Ala Ala Ser Gly Asn Ser G ly Ala Ser Ser Ile Ser
145                 150                 155                 160

Tyr Pro Ala Arg Tyr Ala Asn Ala Met Ala V al Gly Ala Thr Asp Gln
                165                 170                 175

Asn Asn Asn Arg Ala Ser Phe Ser Gln Tyr G ly Ala Gly Leu Asp Ile
            180                 185                 190

Met Ala Pro Gly Val Asn Val Gln Ser Thr T yr Pro Gly Ser Thr Tyr
        195                 200                 205

Ala Ser Leu Asn Gly Thr Ser Met Ala Thr P ro His Val Ala Gly Ala
    210                 215                 220

Ala Ala Leu Val Lys Gln Lys Asn Pro Ser T rp Ser Asn Val Gln Ile
225                 230                 235                 240

Arg Asn His Leu Lys Asn Thr Ala Thr Ser L eu Gly Ser Thr Asn Leu
                245                 250                 255

Tyr Gly Ser Gly Leu Val Asn Ala Glu Ala A la Thr Arg
            260                 265
```

(2) INFORMATION FOR SEQ ID NO (B) STRAIN: Bacillus lentus DSM 5843

(vii) IMMEDIATE SOURCE:
        (B) CLONE: S104T (xi) SEQUENCE D

-continued (xi) SEQUENCE DESCRIPTION: SEQ ID NO:14:

```
Ala Gln Ser Val Pro Trp Gly Ile Ser Arg Val Gln Ala Pro Ala Ala
1               5                  10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
50                  55                  60

His Val Ala Gly Val Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Arg Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265
```

(2) INFORMATION FOR SEQ ID NO:15:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Serine Protease
        (B) STRAIN: Bacillus lentus DSM 5843

(vii) IMMEDIATE SOURCE:
        (B) CLONE: V4I, A188P, V193M (xi) SEQUENCE DESCRIPTION: SEQ ID NO:15:

```
Ala Gln Ser Ile Pro Trp Gly Ile Ser Arg Val Gln Ala Pro Ala Ala
1               5                  10                  15
```

```
His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
            35                  40                  45

Phe Val Pro Gly Glu Pro Ser Thr Gln Asp Gly Asn Gly His Gly Thr
 50                  55                  60

His Val Ala Gly Thr Ile Ala Ala Leu Asn Asn Ser Ile Gly Val Leu
 65                  70                  75                  80

Gly Val Ala Pro Ser Ala Glu Leu Tyr Ala Val Lys Val Leu Gly Ala
                85                  90                  95

Asp Gly Arg Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
            115                 120                 125

Pro Ser Ala Thr Leu Glu Gln Ala Val Asn Ser Ala Thr Ser Arg Gly
            130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Pro Gly Leu Asp Ile
            180                 185                 190

Met Ala Pro Gly Val Asn Val Gln Ser Thr Tyr Pro Gly Ser Thr Tyr
            195                 200                 205

Ala Ser Leu Asn Gly Thr Ser Met Ala Thr Pro His Val Ala Gly Ala
            210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265

(2) INFORMATION FOR SEQ ID NO:16:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
         (A) ORGANISM: Serine Protease
         (B) STRAIN: Bacillus lentus DSM 5843

(vii) IMMEDIATE SOURCE:
          (B) CLONE: A224V (xi) SEQUENCE DESCRIPTION: SEQ ID NO:16:

Ala Gln Ser Val Pro Trp Gly Ile Ser Arg Val Gln Ala Pro Ala Ala
 1               5                  10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
            35                  40                  45
```

-continued

Phe Val Pro Gly Glu Pro Ser Thr Gln Asp Gly Asn Gly His Gly Thr
        50                   55                   60

His Val Ala Gly Thr Ile Ala Ala Leu Asn Asn Ser Ile Gly Val Leu
 65                   70                   75                   80

Gly Val Ala Pro Ser Ala Glu Leu Tyr Ala Val Lys Val Leu Gly Ala
                85                   90                   95

Asp Gly Arg Gly Ala Ile Ser Ser Ile Ala Gln Gly Leu Glu Trp Ala
                100                  105                 110

Gly Asn Asn Gly Met His Val Ala Asn Leu Ser Leu Gly Ser Pro Ser
                115                  120                 125

Pro Ser Ala Thr Leu Glu Gln Ala Val Asn Ser Ala Thr Ser Arg Gly
                130                  135                 140

Val Leu Val Val Ala Ala Ser Gly Asn Ser Gly Ala Ser Ser Ile Ser
145                  150                  155                 160

Tyr Pro Ala Arg Tyr Ala Asn Ala Met Ala Val Gly Ala Thr Asp Gln
                165                  170                 175

Asn Asn Asn Arg Ala Ser Phe Ser Gln Tyr Gly Ala Gly Leu Asp Ile
                180                  185                 190

Val Ala Pro Gly Val Asn Val Gln Ser Thr Tyr Pro Gly Ser Thr Tyr
                195                  200                 205

Ala Ser Leu Asn Gly Thr Ser Met Ala Thr Pro His Val Ala Gly Val
                210                  215                 220

Ala Ala Leu Val Lys Gln Lys Asn Pro Ser Trp Ser Asn Val Gln Ile
225                  230                  235                 240

Arg Asn His Leu Lys Asn Thr Ala Thr Ser Leu Gly Ser Thr Asn Leu
                245                  250                 255

Tyr Gly Ser Gly Leu Val Asn Ala Glu Ala Ala Thr Arg
                260                  265

(2) INFORMATION FOR SEQ ID NO:17:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Serine Protease
        (B) STRAIN: Bacillus lentus DSM 5843

(vii) IMMEDIATE SOURCE:
        (B) CLONE: V199I (xi) SEQUENCE DESCRIPTION: SEQ ID NO:17:

Ala Gln Ser Val Pro Trp Gly Ile Ser Arg Val Gln Ala Pro Ala Ala
 1                    5                   10                  15

His Asn Arg Gly Leu Thr Gly Ser Gly Val Lys Val Ala Val Leu Asp
                20                   25                   30

Thr Gly Ile Ser Thr His Pro Asp Leu Asn Ile Arg Gly Gly Ala Ser
                35                   40                   45

Phe Val Pro Gly Glu Pro Ser Thr Gln Asp Gly Asn Gly His Gly Thr
        50                   55                   60

His Val Ala Gly Thr Ile Ala Ala Leu Asn Asn Ser Ile Gly Val Leu

```
65                      70                      75                      80
Gly Val Ala Pro Ser Ala Glu Leu Tyr Ala V al Lys Val Leu Gly Ala
                    85                      90                      95
Asp Gly Arg Gly Ala Ile Ser Ser Ile Ala G ln Gly Leu Glu Trp Ala
                100                     105                     110
Gly Asn Asn Gly Met His Val Ala Asn Leu S er Leu Gly Ser Pro Ser
            115                     120                     125
Pro Ser Ala Thr Leu Glu Gln Ala Val Asn S er Ala Thr Ser Arg Gly
        130                     135                     140
Val Leu Val Val Ala Ala Ser Gly Asn Ser G ly Ala Ser Ser Ile Ser
145                     150                     155                     160
Tyr Pro Ala Arg Tyr Ala Asn Ala Met Ala V al Gly Ala Thr Asp Gln
                165                     170                     175
Asn Asn Asn Arg Ala Ser Phe Ser Gln Tyr G ly Ala Gly Leu Asp Ile
                180                     185                     190
Val Ala Pro Gly Val Asn Ile Gln Ser Thr T yr Pro Gly Ser Thr Tyr
                195                     200                     205
Ala Ser Leu Asn Gly Thr Ser Met Ala Thr P ro His Val Ala Gly Ala
            210                     215                     220
Ala Ala Leu Val Lys Gln Lys Asn Pro Ser T rp Ser Asn Val Gln Ile
225                     230                     235                     240
Arg Asn His Leu Lys Asn Thr Ala Thr Ser L eu Gly Ser Thr Asn Leu
                    245                     250                     255
Tyr Gly Ser Gly Leu Val Asn Ala Glu Ala A la Thr Arg
                260                     265

(2) INFORMATION FOR SEQ ID NO:18:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Serine P rotease
        (B) STRAIN: Bacillus l entus  DSM 5843

(vii) IMMEDIATE SOURCE:
        (B) CLONE: V4I (xi) SEQUENCE DESCRIPTION: SEQ ID NO:18:

Ala Gln Ser Ile Pro Trp Gly Ile Ser Arg V al Gln Ala Pro Ala Ala
1               5                      10                      15
His Asn Arg Gly Leu Thr Gly Ser Gly Val L ys Val Ala Val Leu Asp
                20                      25                      30
Thr Gly Ile Ser Thr His Pro Asp Leu Asn I le Arg Gly Gly Ala Ser
            35                      40                      45
Phe Val Pro Gly Glu Pro Ser Thr Gln Asp G ly Asn Gly His Gly Thr
        50                      55                      60
His Val Ala Gly Thr Ile Ala Ala Leu Asn A sn Ser Ile Gly Val Leu
65                      70                      75                      80
Gly Val Ala Pro Ser Ala Glu Leu Tyr Ala V al Lys Val Leu Gly Ala
                    85                      90                      95
```

-continued

```
Asp Gly Arg Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
                180                 185                 190

Val Ala Pro Gly Val Asn Val Gln Ser Thr Tyr Pro Gly Ser Thr Tyr
            195                 200                 205

Ala Ser Leu Asn Gly Thr Ser Met Ala Thr Pro His Val Ala Gly Ala
        210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265
```

(2) INFORMATION FOR SEQ ID NO:19:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Serine Protease
        (B) STRAIN: Bacillus lentus DSM 5843

(vii) IMMEDIATE SOURCE:
        (B) CLONE: S3T (xi) SEQUENCE DESCRIPTION: SEQ ID NO:19:

```
Ala Gln Thr Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Arg Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125
```

```
Pro Ser Ala Thr Leu Glu Gln Ala Val Asn S er Ala Thr Ser Arg Gly
        130                 135                 140

Val Leu Val Val Ala Ala Ser Gly Asn Ser G ly Ala Ser Ser Ile Ser
145                 150                 155                 160

Tyr Pro Ala Arg Tyr Ala Asn Ala Met Ala V al Gly Ala Thr Asp Gln
            165                 170                 175

Asn Asn Asn Arg Ala Ser Phe Ser Gln Tyr G ly Ala Gly Leu Asp Ile
            180                 185                 190

Val Ala Pro Gly Val Asn Val Gln Ser Thr T yr Pro Gly Ser Thr Tyr
        195                 200                 205

Ala Ser Leu Asn Gly Thr Ser Met Ala Thr P ro His Val Ala Gly Ala
        210                 215                 220

Ala Ala Leu Val Lys Gln Lys Asn Pro Ser T rp Ser Asn Val Gln Ile
225                 230                 235                 240

Arg Asn His Leu Lys Asn Thr Ala Thr Ser L eu Gly Ser Thr Asn Leu
            245                 250                 255

Tyr Gly Ser Gly Leu Val Asn Ala Glu Ala A la Thr Arg
            260                 265
```

(2) INFORMATION FOR SEQ ID NO:20:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Serine P rotease
        (B) STRAIN: Bacillus l entus  DSM 5843

(vii) IMMEDIATE SOURCE:
        (B) CLONE: S139Y (xi) SEQUENCE DESCRIPTION: SEQ ID NO:20:

Ala Gln Ser Val Pro Trp Gly Ile Ser Arg V al Gln Ala Pro Ala Ala
1               5                   10                  15

His Asn Arg Gly Leu Thr Gly Ser Gly Val L ys Val Ala Val Leu Asp
            20                  25                  30

Thr Gly Ile Ser Thr His Pro Asp Leu Asn I le Arg Gly Gly Ala Ser
        35                  40                  45

Phe Val Pro Gly Glu Pro Ser Thr Gln Asp G ly Asn Gly His Gly Thr
    50                  55                  60

His Val Ala Gly Thr Ile Ala Ala Leu Asn A sn Ser Ile Gly Val Leu
65                  70                  75                  80

Gly Val Ala Pro Ser Ala Glu Leu Tyr Ala V al Lys Val Leu Gly Ala
                85                  90                  95

Asp Gly Arg Gly Ala Ile Ser Ser Ile Ala G ln Gly Leu Glu Trp Ala
            100                 105                 110

Gly Asn Asn Gly Met His Val Ala Asn Leu S er Leu Gly Ser Pro Ser
        115                 120                 125

Pro Ser Ala Thr Leu Glu Gln Ala Val Asn T yr Ala Thr Ser Arg Gly
    130                 135                 140

Val Leu Val Val Ala Ala Ser Gly Asn Ser G ly Ala Ser Ser Ile Ser

-continued

```
                145                 150                 155                 160
Tyr Pro Ala Arg Tyr Ala Asn Ala Met Ala Val Gly Ala Thr Asp Gln
                    165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
                260                 265
```

(2) INFORMATION FOR SEQ ID NO:21:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Serine Protease
        (B) STRAIN: Bacillus lentus DSM 5843

(vii) IMMEDIATE SOURCE:
        (B) CLONE: N242A (xi) SEQUENCE DESCRIPTION: SEQ ID NO:21:

```
Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Arg Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175
```

```
Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Ala His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
                260                 265
```

(2) INFORMATION FOR SEQ ID NO:22:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Serine Protease
        (B) STRAIN: Bacillus lentus DSM 5843

(vii) IMMEDIATE SOURCE:
        (B) CLONE: S236T (xi) SEQUENCE DESCRIPTION: SEQ ID NO:22:

```
Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Arg Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205
```

```
Ala Ser Leu Asn Gly Thr Ser Met Ala Thr Pro His Val Ala Gly Ala
    210                 215                 220

Ala Ala Leu Val Lys Gln Lys Asn Pro Ser Trp Thr Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
                260                 265
```

(2) INFORMATION FOR SEQ ID NO:23:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Serine Protease
        (B) STRAIN: Bacillus lentus DSM 5843

(vii) IMMEDIATE SOURCE:
        (B) CLONE: S36A (xi) SEQUENCE DESCRIPTION: SEQ ID NO:23:

```
Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
                20                  25                  30

Thr Gly Ile Ala Thr His Pro Asp Leu Asn Ile Arg Gly Gly Ala Ser
                35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Arg Gly Ala Ile Ser Ser Ile Ala Gln Gly Leu Glu Trp Ala
                100                 105                 110

Gly Asn Asn Gly Met His Val Ala Asn Leu Ser Leu Gly Ser Pro Ser
                115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
                180                 185                 190

Val Ala Pro Gly Val Asn Val Gln Ser Thr Tyr Pro Gly Ser Thr Tyr
                195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
```

```
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Thr Arg
                260                 265
```

(2) INFORMATION FOR SEQ ID NO:24:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Serine Protease
        (B) STRAIN: Bacillus lentus DSM 5843

(vii) IMMEDIATE SOURCE:
        (B) CLONE: H243A (xi) SEQUENCE DESCRIPTION: SEQ ID NO:24:

```
Ala Gln Ser Val Pro Trp Gly Ile Ser Arg Val Gln Ala Pro Ala Ala
1                5                   10                  15

His Asn Arg Gly Leu Thr Gly Ser Gly Val Lys Val Ala Val Leu Asp
                20                  25                  30

Thr Gly Ile Ser Thr His Pro Asp Leu Asn Ile Arg Gly Gly Ala Ser
            35                  40                  45

Phe Val Pro Gly Glu Pro Ser Thr Gln Asp Gly Asn Gly His Gly Thr
        50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Arg Gly Ala Ile Ser Ser Ile Ala Gln Gly Leu Glu Trp Ala
                100                 105                 110

Gly Asn Asn Gly Met His Val Ala Asn Leu Ser Leu Gly Ser Pro Ser
            115                 120                 125

Pro Ser Ala Thr Leu Glu Gln Ala Val Asn Ser Ala Thr Ser Arg Gly
        130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
                180                 185                 190

Val Ala Pro Gly Val Asn Val Gln Ser Thr Tyr Pro Gly Ser Thr Tyr
            195                 200                 205

Ala Ser Leu Asn Gly Thr Ser Met Ala Thr Pro His Val Ala Gly Ala
        210                 215                 220

Ala Ala Leu Val Lys Gln Lys Asn Pro Ser Trp Ser Asn Val Gln Ile
225                 230                 235                 240

Arg Asn Ala Leu Lys Asn Thr Ala Thr Ser Leu Gly Ser Thr Asn Leu
                245                 250                 255
```

```
Tyr Gly Ser Gly Leu Val Asn Ala Glu Ala Ala Thr Arg
            260                 265

(2) INFORMATION FOR SEQ ID NO:25:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Serine Protease
        (B) STRAIN: Bacillus lentus  DSM 5843

(vii) IMMEDIATE SOURCE:
        (B) CLONE: A101T (xi) SEQUENCE DESCRIPTION: SEQ ID NO:25:

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Arg Gly Thr Ile Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265

(2) INFORMATION FOR SEQ ID NO:26:
```

(i) SEQUENCE CHARACTERISTICS:
    (A) LENGTH: 269 amino acids
    (B) TYPE: amino acid
    (D) TOPOLOGY: unknown (ii) MOLECULE TYPE: protein (iii) HYPOTHETICAL: NO (iv) ANTI-SENSE: NO (vi) ORIGINAL SOURCE:
    (A) ORGANISM: Serine P rotease
    (B) STRAIN: Bacillus l entus  DSM 5843

(vii) IMMEDIATE SOURCE:
    (B) CLONE: S236A (xi) SEQUENCE DESCRIPTION: SEQ ID NO:26:

```
Ala Gln Ser Val Pro Trp Gly Ile Ser Arg V al Gln Ala Pro Ala Ala
 1               5                  10                  15

His Asn Arg Gly Leu Thr Gly Ser Gly Val L ys Val Ala Val Leu Asp
            20                  25                  30

Thr Gly Ile Ser Thr His Pro Asp Leu Asn I le Arg Gly Gly Ala Ser
        35                  40                  45

Phe Val Pro Gly Glu Pro Ser Thr Gln Asp G ly Asn Gly His Gly Thr
    50                  55                  60

His Val Ala Gly Thr Ile Ala Ala Leu Asn A sn Ser Ile Gly Val Leu
65                  70                  75                  80

Gly Val Ala Pro Ser Ala Glu Leu Tyr Ala V al Lys Val Leu Gly Ala
                85                  90                  95

Asp Gly Arg Gly Ala Ile Ser Ser Ile Ala G ln Gly Leu Glu Trp Ala
            100                 105                 110

Gly Asn Asn Gly Met His Val Ala Asn Leu S er Leu Gly Ser Pro Ser
        115                 120                 125

Pro Ser Ala Thr Leu Glu Gln Ala Val Asn S er Ala Thr Ser Arg Gly
    130                 135                 140

Val Leu Val Val Ala Ala Ser Gly Asn Ser G ly Ala Ser Ser Ile Ser
145                 150                 155                 160

Tyr Pro Ala Arg Tyr Ala Asn Ala Met Ala V al Gly Ala Thr Asp Gln
                165                 170                 175

Asn Asn Asn Arg Ala Ser Phe Ser Gln Tyr G ly Ala Gly Leu Asp Ile
            180                 185                 190

Val Ala Pro Gly Val Asn Val Gln Ser Thr T yr Pro Gly Ser Thr Tyr
    195                 200                 205

Ala Ser Leu Asn Gly Thr Ser Met Ala Thr P ro His Val Ala Gly Ala
210                 215                 220

Ala Ala Leu Val Lys Gln Lys Asn Pro Ser T rp Ala Asn Val Gln Ile
225                 230                 235                 240

Arg Asn His Leu Lys Asn Thr Ala Thr Ser L eu Gly Ser Thr Asn Leu
                245                 250                 255

Tyr Gly Ser Gly Leu Val Asn Ala Glu Ala A la Thr Arg
            260                 265
```

(2) INFORMATION FOR SEQ ID NO:27:

(i) SEQUENCE CHARACTERISTICS:
    (A) LENGTH: 269 amino acids
    (B) TYPE: amino acid
    (D) TOPOLOGY: unknown (ii) MOLECULE TYPE: protein (iii) HYPOTHETICAL: NO (iv) ANTI-SENSE: NO (vi) ORIGINAL SOURCE:
         (A) ORGANISM: Serine P rotease
         (B) STRAIN: Bacillus l entus DSM 5843

(vii) IMMEDIATE SOURCE:
         (B) CLONE: E87R (xi) SEQUENCE DESCRIPTION: SEQ ID NO:27:

```
Ala Gln Ser Val Pro Trp Gly Ile Ser Arg V al Gln Ala Pro Ala Ala
1               5                   10                  15

His Asn Arg Gly Leu Thr Gly Ser Gly Val L ys Val Ala Val Leu Asp
            20                  25                  30

Thr Gly Ile Ser Thr His Pro Asp Leu Asn I le Arg Gly Gly Ala Ser
        35                  40                  45

Phe Val Pro Gly Glu Pro Ser Thr Gln Asp G ly Asn Gly His Gly Thr
    50                  55                  60

His Val Ala Gly Thr Ile Ala Ala Leu Asn A sn Ser Ile Gly Val Leu
65                  70                  75                  80

Gly Val Ala Pro Ser Ala Arg Leu Tyr Ala V al Lys Val Leu Gly Ala
                85                  90                  95

Asp Gly Arg Gly Ala Ile Ser Ser Ile Ala G ln Gly Leu Glu Trp Ala
            100                 105                 110

Gly Asn Asn Gly Met His Val Ala Asn Leu S er Leu Gly Ser Pro Ser
        115                 120                 125

Pro Ser Ala Thr Leu Glu Gln Ala Val Asn S er Ala Thr Ser Arg Gly
    130                 135                 140

Val Leu Val Val Ala Ala Ser Gly Asn Ser G ly Ala Ser Ser Ile Ser
145                 150                 155                 160

Tyr Pro Ala Arg Tyr Ala Asn Ala Met Ala V al Gly Ala Thr Asp Gln
                165                 170                 175

Asn Asn Asn Arg Ala Ser Phe Ser Gln Tyr G ly Ala Gly Leu Asp Ile
            180                 185                 190

Val Ala Pro Gly Val Asn Val Gln Ser Thr T yr Pro Gly Ser Thr Tyr
        195                 200                 205

Ala Ser Leu Asn Gly Thr Ser Met Ala Thr P ro His Val Ala Gly Ala
    210                 215                 220

Ala Ala Leu Val Lys Gln Lys Asn Pro Ser T rp Ser Asn Val Gln Ile
225                 230                 235                 240

Arg Asn His Leu Lys Asn Thr Ala Thr Ser L eu Gly Ser Thr Asn Leu
                245                 250                 255

Tyr Gly Ser Gly Leu Val Asn Ala Glu Ala A la Thr Arg
            260                 265
```

(2) INFORMATION FOR SEQ ID NO:28:

(i) SEQUENCE CHARACTERISTICS:
(A) LENGTH: 269 amino acids
(B) TYPE: amino acid
(D) TOPOLOGY: unknown (ii) MOLECULE TYPE: protein (iii) HYPOTHETICAL: NO (iv) ANTI-SENSE: NO (vi) ORIGINAL SOURCE:
            (A) ORGANISM: Serine P rotease
            (B) STRAIN: Bacillus l entus DSM 5843

(vii) IMMEDIATE SOURCE:
            (B) CLONE: N114S (xi) SEQUENCE DESCRIPTION: SEQ ID NO:28:

```

(vii) IMMEDIATE SOURCE:
    (B) CLONE: A47W (xi) SEQUENCE DESCRIPTION: SEQ ID NO:29:

Ala Gln Ser Val Pro Trp Gly Ile Ser Arg Val Gln Ala Pro Ala Ala
1               5                  10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Trp Ser
        35                  40                  45

Phe Val Pro Gly Glu Pro Ser Thr Gln Asp Gly Asn Gly His Gly Thr
50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Arg Gly Ala Ile Ser Ser Ile Ala Gln Gly Leu Glu Trp Ala
                100                 105                 110

Gly Asn Asn Gly Met His Val Ala Asn Leu Ser Leu Gly Ser Pro Ser
            115                 120                 125

Pro Ser Ala Thr Leu Glu Gln Ala Val Asn Ser Ala Thr Ser Arg Gly
        130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
                180                 185                 190

Val Ala Pro Gly Val Asn Val Gln Ser Thr Tyr Pro Gly Ser Thr Tyr
            195                 200                 205

Ala Ser Leu Asn Gly Thr Ser Met Ala Thr Pro His Val Ala Gly Ala
            210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
                260                 265

(2) INFORMATION FOR SEQ ID NO:30:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Serine Protease
        (B) STRAIN: Bacillus lentus DSM 5843

(vii) IMMEDIATE SOURCE:
        (B) CLONE: A120S (xi) SEQUENCE DESCRIPTION: SEQ ID NO:30:

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
                20                  25                  30

Thr Gly Ile Ser Thr His Pro Asp Leu Asn Ile Arg Gly Gly Ala Ser
            35                  40                  45

Phe Val Pro Gly Glu Pro Ser Thr Gln Asp Gly Asn Gly His Gly Thr
        50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Arg Gly Ala Ile Ser Ser Ile Ala Gln Gly Leu Glu Trp Ala
                100                 105                 110

Gly Asn Asn Gly Met His Val Ser Asn Leu Ser Leu Gly Ser Pro Ser
                115                 120                 125

Pro Ser Ala Thr Leu Glu Gln Ala Val Asn Ser Ala Thr Ser Arg Gly
            130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
                180                 185                 190

Val Ala Pro Gly Val Asn Val Gln Ser Thr Tyr Pro Gly Ser Thr Tyr
                195                 200                 205

Ala Ser Leu Asn Gly Thr Ser Met Ala Thr Pro His Val Ala Gly Ala
            210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
                260                 265

(2) INFORMATION FOR SEQ ID NO:31:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Serine Protease
        (B) STRAIN: Bacillus lentus DSM 5843

(vii) IMMEDIATE SOURCE:
        (B) CLONE: T56V (xi) SEQUENCE DESCRIPTION: SEQ ID NO:31:

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp 20                  25                  30
Thr Gly Ile Ser Thr His Pro Asp Leu Asn Ile Arg Gly Gly Ala Ser
            35                  40                  45

Phe Val Pro Gly Glu Pro Ser Val Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Arg Gly Ala Ile Ser Ser Ile Ala Gln Gly Leu Glu Trp Ala
                100                 105                 110

Gly Asn Asn Gly Met His Val Ala Asn Leu Ser Leu Gly Ser Pro Ser
            115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
    195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
                260                 265

(2) INFORMATION FOR SEQ ID NO:32:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Serine Protease
        (B) STRAIN: Bacillus lentus DSM 5843

(vii) IMMEDIATE SOURCE:
        (B) CLONE: A120V (xi) SEQUENCE DESCRIPTION: SEQ ID NO:32:

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
            35                  40                  45

```
Phe Val Pro Gly Glu Pro Ser Thr Gln Asp Gly Asn Gly His Gly Thr
 50                  55                  60

His Val Ala Gly Thr Ile Ala Ala Leu Asn Asn Ser Ile Gly Val Leu
 65                  70              75                      80

Gly Val Ala Pro Ser Ala Glu Leu Tyr Ala Val Lys Val Leu Gly Ala
                 85                  90                  95

Asp Gly Arg Gly Ala Ile Ser Ser Ile Ala Gln Gly Leu Glu Trp Ala
             100                 105                 110

Gly Asn Asn Gly Met His Val Val Asn Leu Ser Leu Gly Ser Pro Ser
             115                 120             125

Pro Ser Ala Thr Leu Glu Gln Ala Val Asn Ser Ala Thr Ser Arg Gly
         130             135             140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
             165                 170                 175

Asn Asn Asn Arg Ala Ser Phe Ser Gln Tyr Gly Ala Gly Leu Asp Ile
             180                 185                 190

Val Ala Pro Gly Val Asn Val Gln Ser Thr Tyr Pro Gly Ser Thr Tyr
         195                 200                 205

Ala Ser Leu Asn Gly Thr Ser Met Ala Thr Pro His Val Ala Gly Ala
         210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
             245                 250                 255

Tyr Gly Ser Gly Leu Val Asn Ala Glu Ala Ala Thr Arg
             260                 265

(2) INFORMATION FOR SEQ ID NO:33:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Serine Protease
        (B) STRAIN: Bacillus lentus  DSM 5843

(vii) IMMEDIATE SOURCE:
        (B) CLONE: G205V (xi) SEQUENCE DESCRIPTION: SEQ ID NO:33:

Ala Gln Ser Val Pro Trp Gly Ile Ser Arg Val Gln Ala Pro Ala Ala
 1               5                  10                  15

His Asn Arg Gly Leu Thr Gly Ser Gly Val Lys Val Ala Val Leu Asp
             20                  25                  30

Thr Gly Ile Ser Thr His Pro Asp Leu Asn Ile Arg Gly Gly Ala Ser
             35                  40                  45

Phe Val Pro Gly Glu Pro Ser Thr Gln Asp Gly Asn Gly His Gly Thr
         50                  55                  60

His Val Ala Gly Thr Ile Ala Ala Leu Asn Asn Ser Ile Gly Val Leu
 65                  70              75                      80
```

```
Gly Val Ala Pro Ser Ala Glu Leu Tyr Ala Val Lys Val Leu Gly Ala
                85                  90                  95

Asp Gly Arg Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
            115                 120                 125

Pro Ser Ala Thr Leu Glu Gln Ala Val Asn Ser Ala Thr Ser Arg Gly
        130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Val Ser Thr Tyr
        195                 200                 205

Ala Ser Leu Asn Gly Thr Ser Met Ala Thr Pro His Val Ala Gly Ala
        210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
                260                 265

(2) INFORMATION FOR SEQ ID NO:34:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Serine Protease
        (B) STRAIN: Bacillus lentus DSM 5843

(vii) IMMEDIATE SOURCE:
        (B) CLONE: S130A (xi) SEQUENCE DESCRIPTION: SEQ ID NO:34:

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Arg Gly Ala Ile Ser Ser Ile Ala Gln Gly Leu Glu Trp Ala
```

-continued

```
              100                 105                 110
Gly Asn Asn Gly Met His Val Ala Asn Leu Ser Leu Gly Ser Pro Ser
            115                 120                 125

Pro Ala Ala Thr Leu Glu Gln Ala Val Asn Ser Ala Thr Ser Arg Gly
            130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
                180                 185                 190

Val Ala Pro Gly Val Asn Val Gln Ser Thr Tyr Pro Gly Ser Thr Tyr
            195                 200                 205

Ala Ser Leu Asn Gly Thr Ser Met Ala Thr Pro His Val Ala Gly Ala
            210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
                260                 265
```

(2) INFORMATION FOR SEQ ID NO:35:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Serine Protease
        (B) STRAIN: Bacillus lentus DSM 5843

(vii) IMMEDIATE SOURCE:
        (B) CLONE: S130T (xi) SEQUENCE DESCRIPTION: SEQ ID NO:35:

```
Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
                20                  25                  30

Thr Gly Ile Ser Thr His Pro Asp Leu Asn Ile Arg Gly Gly Ala Ser
            35                  40                  45

Phe Val Pro Gly Glu Pro Ser Thr Gln Asp Gly Asn Gly His Gly Thr
50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Arg Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
            115                 120                 125
```

```
Pro Thr Ala Thr Leu Glu Gln Ala Val Asn Ser Ala Thr Ser Arg Gly
    130                 135                 140
Val Leu Val Val Ala Ala Ser Gly Asn Ser Gly Ala Ser Ser Ile Ser
145                 150                 155                 160
Tyr Pro Ala Arg Tyr Ala Asn Ala Met Ala Val Gly Ala Thr Asp Gln
                165                 170                 175
Asn Asn Asn Arg Ala Ser Phe Ser Gln Tyr Gly Ala Gly Leu Asp Ile
            180                 185                 190
Val Ala Pro Gly Val Asn Val Gln Ser Thr Tyr Pro Gly Ser Thr Tyr
        195                 200                 205
Ala Ser Leu Asn Gly Thr Ser Met Ala Thr Pro His Val Ala Gly Ala
    210                 215                 220
Ala Ala Leu Val Lys Gln Lys Asn Pro Ser Trp Ser Asn Val Gln Ile
225                 230                 235                 240
Arg Asn His Leu Lys Asn Thr Ala Thr Ser Leu Gly Ser Thr Asn Leu
                245                 250                 255
Tyr Gly Ser Gly Leu Val Asn Ala Glu Ala Ala Thr Arg
            260                 265

(2) INFORMATION FOR SEQ ID NO:36:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Serine Protease
        (B) STRAIN: Bacillus lentus DSM 5843

(vii) IMMEDIATE SOURCE:
        (B) CLONE: A96I (xi) SEQUENCE DESCRIPTION: SEQ ID NO:36:

Ala Gln Ser Val Pro Trp Gly Ile Ser Arg Val Gln Ala Pro Ala Ala
1               5                   10                  15
His Asn Arg Gly Leu Thr Gly Ser Gly Val Lys Val Ala Val Leu Asp
            20                  25                  30
Thr Gly Ile Ser Thr His Pro Asp Leu Asn Ile Arg Gly Gly Ala Ser
        35                  40                  45
Phe Val Pro Gly Glu Pro Ser Thr Gln Asp Gly Asn Gly His Gly Thr
    50                  55                  60
His Val Ala Gly Thr Ile Ala Ala Leu Asn Asn Ser Ile Gly Val Leu
65                  70                  75                  80
Gly Val Ala Pro Ser Ala Glu Leu Tyr Ala Val Lys Val Leu Gly Ile
                85                  90                  95
Asp Gly Arg Gly Ala Ile Ser Ser Ile Ala Gln Gly Leu Glu Trp Ala
            100                 105                 110
Gly Asn Asn Gly Met His Val Ala Asn Leu Ser Leu Gly Ser Pro Ser
        115                 120                 125
Pro Ser Ala Thr Leu Glu Gln Ala Val Asn Ser Ala Thr Ser Arg Gly
    130                 135                 140
Val Leu Val Val Ala Ala Ser Gly Asn Ser Gly Ala Ser Ser Ile Ser
145                 150                 155                 160
```

```
Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
                260                 265
```

(2) INFORMATION FOR SEQ ID NO:37:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Serine Protease
        (B) STRAIN: Bacillus lentus DSM 5843

(vii) IMMEDIATE SOURCE:
        (B) CLONE: S104T, S139Y, A224V (xi) SEQUENCE DESCRIPTION: SEQ ID NO:37:

```
Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Arg Gly Ala Ile Ser Thr Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Tyr Ala Thr Ser Arg Gly
    130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
```

```
                  180              185              190
Val Ala Pro Gly Val Asn Val Gln Ser Thr Tyr Pro Gly Ser Thr Tyr
            195              200              205

Ala Ser Leu Asn Gly Thr Ser Met Ala Thr Pro His Val Ala Gly Val
        210              215              220

Ala Ala Leu Val Lys Gln Lys Asn Pro Ser Trp Ser Asn Val Gln Ile
225              230              235              240

Arg Asn His Leu Lys Asn Thr Ala Thr Ser Leu Gly Ser Thr Asn Leu
                245              250              255

Tyr Gly Ser Gly Leu Val Asn Ala Glu Ala Ala Thr Arg
            260              265
```

(2) INFORMATION FOR SEQ ID NO:38:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Serine P rotease
        (B) STRAIN: Bacillus l entus  DSM 5843

(vii) IMMEDIATE SOURCE:
        (B) CLONE: S139A (xi) SEQUENCE DESCRIPTION: SEQ ID NO:38:

```
Ala Gln Ser Val Pro Trp Gly Ile Ser Arg Val Gln Ala Pro Ala Ala
1               5                  10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
            35                  40                  45

Phe Val Pro Gly Glu Pro Ser Thr Gln Asp Gly Asn Gly His Gly Thr
        50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Arg Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
            115                 120                 125

Pro Ser Ala Thr Leu Glu Gln Ala Val Asn Ala Ala Thr Ser Arg Gly
        130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
            195                 200                 205
```

```
Ala Ser Leu Asn Gly Thr Ser Met Ala Thr Pro His Val Ala Gly Ala
        210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265
```

(2) INFORMATION FOR SEQ ID NO:39:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Serine Protease
        (B) STRAIN: Bacillus lentus DSM 5843

(vii) IMMEDIATE SOURCE:
        (B) CLONE: S142T (xi) SEQUENCE DESCRIPTION: SEQ ID NO:39:

```
Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
                35                  40                  45

Phe Val Pro Gly Glu Pro Ser Thr Gln Asp Gly Asn Gly His Gly Thr
        50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Arg Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
            115                 120                 125

Pro Ser Ala Thr Leu Glu Gln Ala Val Asn Ser Ala Thr Thr Arg Gly
            130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
            195                 200                 205

Ala Ser Leu Asn Gly Thr Ser Met Ala Thr Pro His Val Ala Gly Ala
        210                 215                 220

Ala Ala Leu Val Lys Gln Lys Asn Pro Ser Trp Ser Asn Val Gln Ile
225                 230                 235                 240
```

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265

(2) INFORMATION FOR SEQ ID NO:40:

(i) SEQUENCE CHARACTERISTICS:
       (A) LENGTH: 269 amino acids
       (B) TYPE: amino acid
       (D) TOPOLOGY: unknown (ii) MOLECULE TYPE: protein (iii) HYPOTHETICAL: NO (iv) ANTI-SENSE: NO (vi) ORIGINAL SOURCE:
       (A) ORGANISM: Serine Protease
       (B) STRAIN: Bacillus lentus DSM 5843

(vii) IMMEDIATE SOURCE:
       (B) CLONE: S139T (xi) SEQUENCE DESCRIPTION: SEQ ID NO:40:

Ala Gln Ser Val Pro Trp Gly Ile Ser Arg Val Gln Ala Pro Ala Ala
1               5                  10                  15

His Asn Arg Gly Leu Thr Gly Ser Gly Val Lys Val Ala Val Leu Asp
                20                  25                  30

Thr Gly Ile Ser Thr His Pro Asp Leu Asn Ile Arg Gly Gly Ala Ser
            35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Arg Gly Ala Ile Ser Ser Ile Ala Gln Gly Leu Glu Trp Ala
                100                 105                 110

Gly Asn Asn Gly Met His Val Ala Asn Leu Ser Leu Gly Ser Pro Ser
            115                 120                 125

Pro Ser Ala Thr Leu Glu Gln Ala Val Asn Thr Ala Thr Ser Arg Gly
    130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
    195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265

(2) INFORMATION FOR SEQ ID NO:41:

(i) SEQUENCE CHARACTERISTICS:
       (A) LENGTH: 269 amino acids
       (B) TYPE: amino acid
       (D) TOPOLOGY: unknown (ii) MOLECULE TYPE: protein (iii) HYPOTHETICAL: NO (iv) ANTI-SENSE: NO (vi) ORIGINAL SOURCE:
       (A) ORGANISM: Serine P rotease
       (B) STRAIN: Bacillus l entus  DSM 5843

(vii) IMMEDIATE SOURCE:
       (B) CLONE: I102W (xi) SEQUENCE DESCRIPTION: SEQ ID NO:41:

Ala (i) SEQUENCE CHARACTERISTICS:
    (A) LENGTH: 269 amino acids
    (B) TYPE: amino acid
    (D) TOPOLOGY: unknown (ii) MOLECULE TYPE: protein (iii) HYPOTHETICAL: NO (iv) ANTI-SENSE: NO (vi) ORIGINAL SOURCE:
    (A) ORGANISM: Serine P rotease
    (B) STRAIN: Bacillus l entus DSM 5

-continued

```
    (ii) MOLECULE TYPE: protein (iii) HYPOTHETICAL: NO (iv) ANTI-SENSE: NO (vi) ORIGINAL SOURCE:
         (A) ORGANISM: Serine P rotease
         (B) STRAIN: Bacillus l entus  DSM 5843

(vii) IMMEDIATE SOURCE:
         (B) CLONE: N42F (xi) SEQUENCE DESCRIPTION: SEQ ID NO:43:

Ala Gln Ser Val Pro Trp Gly Ile Ser Arg V al Gln Ala Pro Ala Ala
1               5                  10                  15

His Asn Arg Gly Leu Thr Gly Ser Gly Val L ys Val Ala Val Leu Asp
            20                  25                  30

Thr Gly Ile Ser Thr His Pro Asp Leu Phe I le Arg Gly Gly Ala Ser
        35                  40                  45

Phe Val Pro Gly Glu Pro Ser Thr Gln Asp G ly Asn Gly His Gly Thr
    50                  55                  60

His Val Ala Gly Thr Ile Ala Ala Leu Asn A sn Ser Ile Gly Val Leu
65                  70                  75                  80

Gly Val Ala Pro Ser Ala Glu Leu Tyr Ala V al Lys Val Leu Gly Ala
                85                  90                  95

Asp Gly Arg Gly Ala Ile Ser Ser Ile Ala G ln Gly Leu Glu Trp Ala
            100                 105                 110

Gly Asn Asn Gly Met His Val Ala Asn Leu S er Leu Gly Ser Pro Ser
        115                 120                 125

Pro Ser Ala Thr Leu Glu Gln Ala Val Asn S er Ala Thr Ser Arg Gly
    130                 135                 140

Val Leu Val Val Ala Ala Ser Gly Asn Ser G ly Ala Ser Ser Ile Ser
145                 150                 155                 160

Tyr Pro Ala Arg Tyr Ala Asn Ala Met Ala V al Gly Ala Thr Asp Gln
                165                 170                 175

Asn Asn Asn Arg Ala Ser Phe Ser Gln Tyr G ly Ala Gly Leu Asp Ile
            180                 185                 190

Val Ala Pro Gly Val Asn Val Gln Ser Thr T yr Pro Gly Ser Thr Tyr
        195                 200                 205

Ala Ser Leu Asn Gly Thr Ser Met Ala Thr P ro His Val Ala Gly Ala
    210                 215                 220

Ala Ala Leu Val Lys Gln Lys Asn Pro Ser T rp Ser Asn Val Gln Ile
225                 230                 235                 240

Arg Asn His Leu Lys Asn Thr Ala Thr Ser L eu Gly Ser Thr Asn Leu
                245                 250                 255

Tyr Gly Ser Gly Leu Val Asn Ala Glu Ala A la Thr Arg
            260                 265

(2) INFORMATION FOR SEQ ID NO:44:

(i) SEQUENCE CHARACTERISTICS:
         (A) LENGTH: 269 amino acids
         (B) TYPE: amino acid
         (D) TOPOLOGY: unknown (ii) MOLECULE TYPE: protein (iii) HYPOTHETICAL: NO (iv) ANTI-SENSE: NO
```

(vi) ORIGINAL SOURCE:
    (A) ORGANISM: Serine Protease
    (B) STRAIN: Bacillus lentus DSM 5843

(vii) IMMEDIATE SOURCE:
    (B) CLONE: S142A (xi) SEQUENCE DESCRIPTION: SEQ ID NO:44:

```
Ala Gln Ser Val Pro Trp Gly Ile Ser Arg Val Gln Ala Pro Ala Ala
1               5                  10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Arg Gly Ala Ile Ser Ser Ile Ala Gln Gly Leu Glu Trp Ala
                100                 105                 110

Gly Asn Asn Gly Met His Val Ala Asn Leu Ser Leu Gly Ser Pro Ser
            115                 120                 125

Pro Ser Ala Thr Leu Glu Gln Ala Val Asn Ser Ala Thr Ala Arg Gly
        130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
                180                 185                 190

Val Ala Pro Gly Val Asn Val Gln Ser Thr Tyr Pro Gly Ser Thr Tyr
            195                 200                 205

Ala Ser Leu Asn Gly Thr Ser Met Ala Thr Pro His Val Ala Gly Ala
210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265
```

(2) INFORMATION FOR SEQ ID NO:45:

(i) SEQUENCE CHARACTERISTICS:
      (A) LENGTH: 269 amino acids
      (B) TYPE: amino acid
      (D) TOPOLOGY: unknown (ii) MOLECULE TYPE: protein (iii) HYPOTHETICAL: NO (iv) ANTI-SENSE: NO (vi) ORIGINAL SOURCE:
      (A) ORGANISM: Serine Protease
      (B) STRAIN: Bacillus lentus DSM 5843

(vii) IMMEDIATE SOURCE:
    (B) CLONE: H118F (xi) SEQUENCE DESCRIPTION: SEQ ID NO:45:

Ala Gln Ser Val Pro Trp Gly Ile Ser Arg Val Gln Ala Pro Ala Ala
 1               5                  10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Arg Gly Ala Ile Ser Ser Ile Ala Gln Gly Leu Glu Trp Ala
            100                 105                 110

Gly Asn Asn Gly Met Phe Val Ala Asn Leu Ser Leu Gly Ser Pro Ser
        115                 120                 125

Pro Ser Ala Thr Leu Glu Gln Ala Val Asn Ser Ala Thr Ser Arg Gly
130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265

(2) INFORMATION FOR SEQ ID NO:46:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Serine Protease
        (B) STRAIN: Bacillus lentus DSM 5843

(vii) IMMEDIATE SOURCE:
        (B) CLONE: N237A (xi) SEQUENCE DESCRIPTION: SEQ ID NO:46:

```
Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Arg Gly Ala Ile Ser Ser Ile Ala Gln Gly Leu Glu Trp Ala
                100                 105                 110

Gly Asn Asn Gly Met His Val Ala Asn Leu Ser Leu Gly Ser Pro Ser
            115                 120                 125

Pro Ser Ala Thr Leu Glu Gln Ala Val Asn Ser Ala Thr Ser Arg Gly
130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
            195                 200                 205

Ala Ser Leu Asn Gly Thr Ser Met Ala Thr Pro His Val Ala Gly Ala
210                 215                 220

Ala Ala Leu Val Lys Gln Lys Asn Pro Ser Trp Ser Ala Val Gln Ile
225                 230                 235                 240

Arg Asn His Leu Lys Asn Thr Ala Thr Ser Leu Gly Ser Thr Asn Leu
            245                 250                 255

Tyr Gly Ser Gly Leu Val Asn Ala Glu Ala Ala Thr Arg
            260                 265
```

(2) INFORMATION FOR SEQ ID NO:47:

(i) SEQUENCE CHARACTERISTICS:
      (A) LENGTH: 269 amino acids
      (B) TYPE: amino acid
      (D) TOPOLOGY: unknown (ii) MOLECULE TYPE: protein (iii) HYPOTHETICAL: NO (iv) ANTI-SENSE: NO (vi) ORIGINAL SOURCE:
      (A) ORGANISM: Serine Protease
      (B) STRAIN: Bacillus lentus DSM 5843

(vii) IMMEDIATE SOURCE:
      (B) CLONE: N255P (xi) SEQUENCE DESCRIPTION: SEQ ID NO:47:

```
Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30
```

Thr Gly Ile Ser Thr His Pro Asp Leu Asn Ile Arg Gly Gly Ala Ser
                35                  40                  45

Phe Val Pro Gly Glu Pro Ser Thr Gln Asp Gly Asn Gly His Gly Thr
 50                      55                  60

His Val Ala Gly Thr Ile Ala Ala Leu Asn Asn Ser Ile Gly Val Leu
 65                  70                  75                  80

Gly Val Ala Pro Ser Ala Glu Leu Tyr Ala Val Lys Val Leu Gly Ala
                 85                  90                  95

Asp Gly Arg Gly Ala Ile Ser Ser Ile Ala Gln Gly Leu Glu Trp Ala
                100                 105                 110

Gly Asn Asn Gly Met His Val Ala Asn Leu Ser Leu Gly Ser Pro Ser
            115                 120                 125

Pro Ser Ala Thr Leu Glu Gln Ala Val Asn Ser Ala Thr Ser Arg Gly
        130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
            195                 200                 205

Ala Ser Leu Asn Gly Thr Ser Met Ala Thr Pro His Val Ala Gly Ala
        210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Pro Leu
                245                 250                 255

Tyr Gly Ser Gly Leu Val Asn Ala Glu Ala Ala Thr Arg
            260                 265

(2) INFORMATION FOR SEQ ID NO:48:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Serine Protease
        (B) STRAIN: Bacillus lentus DSM 5843

(vii) IMMEDIATE SOURCE:
        (B) CLONE: T141W, N237A (xi) SEQUENCE DESCRIPTION: SEQ ID NO:48:

Ala Gln Ser Val Pro Trp Gly Ile Ser Arg Val Gln Ala Pro Ala Ala
 1               5                  10                  15

His Asn Arg Gly Leu Thr Gly Ser Gly Val Lys Val Ala Val Leu Asp
             20                  25                  30

Thr Gly Ile Ser Thr His Pro Asp Leu Asn Ile Arg Gly Gly Ala Ser
                35                  40                  45

Phe Val Pro Gly Glu Pro Ser Thr Gln Asp Gly Asn Gly His Gly Thr

-continued

```
                50                  55                  60
His Val Ala Gly Thr Ile Ala Ala Leu Asn Asn Ser Ile Gly Val Leu
 65                  70                  75                  80

Gly Val Ala Pro Ser Ala Glu Leu Tyr Ala Val Lys Val Leu Gly Ala
                 85                  90                  95

Asp Gly Arg Gly Ala Ile Ser Ser Ile Ala Gln Gly Leu Glu Trp Ala
                100                 105                 110

Gly Asn Asn Gly Met His Val Ala Asn Leu Ser Leu Gly Ser Pro Ser
                115                 120                 125

Pro Ser Ala Thr Leu Glu Gln Ala Val Asn Ser Ala Trp Ser Arg Gly
                130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
                180                 185                 190

Val Ala Pro Gly Val Asn Val Gln Ser Thr Tyr Pro Gly Ser Thr Tyr
                195                 200                 205

Ala Ser Leu Asn Gly Thr Ser Met Ala Thr Pro His Val Ala Gly Ala
                210                 215                 220

Ala Ala Leu Val Lys Gln Lys Asn Pro Ser Trp Ser Ala Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
                260                 265
```

(2) INFORMATION FOR SEQ ID NO:49:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Serine Protease
        (B) STRAIN: Bacillus lentus DSM 5843

(vii) IMMEDIATE SOURCE:
        (B) CLONE: T268V (xi) SEQUENCE DESCRIPTION: SEQ ID NO:49:

```
Ala Gln Ser Val Pro Trp Gly Ile Ser Arg Val Gln Ala Pro Ala Ala
  1                   5                  10                  15

His Asn Arg Gly Leu Thr Gly Ser Gly Val Lys Val Ala Val Leu Asp
                 20                  25                  30

Thr Gly Ile Ser Thr His Pro Asp Leu Asn Ile Arg Gly Gly Ala Ser
                 35                  40                  45

Phe Val Pro Gly Glu Pro Ser Thr Gln Asp Gly Asn Gly His Gly Thr
 50                  55                  60

His Val Ala Gly Thr Ile Ala Ala Leu Asn Asn Ser Ile Gly Val Leu
 65                  70                  75                  80
```

-continued

```
Gly Val Ala Pro Ser Ala Glu Leu Tyr Ala Val Lys Val Leu Gly Ala
                 85                  90                  95

Asp Gly Arg Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
            115                 120                 125

Pro Ser Ala Thr Leu Glu Gln Ala Val Asn Ser Ala Thr Ser Arg Gly
            130                 135             140

Val Leu Val Ala Ala Ser Gly Asn Ser Gly Ala Ser Ser Ile Ser
145                 150             155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
            195                 200                 205

Ala Ser Leu Asn Gly Thr Ser Met Ala Thr Pro His Val Ala Gly Ala
            210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Val Arg
            260                 265
```

(2) INFORMATION FOR SEQ ID NO:50:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Serine Protease
        (B) STRAIN: Bacillus lentus DSM 5843

(vii) IMMEDIATE SOURCE:
        (B) CLONE: K229W (xi) SEQUENCE DESCRIPTION: SEQ ID NO:50:

```
Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Arg Gly Ala Ile Ser Ser Ile Ala Gln Gly Leu Glu Trp Ala
            100                 105                 110
```

```
Gly Asn Asn Gly Met His Val Ala Asn Leu Ser Leu Gly Ser Pro Ser
            115                 120                 125

Pro Ser Ala Thr Leu Glu Gln Ala Val Asn Ser Ala Thr Ser Arg Gly
        130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
        210                 215                 220

Ala Ala Leu Val Trp Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
                260                 265

(2) INFORMATION FOR SEQ ID NO:51:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
         (A) ORGANISM: Serine Protease
         (B) STRAIN: Bacillus lentus DSM 5843

(vii) IMMEDIATE SOURCE:
          (B) CLONE: T141W (xi) SEQUENCE DESCRIPTION: SEQ ID NO:51:

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Arg Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
            115                 120                 125

Pro Ser Ala Thr Leu Glu Gln Ala Val Asn Ser Ala Trp Ser Arg Gly
```

```
              130                 135                 140
Val Leu Val Val Ala Ala Ser Gly Asn Ser G ly Ala Ser Ser Ile Ser
145                 150                 155                 160

Tyr Pro Ala Arg Tyr Ala Asn Ala Met Ala V al Gly Ala Thr Asp Gln
                165                 170                 175

Asn Asn Asn Arg Ala Ser Phe Ser Gln Tyr G ly Ala Gly Leu Asp Ile
                180                 185                 190

Val Ala Pro Gly Val Asn Val Gln Ser Thr T yr Pro Gly Ser Thr Tyr
                195                 200                 205

Ala Ser Leu Asn Gly Thr Ser Met Ala Thr P ro His Val Ala Gly Ala
                210                 215                 220

Ala Ala Leu Val Lys Gln Lys Asn Pro Ser T rp Ser Asn Val Gln Ile
225                 230                 235                 240

Arg Asn His Leu Lys Asn Thr Ala Thr Ser L eu Gly Ser Thr Asn Leu
                245                 250                 255

Tyr Gly Ser Gly Leu Val Asn Ala Glu Ala A la Thr Arg
                260                 265

(2) INFORMATION FOR SEQ ID NO:52:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Serine P rotease
        (B) STRAIN: Bacillus l entus  DSM 5843

(vii) IMMEDIATE SOURCE:
        (

```
Tyr Pro Ala Arg Tyr Ala Asn Ala Met Ala V al Gly Ala Thr Asp Gln
                165                 170                 175

Asn Asn Asn Arg Ala Ser Phe Ser Gln Tyr G ly Ala Gly Leu Asp Ile
                180                 185                 190

Val Ala Pro Gly Val Asn Val Gln Ser Thr T yr Pro Gly Ser Thr Tyr
                195                 200                 205

Ala Ser Leu Asn Gly Thr Ser Met Ala Thr P ro His Val Ala Gly Ala
                210                 215                 220

Ala Ala Leu Val Lys Gln Lys Asn Pro Ser T rp Ser Asn Val Gln Ile
225                 230                 235                 240

Arg Asn His Leu Lys Asn Thr Ala Thr Ser L eu Gly Ser Thr Asn Leu
                245                 250                 255

Tyr Gly Ser Gly Leu Val Asn Ala Glu Ala A la Thr Arg
                260                 265
```

(2) INFORMATION FOR SEQ ID NO:53:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (B) STRAIN: Bacillus l entus DSM 5483

(vii) IMMEDIATE SOURCE:
        (B) CLONE: S3T, V4I, A188P, V193M, V199I (xi) SEQUENCE DESCRIPTION: SEQ ID NO:53:

```
GCGCAAACAA TCCCATGGGG AATTAGCCGT GTGCAAGCCC CGGCTGCCCA T AACCGTGGA      60
TTGACAGGTT CTGGTGTAAA AGTTGCTGTC CTCGATACAG GTATTTCCAC T CATCCAGAC     120
TTAAATATTC GTGGTGGCGC TAGCTTTGTA CCAGGGGAAC CATCCACTCA A GATGGGAAT     180
GGGCATGGCA CGCATGTGGC CGGGACGATT GCTGCTTTAA ACAATTCGAT T GGCGTTCTT     240
GGCGTAGCGC CTAGTGCGGA ACTATACGCT GTTAAAGTTT TAGGAGCCGA C GGTAGAGGT     300
GCAATCAGCT CGATTGCCCA AGGGTTGGAA TGGGCAGGGA ACAATGGCAT G CACGTTGCT     360
AATTTGAGTT TAGGAAGCCC TTCGCCAAGT GCCACACTTG AGCAAGCTGT T AATAGCGCG     420
ACTTCTAGAG GCGTTCTTGT TGTAGCGGCA TCTGGGAATT CAGGTGCAAG C TCAATCAGC     480
TATCCGGCCC GTTATGCGAA CGCAATGGCA GTCGGAGCTA CTGACCAAAA C AACAACCGC     540
GCCAGCTTTT CACAGTATGG CCCAGGGCTT GACATTATGG CACCAGGGGT A AACATTCAG     600
AGCACATACC CAGGTTCAAC GTATGCCAGC TTAAACGGTA CATCGATGGC T ACTCCTCAT     660
GTTGCAGGTG CAGCAGCCCT TGTTAAACAA AAGAACCCAT CTTGGTCCAA T GTACAAATC     720
CGCAACCATC TAAAGAATAC GGCAACGAGC TTAGGAAGCA CGAACTTGTA T GGAAGCGGA     780
CTTGTCAATG CAGAAGCGGC AACACGC                                        807
```

(2) INFORMATION FOR SEQ ID NO:54:

(i) SEQUENCE CHARACTERISTICS:
        (A) LENGTH: 807 base pairs
        (B) TYPE: nucleic acid
        (C) STRANDEDNESS: double (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (B) STRAIN: Bacillus l entus DSM 5483

(vii) IMMEDIATE SOURCE:
        (B) CLONE: S3T, A188P,  V193M, V199I (xi) SEQUENCE DESCRIPTION: SEQ ID NO:54:

```
GCGCAAACAG TGCCATGGGG AATTAGCCGT GTGCAAGCCC CGGCTGCCCA T AACCGTGGA      60

TTGACAGGTT CTGGTGTAAA AGTTGCTGTC CTCGATACAG GTATTTCCAC T CATCCAGAC     120

TTAAATATTC GTGGTGGCGC TAGCTTTGTA CCAGGGGAAC CATCCACTCA A GATGGGAAT    180

GGGCATGGCA CGCATGTGGC CGGGACGATT GCTGCTTTAA ACAATTCGAT T GGCGTTCTT    240

GGCGTAGCGC CTAGTGCGGA ACTATACGCT GTTAAAGTTT TAGGAGCCGA C GGTAGAGGT    300

GCAATCAGCT CGATTGCCCA AGGGTTGGAA TGGGCAGGGA ACAATGGCAT G CACGTTGCT   360

AATTTGAGTT TAGGAAGCCC TTCGCCAAGT GCCACACTTG AGCAAGCTGT T AATAGCGCG   420

ACTTCTAGAG GCGTTCTTGT TGTAGCGGCA TCTGGGAATT CAGGTGCAAG C TCAATCAGC   480

TATCCGGCCC GTTATGCGAA CGCAATGGCA GTCGGAGCTA CTGACCAAAA C AACAACCGC  540

GCCAGCTTTT CACAGTATGG CCCAGGGCTT GACATTATGG CACCAGGGGT A AACATTCAG   600

AGCACATACC CAGGTTCAAC GTATGCCAGC TTAAACGGTA CATCGATGGC T ACTCCTCAT   660

GTTGCAGGTG CAGCAGCCCT TGTTAAACAA AAGAACCCAT CTTGGTCCAA T GTACAAATC   720

CGCAACCATC TAAAGAATAC GGCAACGAGC TTAGGAAGCA CGAACTTGTA T GGAAGCGGA   780

CTTGTCAATG CAGAAGCGGC AACACGC                                         807
```

(2) INFORMATION FOR SEQ ID NO:55:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (B) STRAIN: Bacillus l entus DSM 5483

(vii) IMMEDIATE SOURCE:
        (B) CLONE: V4I, A188P,  V193M, V199I (xi) SEQUENCE DESCRIPTION: SEQ ID NO:55:

```
GCGCAATCAA TCCCATGGGG AATTAGCCGT GTGCAAGCCC CGGCTGCCCA T AACCGTGGA      60

TTGACAGGTT CTGGTGTAAA AGTTGCTGTC CTCGATACAG GTATTTCCAC T CATCCAGAC     120

TTAAATATTC GTGGTGGCGC TAGCTTTGTA CCAGGGGAAC CATCCACTCA A GATGGGAAT    180

GGGCATGGCA CGCATGTGGC CGGGACGATT GCTGCTTTAA ACAATTCGAT T GGCGTTCTT    240

GGCGTAGCGC CTAGTGCGGA ACTATACGCT GTTAAAGTTT TAGGAGCCGA C GGTAGAGGT    300

GCAATCAGCT CGATTGCCCA AGGGTTGGAA TGGGCAGGGA ACAATGGCAT G CACGTTGCT   360
```

```
AATTTGAGTT TAGGAAGCCC TTCGCCAAGT GCCACACTTG AGCAAGCTGT T AATAGCGCG      420

ACTTCTAGAG GCGTTCTTGT TGTAGCGGCA TCTGGGAATT CAGGTGCAAG C TCAATCAGC      480

TATCCGGCCC GTTATGCGAA CGCAATGGCA GTCGGAGCTA CTGACCAAAA C AACAACCGC      540

GCCAGCTTTT CACAGTATGG CCCAGGGCTT GACATTATGG CACCAGGGGT A AACATTCAG      600

AGCACATACC CAGGTTCAAC GTATGCCAGC TTAAACGGTA CATCGATGGC T ACTCCTCAT      660

GTTGCAGGTG CAGCAGCCCT TGTTAAACAA AGAACCCAT CTTGGTCCAA T GTACAAATC       720

CGCAACCATC TAAAGAATAC GGCAACGAGC TTAGGAAGCA CGAACTTGTA T GGAAGCGGA      780

CTTGTCAATG CAGAAGCGGC AACACGC                                          807

(2) INFORMATION FOR SEQ ID NO:56:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (B) STRAIN: Bacillus l entus DSM 5483

(vii) IMMEDIATE SOURCE:
          (B) CLONE: S139Y, A188 P, V193M, V199I (xi) SEQUENCE DESCRIPTION: SEQ ID NO:56:

GCGCAATCAG TGCCATGGGG AATTAGCCGT GTGCAAGCCC CGGCTGCCCA T AACCGTGGA       60

TTGACAGGTT CTGGTGTAAA AGTTGCTGTC CTCGATACAG GTATTTCCAC T CATCCAGAC     120

TTAAATATTC GTGGTGGCGC TAGCTTTGTA CCAGGGGAAC CATCCACTCA A GATGGGAAT     180

GGGCATGGCA CGCATGTGGC CGGGACGATT GCTGCTTTAA ACAATTCGAT T GGCGTTCTT     240

GGCGTAGCGC CTAGTGCGGA ACTATACGCT GTTAAAGTTT TAGGAGCCGA C GGTAGAGGT     300

GCAATCAGCT CGATTGCCCA AGGGTTGGAA TGGGCAGGGA ACAATGGCAT G CACGTTGCT     360

AATTTGAGTT TAGGAAGCCC TTCGCCAAGT GCCACACTTG AGCAAGCTGT T AATTATGCG     420

ACTTCTAGAG GCGTTCTTGT TGTAGCGGCA TCTGGGAATT CAGGTGCAAG C TCAATCAGC     480

TATCCGGCCC GTTATGCGAA CGCAATGGCA GTCGGAGCTA CTGACCAAAA C AACAACCGC     540

GCCAGCTTTT CACAGTATGG CCCAGGGCTT GACATTATGG CACCAGGGGT A AACATTCAG     600

AGCACATACC CAGGTTCAAC GTATGCCAGC TTAAACGGTA CATCGATGGC T ACTCCTCAT     660

GTTGCAGGTG CAGCAGCCCT TGTTAAACAA AGAACCCAT CTTGGTCCAA T GTACAAATC      720

CGCAACCATC TAAAGAATAC GGCAACGAGC TTAGGAAGCA CGAACTTGTA T GGAAGCGGA     780

CTTGTCAATG CAGAAGCGGC AACACGC                                          807

(2) INFORMATION FOR SEQ ID NO:57:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO
```

(iv) ANTI-SENSE: NO (vi) ORIGINAL SOURCE:
(B) STRAIN: Bacillus l entus DSM 5483

(vii) IMMEDIATE SOURCE:
(B) CLONE: S130T, S139 Y, A188P, V193M, V199I (xi) SEQUENCE DESCRIPTION: SEQ ID NO:57:

```
GCGCAATCAG TGCCATGGGG AATTAGCCGT GTGCAAGCCC CGGCTGCCCA T AACCGTGGA      60
TTGACAGGTT CTGGTGTAAA AGTTGCTGTC CTCGATACAG GTATTTCCAC T CATCCAGAC    120
TTAAATATTC GTGGTGGCGC TAGCTTTGTA CCAGGGGAAC CATCCACTCA A GATGGGAAT    180
GGGCATGGCA CGCATGTGGC CGGGACGATT GCTGCTTTAA ACAATTCGAT T GGCGTTCTT    240
GGCGTAGCGC CTAGTGCGGA ACTATACGCT GTTAAAGTTT TAGGAGCCGA C GGTAGAGGT    300
GCAATCAGCT CGATTGCCCA AGGGTTGGAA TGGGCAGGGA ACAATGGCAT G CACGTTGCT    360
AATTTGAGTT TAGGAAGCCC TTCGCCAACA GCCACACTTG AGCAAGCTGT T AATTATGCG    420
ACTTCTAGAG GCGTTCTTGT TGTAGCGGCA TCTGGGAATT CAGGTGCAAG C TCAATCAGC    480
TATCCGGCCC GTTATGCGAA CGCAATGGCA GTCGGAGCTA CTGACCAAAA C AACAACCGC    540
GCCAGCTTTT CACAGTATGG CCCAGGGCTT GACATTATGG CACCAGGGGT A AACATTCAG    600
AGCACATACC CAGGTTCAAC GTATGCCAGC TTAAACGGTA CATCGATGGC T ACTCCTCAT    660
GTTGCAGGTG CAGCAGCCCT TGTTAAACAA AAGAACCCAT CTTGGTCCAA T GTACAAATC    720
CGCAACCATC TAAAGAATAC GGCAACGAGC TTAGGAAGCA CGAACTTGTA T GGAAGCGGA    780
CTTGTCAATG CAGAAGCGGC AACACGC                                        807
```

(2) INFORMATION FOR SEQ ID NO:58:

(i) SEQUENCE CHARACTERISTICS:
(A) LENGTH: 807 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(B) STRAIN: Bacillus l entus DSM 5483

(vii) IMMEDIATE SOURCE:
(B) CLONE: A188P, V193 M, V199I (xi) SEQUENCE DESCRIPTION: SEQ ID NO:58:

```
GCGCAATCAG TGCCATGGGG AATTAGCCGT GTGCAAGCCC CGGCTGCCCA T AACCGTGGA      60
TTGACAGGTT CTGGTGTAAA AGTTGCTGTC CTCGATACAG GTATTTCCAC T CATCCAGAC    120
TTAAATATTC GTGGTGGCGC TAGCTTTGTA CCAGGGGAAC CATCCACTCA A GATGGGAAT    180
GGGCATGGCA CGCATGTGGC CGGGACGATT GCTGCTTTAA ACAATTCGAT T GGCGTTCTT    240
GGCGTAGCGC CTAGTGCGGA ACTATACGCT GTTAAAGTTT TAGGAGCCGA C GGTAGAGGT    300
GCAATCAGCT CGATTGCCCA AGGGTTGGAA TGGGCAGGGA ACAATGGCAT G CACGTTGCT    360
AATTTGAGTT TAGGAAGCCC TTCGCCAAGT GCCACACTTG AGCAAGCTGT T AATAGCGCG    420
ACTTCTAGAG GCGTTCTTGT TGTAGCGGCA TCTGGGAATT CAGGTGCAAG C TCAATCAGC    480
TATCCGGCCC GTTATGCGAA CGCAATGGCA GTCGGAGCTA CTGACCAAAA C AACAACCGC    540
```

GCCAGCTTTT CACAGTATGG CCCAGGGCTT GACATTATGG CACCAGGGGT A AACATTCAG    600

AGCACATACC CAGGTTCAAC GTATGCCAGC TTAAACGGTA CATCGATGGC T ACTCCTCAT    660

GTTGCAGGTG CAGCAGCCCT TGTTAAACAA AAGAACCCAT CTTGGTCCAA T GTACAAATC    720

CGCAACCATC TAAAGAATAC GGCAACGAGC TTAGGAAGCA CGAACTTGTA T GGAAGCGGA    780

CTTGTCAATG CAGAAGCGGC AACACGC                                        807

(2) INFORMATION FOR SEQ ID NO:59:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (B) STRAIN: Bacillus l entus DSM 5483

(vii) IMMEDIATE SOURCE:
        (B) CLONE: S3T, A188P, V193M (xi) SEQUENCE DESCRIPTION: SEQ ID NO:59:

GCGCAAACAG TGCCATGGGG AATTAGCCGT GTGCAAGCCC CGGCTGCCCA T AACCGTGGA    60

TTGACAGGTT CTGGTGTAAA AGTTGCTGTC CTCGATACAG GTATTTCCAC T CATCCAGAC   120

TTAAATATTC GTGGTGGCGC TAGCTTTGTA CCAGGGGAAC CATCCACTCA A GATGGGAAT   180

GGGCATGGCA CGCATGTGGC CGGGACGATT GCTGCTTTAA ACAATTCGAT T GGCGTTCTT   240

GGCGTAGCGC CTAGTGCGGA ACTATACGCT GTTAAAGTTT TAGGAGCCGA C GGTAGAGGT   300

GCAATCAGCT CGATTGCCCA AGGGTTGGAA TGGGCAGGGA ACAATGGCAT G CACGTTGCT   360

AATTTGAGTT TAGGAAGCCC TTCGCCAAGT GCCACACTTG AGCAAGCTGT T AATAGCGCG   420

ACTTCTAGAG GCGTTCTTGT TGTAGCGGCA TCTGGGAATT CAGGTGCAAG C TCAATCAGC   480

TATCCGGCCC GTTATGCGAA CGCAATGGCA GTCGGAGCTA CTGACCAAAA C AACAACCGC   540

GCCAGCTTTT CACAGTATGG CCCAGGGCTT GACATTATGG CACCAGGGGT A AACGTGCAG    600

AGCACATACC CAGGTTCAAC GTATGCCAGC TTAAACGGTA CATCGATGGC T ACTCCTCAT   660

GTTGCAGGTG CAGCAGCCCT TGTTAAACAA AAGAACCCAT CTTGGTCCAA T GTACAAATC   720

CGCAACCATC TAAAGAATAC GGCAACGAGC TTAGGAAGCA CGAACTTGTA T GGAAGCGGA   780

CTTGTCAATG CAGAAGCGGC AACACGC                                       807

(2) INFORMATION FOR SEQ ID NO:60:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (B) STRAIN: Bacillus l entus DSM 5483

(vii) IMMEDIATE SOURCE:
    (B) CLONE: S157T (xi) SEQUENCE DESCRIPTION: SEQ ID NO:60:

```
GCGCAATCAG TGCCATGGGG AATTAGCCGT GTGCAAGCCC CGGCTGCCCA T AACCGTGGA      60
TTGACAGGTT CTGGTGTAAA AGTTGCTGTC CTCGATACAG GTATTTCCAC T CATCCAGAC     120
TTAAATATTC GTGGTGGCGC TAGCTTTGTA CCAGGGGAAC CATCCACTCA A GATGGGAAT    180
GGGCATGGCA CGCATGTGGC CGGGACGATT GCTGCTTTAA ACAATTCGAT T GGCGTTCTT    240
GGCGTAGCGC CTAGTGCGGA ACTATACGCT GTTAAAGTTT TAGGAGCCGA C GGTAGAGGT    300
GCAATCAGCT CGATTGCCCA AGGGTTGGAA TGGGCAGGGA ACAATGGCAT G CACGTTGCT    360
AATTTGAGTT TAGGAAGCCC TTCGCCAAGT GCCACACTTG AGCAAGCTGT T AATAGCGCG    420
ACTTCTAGAG GCGTTCTTGT TGTAGCGGCA TCTGGGAATT CAGGTGCAAC A TCAATCAGC    480
TATCCGGCCC GTTATGCGAA CGCAATGGCA GTCGGAGCTA CTGACCAAAA C AACAACCGC    540
GCCAGCTTTT CACAGTATGG CGCAGGGCTT GACATTGTCG CACCAGGGGT A AACGTGCAG    600
AGCACATACC CAGGTTCAAC GTATGCCAGC TTAAACGGTA CATCGATGGC T ACTCCTCAT    660
GTTGCAGGTG CAGCAGCCCT TGTTAAACAA AAGAACCCAT CTTGGTCCAA T GTACAAATC    720
CGCAACCATC TAAAGAATAC GGCAACGAGC TTAGGAAGCA CGAACTTGTA T GGAAGCGGA    780
CTTGTCAATG CAGAAGCGGC AACACGC                                         807
```

(2) INFORMATION FOR SEQ ID NO:61:

(i) SEQUENCE CHARACTERISTICS:
       (A) LENGTH: 807 base pairs
       (B) TYPE: nucleic acid
       (C) STRANDEDNESS: double
       (D) TOPOLOGY: linear (ii) MOLECULE TYPE: DNA (genomic)

(iii) HYPOTHETICAL: NO (iv) ANTI-SENSE: NO (vi) ORIGINAL SOURCE:
       (B) STRAIN: Bacillus l entus DSM 5483

(vii) IMMEDIATE SOURCE:
       (B) CLONE: A188P, V193 M (xi) SEQUENCE DESCRIPTION: SEQ ID NO:61:

```
GCGCAATCAG TGCCATGGGG AATTAGCCGT GTGCAAGCCC CGGCTGCCCA T AACCGTGGA      60
TTGACAGGTT CTGGTGTAAA AGTTGCTGTC CTCGATACAG GTATTTCCAC T CATCCAGAC     120
TTAAATATTC GTGGTGGCGC TAGCTTTGTA CCAGGGGAAC CATCCACTCA A GATGGGAAT    180
GGGCATGGCA CGCATGTGGC CGGGACGATT GCTGCTTTAA ACAATTCGAT T GGCGTTCTT    240
GGCGTAGCGC CTAGTGCGGA ACTATACGCT GTTAAAGTTT TAGGAGCCGA C GGTAGAGGT    300
GCAATCAGCT CGATTGCCCA AGGGTTGGAA TGGGCAGGGA ACAATGGCAT G CACGTTGCT    360
AATTTGAGTT TAGGAAGCCC TTCGCCAAGT GCCACACTTG AGCAAGCTGT T AATAGCGCG    420
ACTTCTAGAG GCGTTCTTGT TGTAGCGGCA TCTGGGAATT CAGGTGCAAG C TCAATCAGC    480
TATCCGGCCC GTTATGCGAA CGCAATGGCA GTCGGAGCTA CTGACCAAAA C AACAACCGC    540
GCCAGCTTTT CACAGTATGG CCCAGGGCTT GACATTATGG CACCAGGGGT A AACGTGCAG    600
AGCACATACC CAGGTTCAAC GTATGCCAGC TTAAACGGTA CATCGATGGC T ACTCCTCAT    660
```

```
GTTGCAGGTG CAGCAGCCCT TGTTAAACAA AAGAACCCAT CTTGGTCCAA T GTACAAATC      720

CGCAACCATC TAAAGAATAC GGCAACGAGC TTAGGAAGCA CGAACTTGTA T GGAAGCGGA      780

CTTGTCAATG CAGAAGCGGC AACACGC                                          807
```

(2) INFORMATION FOR SEQ ID NO:62:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (B) STRAIN: Bacillus l entus DSM 5483

(vii) IMMEDIATE SOURCE:
        (B) CLONE: A188P (xi) SEQUENCE DESCRIPTION: SEQ ID NO:62:

```
GCGCAATCAG TGCCATGGGG AATTAGCCGT GTGCAAGCCC CGGCTGCCCA T AACCGTGGA       60

TTGACAGGTT CTGGTGTAAA AGTTGCTGTC CTCGATACAG GTATTTCCAC T CATCCAGAC     120

TTAAATATTC GTGGTGGCGC TAGCTTTGTA CCAGGGGAAC CATCCACTCA A GATGGAAT      180

GGGCATGGCA CGCATGTGGC CGGGACGATT GCTGCTTTAA ACAATTCGAT T GGCGTTCTT     240

GGCGTAGCGC CTAGTGCGGA ACTATACGCT GTTAAAGTTT TAGGAGCCGA C GGTAGAGGT     300

GCAATCAGCT CGATTGCCCA AGGGTTGGAA TGGGCAGGGA ACAATGGCAT G CACGTTGCT     360

AATTTGAGTT TAGGAAGCCC TTCGCCAAGT GCCACACTTG AGCAAGCTGT T AATAGCGCG     420

ACTTCTAGAG GCGTTCTTGT TGTAGCGGCA TCTGGGAATT CAGGTGCAAG C TCAATCAGC     480

TATCCGGCCC GTTATGCGAA CGCAATGGCA GTCGGAGCTA CTGACCAAAA C AACAACCGC     540

GCCAGCTTTT CACAGTATGG CCCAGGGCTT GACATTGTCG CACCAGGGGT A AACGTGCAG     600

AGCACATACC CAGGTTCAAC GTATGCCAGC TTAAACGGTA CATCGATGGC T ACTCCTCAT     660

GTTGCAGGTG CAGCAGCCCT TGTTAAACAA AAGAACCCAT CTTGGTCCAA T GTACAAATC     720

CGCAACCATC TAAAGAATAC GGCAACGAGC TTAGGAAGCA CGAACTTGTA T GGAAGCGGA     780

CTTGTCAATG CAGAAGCGGC AACACGC                                         807
```

(2) INFORMATION FOR SEQ ID NO:63:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (B) STRAIN: Bacillus l entus DSM 5483

(vii) IMMEDIATE SOURCE:
        (B) CLONE: S3T, V4I, A188P, V193M (xi) SEQUENCE DESCRIPTION: SEQ ID NO:63:

```
GCGCAAACAA TCCCATGGGG AATTAGCCGT GTGCAAGCCC CGGCTGCCCA T AACCGTGGA      60

TTGACAGGTT CTGGTGTAAA AGTTGCTGTC CTCGATACAG GTATTTCCAC T CATCCAGAC    120

TTAAATATTC GTGGTGGCGC TAGCTTTGTA CCAGGGGAAC CATCCACTCA A GATGGGAAT    180

GGGCATGGCA CGCATGTGGC CGGGACGATT GCTGCTTTAA ACAATTCGAT T GGCGTTCTT    240

GGCGTAGCGC CTAGTGCGGA ACTATACGCT GTTAAAGTTT AGGAGCCGA  C GGTAGAGGT    300

GCAATCAGCT CGATTGCCCA AGGGTTGGAA TGGGCAGGGA ACAATGGCAT G CACGTTGCT    360

AATTTGAGTT TAGGAAGCCC TTCGCCAAGT GCCACACTTG AGCAAGCTGT T AATAGCGCG    420

ACTTCTAGAG GCGTTCTTGT TGTAGCGGCA TCTGGGAATT CAGGTGCAAG C TCAATCAGC    480

TATCCGGCCC GTTATGCGAA CGCAATGGCA GTCGGAGCTA CTGACCAAAA C AACAACCGC    540

GCCAGCTTTT CACAGTATGG CCCAGGGCTT GACATTATGG CACCAGGGGT A AACGTGCAG    600

AGCACATACC CAGGTTCAAC GTATGCCAGC TTAAACGGTA CATCGATGGC T ACTCCTCAT    660

GTTGCAGGTG CAGCAGCCCT TGTTAAACAA AGAACCCAT  CTTGGTCCAA T GTACAAATC    720

CGCAACCATC TAAAGAATAC GGCAACGAGC TTAGGAAGCA CGAACTTGTA T GGAAGCGGA    780

CTTGTCAATG CAGAAGCGGC AACACGC                                         807
```

(2) INFORMATION FOR SEQ ID NO:64:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (B) STRAIN: Bacillus l entus DSM 5483

(vii) IMMEDIATE SOURCE:
        (B) CLONE: V193M (xi) SEQUENCE DESCRIPTION: SEQ ID NO:64:

```
GCGCAATCAG TGCCATGGGG AATTAGCCGT GTGCAAGCCC CGGCTGCCCA T AACCGTGGA     60

TTGACAGGTT CTGGTGTAAA AGTTGCTGTC CTCGATACAG GTATTTCCAC T CATCCAGAC   120

TTAAATATTC GTGGTGGCGC TAGCTTTGTA CCAGGGGAAC CATCCACTCA A GATGGGAAT   180

GGGCATGGCA CGCATGTGGC CGGGACGATT GCTGCTTTAA ACAATTCGAT T GGCGTTCTT   240

GGCGTAGCGC CTAGTGCGGA ACTATACGCT GTTAAAGTTT AGGAGCCGA  C GGTAGAGGT   300

GCAATCAGCT CGATTGCCCA AGGGTTGGAA TGGGCAGGGA ACAATGGCAT G CACGTTGCT   360

AATTTGAGTT TAGGAAGCCC TTCGCCAAGT GCCACACTTG AGCAAGCTGT T AATAGCGCG   420

ACTTCTAGAG GCGTTCTTGT TGTAGCGGCA TCTGGGAATT CAGGTGCAAG C TCAATCAGC   480

TATCCGGCCC GTTATGCGAA CGCAATGGCA GTCGGAGCTA CTGACCAAAA C AACAACCGC   540

GCCAGCTTTT CACAGTATGG CGCAGGGCTT GACATTATGG CACCAGGGGT A AACGTGCAG   600

AGCACATACC CAGGTTCAAC GTATGCCAGC TTAAACGGTA CATCGATGGC T ACTCCTCAT   660

GTTGCAGGTG CAGCAGCCCT TGTTAAACAA AGAACCCAT  CTTGGTCCAA T GTACAAATC   720

CGCAACCATC TAAAGAATAC GGCAACGAGC TTAGGAAGCA CGAACTTGTA T GGAAGCGGA   780

CTTGTCAATG CAGAAGCGGC AACACGC                                        807
```

(2) INFORMATION FOR SEQ ID NO:65:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (B) STRAIN: Bacillus l entus DSM 5483

(vii) IMMEDIATE SOURCE:
        (B) CLONE: S104T (xi) SEQUENCE DESCRIPTION: SEQ ID NO:65:

```
GCGCAATCAG TGCCATGGGG AATTAGCCGT GTGCAAGCCC CGGCTGCCCA T AACCGTGGA      60

TTGACAGGTT CTGGTGTAAA AGTTGCTGTC CTCGATACAG GTATTTCCAC T CATCCAGAC     120

TTAAATATTC GTGGTGGCGC TAGCTTTGTA CCAGGGGAAC CATCCACTCA A GATGGGAAT    180

GGGCATGGCA CGCATGTGGC CGGGACGATT GCTGCTTTAA ACAATTCGAT T GGCGTTCTT    240

GGCGTAGCGC CTAGTGCGGA ACTATACGCT GTTAAAGTTT TAGGAGCCGA C GGTAGAGGT    300

GCAATCAGCA CGATTGCCCA AGGGTTGGAA TGGGCAGGGA ACAATGGCAT G CACGTTGCT    360

AATTTGAGTT TAGGAAGCCC TTCGCCAAGT GCCACACTTG AGCAAGCTGT T AATAGCGCG    420

ACTTCTAGAG GCGTTCTTGT TGTAGCGGCA TCTGGGAATT CAGGTGCAAG C TCAATCAGC    480

TATCCGGCCC GTTATGCGAA CGCAATGGCA GTCGGAGCTA CTGACCAAAA C AACAACCGC    540

GCCAGCTTTT CACAGTATGG CGCAGGGCTT GACATTGTCG CACCAGGGGT A AACGTGCAG    600

AGCACATACC CAGGTTCAAC GTATGCCAGC TTAAACGGTA CATCGATGGC T ACTCCTCAT    660

GTTGCAGGTG CAGCAGCCCT TGTTAAACAA AAGAACCCAT CTTGGTCCAA T GTACAAATC    720

CGCAACCATC TAAAGAATAC GGCAACGAGC TTAGGAAGCA CGAACTTGTA T GGAAGCGGA    780

CTTGTCAATG CAGAAGCGGC AACACGC                                         807
```

(2) INFORMATION FOR SEQ ID NO:66:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (B) STRAIN: Bacillus l entus DSM 5483

(vii) IMMEDIATE SOURCE:
        (B) CLONE: T69V (xi) SEQUENCE DESCRIPTION: SEQ ID NO:66:

```
GCGCAATCAG TGCCATGGGG AATTAGCCGT GTGCAAGCCC CGGCTGCCCA T AACCGTGGA      60

TTGACAGGTT CTGGTGTAAA AGTTGCTGTC CTCGATACAG GTATTTCCAC T CATCCAGAC    120
```

-continued

```
TTAAATATTC GTGGTGGCGC TAGCTTTGTA CCAGGGGAAC CATCCACTCA A GATGGGAAT      180

GGGCATGGCA CGCATGTGGC CGGGGTTATT GCTGCTTTAA ACAATTCGAT T GGCGTTCTT      240

GGCGTAGCGC CTAGTGCGGA ACTATACGCT GTTAAAGTTT TAGGAGCCGA C GGTAGAGGT      300

GCAATCAGCT CGATTGCCCA AGGGTTGGAA TGGGCAGGGA ACAATGGCAT G CACGTTGCT      360

AATTTGAGTT TAGGAAGCCC TTCGCCAAGT GCCACACTTG AGCAAGCTGT T AATAGCGCG      420

ACTTCTAGAG GCGTTCTTGT TGTAGCGGCA TCTGGGAATT CAGGTGCAAG C TCAATCAGC      480

TATCCGGCCC GTTATGCGAA CGCAATGGCA GTCGGAGCTA CTGACCAAAA C AACAACCGC      540

GCCAGCTTTT CACAGTATGG CGCAGGGCTT GACATTGTCG CACCAGGGGT A AACGTGCAG      600

AGCACATACC CAGGTTCAAC GTATGCCAGC TTAAACGGTA CATCGATGGC T ACTCCTCAT      660

GTTGCAGGTG CAGCAGCCCT TGTTAAACAA AAGAACCCAT CTTGGTCCAA T GTACAAATC      720

CGCAACCATC TAAAGAATAC GGCAACGAGC TTAGGAAGCA CGAACTTGTA T GGAAGCGGA      780

CTTGTCAATG CAGAAGCGGC AACACGC                                          807
```

(2) INFORMATION FOR SEQ ID NO:67:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (B) STRAIN: Bacillus l entus DSM 5483

(vii) IMMEDIATE SOURCE:
        (B) CLONE: V4I, A188P, V193M (xi) SEQUENCE DESCRIPTION: SEQ ID NO:67:

```
GCGCAATCAA TCCCATGGGG AATTAGCCGT GTGCAAGCCC CGGCTGCCCA T AACCGTGGA       60

TTGACAGGTT CTGGTGTAAA AGTTGCTGTC CTCGATACAG GTATTTCCAC T CATCCAGAC      120

TTAAATATTC GTGGTGGCGC TAGCTTTGTA CCAGGGGAAC CATCCACTCA A GATGGGAAT      180

GGGCATGGCA CGCATGTGGC CGGGACGATT GCTGCTTTAA ACAATTCGAT T GGCGTTCTT      240

GGCGTAGCGC CTAGTGCGGA ACTATACGCT GTTAAAGTTT TAGGAGCCGA C GGTAGAGGT      300

GCAATCAGCT CGATTGCCCA AGGGTTGGAA TGGGCAGGGA ACAATGGCAT G CACGTTGCT      360

AATTTGAGTT TAGGAAGCCC TTCGCCAAGT GCCACACTTG AGCAAGCTGT T AATAGCGCG      420

ACTTCTAGAG GCGTTCTTGT TGTAGCGGCA TCTGGGAATT CAGGTGCAAG C TCAATCAGC      480

TATCCGGCCC GTTATGCGAA CGCAATGGCA GTCGGAGCTA CTGACCAAAA C AACAACCGC      540

GCCAGCTTTT CACAGTATGG CCCAGGGCTT GACATTATGG CACCAGGGGT A AACGTGCAG      600

AGCACATACC CAGGTTCAAC GTATGCCAGC TTAAACGGTA CATCGATGGC T ACTCCTCAT      660

GTTGCAGGTG CAGCAGCCCT TGTTAAACAA AAGAACCCAT CTTGGTCCAA T GTACAAATC      720

CGCAACCATC TAAAGAATAC GGCAACGAGC TTAGGAAGCA CGAACTTGTA T GGAAGCGGA      780

CTTGTCAATG CAGAAGCGGC AACACGC                                          807
```

(2) INFORMATION FOR SEQ ID NO:68:

(i) SEQUENCE CHARACTERISTICS:

(A) LENGTH: 807 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(B) STRAIN: Bacillus l entus DSM 5483

(vii) IMMEDIATE SOURCE:
(B) CLONE: A224V (xi) SEQUENCE DESCRIPTION: SEQ ID NO:68:

```
GCGCAATCAG TGCCATGGGG AATTAGCCGT GTGCAAGCCC CGGCTGCCCA T AACCGTGGA      60
TTGACAGGTT CTGGTGTAAA AGTTGCTGTC CTCGATACAG GTATTTCCAC T CATCCAGAC    120
TTAAATATTC GTGGTGGCGC TAGCTTTGTA CCAGGGGAAC CATCCACTCA A GATGGGAAT    180
GGGCATGGCA CGCATGTGGC CGGGACGATT GCTGCTTTAA ACAATTCGAT T GGCGTTCTT    240
GGCGTAGCGC CTAGTGCGGA ACTATACGCT GTTAAAGTTT TAGGAGCCGA C GGTAGAGGT    300
GCAATCAGCT CGATTGCCCA AGGGTTGGAA TGGGCAGGGA ACAATGGCAT G CACGTTGCT    360
AATTTGAGTT TAGGAAGCCC TTCGCCAAGT GCCACACTTG AGCAAGCTGT T AATAGCGCG    420
ACTTCTAGAG GCGTTCTTGT TGTAGCGGCA TCTGGGAATT CAGGTGCAAG C TCAATCAGC    480
TATCCGGCCC GTTATGCGAA CGCAATGGCA GTCGGAGCTA CTGACCAAAA C AACAACCGC    540
GCCAGCTTTT CACAGTATGG CGCAGGGCTT GACATTGTCG CACCAGGGGT A AACGTGCAG    600
AGCACATACC CAGGTTCAAC GTATGCCAGC TTAAACGGTA CATCGATGGC T ACTCCTCAT    660
GTTGCAGGTG TTGCAGCCCT TGTTAAACAA AAGAACCCAT CTTGGTCCAA T GTACAAATC    720
CGCAACCATC TAAAGAATAC GGCAACGAGC TTAGGAAGCA CGAACTTGTA T GGAAGCGGA    780
CTTGTCAATG CAGAAGCGGC AACACGC                                         807
```

(2) INFORMATION FOR SEQ ID NO:69:

(i) SEQUENCE CHARACTERISTICS:
(A) LENGTH: 807 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(B) STRAIN: Bacillus l entus DSM 5483

(vii) IMMEDIATE SOURCE:
(B) CLONE: V199I (xi) SEQUENCE DESCRIPTION: SEQ ID NO:69:

```
GCGCAATCAG TGCCATGGGG AATTAGCCGT GTGCAAGCCC CGGCTGCCCA T AACCGTGGA      60
TTGACAGGTT CTGGTGTAAA AGTTGCTGTC CTCGATACAG GTATTTCCAC T CATCCAGAC    120
TTAAATATTC GTGGTGGCGC TAGCTTTGTA CCAGGGGAAC CATCCACTCA A GATGGGAAT    180
GGGCATGGCA CGCATGTGGC CGGGACGATT GCTGCTTTAA ACAATTCGAT T GGCGTTCTT    240
GGCGTAGCGC CTAGTGCGGA ACTATACGCT GTTAAAGTTT TAGGAGCCGA C GGTAGAGGT    300
```

-continued

```
GCAATCAGCT CGATTGCCCA AGGGTTGGAA TGGGCAGGGA ACAATGGCAT G CACGTTGCT      360

AATTTGAGTT TAGGAAGCCC TTCGCCAAGT GCCACACTTG AGCAAGCTGT T AATAGCGCG      420

ACTTCTAGAG GCGTTCTTGT TGTAGCGGCA TCTGGGAATT CAGGTGCAAG C TCAATCAGC      480

TATCCGGCCC GTTATGCGAA CGCAATGGCA GTCGGAGCTA CTGACCAAAA C AACAACCGC      540

GCCAGCTTTT CACAGTATGG CGCAGGGCTT GACATTGTCG CACCAGGGGT A AACATTCAG      600

AGCACATACC CAGGTTCAAC GTATGCCAGC TTAAACGGTA CATCGATGGC T ACTCCTCAT      660

GTTGCAGGTG CAGCAGCCCT TGTTAAACAA AAGAACCCAT CTTGGTCCAA T GTACAAATC      720

CGCAACCATC TAAAGAATAC GGCAACGAGC TTAGGAAGCA CGAACTTGTA T GGAAGCGGA      780

CTTGTCAATG CAGAAGCGGC AACACGC                                          807
```

(2) INFORMATION FOR SEQ ID NO:70:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (B) STRAIN: Bacillus l entus DSM 5483

(vii) IMMEDIATE SOURCE:
        (B) CLONE: V4I (xi) SEQUENCE DESCRIPTION: SEQ ID NO:70:

```
GCGCAATCAA TCCCATGGGG AATTAGCCGT GTGCAAGCCC CGGCTGCCCA T AACCGTGGA      60

TTGACAGGTT CTGGTGTAAA AGTTGCTGTC CTCGATACAG GTATTTCCAC T CATCCAGAC     120

TTAAATATTC GTGGTGGCGC TAGCTTTGTA CCAGGGGAAC CATCCACTCA A GATGGGAAT     180

GGGCATGGCA CGCATGTGGC CGGGACGATT GCTGCTTTAA ACAATTCGAT T GGCGTTCTT     240

GGCGTAGCGC CTAGTGCGGA ACTATACGCT GTTAAAGTTT TAGGAGCCGA C GGTAGAGGT     300

GCAATCAGCT CGATTGCCCA AGGGTTGGAA TGGGCAGGGA ACAATGGCAT G CACGTTGCT     360

AATTTGAGTT TAGGAAGCCC TTCGCCAAGT GCCACACTTG AGCAAGCTGT T AATAGCGCG     420

ACTTCTAGAG GCGTTCTTGT TGTAGCGGCA TCTGGGAATT CAGGTGCAAG C TCAATCAGC     480

TATCCGGCCC GTTATGCGAA CGCAATGGCA GTCGGAGCTA CTGACCAAAA C AACAACCGC     540

GCCAGCTTTT CACAGTATGG CGCAGGGCTT GACATTGTCG CACCAGGGGT A AACGTGCAG     600

AGCACATACC CAGGTTCAAC GTATGCCAGC TTAAACGGTA CATCGATGGC T ACTCCTCAT     660

GTTGCAGGTG CAGCAGCCCT TGTTAAACAA AAGAACCCAT CTTGGTCCAA T GTACAAATC     720

CGCAACCATC TAAAGAATAC GGCAACGAGC TTAGGAAGCA CGAACTTGTA T GGAAGCGGA     780

CTTGTCAATG CAGAAGCGGC AACACGC                                         807
```

(2) INFORMATION FOR SEQ ID NO:71:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
    (B) STRAIN: Bacillus l entus DSM 5483

(vii) IMMEDIATE SOURCE:
    (B) CLONE: S3T (xi) SEQUENCE DESCRIPTION: SEQ ID NO:71:

```
GCGCAAACAG TGCCATGGGG AATTAGCCGT GTGCAAGCCC CGGCTGCCCA T AACCGTGGA      60

TTGACAGGTT CTGGTGTAAA AGTTGCTGTC CTCGATACAG GTATTTCCAC T CATCCAGAC    120

TTAAATATTC GTGGTGGCGC TAGCTTTGTA CCAGGGGAAC CATCCACTCA A GATGGGAAT    180

GGGCATGGCA CGCATGTGGC CGGGACGATT GCTGCTTTAA ACAATTCGAT T GGCGTTCTT    240

GGCGTAGCGC CTAGTGCGGA ACTATACGCT GTTAAAGTTT TAGGAGCCGA C GGTAGAGGT    300

GCAATCAGCT CGATTGCCCA AGGGTTGGAA TGGGCAGGGA ACAATGGCAT G CACGTTGCT    360

AATTTGAGTT TAGGAAGCCC TTCGCCAAGT GCCACACTTG AGCAAGCTGT T AATAGCGCG    420

ACTTCTAGAG GCGTTCTTGT TGTAGCGGCA TCTGGGAATT CAGGTGCAAG C TCAATCAGC    480

TATCCGGCCC GTTATGCGAA CGCAATGGCA GTCGGAGCTA CTGACCAAAA C AACAACCGC    540

GCCAGCTTTT CACAGTATGG CGCAGGGCTT GACATTGTCG CACCAGGGGT A AACGTGCAG    600

AGCACATACC CAGGTTCAAC GTATGCCAGC TTAAACGGTA CATCGATGGC T ACTCCTCAT    660

GTTGCAGGTG CAGCAGCCCT TGTTAAACAA AAGAACCCAT CTTGGTCCAA T GTACAAATC    720

CGCAACCATC TAAAGAATAC GGCAACGAGC TTAGGAAGCA CGAACTTGTA T GGAAGCGGA    780

CTTGTCAATG CAGAAGCGGC AACACGC                                         807
```

(2) INFORMATION FOR SEQ ID NO:72:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (B) STRAIN: Bacillus l entus DSM 5483

(vii) IMMEDIATE SOURCE:
        (B) CLONE: S139Y (xi) SEQUENCE DESCRIPTION: SEQ ID NO:72:

```
GCGCAATCAG TGCCATGGGG AATTAGCCGT GTGCAAGCCC CGGCTGCCCA T AACCGTGGA      60

TTGACAGGTT CTGGTGTAAA AGTTGCTGTC CTCGATACAG GTATTTCCAC T CATCCAGAC    120

TTAAATATTC GTGGTGGCGC TAGCTTTGTA CCAGGGGAAC CATCCACTCA A GATGGGAAT    180

GGGCATGGCA CGCATGTGGC CGGGACGATT GCTGCTTTAA ACAATTCGAT T GGCGTTCTT    240

GGCGTAGCGC CTAGTGCGGA ACTATACGCT GTTAAAGTTT TAGGAGCCGA C GGTAGAGGT    300

GCAATCAGCT CGATTGCCCA AGGGTTGGAA TGGGCAGGGA ACAATGGCAT G CACGTTGCT    360

AATTTGAGTT TAGGAAGCCC TTCGCCAAGT GCCACACTTG AGCAAGCTGT T AATTATGCG    420
```

```
ACTTCTAGAG GCGTTCTTGT TGTAGCGGCA TCTGGGAATT CAGGTGCAAG C TCAATCAGC      480

TATCCGGCCC GTTATGCGAA CGCAATGGCA GTCGGAGCTA CTGACCAAAA C AACAACCGC      540

GCCAGCTTTT CACAGTATGG CGCAGGGCTT GACATTGTCG CACCAGGGGT A AACGTGCAG      600

AGCACATACC CAGGTTCAAC GTATGCCAGC TTAAACGGTA CATCGATGGC T ACTCCTCAT      660

GTTGCAGGTG CAGCAGCCCT TGTTAAACAA AAGAACCCAT CTTGGTCCAA T GTACAAATC      720

CGCAACCATC TAAAGAATAC GGCAACGAGC TTAGGAAGCA CGAACTTGTA T GGAAGCGGA      780

CTTGTCAATG CAGAAGCGGC AACACGC                                           807
```

(2) INFORMATION FOR SEQ ID NO:73:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (B) STRAIN: Bacillus l entus DSM 5483

(vii) IMMEDIATE SOURCE:
        (B) CLONE: N242A (xi) SEQUENCE DESCRIPTION: SEQ ID NO:73:

```
GCGCAATCAG TGCCATGGGG AATTAGCCGT GTGCAAGCCC CGGCTGCCCA T AACCGTGGA      60

TTGACAGGTT CTGGTGTAAA AGTTGCTGTC CTCGATACAG GTATTTCCAC T CATCCAGAC     120

TTAAATATTC GTGGTGGCGC TAGCTTTGTA CCAGGGGAAC CATCCACTCA A GATGGGAAT     180

GGGCATGGCA CGCATGTGGC CGGGACGATT GCTGCTTTAA ACAATTCGAT T GGCGTTCTT     240

GGCGTAGCGC CTAGTGCGGA ACTATACGCT GTTAAAGTTT TAGGAGCCGA C GGTAGAGGT     300

GCAATCAGCT CGATTGCCCA AGGGTTGGAA TGGGCAGGGA ACAATGGCAT G CACGTTGCT     360

AATTTGAGTT TAGGAAGCCC TTCGCCAAGT GCCACACTTG AGCAAGCTGT T AATAGCGCG     420

ACTTCTAGAG GCGTTCTTGT TGTAGCGGCA TCTGGGAATT CAGGTGCAAG C TCAATCAGC     480

TATCCGGCCC GTTATGCGAA CGCAATGGCA GTCGGAGCTA CTGACCAAAA C AACAACCGC     540

GCCAGCTTTT CACAGTATGG CGCAGGGCTT GACATTGTCG CACCAGGGGT A AACGTGCAG     600

AGCACATACC CAGGTTCAAC GTATGCCAGC TTAAACGGTA CATCGATGGC T ACTCCTCAT     660

GTTGCAGGTG CAGCAGCCCT TGTTAAACAA AAGAACCCAT CTTGGTCCAA T GTACAAATC     720

CGCGCACATC TAAAGAATAC GGCAACGAGC TTAGGAAGCA CGAACTTGTA T GGAAGCGGA     780

CTTGTCAATG CAGAAGCGGC AACACGC                                          807
```

(2) INFORMATION FOR SEQ ID NO:74:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (B) STRAIN: Bacillus l entus DSM 5483

(vii) IMMEDIATE SOURCE:
         (B) CLONE: S236T (xi) SEQUENCE DESCRIPTION: SEQ ID NO:74:

| | | | | | |
|---|---|---|---|---|---|
| GCGCAATCAG | TGCCATGGGG | AATTAGCCGT | GTGCAAGCCC | CGGCTGCCCA T AACCGTGGA | 60 |
| TTGACAGGTT | CTGGTGTAAA | AGTTGCTGTC | CTCGATACAG | GTATTTCCAC T CATCCAGAC | 120 |
| TTAAATATTC | GTGGTGGCGC | TAGCTTTGTA | CCAGGGGAAC | CATCCACTCA A GATGGGAAT | 180 |
| GGGCATGGCA | CGCATGTGGC | CGGGACGATT | GCTGCTTTAA | ACAATTCGAT T GGCGTTCTT | 240 |
| GGCGTAGCGC | CTAGTGCGGA | ACTATACGCT | GTTAAAGTTT | TAGGAGCCGA C GGTAGAGGT | 300 |
| GCAATCAGCT | CGATTGCCCA | AGGGTTGGAA | TGGGCAGGGA | ACAATGGCAT G CACGTTGCT | 360 |
| AATTTGAGTT | TAGGAAGCCC | TTCGCCAAGT | GCCACACTTG | AGCAAGCTGT T AATAGCGCG | 420 |
| ACTTCTAGAG | GCGTTCTTGT | TGTAGCGGCA | TCTGGGAATT | CAGGTGCAAG C TCAATCAGC | 480 |
| TATCCGGCCC | GTTATGCGAA | CGCAATGGCA | GTCGGAGCTA | CTGACCAAAA C AACAACCGC | 540 |
| GCCAGCTTTT | CACAGTATGG | CGCAGGGCTT | GACATTGTCG | CACCAGGGGT A AACGTGCAG | 600 |
| AGCACATACC | CAGGTTCAAC | GTATGCCAGC | TTAAACGGTA | CATCGATGGC T ACTCCTCAT | 660 |
| GTTGCAGGTG | CAGCAGCCCT | TGTTAAACAA | AAGAACCCAT | CTTGGACAAA T GTACAAATC | 720 |
| CGCAACCATC | TAAAGAATAC | GGCAACGAGC | TTAGGAAGCA | CGAACTTGTA T GGAAGCGGA | 780 |
| CTTGTCAATG | CAGAAGCGGC | AACACGC | | | 807 |

(2) INFORMATION FOR SEQ ID NO:75:

(i) SEQUENCE CHARACTERISTICS:
         (A) LENGTH: 807 base pairs
         (B) TYPE: nucleic acid
         (C) STRANDEDNESS: double
         (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (B) STRAIN: Bacillus l entus DSM 5483

(vii) IMMEDIATE SOURCE:
         (B) CLONE: S36A (xi) SEQUENCE DESCRIPTION: SEQ ID NO:75:

| | | | | | |
|---|---|---|---|---|---|
| GCGCAATCAG | TGCCATGGGG | AATTAGCCGT | GTGCAAGCCC | CGGCTGCCCA T AACCGTGGA | 60 |
| TTGACAGGTT | CTGGTGTAAA | AGTTGCTGTC | CTCGATACAG | GTATTGCAAC T CATCCAGAC | 120 |
| TTAAATATTC | GTGGTGGCGC | TAGCTTTGTA | CCAGGGGAAC | CATCCACTCA A GATGGGAAT | 180 |
| GGGCATGGCA | CGCATGTGGC | CGGGACGATT | GCTGCTTTAA | ACAATTCGAT T GGCGTTCTT | 240 |
| GGCGTAGCGC | CTAGTGCGGA | ACTATACGCT | GTTAAAGTTT | TAGGAGCCGA C GGTAGAGGT | 300 |
| GCAATCAGCT | CGATTGCCCA | AGGGTTGGAA | TGGGCAGGGA | ACAATGGCAT G CACGTTGCT | 360 |
| AATTTGAGTT | TAGGAAGCCC | TTCGCCAAGT | GCCACACTTG | AGCAAGCTGT T AATAGCGCG | 420 |
| ACTTCTAGAG | GCGTTCTTGT | TGTAGCGGCA | TCTGGGAATT | CAGGTGCAAG C TCAATCAGC | 480 |
| TATCCGGCCC | GTTATGCGAA | CGCAATGGCA | GTCGGAGCTA | CTGACCAAAA C AACAACCGC | 540 |
| GCCAGCTTTT | CACAGTATGG | CGCAGGGCTT | GACATTGTCG | CACCAGGGGT A AACGTGCAG | 600 |

```
AGCACATACC CAGGTTCAAC GTATGCCAGC TTAAACGGTA CATCGATGGC T ACTCCTCAT      660

GTTGCAGGTG CAGCAGCCCT TGTTAAACAA AAGAACCCAT CTTGGTCCAA T GTACAAATC      720

CGCAACCATC TAAAGAATAC GGCAACGAGC TTAGGAAGCA CGAACTTGTA T GGAAGCGGA      780

CTTGTCAATG CAGAAGCGGC AACACGC                                          807
```

(2) INFORMATION FOR SEQ ID NO:76:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (B) STRAIN: Bacillus l entus DSM 5483

(vii) IMMEDIATE SOURCE:
        (B) CLONE: H243A (xi) SEQUENCE DESCRIPTION: SEQ ID NO:76:

```
GCGCAATCAG TGCCATGGGG AATTAGCCGT GTGCAAGCCC CGGCTGCCCA T AACCGTGGA      60

TTGACAGGTT CTGGTGTAAA AGTTGCTGTC CTCGATACAG GTATTTCCAC T CATCCAGAC    120

TTAAATATTC GTGGTGGCGC TAGCTTTGTA CCAGGGGAAC CATCCACTCA A GATGGGAAT    180

GGGCATGGCA CGCATGTGGC CGGGACGATT GCTGCTTTAA ACAATTCGAT T GGCGTTCTT    240

GGCGTAGCGC CTAGTGCGGA ACTATACGCT GTTAAAGTTT TAGGAGCCGA C GGTAGAGGT    300

GCAATCAGCT CGATTGCCCA AGGGTTGGAA TGGGCAGGGA ACAATGGCAT G CACGTTGCT    360

AATTTGAGTT TAGGAAGCCC TTCGCCAAGT GCCACACTTG AGCAAGCTGT T AATAGCGCG    420

ACTTCTAGAG GCGTTCTTGT TGTAGCGGCA TCTGGGAATT CAGGTGCAAG C TCAATCAGC    480

TATCCGGCCC GTTATGCGAA CGCAATGGCA GTCGGAGCTA CTGACCAAAA C AACAACCGC    540

GCCAGCTTTT CACAGTATGG CGCAGGGCTT GACATTGTCG CACCAGGGGT A AACGTGCAG    600

AGCACATACC CAGGTTCAAC GTATGCCAGC TTAAACGGTA CATCGATGGC T ACTCCTCAT    660

GTTGCAGGTG CAGCAGCCCT TGTTAAACAA AAGAACCCAT CTTGGTCCAA T GTACAAATC    720

CGCAACGCAC TAAAGAATAC GGCAACGAGC TTAGGAAGCA CGAACTTGTA T GGAAGCGGA    780

CTTGTCAATG CAGAAGCGGC AACACGC                                         807
```

(2) INFORMATION FOR SEQ ID NO:77:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (B) STRAIN: Bacillus l entus DSM 5483

(vii) IMMEDIATE SOURCE:

-continued (B) CLONE: A101T (xi) SEQUENCE DESCRIPTION: SEQ ID NO:77:

GCGCAATCAG TGCCATGGGG AATTAGCCGT GTGCAAGCCC CGGCTGCCCA T AACCGTGGA        60

TTGACAGGTT CTGGTGTAAA AGTTGCTGTC CTCGATACAG GTATTTCCAC T CATCCAGAC       120

TTAAATATTC GTGGTGGCGC TAGCTTTGTA CCAGGGGAAC CATCCACTCA A GATGGGAAT      180

GGGCATGGCA CGCATGTGGC CGGGACGATT GCTGCTTTAA ACAATTCGAT T GGCGTTCTT      240

GGCGTAGCGC CTAGTGCGGA ACTATACGCT GTTAAAGTTT TAGGAGCCGA C GGTAGAGGT      300

ACAATCAGCT CGATTGCCCA AGGGTTGGAA TGGGCAGGGA ACAATGGCAT G CACGTTGCT      360

AATTTGAGTT TAGGAAGCCC TTCGCCAAGT GCCACACTTG AGCAAGCTGT T AATAGCGCG      420

ACTTCTAGAG GCGTTCTTGT TGTAGCGGCA TCTGGGAATT CAGGTGCAAG C TCAATCAGC      480

TATCCGGCCC GTTATGCGAA CGCAATGGCA GTCGGAGCTA CTGACCAAAA C AACAACCGC      540

GCCAGCTTTT CACAGTATGG CGCAGGGCTT GACATTGTCG CACCAGGGGT A AACGTGCAG      600

AGCACATACC CAGGTTCAAC GTATGCCAGC TTAAACGGTA CATCGATGGC T ACTCCTCAT      660

GTTGCAGGTG CAGCAGCCCT TGTTAAACAA AAGAACCCAT CTTGGTCCAA T GTACAAATC     720

CGCAACCATC TAAAGAATAC GGCAACGAGC TTAGGAAGCA CGAACTTGTA T GGAAGCGGA      780

CTTGTCAATG CAGAAGCGGC AACACGC                                          807

(2) INFORMATION FOR SEQ ID NO:78:

(i) SEQUENCE CHARACTERISTICS:
         (A) LENGTH: 807 base pairs
         (B) TYPE: nucleic acid
         (C) STRANDEDNESS: double
         (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (B) STRAIN: Bacillus l entus DSM 5483

(vii) IMMEDIATE SOURCE:
         (B) CLONE: S236A (xi) SEQUENCE DESCRIPTION: SEQ ID NO:78:

GCGCAATCAG TGCCATGGGG AATTAGCCGT GTGCAAGCCC CGGCTGCCCA T AACCGTGGA       60

TTGACAGGTT CTGGTGTAAA AGTTGCTGTC CTCGATACAG GTATTTCCAC T CATCCAGAC      120

TTAAATATTC GTGGTGGCGC TAGCTTTGTA CCAGGGGAAC CATCCACTCA A GATGGGAAT      180

GGGCATGGCA CGCATGTGGC CGGGACGATT GCTGCTTTAA ACAATTCGAT T GGCGTTCTT      240

GGCGTAGCGC CTAGTGCGGA ACTATACGCT GTTAAAGTTT TAGGAGCCGA C GGTAGAGGT      300

GCAATCAGCT CGATTGCCCA AGGGTTGGAA TGGGCAGGGA ACAATGGCAT G CACGTTGCT      360

AATTTGAGTT TAGGAAGCCC TTCGCCAAGT GCCACACTTG AGCAAGCTGT T AATAGCGCG      420

ACTTCTAGAG GCGTTCTTGT TGTAGCGGCA TCTGGGAATT CAGGTGCAAG C TCAATCAGC      480

TATCCGGCCC GTTATGCGAA CGCAATGGCA GTCGGAGCTA CTGACCAAAA C AACAACCGC      540

GCCAGCTTTT CACAGTATGG CGCAGGGCTT GACATTGTCG CACCAGGGGT A AACGTGCAG      600

AGCACATACC CAGGTTCAAC GTATGCCAGC TTAAACGGTA CATCGATGGC T ACTCCTCAT      660

GTTGCAGGTG CAGCAGCCCT TGTTAAACAA AAGAACCCAT CTTGGGCAAA T GTACAAATC     720

```
CGCAACCATC TAAAGAATAC GGCAACGAGC TTAGGAAGCA CGAACTTGTA T GGAAGCGGA      780

CTTGTCAATG CAGAAGCGGC AACACGC                                          807
```

(2) INFORMATION FOR SEQ ID NO:79:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (B) STRAIN: Bacillus l entus DSM 5483

(vii) IMMEDIATE SOURCE:
        (B) CLONE: E87R (xi) SEQUENCE DESCRIPTION: SEQ ID NO:79:

```
GCGCAATCAG TGCCATGGGG AATTAGCCGT GTGCAAGCCC CGGCTGCCCA T AACCGTGGA      60

TTGACAGGTT CTGGTGTAAA AGTTGCTGTC CTCGATACAG GTATTTCCAC T CATCCAGAC    120

TTAAATATTC GTGGTGGCGC TAGCTTTGTA CCAGGGGAAC CATCCACTCA A GATGGGAAT    180

GGGCATGGCA CGCATGTGGC CGGGACGATT GCTGCTTTAA ACAATTCGAT T GGCGTTCTT    240

GGCGTAGCGC CTAGTGCGCG TCTATACGCT GTTAAAGTTT TAGGAGCCGA C GGTAGAGGT    300

GCAATCAGCT CGATTGCCCA AGGGTTGGAA TGGGCAGGGA ACAATGGCAT G CACGTTGCT    360

AATTTGAGTT TAGGAAGCCC TTCGCCAAGT GCCACACTTG AGCAAGCTGT T AATAGCGCG    420

ACTTCTAGAG GCGTTCTTGT TGTAGCGGCA TCTGGGAATT CAGGTGCAAG C TCAATCAGC    480

TATCCGGCCC GTTATGCGAA CGCAATGGCA GTCGGAGCTA CTGACCAAAA C AACAACCGC    540

GCCAGCTTTT CACAGTATGG CGCAGGGCTT GACATTGTCG CACCAGGGGT A AACGTGCAG    600

AGCACATACC CAGGTTCAAC GTATGCCAGC TTAAACGGTA CATCGATGGC T ACTCCTCAT    660

GTTGCAGGTG CAGCAGCCCT TGTTAAACAA AAGAACCCAT CTTGGTCCAA T GTACAAATC    720

CGCAACCATC TAAAGAATAC GGCAACGAGC TTAGGAAGCA CGAACTTGTA T GGAAGCGGA    780

CTTGTCAATG CAGAAGCGGC AACACGC                                         807
```

(2) INFORMATION FOR SEQ ID NO:80:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (B) STRAIN: Bacillus l entus DSM 5483

(vii) IMMEDIATE SOURCE:
        (B) CLONE: N114S (xi) SEQUENCE DESCRIPTION: SEQ ID NO:80:

```
GCGCAATCAG TGCCATGGGG AATTAGCCGT GTGCAAGCCC CGGCTGCCCA T AACCGTGGA      60
```

-continued

```
TTGACAGGTT CTGGTGTAAA AGTTGCTGTC CTCGATACAG GTATTTCCAC T CATCCAGAC        120

TTAAATATTC GTGGTGGCGC TAGCTTTGTA CCAGGGGAAC CATCCACTCA A GATGGGAAT        180

GGGCATGGCA CGCATGTGGC CGGGACGATT GCTGCTTTAA ACAATTCGAT T GGCGTTCTT        240

GGCGTAGCGC CTAGTGCGGA ACTATACGCT GTTAAAGTTT TAGGAGCCGA C GGTAGAGGT        300

GCAATCAGCT CGATTGCCCA AGGGTTGGAA TGGGCAGGGA GCAATGGCAT G CACGTTGCT        360

AATTTGAGTT TAGGAAGCCC TTCGCCAAGT GCCACACTTG AGCAAGCTGT T AATAGCGCG        420

ACTTCTAGAG GCGTTCTTGT TGTAGCGGCA TCTGGGAATT CAGGTGCAAG C TCAATCAGC        480

TATCCGGCCC GTTATGCGAA CGCAATGGCA GTCGGAGCTA CTGACCAAAA C AACAACCGC        540

GCCAGCTTTT CACAGTATGG CGCAGGGCTT GACATTGTCG CACCAGGGGT A AACGTGCAG        600

AGCACATACC CAGGTTCAAC GTATGCCAGC TTAAACGGTA CATCGATGGC T ACTCCTCAT        660

GTTGCAGGTG CAGCAGCCCT TGTTAAACAA AAGAACCCAT CTTGGTCCAA T GTACAAATC        720

CGCAACCATC TAAAGAATAC GGCAACGAGC TTAGGAAGCA CGAACTTGTA T GGAAGCGGA        780

CTTGTCAATG CAGAAGCGGC AACACGC                                            807
```

(2) INFORMATION FOR SEQ ID NO:81:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (B) STRAIN: Bacillus l entus DSM 5483

(vii) IMMEDIATE SOURCE:
        (B) CLONE: A47W (xi) SEQUENCE DESCRIPTION: SEQ ID NO:81:

```
GCGCAATCAG TGCCATGGGG AATTAGCCGT GTGCAAGCCC CGGCTGCCCA T AACCGTGGA         60

TTGACAGGTT CTGGTGTAAA AGTTGCTGTC CTCGATACAG GTATTTCCAC T CATCCAGAC        120

TTAAATATTC GTGGTGGCTG GAGCTTTGTA CCAGGGGAAC CATCCACTCA A GATGGGAAT        180

GGGCATGGCA CGCATGTGGC CGGGACGATT GCTGCTTTAA ACAATTCGAT T GGCGTTCTT        240

GGCGTAGCGC CTAGTGCGGA ACTATACGCT GTTAAAGTTT TAGGAGCCGA C GGTAGAGGT        300

GCAATCAGCT CGATTGCCCA AGGGTTGGAA TGGGCAGGGA ACAATGGCAT G CACGTTGCT        360

AATTTGAGTT TAGGAAGCCC TTCGCCAAGT GCCACACTTG AGCAAGCTGT T AATAGCGCG        420

ACTTCTAGAG GCGTTCTTGT TGTAGCGGCA TCTGGGAATT CAGGTGCAAG C TCAATCAGC        480

TATCCGGCCC GTTATGCGAA CGCAATGGCA GTCGGAGCTA CTGACCAAAA C AACAACCGC        540

GCCAGCTTTT CACAGTATGG CGCAGGGCTT GACATTGTCG CACCAGGGGT A AACGTGCAG        600

AGCACATACC CAGGTTCAAC GTATGCCAGC TTAAACGGTA CATCGATGGC T ACTCCTCAT        660

GTTGCAGGTG CAGCAGCCCT TGTTAAACAA AAGAACCCAT CTTGGTCCAA T GTACAAATC        720

CGCAACCATC TAAAGAATAC GGCAACGAGC TTAGGAAGCA CGAACTTGTA T GGAAGCGGA        780

CTTGTCAATG CAGAAGCGGC AACACGC                                            807
```

(2) INFORMATION FOR SEQ ID NO:82:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (B) STRAIN: Bacillus l entus DSM 5483

(vii) IMMEDIATE SOURCE:
        (B) CLONE: A120S (xi) SEQUENCE DESCRIPTION: SEQ ID NO:82:

```
GCGCAATCAG TGCCATGGGG AATTAGCCGT GTGCAAGCCC CGGCTGCCCA T AACCGTGGA      60
TTGACAGGTT CTGGTGTAAA AGTTGCTGTC CTCGATACAG GTATTTCCAC T CATCCAGAC     120
TTAAATATTC GTGGTGGCGC TAGCTTTGTA CCAGGGGAAC CATCCACTCA A GATGGGAAT     180
GGGCATGGCA CGCATGTGGC CGGGACGATT GCTGCTTTAA ACAATTCGAT T GGCGTTCTT     240
GGCGTAGCGC CTAGTGCGGA ACTATACGCT GTTAAAGTTT TAGGAGCCGA C GGTAGAGGT     300
GCAATCAGCT CGATTGCCCA AGGGTTGGAA TGGGCAGGGA ACAATGGCAT G CACGTTAGC     360
AATTTGAGTT TAGGAAGCCC TTCGCCAAGT GCCACACTTG AGCAAGCTGT T AATAGCGCG     420
ACTTCTAGAG GCGTTCTTGT TGTAGCGGCA TCTGGGAATT CAGGTGCAAG C TCAATCAGC     480
TATCCGGCCC GTTATGCGAA CGCAATGGCA GTCGGAGCTA CTGACCAAAA C AACAACCGC     540
GCCAGCTTTT CACAGTATGG CGCAGGGCTT GACATTGTCG CACCAGGGGT A AACGTGCAG     600
AGCACATACC CAGGTTCAAC GTATGCCAGC TTAAACGGTA CATCGATGGC T ACTCCTCAT     660
GTTGCAGGTG CAGCAGCCCT TGTTAAACAA AAGAACCCAT CTTGGTCCAA T GTACAAATC     720
CGCAACCATC TAAAGAATAC GGCAACGAGC TTAGGAAGCA CGAACTTGTA T GGAAGCGGA     780
CTTGTCAATG CAGAAGCGGC AACACGC                                         807
```

(2) INFORMATION FOR SEQ ID NO:83:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (B) STRAIN: Bacillus l entus DSM 5483

(vii) IMMEDIATE SOURCE:
        (B) CLONE: T56V (xi) SEQUENCE DESCRIPTION: SEQ ID NO:83:

```
GCGCAATCAG TGCCATGGGG AATTAGCCGT GTGCAAGCCC CGGCTGCCCA T AACCGTGGA      60
TTGACAGGTT CTGGTGTAAA AGTTGCTGTC CTCGATACAG GTATTTCCAC T CATCCAGAC     120
TTAAATATTC GTGGTGGCGC TAGCTTTGTA CCAGGGGAAC CATCCGTTCA A GATGGGAAT     180
```

```
GGGCATGGCA CGCATGTGGC CGGGACGATT GCTGCTTTAA ACAATTCGAT T GGCGTTCTT      240

GGCGTAGCGC CTAGTGCGGA ACTATACGCT GTTAAAGTTT TAGGAGCCGA C GGTAGAGGT      300

GCAATCAGCT CGATTGCCCA AGGGTTGGAA TGGGCAGGGA ACAATGGCAT G CACGTTGCT      360

AATTTGAGTT TAGGAAGCCC TTCGCCAAGT GCCACACTTG AGCAAGCTGT T AATAGCGCG      420

ACTTCTAGAG GCGTTCTTGT TGTAGCGGCA TCTGGGAATT CAGGTGCAAG C TCAATCAGC      480

TATCCGGCCC GTTATGCGAA CGCAATGGCA GTCGGAGCTA CTGACCAAAA C AACAACCGC      540

GCCAGCTTTT CACAGTATGG CGCAGGGCTT GACATTGTCG CACCAGGGGT A AACGTGCAG      600

AGCACATACC CAGGTTCAAC GTATGCCAGC TTAAACGGTA CATCGATGGC T ACTCCTCAT      660

GTTGCAGGTG CAGCAGCCCT TGTTAAACAA AAGAACCCAT CTTGGTCCAA T GTACAAATC      720

CGCAACCATC TAAAGAATAC GGCAACGAGC TTAGGAAGCA CGAACTTGTA T GGAAGCGGA      780

CTTGTCAATG CAGAAGCGGC AACACGC                                          807
```

(2) INFORMATION FOR SEQ ID NO:84:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (B) STRAIN: Bacillus l entus DSM 5483

(vii) IMMEDIATE SOURCE:
        (B) CLONE: A120V (xi) SEQUENCE DESCRIPTION: SEQ ID NO:84:

```
GCGCAATCAG TGCCATGGGG AATTAGCCGT GTGCAAGCCC CGGCTGCCCA T AACCGTGGA       60

TTGACAGGTT CTGGTGTAAA AGTTGCTGTC CTCGATACAG GTATTTCCAC T CATCCAGAC      120

TTAAATATTC GTGGTGGCGC TAGCTTTGTA CCAGGGGAAC CATCCACTCA A GATGGGAAT      180

GGGCATGGCA CGCATGTGGC CGGGACGATT GCTGCTTTAA ACAATTCGAT T GGCGTTCTT      240

GGCGTAGCGC CTAGTGCGGA ACTATACGCT GTTAAAGTTT TAGGAGCCGA C GGTAGAGGT      300

GCAATCAGCT CGATTGCCCA AGGGTTGGAA TGGGCAGGGA ACAATGGCAT G CACGTTGTT      360

AATTTGAGTT TAGGAAGCCC TTCGCCAAGT GCCACACTTG AGCAAGCTGT T AATAGCGCG      420

ACTTCTAGAG GCGTTCTTGT TGTAGCGGCA TCTGGGAATT CAGGTGCAAG C TCAATCAGC      480

TATCCGGCCC GTTATGCGAA CGCAATGGCA GTCGGAGCTA CTGACCAAAA C AACAACCGC      540

GCCAGCTTTT CACAGTATGG CGCAGGGCTT GACATTGTCG CACCAGGGGT A AACGTGCAG      600

AGCACATACC CAGGTTCAAC GTATGCCAGC TTAAACGGTA CATCGATGGC T ACTCCTCAT      660

GTTGCAGGTG CAGCAGCCCT TGTTAAACAA AAGAACCCAT CTTGGTCCAA T GTACAAATC      720

CGCAACCATC TAAAGAATAC GGCAACGAGC TTAGGAAGCA CGAACTTGTA T GGAAGCGGA      780

CTTGTCAATG CAGAAGCGGC AACACGC                                          807
```

(2) INFORMATION FOR SEQ ID NO:85:

(i) SEQUENCE CHARACTERISTICS:
        (A) LENGTH: 807 base pairs
        (B) TYPE: nucleic acid (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (B) STRAIN: Bacillus l entus DSM 5483

(vii) IMMEDIATE SOURCE:
        (B) CLONE: G205V (xi) SEQUENCE DESCRIPTION: SEQ ID NO:85:

GCGCAATCAG TGCCATGGGG AATTAGCCGT GTGCAAGCCC CGGCTGCCCA T AACCGTGGA      60

TTGACAGGTT CTGGTGTAAA AGTTGCTGTC CTCGATACAG GTATTTCCAC T CATCCAGAC    120

TTAAATATTC GTGGTGGCGC TAGCTTTGTA CCAGGGGAAC CATCCACTCA A GATGGGAAT    180

GGGCATGGCA CGCATGTGGC CGGGACGATT GCTGCTTTAA ACAATTCGAT T GGCGTTCTT    240

GGCGTAGCGC CTAGTGCGGA ACTATACGCT GTTAAAGTTT TAGGAGCCGA C GGTAGAGGT    300

GCAATCAGCT CGATTGCCCA AGGGTTGGAA TGGGCAGGGA ACAATGGCAT G CACGTTGCT    360

AATTTGAGTT TAGGAAGCCC TTCGCCAAGT GCCACACTTG AGCAAGCTGT T AATAGCGCG    420

ACTTCTAGAG GCGTTCTTGT TGTAGCGGCA TCTGGGAATT CAGGTGCAAG C TCAATCAGC    480

TATCCGGCCC GTTATGCGAA CGCAATGGCA GTCGGAGCTA CTGACCAAAA C AACAACCGC    540

GCCAGCTTTT CACAGTATGG CGCAGGGCTT GACATTGTCG CACCAGGGGT A AACGTGCAG    600

AGCACATACC CAGTTTCAAC GTATGCCAGC TTAAACGGTA CATCGATGGC T ACTCCTCAT    660

GTTGCAGGTG CAGCAGCCCT TGTTAAACAA AAGAACCCAT CTTGGTCCAA T GTACAAATC    720

CGCAACCATC TAAAGAATAC GGCAACGAGC TTAGGAAGCA CGAACTTGTA T GGAAGCGGA    780

CTTGTCAATG CAGAAGCGGC AACACGC                                        807

(2) INFORMATION FOR SEQ ID NO:86:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (B) STRAIN: Bacillus l entus DSM 5483

(vii) IMMEDIATE SOURCE:
        (B) CLONE: S130A (xi) SEQUENCE DESCRIPTION: SEQ ID NO:86:

GCGCAATCAG TGCCATGGGG AATTAGCCGT GTGCAAGCCC CGGCTGCCCA T AACCGTGGA      60

TTGACAGGTT CTGGTGTAAA AGTTGCTGTC CTCGATACAG GTATTTCCAC T CATCCAGAC    120

TTAAATATTC GTGGTGGCGC TAGCTTTGTA CCAGGGGAAC CATCCACTCA A GATGGGAAT    180

GGGCATGGCA CGCATGTGGC CGGGACGATT GCTGCTTTAA ACAATTCGAT T GGCGTTCTT    240

GGCGTAGCGC CTAGTGCGGA ACTATACGCT GTTAAAGTTT TAGGAGCCGA C GGTAGAGGT    300

GCAATCAGCT CGATTGCCCA AGGGTTGGAA TGGGCAGGGA ACAATGGCAT G CACGTTGCT    360

```
AATTTGAGTT TAGGAAGCCC TTCGCCAGCA GCCACACTTG AGCAAGCTGT T AATAGCGCG      420

ACTTCTAGAG GCGTTCTTGT TGTAGCGGCA TCTGGGAATT CAGGTGCAAG C TCAATCAGC      480

TATCCGGCCC GTTATGCGAA CGCAATGGCA GTCGGAGCTA CTGACCAAAA C AACAACCGC      540

GCCAGCTTTT CACAGTATGG CGCAGGGCTT GACATTGTCG CACCAGGGGT A AACGTGCAG      600

AGCACATACC CAGGTTCAAC GTATGCCAGC TTAAACGGTA CATCGATGGC T ACTCCTCAT      660

GTTGCAGGTG CAGCAGCCCT TGTTAAACAA AAGAACCCAT CTTGGTCCAA T GTACAAATC      720

CGCAACCATC TAAAGAATAC GGCAACGAGC TTAGGAAGCA CGAACTTGTA T GGAAGCGGA      780

CTTGTCAATG CAGAAGCGGC AACACGC                                          807

(2) INFORMATION FOR SEQ ID NO:87:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (B) STRAIN: Bacillus l entus DSM 5483

(vii) IMMEDIATE SOURCE:
          (B) CLONE: S130T (xi) SEQUENCE DESCRIPTION: SEQ ID NO:87:

GCGCAATCAG TGCCATGGGG AATTAGCCGT GTGCAAGCCC CGGCTGCCCA T AACCGTGGA       60

TTGACAGGTT CTGGTGTAAA AGTTGCTGTC CTCGATACAG GTATTTCCAC T CATCCAGAC      120

TTAAATATTC GTGGTGGCGC TAGCTTTGTA CCAGGGGAAC CATCCACTCA A GATGGGAAT      180

GGGCATGGCA CGCATGTGGC CGGGACGATT GCTGCTTTAA ACAATTCGAT T GGCGTTCTT      240

GGCGTAGCGC CTAGTGCGGA ACTATACGCT GTTAAAGTTT TAGGAGCCGA C GGTAGAGGT      300

GCAATCAGCT CGATTGCCCA AGGGTTGGAA TGGGCAGGGA ACAATGGCAT G CACGTTGCT      360

AATTTGAGTT TAGGAAGCCC TTCGCCAACA GCCACACTTG AGCAAGCTGT T AATAGCGCG      420

ACTTCTAGAG GCGTTCTTGT TGTAGCGGCA TCTGGGAATT CAGGTGCAAG C TCAATCAGC      480

TATCCGGCCC GTTATGCGAA CGCAATGGCA GTCGGAGCTA CTGACCAAAA C AACAACCGC      540

GCCAGCTTTT CACAGTATGG CGCAGGGCTT GACATTGTCG CACCAGGGGT A AACGTGCAG      600

AGCACATACC CAGGTTCAAC GTATGCCAGC TTAAACGGTA CATCGATGGC T ACTCCTCAT      660

GTTGCAGGTG CAGCAGCCCT TGTTAAACAA AAGAACCCAT CTTGGTCCAA T GTACAAATC      720

CGCAACCATC TAAAGAATAC GGCAACGAGC TTAGGAAGCA CGAACTTGTA T GGAAGCGGA      780

CTTGTCAATG CAGAAGCGGC AACACGC                                          807

(2) INFORMATION FOR SEQ ID NO:88:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)
```

(iii) HYPOTHETICAL: NO (iv) ANTI-SENSE: NO (vi) ORIGINAL SOURCE:
            (B) STRAIN: Bacillus l entus DSM 5483

(vii) IMMEDIATE SOURCE:
            (B) CLONE: A96I (xi) SEQUENCE DESCRIPTION: SEQ ID NO:88:

```
GCGCAATCAG TGCCATGGGG AATTAGCCGT GTGCAAGCCC CGGCTGCCCA T AACCGTGGA      60

TTGACAGGTT CTGGTGTAAA AGTTGCTGTC CTCGATACAG GTATTTCCAC T CATCCAGAC    120

TTAAATATTC GTGGTGGCGC TAGCTTTGTA CCAGGGGAAC CATCCACTCA A GATGGGAAT    180

GGGCATGGCA CGCATGTGGC CGGGACGATT GCTGCTTTAA ACAATTCGAT T GGCGTTCTT    240

GGCGTAGCGC CTAGTGCGGA ACTATACGCT GTTAAAGTTT TAGGAATTGA C GGTAGAGGT    300

GCAATCAGCT CGATTGCCCA AGGGTTGGAA TGGGCAGGGA ACAATGGCAT G CACGTTGCT    360

AATTTGAGTT TAGGAAGCCC TTCGCCAAGT GCCACACTTG AGCAAGCTGT T AATAGCGCG    420

ACTTCTAGAG GCGTTCTTGT TGTAGCGGCA TCTGGGAATT CAGGTGCAAG C TCAATCAGC    480

TATCCGGCCC GTTATGCGAA CGCAATGGCA GTCGGAGCTA CTGACCAAAA C AACAACCGC    540

GCCAGCTTTT CACAGTATGG CGCAGGGCTT GACATTGTCG CACCAGGGGT A AACGTGCAG    600

AGCACATACC CAGGTTCAAC GTATGCCAGC TTAAACGGTA CATCGATGGC T ACTCCTCAT    660

GTTGCAGGTG CAGCAGCCCT TGTTAAACAA AAGAACCCAT CTTGGTCCAA T GTACAAATC    720

CGCAACCATC TAAAGAATAC GGCAACGAGC TTAGGAAGCA CGAACTTGTA T GGAAGCGGA    780

CTTGTCAATG CAGAAGCGGC AACACGC                                         807
```

(2) INFORMATION FOR SEQ ID NO:89:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (B) STRAIN: Bacillus l entus DSM 5483

(vii) IMMEDIATE SOURCE:
        (B) CLONE: S104T, S139 Y, A224V (xi) SEQUENCE DESCRIPTION: SEQ ID NO:89:

```
GCGCAATCAG TGCCATGGGG AATTAGCCGT GTGCAAGCCC CGGCTGCCCA T AACCGTGGA      60

TTGACAGGTT CTGGTGTAAA AGTTGCTGTC CTCGATACAG GTATTTCCAC T CATCCAGAC    120

TTAAATATTC GTGGTGGCGC TAGCTTTGTA CCAGGGGAAC CATCCACTCA A GATGGGAAT    180

GGGCATGGCA CGCATGTGGC CGGGACGATT GCTGCTTTAA ACAATTCGAT T GGCGTTCTT    240

GGCGTAGCGC CTAGTGCGGA ACTATACGCT GTTAAAGTTT TAGGAGCCGA C GGTAGAGGT    300

GCAATCAGCA CGATTGCCCA AGGGTTGGAA TGGGCAGGGA ACAATGGCAT G CACGTTGCT    360

AATTTGAGTT TAGGAAGCCC TTCGCCAAGT GCCACACTTG AGCAAGCTGT T AATTATGCG    420

ACTTCTAGAG GCGTTCTTGT TGTAGCGGCA TCTGGGAATT CAGGTGCAAG C TCAATCAGC    480
```

```
TATCCGGCCC GTTATGCGAA CGCAATGGCA GTCGGAGCTA CTGACCAAAA C AACAACCGC      540

GCCAGCTTTT CACAGTATGG CGCAGGGCTT GACATTGTCG CACCAGGGGT A AACGTGCAG      600

AGCACATACC CAGGTTCAAC GTATGCCAGC TTAAACGGTA CATCGATGGC T ACTCCTCAT      660

GTTGCAGGTG TTGCAGCCCT TGTTAAACAA AAGAACCCAT CTTGGTCCAA T GTACAAATC      720

CGCAACCATC TAAAGAATAC GGCAACGAGC TTAGGAAGCA CGAACTTGTA T GGAAGCGGA      780

CTTGTCAATG CAGAAGCGGC AACACGC                                          807
```

(2) INFORMATION FOR SEQ ID NO:90:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (B) STRAIN: Bacillus l entus DSM 5483

(vii) IMMEDIATE SOURCE:
        (B) CLONE: S139A (xi) SEQUENCE DESCRIPTION: SEQ ID NO:90:

```
GCGCAATCAG TGCCATGGGG AATTAGCCGT GTGCAAGCCC CGGCTGCCCA T AACCGTGGA       60

TTGACAGGTT CTGGTGTAAA AGTTGCTGTC CTCGATACAG GTATTTCCAC T CATCCAGAC      120

TTAAATATTC GTGGTGGCGC TAGCTTTGTA CCAGGGGAAC CATCCACTCA A GATGGGAAT      180

GGGCATGGCA CGCATGTGGC CGGGACGATT GCTGCTTTAA ACAATTCGAT T GGCGTTCTT      240

GGCGTAGCGC CTAGTGCGGA ACTATACGCT GTTAAAGTTT TAGGAGCCGA C GGTAGAGGT      300

GCAATCAGCT CGATTGCCCA AGGGTTGGAA TGGGCAGGGA ACAATGGCAT G CACGTTGCT      360

AATTTGAGTT TAGGAAGCCC TTCGCCAAGT GCCACACTTG AGCAAGCTGT T AATGCAGCG      420

ACTTCTAGAG GCGTTCTTGT TGTAGCGGCA TCTGGGAATT CAGGTGCAAG C TCAATCAGC      480

TATCCGGCCC GTTATGCGAA CGCAATGGCA GTCGGAGCTA CTGACCAAAA C AACAACCGC      540

GCCAGCTTTT CACAGTATGG CGCAGGGCTT GACATTGTCG CACCAGGGGT A AACGTGCAG      600

AGCACATACC CAGGTTCAAC GTATGCCAGC TTAAACGGTA CATCGATGGC T ACTCCTCAT      660

GTTGCAGGTG CAGCAGCCCT TGTTAAACAA AAGAACCCAT CTTGGTCCAA T GTACAAATC      720

CGCAACCATC TAAAGAATAC GGCAACGAGC TTAGGAAGCA CGAACTTGTA T GGAAGCGGA      780

CTTGTCAATG CAGAAGCGGC AACACGC                                          807
```

(2) INFORMATION FOR SEQ ID NO:91:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:

(B) STRAIN: Bacillus l entus DSM 5483

(vii) IMMEDIATE SOURCE:
          (B) CLONE: S142T (xi) SEQUENCE DESCRIPTION: SEQ ID NO:91:

GCGCAATCAG TGCCATGGGG AATTAGCCGT GTGCAAGCCC CGGCTGCCCA T AACCGTGGA      60

TTGACAGGTT CTGGTGTAAA AGTTGCTGTC CTCGATACAG GTATTTCCAC T CATCCAGAC     120

TTAAATATTC GTGGTGGCGC TAGCTTTGTA CCAGGGGAAC CATCCACTCA A GATGGGAAT     180

GGGCATGGCA CGCATGTGGC CGGGACGATT GCTGCTTTAA ACAATTCGAT T GGCGTTCTT     240

GGCGTAGCGC CTAGTGCGGA ACTATACGCT GTTAAAGTTT TAGGAGCCGA C GGTAGAGGT    300

GCAATCAGCT CGATTGCCCA AGGGTTGGAA TGGGCAGGGA ACAATGGCAT G CACGTTGCT    360

AATTTGAGTT TAGGAAGCCC TTCGCCAAGT GCCACACTTG AGCAAGCTGT T AATAGCGCG    420

ACTACAAGAG GCGTTCTTGT TGTAGCGGCA TCTGGGAATT CAGGTGCAAG C TCAATCAGC    480

TATCCGGCCC GTTATGCGAA CGCAATGGCA GTCGGAGCTA CTGACCAAAA C AACAACCGC    540

GCCAGCTTTT CACAGTATGG CGCAGGGCTT GACATTGTCG CACCAGGGGT A AACGTGCAG    600

AGCACATACC CAGGTTCAAC GTATGCCAGC TTAAACGGTA CATCGATGGC T ACTCCTCAT    660

GTTGCAGGTG CAGCAGCCCT TGTTAAACAA AAGAACCCAT CTTGGTCCAA T GTACAAATC    720

CGCAACCATC TAAAGAATAC GGCAACGAGC TTAGGAAGCA CGAACTTGTA T GGAAGCGGA    780

CTTGTCAATG CAGAAGCGGC AACACGC                                         807

(2) INFORMATION FOR SEQ ID NO:92:

(i) SEQUENCE CHARACTERISTICS:
          (A) LENGTH: 807 base pairs
          (B) TYPE: nucleic acid
          (C) STRANDEDNESS: double
          (D) TOPOLOGY: linear (ii) MOLECULE TYPE: DNA (genomic)

(iii) HYPOTHETICAL: NO (iv) ANTI-SENSE: NO (vi) ORIGINAL SOURCE:
          (B) STRAIN: Bacillus l entus DSM 5483

(vii) IMMEDIATE SOURCE:
          (B) CLONE: S139T (xi) SEQUENCE DESCRIPTION: SEQ ID NO:92:

GCGCAATCAG TGCCATGGGG AATTAGCCGT GTGCAAGCCC CGGCTGCCCA T AACCGTGGA      60

TTGACAGGTT CTGGTGTAAA AGTTGCTGTC CTCGATACAG GTATTTCCAC T CATCCAGAC     120

TTAAATATTC GTGGTGGCGC TAGCTTTGTA CCAGGGGAAC CATCCACTCA A GATGGGAAT     180

GGGCATGGCA CGCATGTGGC CGGGACGATT GCTGCTTTAA ACAATTCGAT T GGCGTTCTT     240

GGCGTAGCGC CTAGTGCGGA ACTATACGCT GTTAAAGTTT TAGGAGCCGA C GGTAGAGGT    300

GCAATCAGCT CGATTGCCCA AGGGTTGGAA TGGGCAGGGA ACAATGGCAT G CACGTTGCT    360

AATTTGAGTT TAGGAAGCCC TTCGCCAAGT GCCACACTTG AGCAAGCTGT T AATACAGCG    420

ACTTCTAGAG GCGTTCTTGT TGTAGCGGCA TCTGGGAATT CAGGTGCAAG C TCAATCAGC    480

TATCCGGCCC GTTATGCGAA CGCAATGGCA GTCGGAGCTA CTGACCAAAA C AACAACCGC    540

GCCAGCTTTT CACAGTATGG CGCAGGGCTT GACATTGTCG CACCAGGGGT A AACGTGCAG    600

AGCACATACC CAGGTTCAAC GTATGCCAGC TTAAACGGTA CATCGATGGC T ACTCCTCAT    660

```
GTTGCAGGTG CAGCAGCCCT TGTTAAACAA AGAACCCAT CTTGGTCCAA T GTACAAATC      720

CGCAACCATC TAAAGAATAC GGCAACGAGC TTAGGAAGCA CGAACTTGTA T GGAAGCGGA      780

CTTGTCAATG CAGAAGCGGC AACACGC                                          807
```

(2) INFORMATION FOR SEQ ID NO:93:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (B) STRAIN: Bacillus l entus DSM 5483

(vii) IMMEDIATE SOURCE:
        (B) CLONE: I102W (xi) SEQUENCE DESCRIPTION: SEQ ID NO:93:

```
GCGCAATCAG TGCCATGGGG AATTAGCCGT GTGCAAGCCC CGGCTGCCCA T AACCGTGGA       60

TTGACAGGTT CTGGTGTAAA AGTTGCTGTC CTCGATACAG GTATTTCCAC T CATCCAGAC      120

TTAAATATTC GTGGTGGCGC TAGCTTTGTA CCAGGGGAAC CATCCACTCA A GATGGGAAT      180

GGGCATGGCA CGCATGTGGC CGGGACGATT GCTGCTTTAA ACAATTCGAT T GGCGTTCTT      240

GGCGTAGCGC CTAGTGCGGA ACTATACGCT GTTAAAGTTT TAGGAGCCGA C GGTAGAGGT      300

GCATGGAGCT CGATTGCCCA AGGGTTGGAA TGGGCAGGGA ACAATGGCAT G CACGTTGCT      360

AATTTGAGTT TAGGAAGCCC TTCGCCAAGT GCCACACTTG AGCAAGCTGT T AATAGCGCG      420

ACTTCTAGAG GCGTTCTTGT TGTAGCGGCA TCTGGGAATT CAGGTGCAAG C TCAATCAGC      480

TATCCGGCCC GTTATGCGAA CGCAATGGCA GTCGGAGCTA CTGACCAAAA C AACAACCGC      540

GCCAGCTTTT CACAGTATGG CGCAGGGCTT GACATTGTCG CACCAGGGGT A AACGTGCAG      600

AGCACATACC CAGGTTCAAC GTATGCCAGC TTAAACGGTA CATCGATGGC T ACTCCTCAT      660

GTTGCAGGTG CAGCAGCCCT TGTTAAACAA AGAACCCAT CTTGGTCCAA T GTACAAATC      720

CGCAACCATC TAAAGAATAC GGCAACGAGC TTAGGAAGCA CGAACTTGTA T GGAAGCGGA      780

CTTGTCAATG CAGAAGCGGC AACACGC                                          807
```

(2) INFORMATION FOR SEQ ID NO:94:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (B) STRAIN: Bacillus l entus DSM 5483

(vii) IMMEDIATE SOURCE:
        (B) CLONE: A96N

-continued (xi) SEQUENCE DESCRIPTION: SEQ ID NO:94:

```
GCGCAATCAG TGCCATGGGG AATTAGCCGT GTGCAAGCCC CGGCTGCCCA T AACCGTGGA        60
TTGACAGGTT CTGGTGTAAA AGTTGCTGTC CTCGATACAG GTATTTCCAC T CATCCAGAC       120
TTAAATATTC GTGGTGGCGC TAGCTTTGTA CCAGGGGAAC CATCCACTCA A GATGGGAAT       180
GGGCATGGCA CGCATGTGGC CGGGACGATT GCTGCTTTAA ACAATTCGAT T GGCGTTCTT       240
GGCGTAGCGC CTAGTGCGGA ACTATACGCT GTTAAAGTTT TAGGAAACGA C GGTAGAGGT       300
GCAATCAGCT CGATTGCCCA AGGGTTGGAA TGGGCAGGGA ACAATGGCAT G CACGTTGCT       360
AATTTGAGTT TAGGAAGCCC TTCGCCAAGT GCCACACTTG AGCAAGCTGT T AATAGCGCG       420
ACTTCTAGAG GCGTTCTTGT TGTAGCGGCA TCTGGGAATT CAGGTGCAAG C TCAATCAGC       480
TATCCGGCCC GTTATGCGAA CGCAATGGCA GTCGGAGCTA CTGACCAAAA C AACAACCGC       540
GCCAGCTTTT CACAGTATGG CGCAGGGCTT GACATTGTCG CACCAGGGGT A AACGTGCAG       600
AGCACATACC CAGGTTCAAC GTATGCCAGC TTAAACGGTA CATCGATGGC T ACTCCTCAT       660
GTTGCAGGTG CAGCAGCCCT TGTTAAACAA AAGAACCCAT CTTGGTCCAA T GTACAAATC       720
CGCAACCATC TAAAGAATAC GGCAACGAGC TTAGGAAGCA CGAACTTGTA T GGAAGCGGA       780
CTTGTCAATG CAGAAGCGGC AACACGC                                            807
```

(2) INFORMATION FOR SEQ ID NO:95:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (B) STRAIN: Bacillus l entus DSM 5483

(vii) IMMEDIATE SOURCE:
        (B) CLONE: N42F (xi) SEQUENCE DESCRIPTION: SEQ ID NO:95:

```
GCGCAATCAG TGCCATGGGG AATTAGCCGT GTGCAAGCCC CGGCTGCCCA T AACCGTGGA        60
TTGACAGGTT CTGGTGTAAA AGTTGCTGTC CTCGATACAG GTATTTCCAC T CATCCAGAC       120
TTATTTATTC GTGGTGGCGC TAGCTTTGTA CCAGGGGAAC CATCCACTCA A GATGGGAAT       180
GGGCATGGCA CGCATGTGGC CGGGACGATT GCTGCTTTAA ACAATTCGAT T GGCGTTCTT       240
GGCGTAGCGC CTAGTGCGGA ACTATACGCT GTTAAAGTTT TAGGAGCCGA C GGTAGAGGT       300
GCAATCAGCT CGATTGCCCA AGGGTTGGAA TGGGCAGGGA ACAATGGCAT G CACGTTGCT       360
AATTTGAGTT TAGGAAGCCC TTCGCCAAGT GCCACACTTG AGCAAGCTGT T AATAGCGCG       420
ACTTCTAGAG GCGTTCTTGT TGTAGCGGCA TCTGGGAATT CAGGTGCAAG C TCAATCAGC       480
TATCCGGCCC GTTATGCGAA CGCAATGGCA GTCGGAGCTA CTGACCAAAA C AACAACCGC       540
GCCAGCTTTT CACAGTATGG CGCAGGGCTT GACATTGTCG CACCAGGGGT A AACGTGCAG       600
AGCACATACC CAGGTTCAAC GTATGCCAGC TTAAACGGTA CATCGATGGC T ACTCCTCAT       660
GTTGCAGGTG CAGCAGCCCT TGTTAAACAA AAGAACCCAT CTTGGTCCAA T GTACAAATC       720
CGCAACCATC TAAAGAATAC GGCAACGAGC TTAGGAAGCA CGAACTTGTA T GGAAGCGGA       780
```

```
CTTGTCAATG CAGAAGCGGC AACACGC                                              807
```

(2) INFORMATION FOR SEQ ID NO:96:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (B) STRAIN: Bacillus l entus DSM 5483

(vii) IMMEDIATE SOURCE:
        (B) CLONE: S142A (xi) SEQUENCE DESCRIPTION: SEQ ID NO:96:

```
GCGCAATCAG TGCCATGGGG AATTAGCCGT GTGCAAGCCC CGGCTGCCCA T AACCGTGGA    60
TTGACAGGTT CTGGTGTAAA AGTTGCTGTC CTCGATACAG GTATTTCCAC T CATCCAGAC   120
TTAAATATTC GTGGTGGCGC TAGCTTTGTA CCAGGGGAAC CATCCACTCA A GATGGGAAT   180
GGGCATGGCA CGCATGTGGC CGGGACGATT GCTGCTTTAA ACAATTCGAT T GGCGTTCTT   240
GGCGTAGCGC CTAGTGCGGA ACTATACGCT GTTAAAGTTT TAGGAGCCGA C GGTAGAGGT   300
GCAATCAGCT CGATTGCCCA AGGGTTGGAA TGGGCAGGGA ACAATGGCAT G CACGTTGCT   360
AATTTGAGTT TAGGAAGCCC TTCGCCAAGT GCCACACTTG AGCAAGCTGT T AATAGCGCG   420
ACTGCAAGAG GCGTTCTTGT TGTAGCGGCA TCTGGGAATT CAGGTGCAAG C TCAATCAGC   480
TATCCGGCCC GTTATGCGAA CGCAATGGCA GTCGGAGCTA CTGACCAAAA C AACAACCGC   540
GCCAGCTTTT CACAGTATGG CGCAGGGCTT GACATTGTCG CACCAGGGGT A AACGTGCAG   600
AGCACATACC CAGGTTCAAC GTATGCCAGC TTAAACGGTA CATCGATGGC T ACTCCTCAT   660
GTTGCAGGTG CAGCAGCCCT TGTTAAACAA AAGAACCCAT CTTGGTCCAA T GTACAAATC   720
CGCAACCATC TAAAGAATAC GGCAACGAGC TTAGGAAGCA CGAACTTGTA T GGAAGCGGA   780
CTTGTCAATG CAGAAGCGGC AACACGC                                        807
```

(2) INFORMATION FOR SEQ ID NO:97:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (B) STRAIN: Bacillus l entus DSM 5483

(vii) IMMEDIATE SOURCE:
        (B) CLONE: H118F (xi) SEQUENCE DESCRIPTION: SEQ ID NO:97:

```
GCGCAATCAG TGCCATGGGG AATTAGCCGT GTGCAAGCCC CGGCTGCCCA T AACCGTGGA    60
TTGACAGGTT CTGGTGTAAA AGTTGCTGTC CTCGATACAG GTATTTCCAC T CATCCAGAC   120
```

```
TTAAATATTC GTGGTGGCGC TAGCTTTGTA CCAGGGGAAC CATCCACTCA A GATGGGAAT      180

GGGCATGGCA CGCATGTGGC CGGGACGATT GCTGCTTTAA ACAATTCGAT T GGCGTTCTT      240

GGCGTAGCGC CTAGTGCGGA ACTATACGCT GTTAAAGTTT TAGGAGCCGA C GGTAGAGGT      300

GCAATCAGCT CGATTGCCCA AGGGTTGGAA TGGGCAGGGA ACAATGGCAT G TTTGTTGCT      360

AATTTGAGTT TAGGAAGCCC TTCGCCAAGT GCCACACTTG AGCAAGCTGT T AATAGCGCG      420

ACTTCTAGAG GCGTTCTTGT TGTAGCGGCA TCTGGGAATT CAGGTGCAAG C TCAATCAGC      480

TATCCGGCCC GTTATGCGAA CGCAATGGCA GTCGGAGCTA CTGACCAAAA C AACAACCGC      540

GCCAGCTTTT CACAGTATGG CGCAGGGCTT GACATTGTCG CACCAGGGGT A AACGTGCAG      600

AGCACATACC CAGGTTCAAC GTATGCCAGC TTAAACGGTA CATCGATGGC T ACTCCTCAT      660

GTTGCAGGTG CAGCAGCCCT TGTTAAACAA AGAACCCAT CTTGGTCCAA T GTACAAATC       720

CGCAACCATC TAAAGAATAC GGCAACGAGC TTAGGAAGCA CGAACTTGTA T GGAAGCGGA      780

CTTGTCAATG CAGAAGCGGC AACACGC                                          807
```

(2) INFORMATION FOR SEQ ID NO:98:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (B) STRAIN: Bacillus l entus DSM 5483

(vii) IMMEDIATE SOURCE:
        (B) CLONE: N237A (xi) SEQUENCE DESCRIPTION: SEQ ID NO:98:

```
GCGCAATCAG TGCCATGGGG AATTAGCCGT GTGCAAGCCC CGGCTGCCCA T AACCGTGGA       60

TTGACAGGTT CTGGTGTAAA AGTTGCTGTC CTCGATACAG GTATTTCCAC T CATCCAGAC      120

TTAAATATTC GTGGTGGCGC TAGCTTTGTA CCAGGGGAAC CATCCACTCA A GATGGGAAT      180

GGGCATGGCA CGCATGTGGC CGGGACGATT GCTGCTTTAA ACAATTCGAT T GGCGTTCTT      240

GGCGTAGCGC CTAGTGCGGA ACTATACGCT GTTAAAGTTT TAGGAGCCGA C GGTAGAGGT      300

GCAATCAGCT CGATTGCCCA AGGGTTGGAA TGGGCAGGGA ACAATGGCAT G CACGTTGCT      360

AATTTGAGTT TAGGAAGCCC TTCGCCAAGT GCCACACTTG AGCAAGCTGT T AATAGCGCG      420

ACTTCTAGAG GCGTTCTTGT TGTAGCGGCA TCTGGGAATT CAGGTGCAAG C TCAATCAGC      480

TATCCGGCCC GTTATGCGAA CGCAATGGCA GTCGGAGCTA CTGACCAAAA C AACAACCGC      540

GCCAGCTTTT CACAGTATGG CGCAGGGCTT GACATTGTCG CACCAGGGGT A AACGTGCAG      600

AGCACATACC CAGGTTCAAC GTATGCCAGC TTAAACGGTA CATCGATGGC T ACTCCTCAT      660

GTTGCAGGTG CAGCAGCCCT TGTTAAACAA AGAACCCAT CTTGGTCCGC T GTACAAATC       720

CGCAACCATC TAAAGAATAC GGCAACGAGC TTAGGAAGCA CGAACTTGTA T GGAAGCGGA      780

CTTGTCAATG CAGAAGCGGC AACACGC                                          807
```

(2) INFORMATION FOR SEQ ID NO:99:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (B) STRAIN: Bacillus l entus DSM 5483

(vii) IMMEDIATE SOURCE:
        (B) CLONE: N255P (xi) SEQUENCE DESCRIPTION: SEQ ID NO:99:

| | | | | | |
|---|---|---|---|---|---|
| GCGCAATCAG | TGCCATGGGG | AATTAGCCGT | GTGCAAGCCC | CGGCTGCCCA T | AACCGTGGA       60 |
| TTGACAGGTT | CTGGTGTAAA | AGTTGCTGTC | CTCGATACAG | GTATTTCCAC T | CATCCAGAC      120 |
| TTAAATATTC | GTGGTGGCGC | TAGCTTTGTA | CCAGGGGAAC | CATCCACTCA A | GATGGGAAT      180 |
| GGGCATGGCA | CGCATGTGGC | CGGGACGATT | GCTGCTTTAA | ACAATTCGAT T | GGCGTTCTT      240 |
| GGCGTAGCGC | CTAGTGCGGA | ACTATACGCT | GTTAAAGTTT | TAGGAGCCGA C | GGTAGAGGT      300 |
| GCAATCAGCT | CGATTGCCCA | AGGGTTGGAA | TGGGCAGGGA | ACAATGGCAT G | CACGTTGCT      360 |
| AATTTGAGTT | TAGGAAGCCC | TTCGCCAAGT | GCCACACTTG | AGCAAGCTGT T | AATAGCGCG      420 |
| ACTTCTAGAG | GCGTTCTTGT | TGTAGCGGCA | TCTGGGAATT | CAGGTGCAAG C | TCAATCAGC      480 |
| TATCCGGCCC | GTTATGCGAA | CGCAATGGCA | GTCGGAGCTA | CTGACCAAAA C | AACAACCGC      540 |
| GCCAGCTTTT | CACAGTATGG | CGCAGGGCTT | GACATTGTCG | CACCAGGGGT A | AACGTGCAG      600 |
| AGCACATACC | CAGGTTCAAC | GTATGCCAGC | TTAAACGGTA | CATCGATGGC T | ACTCCTCAT      660 |
| GTTGCAGGTG | CAGCAGCCCT | TGTTAAACAA | AAGAACCCAT | CTTGGTCCAA T | GTACAAATC      720 |
| CGCAACCATC | TAAAGAATAC | GGCAACGAGC | TTAGGAAGCA | CGCCATTGTA T | GGAAGCGGA      780 |
| CTTGTCAATG | CAGAAGCGGC | AACACGC     | | |            807 |

(2) INFORMATION FOR SEQ ID NO:100:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (B) STRAIN: Bacillus l entus DSM 5483

(vii) IMMEDIATE SOURCE:
        (B) CLONE: T141W, N237 A (xi) SEQUENCE DESCRIPTION: SEQ ID NO:100 :

| | | | | | |
|---|---|---|---|---|---|
| GCGCAATCAG | TGCCATGGGG | AATTAGCCGT | GTGCAAGCCC | CGGCTGCCCA T | AACCGTGGA       60 |
| TTGACAGGTT | CTGGTGTAAA | AGTTGCTGTC | CTCGATACAG | GTATTTCCAC T | CATCCAGAC      120 |
| TTAAATATTC | GTGGTGGCGC | TAGCTTTGTA | CCAGGGGAAC | CATCCACTCA A | GATGGGAAT      180 |
| GGGCATGGCA | CGCATGTGGC | CGGGACGATT | GCTGCTTTAA | ACAATTCGAT T | GGCGTTCTT      240 |

| | | |
|---|---|---|
| GGCGTAGCGC CTAGTGCGGA ACTATACGCT GTTAAAGTTT TAGGAGCCGA C GGTAGAGGT | 300 | |
| GCAATCAGCT CGATTGCCCA AGGGTTGGAA TGGGCAGGGA ACAATGGCAT G CACGTTGCT | 360 | |
| AATTTGAGTT TAGGAAGCCC TTCGCCAAGT GCCACACTTG AGCAAGCTGT T AATAGCGCG | 420 | |
| TGGTCTAGAG GCGTTCTTGT TGTAGCGGCA TCTGGGAATT CAGGTGCAAG C TCAATCAGC | 480 | |
| TATCCGGCCC GTTATGCGAA CGCAATGGCA GTCGGAGCTA CTGACCAAAA C AACAACCGC | 540 | |
| GCCAGCTTTT CACAGTATGG CGCAGGGCTT GACATTGTCG CACCAGGGGT A AACGTGCAG | 600 | |
| AGCACATACC CAGGTTCAAC GTATGCCAGC TTAAACGGTA CATCGATGGC T ACTCCTCAT | 660 | |
| GTTGCAGGTG CAGCAGCCCT TGTTAAACAA AGAACCCAT CTTGGTCCGC T GTACAAATC | 720 | |
| CGCAACCATC TAAAGAATAC GGCAACGAGC TTAGGAAGCA CGAACTTGTA T GGAAGCGGA | 780 | |
| CTTGTCAATG CAGAAGCGGC AACACGC | 807 | |

(2) INFORMATION FOR SEQ ID NO:101:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (B) STRAIN: Bacillus l entus DSM 5483

(vii) IMMEDIATE SOURCE:
        (B) CLONE: T268V (xi) SEQUENCE DESCRIPTION: SEQ ID NO:101 :

| | | |
|---|---|---|
| GCGCAATCAG TGCCATGGGG AATTAGCCGT GTGCAAGCCC CGGCTGCCCA T AACCGTGGA | 60 | |
| TTGACAGGTT CTGGTGTAAA AGTTGCTGTC CTCGATACAG GTATTTCCAC T CATCCAGAC | 120 | |
| TTAAATATTC GTGGTGGCGC TAGCTTTGTA CCAGGGGAAC CATCCACTCA A GATGGGAAT | 180 | |
| GGGCATGGCA CGCATGTGGC CGGGACGATT GCTGCTTTAA ACAATTCGAT T GGCGTTCTT | 240 | |
| GGCGTAGCGC CTAGTGCGGA ACTATACGCT GTTAAAGTTT TAGGAGCCGA C GGTAGAGGT | 300 | |
| GCAATCAGCT CGATTGCCCA AGGGTTGGAA TGGGCAGGGA ACAATGGCAT G CACGTTGCT | 360 | |
| AATTTGAGTT TAGGAAGCCC TTCGCCAAGT GCCACACTTG AGCAAGCTGT T AATAGCGCG | 420 | |
| ACTTCTAGAG GCGTTCTTGT TGTAGCGGCA TCTGGGAATT CAGGTGCAAG C TCAATCAGC | 480 | |
| TATCCGGCCC GTTATGCGAA CGCAATGGCA GTCGGAGCTA CTGACCAAAA C AACAACCGC | 540 | |
| GCCAGCTTTT CACAGTATGG CGCAGGGCTT GACATTGTCG CACCAGGGGT A AACGTGCAG | 600 | |
| AGCACATACC CAGGTTCAAC GTATGCCAGC TTAAACGGTA CATCGATGGC T ACTCCTCAT | 660 | |
| GTTGCAGGTG CAGCAGCCCT TGTTAAACAA AGAACCCAT CTTGGTCCAA T GTACAAATC | 720 | |
| CGCAACCATC TAAAGAATAC GGCAACGAGC TTAGGAAGCA CGAACTTGTA T GGAAGCGGA | 780 | |
| CTTGTCAATG CAGAAGCGGC AGTTCGC | 807 | |

(2) INFORMATION FOR SEQ ID NO:102:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (B) STRAIN: Bacillus l entus DSM 5483

(vii) IMMEDIATE SOURCE:
             (B) CLONE: K229W (xi) SEQUENCE DESCRIPTION: SEQ ID NO:102 :

```
GCGCAATCAG TGCCATGGGG AATTAGCCGT GTGCAAGCCC CGGCTGCCCA T AACCGTGGA      60

TTGACAGGTT CTGGTGTAAA AGTTGCTGTC CTCGATACAG GTATTTCCAC T CATCCAGAC     120

TTAAATATTC GTGGTGGCGC TAGCTTTGTA CCAGGGGAAC CATCCACTCA A GATGGGAAT    180

GGGCATGGCA CGCATGTGGC CGGGACGATT GCTGCTTTAA ACAATTCGAT T GGCGTTCTT    240

GGCGTAGCGC CTAGTGCGGA ACTATACGCT GTTAAAGTTT TAGGAGCCGA C GGTAGAGGT    300

GCAATCAGCT CGATTGCCCA AGGGTTGGAA TGGGCAGGGA ACAATGGCAT G CACGTTGCT    360

AATTTGAGTT TAGGAAGCCC TTCGCCAAGT GCCACACTTG AGCAAGCTGT T AATAGCGCG    420

ACTTCTAGAG GCGTTCTTGT TGTAGCGGCA TCTGGGAATT CAGGTGCAAG C TCAATCAGC    480

TATCCGGCCC GTTATGCGAA CGCAATGGCA GTCGGAGCTA CTGACCAAAA C AACAACCGC    540

GCCAGCTTTT CACAGTATGG CGCAGGGCTT GACATTGTCG CACCAGGGGT A AACGTGCAG    600

AGCACATACC CAGGTTCAAC GTATGCCAGC TTAAACGGTA CATCGATGGC T ACTCCTCAT    660

GTTGCAGGTG CAGCAGCCCT TGTTTGGCAA AAGAACCCAT CTTGGTCCAA T GTACAAATC    720

CGCAACCATC TAAAGAATAC GGCAACGAGC TTAGGAAGCA CGAACTTGTA T GGAAGCGGA    780

CTTGTCAATG CAGAAGCGGC AACACGC                                         807
```

(2) INFORMATION FOR SEQ ID NO:103:

(i) SEQUENCE CHARACTERISTICS:
             (A) LENGTH: 807 base pairs
             (B) TYPE: nucleic acid
             (C) STRANDEDNESS: double
             (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (B) STRAIN: Bacillus l entus DSM 5483

(vii) IMMEDIATE SOURCE:
             (B) CLONE: T141W (xi) SEQUENCE DESCRIPTION: SEQ ID NO:103 :

```
GCGCAATCAG TGCCATGGGG AATTAGCCGT GTGCAAGCCC CGGCTGCCCA T AACCGTGGA      60

TTGACAGGTT CTGGTGTAAA AGTTGCTGTC CTCGATACAG GTATTTCCAC T CATCCAGAC    120

TTAAATATTC GTGGTGGCGC TAGCTTTGTA CCAGGGGAAC CATCCACTCA A GATGGGAAT    180

GGGCATGGCA CGCATGTGGC CGGGACGATT GCTGCTTTAA ACAATTCGAT T GGCGTTCTT    240

GGCGTAGCGC CTAGTGCGGA ACTATACGCT GTTAAAGTTT TAGGAGCCGA C GGTAGAGGT    300

GCAATCAGCT CGATTGCCCA AGGGTTGGAA TGGGCAGGGA ACAATGGCAT G CACGTTGCT    360

AATTTGAGTT TAGGAAGCCC TTCGCCAAGT GCCACACTTG AGCAAGCTGT T AATAGCGCG    420
```

-continued

```
TGGTCTAGAG GCGTTCTTGT TGTAGCGGCA TCTGGGAATT CAGGTGCAAG C TCAATCAGC        480

TATCCGGCCC GTTATGCGAA CGCAATGGCA GTCGGAGCTA CTGACCAAAA C AACAACCGC        540

GCCAGCTTTT CACAGTATGG CGCAGGGCTT GACATTGTCG CACCAGGGGT A AACGTGCAG        600

AGCACATACC CAGGTTCAAC GTATGCCAGC TTAAACGGTA CATCGATGGC T ACTCCTCAT        660

GTTGCAGGTG CAGCAGCCCT TGTTAAACAA AAGAACCCAT CTTGGTCCAA T GTACAAATC        720

CGCAACCATC TAAAGAATAC GGCAACGAGC TTAGGAAGCA CGAACTTGTA T GGAAGCGGA        780

CTTGTCAATG CAGAAGCGGC AACACGC                                             807

(2) INFORMATION FOR SEQ ID NO:104:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Bacillus lentus
        (B) STRAIN: DSM 5483

(vii) IMMEDIATE SOURCE:
        (B) CLONE: wild type (xi) SEQUENCE DESCRIPTION: SEQ ID NO:104 :

GCGCAATCAG TGCCATGGGG AATTAGCCGT GTGCAAGCCC CGGCTGCCCA T AACCGTGGA         60

TTGACAGGTT CTGGTGTAAA AGTTGCTGTC CTCGATACAG GTATTTCCAC T CATCCAGAC        120

TTAAATATTC GTGGTGGCGC TAGCTTTGTA CCAGGGGAAC CATCCACTCA A GATGGGAAT       180

GGGCATGGCA CGCATGTGGC CGGGACGATT GCTGCTTTAA ACAATTCGAT T GGCGTTCTT        240

GGCGTAGCGC CTAGTGCGGA ACTATACGCT GTTAAAGTTT TAGGAGCCGA C GGTAGAGGT        300

GCAATCAGCT CGATTGCCCA AGGGTTGGAA TGGGCAGGGA ACAATGGCAT G CACGTTGCT        360

AATTTGAGTT TAGGAAGCCC TTCGCCAAGT GCCACACTTG AGCAAGCTGT T AATAGCGCG        420

ACTTCTAGAG GCGTTCTTGT TGTAGCGGCA TCTGGGAATT CAGGTGCAAG C TCAATCAGC        480

TATCCGGCCC GTTATGCGAA CGCAATGGCA GTCGGAGCTA CTGACCAAAA C AACAACCGC        540

GCCAGCTTTT CACAGTATGG CGCAGGGCTT GACATTGTCG CACCAGGGGT A AACGTGCAG        600

AGCACATACC CAGGTTCAAC GTATGCCAGC TTAAACGGTA CATCGATGGC T ACTCCTCAT        660

GTTGCAGGTG CAGCAGCCCT TGTTAAACAA AAGAACCCAT CTTGGTCCAA T GTACAAATC        720

CGCAACCATC TAAAGAATAC GGCAACGAGC TTAGGAAGCA CGAACTTGTA T GGAAGCGGA        780

CTTGTCAATG CAGAAGCGGC AACACGC                                             807
```